(12) United States Patent
Matsui et al.

(10) Patent No.: US 7,838,087 B2
(45) Date of Patent: *Nov. 23, 2010

(54) BENZENE DERIVATIVE, LIQUID CRYSTAL COMPOSITION AND LIQUID CRYSTAL DISPLAY DEVICE

(75) Inventors: Syuichi Matsui, Chiba (JP); Yasuyuki Sasada, Chiba (JP)

(73) Assignees: Chisso Corporation, Osaka (JP); Chisso Petrochemical Corporation, Tokyo (JP)

( * ) Notice: Subject to any disclaimer, the term of this patent is extended or adjusted under 35 U.S.C. 154(b) by 368 days.

This patent is subject to a terminal disclaimer.

(21) Appl. No.: 10/593,874

(22) PCT Filed: Mar. 29, 2005

(86) PCT No.: PCT/JP2005/005837

§ 371 (c)(1),
(2), (4) Date: Nov. 8, 2006

(87) PCT Pub. No.: WO2005/095311

PCT Pub. Date: Oct. 13, 2005

(65) Prior Publication Data

US 2007/0200092 A1 Aug. 30, 2007

(30) Foreign Application Priority Data

Apr. 1, 2004 (JP) .............................. 2004-108969

(51) Int. Cl.
*C09K 19/34* (2006.01)
*C09K 19/30* (2006.01)
*C09K 19/12* (2006.01)
*C09K 19/20* (2006.01)
*C07D 309/06* (2006.01)
*C07C 25/13* (2006.01)
*C07C 25/18* (2006.01)
*C07C 25/24* (2006.01)

(52) U.S. Cl. .............. 428/1.1; 252/299.61; 252/299.63; 252/299.66; 252/299.67; 549/380; 570/127; 570/128; 570/129

(58) Field of Classification Search ............ 252/299.61, 252/299.62, 299.63, 299.66, 299.67; 570/129, 570/127, 128; 428/1.1; 549/380
See application file for complete search history.

(56) References Cited

U.S. PATENT DOCUMENTS 6,576,303 B1 6/2003 Tamura et al.
7,306,831 B1* 12/2007 Yamamoto ................... 428/1.1
7,348,043 B2* 3/2008 Fujita et al. ................... 428/1.1
2005/0230661 A1* 10/2005 Hattori et al. ........... 252/299.63

FOREIGN PATENT DOCUMENTS

DE 43 38 348 5/1994
JP 8-40953 2/1996
JP 2004-75667 3/2004

OTHER PUBLICATIONS

Pamphlet of WO 0039063, Jul. 6, 2000.
Peer Kirsch et al., "Nematic Liquid Crystals with Negative Dielectric Anisotropy: Molecular Design and Synthesis", Synlett, No. 4, ISSN: 0936-5214, pp. 389-396, 1999.
Peer Kirsch et al., "Nematic Liquid Crystals for Active Matrix Displays: Molecular Design and Synthesis", Angew. Chem. Int. Ed., 39, pp. 4216-4235, 2000.

* cited by examiner

*Primary Examiner*—Shean C Wu
(74) *Attorney, Agent, or Firm*—Wenderoth, Lind & Ponack, L.L.P.

(57) ABSTRACT

Known compounds showing negative dielectric anisotropy show negative dielectric anisotropy of relatively large values but are not satisfactory in view of the balance of the physical property as the liquid crystal material such as having low clearing point and showing high viscosity. The present invention intends to provide a liquid crystalline compound showing a negative dielectric anisotropy, as well as having excellent balance for physical property such as having relatively high clearing point, relatively low viscosity, appropriate optical anisotropy, and excellent compatibility with other liquid crystalline compounds.

The compound of the invention is a compound represented by Formula (1) or Formula (2). In the formulae, Ra and Rb each independently is hydrogen or alkyl of 1 to 20 carbon atoms, $A^1, A^{11}, A^{12}, A^2, A^{21}$ and $A^{22}$ each independently is a cyclic group, Y, W, $Z^{11}, Z^{12}, Z^2, Z^{21}$ and $Z^{22}$ each independently is a bonding group, and j, k, m, n, p and q each independently is 0 or 1 and the sum of them is 1, 2 or 3;

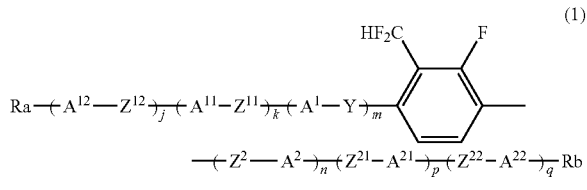

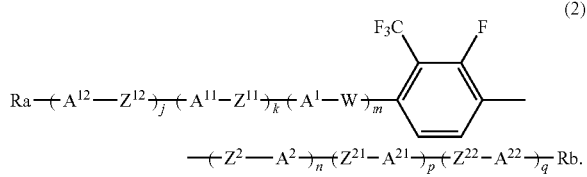

39 Claims, No Drawings

BENZENE DERIVATIVE, LIQUID CRYSTAL COMPOSITION AND LIQUID CRYSTAL DISPLAY DEVICE

TECHNICAL FIELD

The present invention concerns a liquid crystalline compound, a liquid crystal composition, and a liquid crystal display device. More specifically, it relates to a benzene derivative, a liquid crystal composition containing the same and having a nematic phase, and a liquid crystal display device containing the composition.

BACKGROUND ART

The liquid crystal display device is classified based on the operation mode of liquid crystals, for example, into PC (phase change), TN (twisted nematic), STN (super twisted nematic), BTN (bistable twisted nematic), ECB (electrically controlled birefringence), OCB (optically compensated bend), IPS (in-plane switching), and VA (vertical alignment). The device is classified based on the driving system as PM (passive matrix) and AM (active matrix). PM (passive matrix) is classified into static, multiplex, etc. and AM is classified into TFT (thin film transistor), MIM (metal insulator metal), etc.

The liquid crystal display devices contain liquid crystal compositions. In the following description, the liquid crystal display device is sometimes referred to merely as a device. The liquid crystal composition is sometimes referred merely to as a composition. The liquid crystalline compound is sometimes referred to merely as a compound. In order to improve the characteristics of the device, it is preferred that the composition has appropriate physical properties. General physical properties necessary for compound as an ingredient of the composition are as described below.
(1) Chemical stability and physical stability
(2) High clearing point
(3) Low lower limit temperature of a liquid crystal phase
(4) Low viscosity
(5) Appropriate optical anisotropy
(6) Appropriate dielectric anisotropy
(7) High specific resistivity The clearing point is a transition temperature from liquid crystal phase to isotropic phase. The liquid crystal phase means nematic phase, smectic phase, etc. Compounds having high dielectric anisotropy often have high viscosity.

The composition is prepared by mixing various compounds. Accordingly, it is preferred that the compounds are well mixed with other compounds. Since the device is sometimes used at a temperature below a freezing point, compounds having favorable compatibility at a low temperature are preferred. Compounds having high clearing point or low lower limit temperature of a liquid crystal phase contribute to a wide temperature range of the nematic phase in the composition. A preferred composition has an optical anisotropy suitable to the low viscosity and the mode of the device. A high dielectric anisotropy of the compound contributes to a low threshold voltage of the composition. Such a composition can provide a device having such characteristics as usable wide temperature range, short response time, large contrast ratio, low driving voltage, small power consumption, and large voltage holding ratio.

As a compound showing a negative dielectric anisotropy, a compound (i) having 2,3-difluoro-1,4-phenylene in a partial structure has been known generally (refer to Non-Patent Document 2). As a compound for improving the dielectric anisotropy, a compound (ii) having trifluoromethyl laterally bonded, and a compound (iii) and a compound (iv) in which difluoromethyl is bonded for making the negative dielectric anisotropy to a more larger value have been reported (refer to Patent document 1, Non-Patent Document 1, Non-Patent Document 2, and Patent Document 2). However, while such compounds show negative dielectric anisotropy of relatively large values, balance of the physical properties as the liquid crystal material is not preferred such that the clearing point is low or they show high viscosity. Further preferred liquid crystalline compounds, liquid crystal compositions, and liquid crystal display devices are demanded.

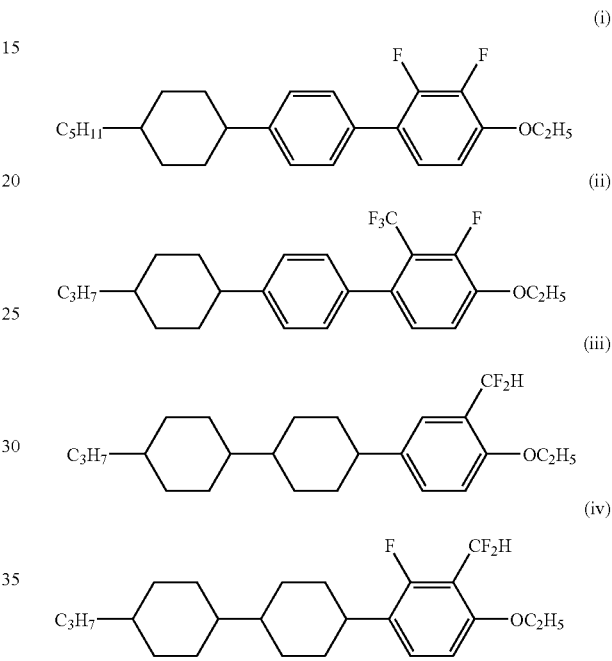

[Patent Document 1] JP-A No. 8-040953
[Patent Document 2] Pamphlet of WO2000/39063
[Non-Patent Document 1] Synlett. 1999, No. 4, 389-396
[Non-Patent Document 2] Angew. Chem. Int. Ed. 2000, 39, 4216-4235

DISCLOSURE OF THE INVENTION

Subject to be Solved by the Invention

A first object of the present invention is to provide a liquid crystalline compound showing negative dielectric anisotropy and having excellent balance of physical properties such as relatively high clearing point, relatively low viscosity, appropriate optical anisotropy, and excellent compatibility with other liquid crystalline compounds. A second object is to provide a liquid crystal composition containing the compound and having a wide temperature range for the nematic phase, low viscosity, appropriate optical anisotropy, and low threshold voltage. A third object is to provide a liquid crystal display device containing the composition and having a quick response, small power consumption, high contrast, and high voltage holding ratio.

Means for the Solution of the Subject

At first, terms in the present invention are to be described. The liquid crystalline compound is a collective name of compounds having liquid crystal phases such as nematic phase and smectic phase and compounds not having the liquid crystal phase but useful as the ingredient for the liquid crystal composition. The liquid crystal display device is a collective name of liquid crystal display panels and liquid crystal display modules. The upper limit temperature of the nematic phase is a phase transition temperature from the nematic phase to the isotropic phase and it is sometimes referred to simply as an upper limit temperature. The lower limit temperature of the nematic phase is sometimes referred to simply as a lower limit temperature. The compound represented by Formula (1) is sometimes described as Compound (1). The indication is sometimes applied also to the compound represented by Formula (2), etc. "Arbitrary" means not only the position but also the number are optional. Then, the description that arbitrary A may be replaced by B, C or D has a meaning that at least two of A replaced by B, A replaced by C, and A replaced by D are present together, as well as a meaning that an A may be replaced by B, C or D, and a meaning that any of plural A may be replaced by one of B, C and D. For example, n-butyl in which arbitrary —CH$_2$— may be replaced by —O— or —CH=CH— includes CH$_3$(CH$_2$)$_3$— and, in addition, CH$_3$ (CH$_2$)$_2$O—, CH$_3$—O— (CH$_2$)$_2$—, CH$_3$—O—CH$_2$—O—, CH$_2$=CH— (CH$_2$)$_3$—, CH$_3$—CH=CH—(CH$_2$)$_2$—, CH$_3$—CH=CH—CH$_2$—O—, etc. Then, in such a case, in view of the stability of the compound, it is preferred that a plurality of successive —CH$_2$— are not replaced by —O—. Any of alkyl and alkylene may be linear group, or branched group. This is identical also in a case where arbitrary —CH$_2$— in the groups is replaced by —O— or —CH=CH—. Then, the amount of the compound represented by percentage in the composition is weight percent (wt %) based on the entire weight of the composition.

The present invention comprises each of the following items.

[1] A compound represented by Formula (1) or Formula (2):

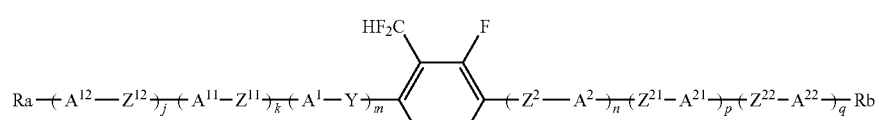

(1)

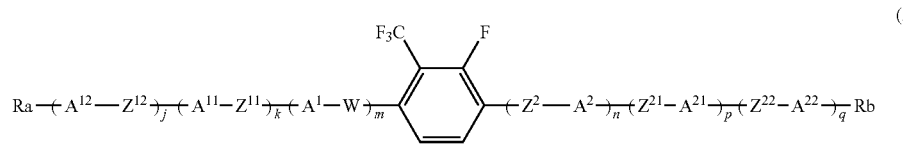

(2)

in which Ra and Rb each independently is hydrogen or alkyl of 1 to 20 carbon atoms; and in the alkyl, arbitrary —CH$_2$— may be replaced by —O—, —S—, —CO— or —SiH$_2$—, arbitrary —(CH$_2$)$_2$— may be replaced by —CH=CH—, and arbitrary hydrogen may be replaced by halogen;

$A^1$, $A^{11}$, $A^{12}$, $A^2$, $A^{21}$ and $A^{22}$ each independently is 1,4-cyclohexylene, 1,4-phenylene, decahydronaphthalene-2,6-diyl, 1,2,3,4-tetrahydronaphthalene-2,6-diyl, or naphthale-2,6-diyl; and in the rings, one or not-adjacent two —CH$_2$— may be replaced by —O—, —S—, —CO—, or —SiH$_2$—, and arbitrary hydrogen may be replaced by halogen;

Y is a single bond, —(CH$_2$)$_2$—, —CH=CH—, —CF=CF—, —CF$_2$O—, —OCF$_2$—, —CH$_2$CO—, —COCH$_2$—, —CH$_2$SiH$_2$—, —SiH$_2$CH$_2$—, —(CH$_2$)$_4$—, —CH=CH—(CH$_2$)$_2$—, —(CH$_2$)$_2$—CH=CH—, —(CH$_2$)$_2$CF$_2$O—, or —OCF$_2$(CH$_2$)$_2$—;

W is —(CH$_2$)$_2$—, —CH=CH—, —CF=CF—, —CH$_2$O—, —OCH$_2$—, —CF$_2$O—, —OCF$_2$—, —CH$_2$CO—, —COCH$_2$—, —CH$_2$SiH$_2$—, —SiH$_2$CH$_2$—, —(CH$_2$)$_4$—, —(CH$_2$)$_3$—O—, —O—(CH$_2$)$_3$—, —CH=CH—(CH$_2$)$_2$—, —(CH$_2$)$_2$—CH=CH—, —(CH$_2$)$_2$CF$_2$O—, or —OCF$_2$(CH$_2$)$_2$—;

$Z^{11}$, $Z^{12}$, $Z^2$, $Z^{21}$ and $Z^{22}$ each independently is a single bond, —(CH$_2$)$_2$—, —COO—, —OCO—, —CH$_2$O—, —OCH$_2$—, —CF$_2$O—, —OCF$_2$—, —CH=CH—, —CF=CF—, —CH$_2$CO—, —COCH$_2$—, —(CH$_2$)$_4$—, —(CH$_2$)$_3$—O—, —O—(CH$_2$)$_3$—, —CH=CH—(CH$_2$)$_2$—, —(CH$_2$)$_2$—CH=CH—, —(CH$_2$)$_2$CF$_2$O—, or —OCF$_2$(CH$_2$)$_2$—;

j, k, m, n, p and q each independently is 0 or 1 and the sum of them is 1, 2 or 3;

when m is 0, each of j and k is 0, Ra in Formula (1) is none of hydrogen, alkoxy and alkoxymethyl, and Ra in Formula (2) is 1-alkenyl.

[2] The compound described in the item [1], wherein the sum of j, k and m, and the sum of n, p and q each independently is 1 or 2.

[3] The compound described in the item [1], which is represented by any one of Formula (1-1) to Formula (1-9) and Formula (2-1) to Formula (2-9):

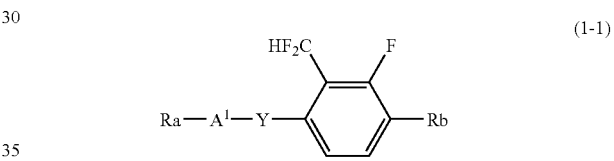

(1-1)

-continued

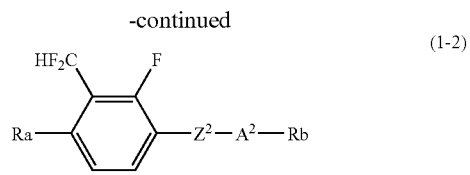

(1-2)

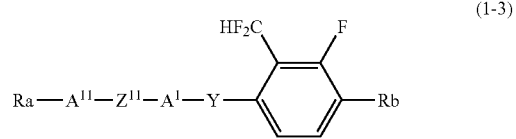

(1-3)

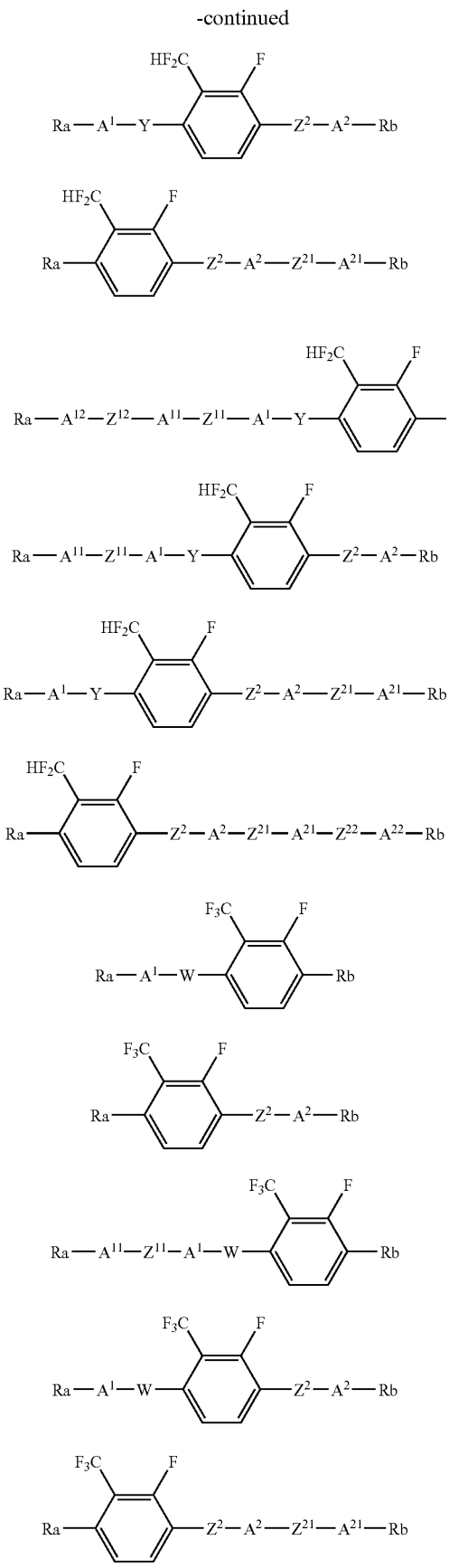
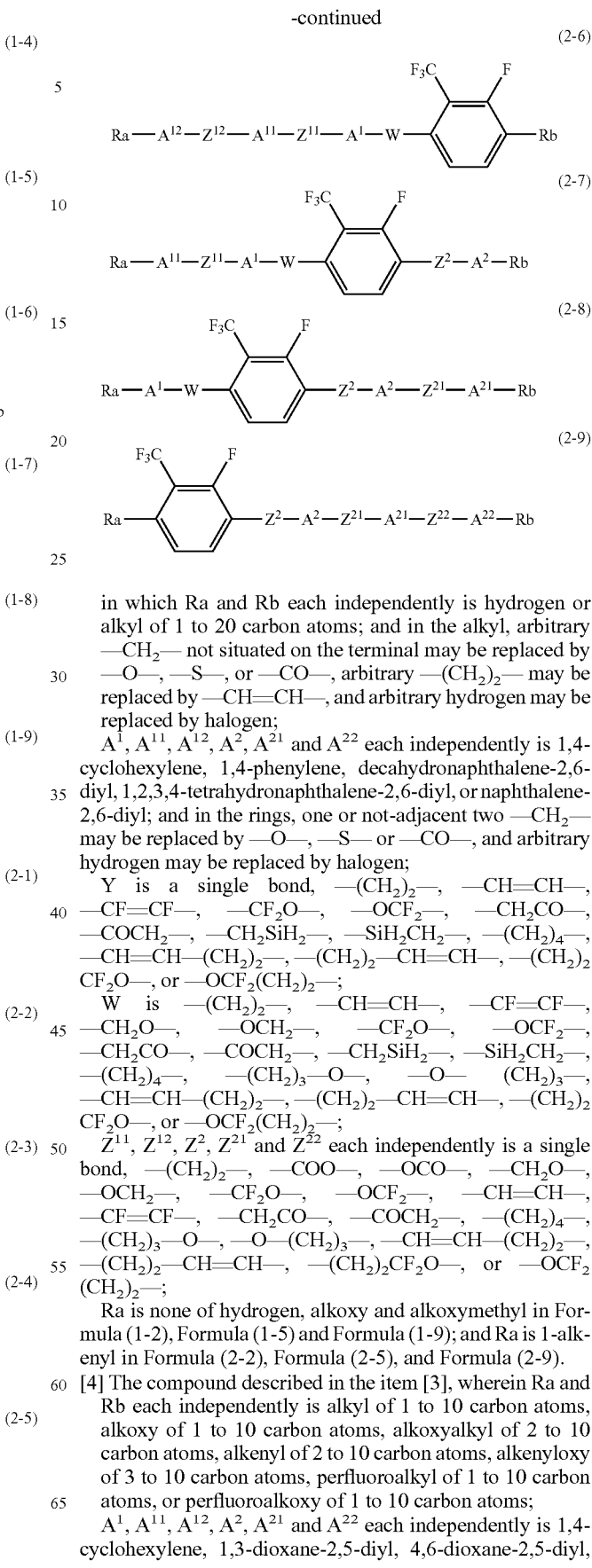

in which Ra and Rb each independently is hydrogen or alkyl of 1 to 20 carbon atoms; and in the alkyl, arbitrary —$CH_2$— not situated on the terminal may be replaced by —O—, —S—, or —CO—, arbitrary —$(CH_2)_2$— may be replaced by —CH=CH—, and arbitrary hydrogen may be replaced by halogen;

$A^1$, $A^{11}$, $A^{12}$, $A^2$, $A^{21}$ and $A^{22}$ each independently is 1,4-cyclohexylene, 1,4-phenylene, decahydronaphthalene-2,6-diyl, 1,2,3,4-tetrahydronaphthalene-2,6-diyl, or naphthalene-2,6-diyl; and in the rings, one or not-adjacent two —$CH_2$— may be replaced by —O—, —S— or —CO—, and arbitrary hydrogen may be replaced by halogen;

Y is a single bond, —$(CH_2)_2$—, —CH=CH—, —CF=CF—, —$CF_2O$—, —$OCF_2$—, —$CH_2CO$—, —$COCH_2$—, —$CH_2SiH_2$—, —$SiH_2CH_2$—, —$(CH_2)_4$—, —CH=CH—$(CH_2)_2$—, —$(CH_2)_2$—CH=CH—, —$(CH_2)_2CF_2O$—, or —$OCF_2(CH_2)_2$—;

W is —$(CH_2)_2$—, —CH=CH—, —CF=CF—, —$CH_2O$—, —$OCH_2$—, —$CF_2O$—, —$OCF_2$—, —$CH_2CO$—, —$COCH_2$—, —$CH_2SiH_2$—, —$SiH_2CH_2$—, —$(CH_2)_4$—, —$(CH_2)_3$—O—, —O—$(CH_2)_3$—, —CH=CH—$(CH_2)_2$—, —$(CH_2)_2$—CH=CH—, —$(CH_2)_2CF_2O$—, or —$OCF_2(CH_2)_2$—;

$Z^{11}$, $Z^{12}$, $Z^2$, $Z^{21}$ and $Z^{22}$ each independently is a single bond, —$(CH_2)_2$—, —COO—, —OCO—, —$CH_2O$—, —$OCH_2$—, —$CF_2O$—, —$OCF_2$—, —CH=CH—, —CF=CF—, —$CH_2CO$—, —$COCH_2$—, —$(CH_2)_4$—, —$(CH_2)_3$—O—, —O—$(CH_2)_3$—, —CH=CH—$(CH_2)_2$—, —$(CH_2)_2$—CH=CH—, —$(CH_2)_2CF_2O$—, or —$OCF_2(CH_2)_2$—;

Ra is none of hydrogen, alkoxy and alkoxymethyl in Formula (1-2), Formula (1-5) and Formula (1-9); and Ra is 1-alkenyl in Formula (2-2), Formula (2-5), and Formula (2-9).

[4] The compound described in the item [3], wherein Ra and Rb each independently is alkyl of 1 to 10 carbon atoms, alkoxy of 1 to 10 carbon atoms, alkoxyalkyl of 2 to 10 carbon atoms, alkenyl of 2 to 10 carbon atoms, alkenyloxy of 3 to 10 carbon atoms, perfluoroalkyl of 1 to 10 carbon atoms, or perfluoroalkoxy of 1 to 10 carbon atoms;

$A^1$, $A^{11}$, $A^{12}$, $A^2$, $A^{21}$ and $A^{22}$ each independently is 1,4-cyclohexylene, 1,3-dioxane-2,5-diyl, 4,6-dioxane-2,5-diyl, 1,4-phenylene, 2-fluoro-1,4-pyenylene, 3-fluoro-1,4-phenylene, 2,3-difluoro-1,4-phenylene, decahydronaphthalene-2,6-diyl, 1,2,3,4-tetrahydronaphthalene-2,6-diyl, or naphthalene-2,6-diyl;

$Z^{11}$ and $Z^{12}$ each independently is a single bond, —$(CH_2)_2$—, —COO—, —OCO—, —$CF_2O$—, —$OCF_2$—, —CH═CH—, —$(CH_2)_4$—, —CH═CH—$(CH_2)_2$—, —$(CH_2)_2$—CH═CH—, —$(CH_2)_2CF_2O$—, or —$OCF_2(CH_2)_2$—;

$Z^2$, $Z^{21}$ and $Z^{22}$ each independently is a single bond, —$(CH_2)_2$—, —COO—, —OCO—, —$CH_2O$—, —$OCH_2$—, —$CF_2O$—, —$OCF_2$—, —CH═CH—, —CF═CF—, —$(CH_2)_4$—, —$(CH_2)_3$—O—, —O—$(CH_2)_3$—, —CH═CH—$(CH_2)_2$—, —$(CH_2)_2$—CH═CH—, —$(CH_2)_2CF_2O$—, or —$OCF_2(CH_2)_2$—;

Y is a single band, —$(CH_2)_2$—, —CH═CH—, —$CF_2O$—, —$OCF_2$, —$(CH_2)_4$—, —$(CH_2)_2CF_2O$—, or —$OCF_2(CH_2)_2$—; and W is —$(CH_2)_2$—, —$CH_2O$—, —$OCH_2$—, —$CF_2O$—, —$OCF_2$—, —CH═CH—, —$(CH_2)_4$—, —$(CH_2)_3$—O—, —O—$(CH_2)_3$—, —$(CH_2)_2CF_2O$—, or —$OCF_2(CH_2)_2$—.

[5] The compound described in the item [3], wherein Ra and Rb each independently is alkyl of 1 to 10 carbon atoms, alkoxy of 1 to 10 carbon atoms, alkoxyalkyl of 2 to 10 carbon atoms or alkenyl of 2 to 10 carbon atoms;

$A^1$, $A^{11}$, $A^{12}$, $A^2$, $A^{21}$ and $A^{22}$ each independently is 1,4-cyclohexylene, 1,4-phenylene, 2-fluoro-1,4-phenylene, 3-fluoro-1,4-phenylene, or 2,3-difluoro-1,4-phenylene; $Z^{11}$ and $Z^{12}$ each independently is a single bond, —$(CH_2)_2$—, —$CF_2O$—, —$OCF_2$—, —CH═CH—, —$(CH_2)_4$—, CH═CH—$(CH_2)_2$—, —$(CH_2)_2$—CH═CH—, —$(CH_2)_2CF_2O$—, or —$OCF_2(CH_2)_2$—;

$Z^2$, $Z^{21}$ and $Z^{22}$ each independently is a single bond, —$(CH_2)_2$—, —$CH_2O$—, —$OCH_2$—, —$CF_2O$—, —$OCF_2$—, —CH═CH—, —$(CH_2)_2CF_2O$—, or —$OCF_2(CH_2)_2$—;

Y is a single bond, —$(CH_2)_2$—, —CH═CH—, —$CF_2O$—, —$OCF_2$, —$(CH_2)_4$—, —$(CH_2)_2CF_2O$—, or —$OCF_2(CH_2)_2$—; and W is —$(CH_2)_2$—, —$CH_2O$—, —$OCH_2$—, —$CF_2O$—, —$OCF_2$—, —CH═CH—, —$(CH_2)_4$—, —$(CH_2)_3$—O—, —O—$(CH_2)_3$—, —$(CH_2)_2CF_2O$—, or —$OCF_2(CH_2)_2$—.

[6] The compound described in the item [3], wherein Ra is alkyl of 1 to 10 carbon atoms, or alkenyl of 2 to 10 carbon atoms, and Rb is alkoxy of 1 to 10 carbon atoms;

$A^1$, $A^{11}$, $A^{12}$, $A^2$, $A^{21}$ and $A^{22}$ each independently is 1,4-cyclohexylene, 1,4-phenylene, 2-fluoro-1,4-phenylene, or 3-fluoro-1,4-phenylene, $Z^{11}$ and $Z^{12}$ each independently is a single bond, or —CH═CH—;

$Z^2$, $Z^{21}$ and $Z^{22}$ each independently is a single bond, —$CH_2O$—, —$OCH_2$—, —$CF_2O$—, or —$OCF_2$—;

Y is a single bond, —$(CH_2)_2$—, —CH═CH—, —$CF_2O$—, —$OCF_2$—, —$(CH_2)_4$—, —$(CH_2)_2CF_2O$—, or —$OCF_2(CH_2)_2$—; and W is —$(CH_2)_2$—, —$CH_2O$—, —$OCH_2$—, —$CF_2O$—, —$OCF_2$—, —CH═CH—, —$(CH_2)_4$—, —$(CH_2)_3$—O—, —O—$(CH_2)_3$—, —$(CH_2)_2CF_2O$—, or —$OCF_2(CH_2)_2$—.

[7] The compound described in any one of the items [3] to [6], wherein $A^1$ or $A^2$ is 1,4-cyclohexylene.

[8] The compound described in any one of the items [3] to [6], wherein $A^1$ or $A^2$ is 1,4-phenylene.

[9] The compound described in any one of the items [3] to [6], wherein Y or $Z^2$ is a single bond in Formula (1-1) to Formula (1-9), and $Z^2$ is a single bond in Formula (2-1) to Formula (2-9).

[10] The compound described in any one of the items [3] to [6], wherein $A^1$ or $A^2$ is 1,4-cyclohexylene, Y or $Z^2$ is a single bond in Formula (1-1) to Formula (1-9), and $Z^2$ is a single bond in Formula (2-1) to Formula (2-9).

[11] The compound described in any one of the items [3] to [6], wherein $A^1$ or $A^2$ is 1,4-cyclohexylene, Y or $Z^2$ is a single bond in Formula (1-1) to Formula (1-9), and $Z^2$ is a single bond in Formula (2-1) to Formula (2-9).

[12] The compound described in any one of the items [3] to [6], which is represented by any one of Formula (2-1), Formula (2-3), Formula (2-4), Formula (2-6), Formula (2-7) and Formula (2-8); in which $A^1$ is 1,4-cyclohexylene.

[13] The compound described in any one of the items [3] to [6], which is represented by Formula (2-1); in which $A^1$ is 1,4-cyclohexylene, and W is —$(CH_2)_2$—, —$CH_2O$—, or —$CF_2O$—.

[14] The compound described in any one of the items [3] to [6], which is represented by Formula (2-3); in which any of $A^1$ and $A^{11}$ is 1,4-cyclohexylene, $Z^{11}$ is a single bond, and W is —$(CH_2)_2$—, —$CH_2O$—, or —$CF_2O$—.

[15] The compound described in any one of the items [3] to [6], which is represented by Formula (2-6); in which any of $A^1$, $A^{11}$ and $A^{12}$ is 1,4-cyclohexylene, any of $Z^{11}$ and $Z^{12}$ is a single bond, and W is —$(CH_2)_2$—, —$CH_2$—O— or —$CF_2O$—.

[16] The compound described in any one of the items [3] to [6], which is represented by any one of Formula (1-2), Formula (1-4), Formula (1-5), Formula (1-7), Formula (1-8), and Formula (1-9); in which $Z^2$ is —$CH_2O$—, —$OCH_2$—, —$CF_2O$— or —$OCF_2$—.

[17] The compound described in the item [3], which is represented by Formula (1-3); in which Ra is alkyl of 1 to 10 carbon atoms or alkenyl of 2 to 10 carbon atoms, Rb is alkoxy of 1 to 10 carbon atoms, any of $A^1$ and $A^{11}$ is 1,4-cyclohexylene, and any of Y and $Z^{11}$ is a single bond.

[18] The compound described in the item [3], which is represented by Formula (1-3); in which Ra is alkyl of 1 to 10 carbon atoms or alkenyl of 2 to 10 carbon atoms, Rb is alkoxy of 1 to 10 carbon atoms, any of $A^1$ and $A^{11}$ is 1,4-cyclohexylene, Y is —$CH_2CH_2$—, and $Z^{11}$ is a single bond.

[19] The compound described in the item [3], which is represented by Formula (1-3); in which Ra is alkyl of 1 to 10 carbon atoms or alkenyl of 2 to 10 carbon atoms, Rb is alkoxy f 1 to 10 carbon atoms, $A^1$ is 1,4-phenylene, $A^{11}$ is 1,4-cyclohexylene, and any of Y and $Z^{11}$ is a single bond.

[20] The compound described in any one of the items [3] to [6], which is represented by Formula (1-3); in which Ra is alkyl of 1 to 10 carbon atoms or alkenyl of 2 to 10 carbon atoms, Rb is alkoxy of 1 to 10 carbon atoms, any of $A^1$ and $A^{11}$ is 1,4-phenylene, and any of Y and $Z^{11}$ is a single bond.

[21] The compound described in the item [3], which is represented by Formula (1-1); in which Ra is alkyl of 1 to 10 carbon atoms or alkenyl of 2 to 10 carbon atoms, Rb is alkoxy of 1 to 10 carbon atoms, $A^1$ is 1,4-cyclohexylene, and Y is a single bond.

[22] The compound described in the item [3], which is represented by Formula (1-1); in which Ra is alkyl of 1 to 10 carbon atoms or alkenyl of 2 to 10 carbon atoms, Rb is alkoxy of 1 to 10 carbon atoms, $A^1$ is 1,4-cyclohexylene, and Y is —$CH_2CH_2$—.

[23] The compound described in the item [3], which is represented by Formula (2-1); in which Ra is alkyl of 1 to 10 carbon atoms or alkenyl of 2 to 10 carbon atoms, Rb is alkoxy of 1 to 10 carbon atoms, $A^1$ is 1,4-cyclohexylene, and W is —$(CH_2)_2$—.

[24] The compound described in the item [3], which is represented by Formula (2-1); in which Ra is alkyl of 1 to 10 carbon atoms or alkenyl of 2 to 10 carbon atoms, Rb is alkoxy of 1 to 10 carbon atoms, $A^1$ is 1,4-cyclohexylene, and W is —CH$_2$O—.

[25] The compound described in the item [3], which is represented by Formula (2-1); in which Ra is alkyl of 1 to 10 carbon atoms or alkenyl of 2 to 10 carbon atoms, Rb is alkoxy of 1 to 10 carbon atoms, $A^1$ is 1,4-phenylene, and W is —(CH$_2$)$_2$—.

[26] The compound described in the item [3], which is represented by Formula (2-3); in which Ra is alkyl of 1 to 10 carbon atoms or alkenyl of 2 to 10 carbon atoms, Rb is alkoxy of 1 to 10 carbon atoms, any of $A^1$ and $A^{11}$ is 1,4-cyclohexylene, $Z^{11}$ is a single bond, and W is —(CH$_2$)$_2$—.

[27] The compound described in the item [3], which is represented by Formula (2-3); in which Ra is alkyl of 1 to 10 carbon atoms or alkenyl of 2 to 10 carbon atoms, Rb is alkoxy of 1 to 10 carbon atoms, any of $A^1$ and $A^{11}$ is 1,4-cyclohexylene, $Z^{11}$ is a single bond, and W is —CH$_2$O—.

[28] The compound described in the item [3], which is represented by Formula (2-3); in which Ra is alkyl of 1 to 10 carbon atoms or alkenyl of 2 to 10 carbon atoms, Rb is alkoxy of 1 to 10 carbon atoms, $A^1$ is 1,4-phenylene, $A^{11}$ is 1,4-cyclohexylene, $Z^{11}$ is a single bond, and W is —(CH$_2$)$_2$—.

[29] The compound described in the item [3], which is represented by Formula (2-3); in which Ra is alkyl of 1 to 10 carbon atoms or alkenyl of 2 to 10 carbon atoms, Rb is alkoxy of 1 to 10 carbon atoms, any of $A^1$ and $A^{11}$ is 1,4-phenylene, $Z^{11}$ is a single bond, and W is —(CH$_2$)$_2$—.

[30] The compound described in the item [3], which is represented by Formula (2-6); in which Ra is alkyl of 1 to 10 carbon atoms or alkenyl of 2 to 10 carbon atoms, Rb is alkoxy of 1 to 10 carbon atoms, any of $A^1$, $A^{11}$ and $A^{12}$ is 1,4-cyclohexylene, any of $Z^{11}$ and $Z^{12}$ is a single bond, and W is —(CH$_2$)$_2$— or —CH$_2$O—.

[31] The compound described in the item [3], which is represented by Formula (1-2); in which Ra is alkyl of 1 to 10 carbon atoms, Rb is alkyl of 1 to 10 carbon atoms or alkenyl of 2 to 10 carbon atoms, $A^2$ is 1,4-cyclohexylene, and $Z^2$ is —OCH$_2$—.

[32] The compound described in the item [3], which is represented by Formula (1-5); in which Ra is alkyl of 1 to 10 carbon atoms, Rb is alkyl of 1 to 10 carbon atoms or alkenyl of 2 to 10 carbon atoms, any of $A^2$ and $A^{21}$ is 1,4-cyclohexylene, $Z^2$ is —OCH$_2$—, and $Z^{21}$ is a single bond.

[33] The compound described in the item [3], which is represented by Formula (1-4); in which Ra and Rb each independently is alkyl of 1 to 10 carbon atoms or alkenyl of 2 to 10 carbon atoms, any of $A^1$ and $A^2$ is 1,4-phenylene, and any of Y and $Z^2$ is a single bond.

[34] The compound described in the item [3], which is represented by Formula (1-4); in which Ra and Rb each independently is alkyl of 1 to 10 carbon atoms or alkenyl of 2 to 10 carbon atoms, $A^1$ is 1,4-cyclohexylene, $A^2$ is 1,4-phenylene, and any of Y and $Z^2$ is a single bond.

[35] The compound described in the item [3], which is represented by Formula (1-4); in which Ra and Rb each independently is alkyl of 1 to 10 carbon atoms or alkenyl of 2 to 10 carbon atoms, $A^1$ is 1,4-phenylene, $A^2$ is 1,4-cyclohexylene, and any of Y and $Z^2$ is a single bond.

[36] A liquid crystal composition which contains at least one of the compounds described in the item [1] and may contain at least one optically active compound.

[37] A liquid crystal composition which contains at least one of the compound described in the item [1] and at least one compound selected from the group consisting of the compounds represented by Formula (3), Formula (4), and Formula (5) respectively, and may contain at least one optically active compound:

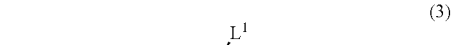

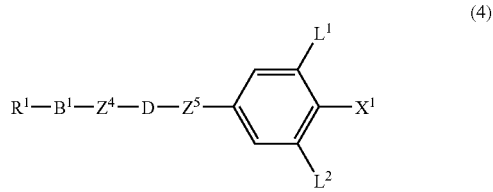

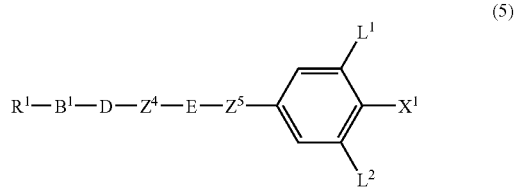

in which $R^1$ is alkyl of 1 to 10 carbon atoms; in the alkyl, arbitrary —CH$_2$— may be replaced by —O—, arbitrary —(CH$_2$)$_2$— may be replaced by —CH=CH—, and arbitrary hydrogen may be replaced by fluorine; $X^1$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$; $B^1$ and D each independently is 1,4-cyclohexylene, 1,4-phenylene, 1,3-dioxane-2,5-diyl, or 1,4-phenylene in which at least one hydrogen is replaced by fluorine; E is 1,4-cyclohexylene, 1,4-phenylene, or 1,4-phenylene in which at least one hydrogen is replaced by fluorine; $Z^4$ and $Z^5$ each independently is —(CH$_2$)$_2$—, —(CH$_2$)$_4$—, —COO—, —CF$_2$O—, —OCF$_2$—, —CH=CH—, or a single bond; and $L^1$ and $L^2$ each independently is hydrogen or fluorine.

[38] A liquid crystal composition which contains at least one of the compounds described in the item [1], and at least one compound selected from the group consisting of the compounds represented by Formula (6-1), Formula (6-2), and Formula (7) respectively, and may contain at least one optically active compound:

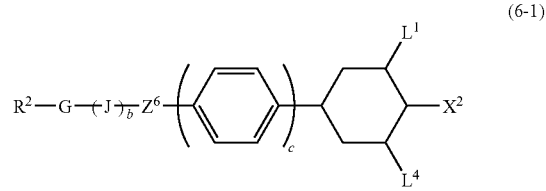

(6-2)

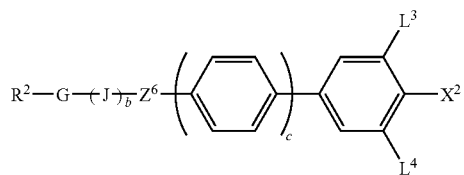

(7)

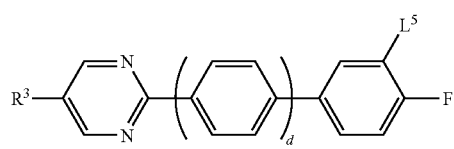

in which $R^2$ and $R^3$ each independently is alkyl of 1 to 10 carbon atoms; in the alkyl, arbitrary —$CH_2$— may be replaced by —O—, arbitrary —$(CH_2)_2$— may be replaced by —CH=CH—, and arbitrary hydrogen may be replaced by fluorine; $X^2$ is —CN or —C≡C—CN; G is 1,4-cyclohexylene, 1,4-phenylene, 1,3-dioxane-2,5-diyl, or pyrimidine-2,5-diyl; J is 1,4-cyclohexylene, 1,4-phenylene, pyrimidine-2,5-diyl or 1,4-phenylne in which at least one hydrogen is replaced by fluorine; $Z^6$ is —$(CH_2)_2$—, —COO—, —$CF_2O$—, —$OCF_2$— or a single bond; $L^3$, $L^4$ and $L^5$ each independently is hydrogen or fluorine; and b, c and d each independently is 0 or 1.

[39] A liquid crystal composition which contains at least one of the compounds described in the item [1], and at least one compound selected from the group consisting of the compounds represented by Formula (8), Formula (9), Formula (10), Formula (11) and Formula (12) respectively, and may contain at least one optically active compound:

(8)

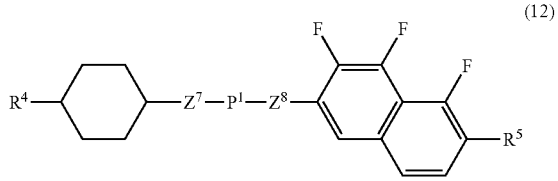

(9)

(10)

(11)

(12)

in which $R^4$ is alkyl of 1 to 10 carbon atoms and $R^5$ is fluorine or alkyl of 1 to 10 carbon atoms; in the alkyls, arbitrary —$CH_2$— may be replaced by —O—, arbitrary —$(CH_2)_2$— may be replaced by —CH=CH— and arbitrary hydrogen may be replaced by fluorine; M and $P^1$ each independently is 1,4-cyclohexylene, 1,4-phenylene, or decahydro-2,6-naphthylene; $Z^7$ and $Z^8$ each independently is —$(CH_2)_2$—, —COO—, or a single bond; $L^6$ and $L^7$ each independently is hydrogen or fluorine; and at least one of $L^6$ and $L^7$ is fluorine.

[40] A liquid crystal composition which contains at least one of the compounds described in the item [1], and at least one compound selected from the group consisting of the compounds represented by Formula (13), Formula (14) and Formula (15) respectively, and may contain at least one optically active compound:

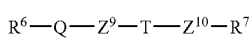 (13)

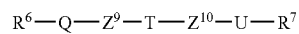 (14)

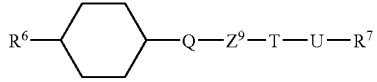 (15)

in which $R^6$ and $R^7$ each independently is alkyl of 1 to 10 carbon atoms; in the alkyl, arbitrary —$CH_2$— may be replaced by —O—, arbitrary —$(CH_2)_2$— may be replaced by —CH=CH—, and arbitrary hydrogen may be replaced by fluorine; Q, T and U each independently is 1,4-cyclohexylene, 1,4-phenylene, pyrimidine-2,5-diyl, or 1,4-phenylene in which at least one hydrogen is replaced by fluorine; and $Z^9$ and $Z^{10}$ each independently is —C≡C—, —COO—, —$(CH_2)_2$—, —CH=CH—, —$CH_2O$—, or a single bond.

[41] The liquid crystal composition described in the item [37], which further contains at least one compound selected from the group consisting of the compounds represented by Formula (6-1), Formula (6-2) and Formula (7), respectively:

(6-1)

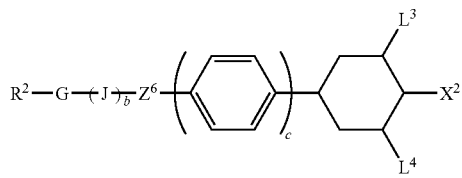

-continued

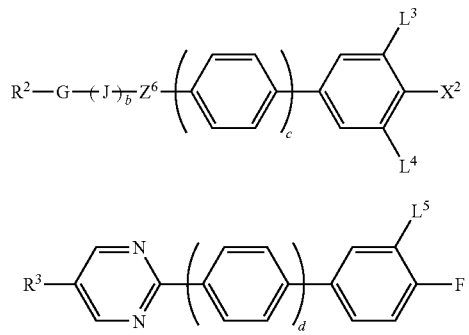

(6-2)

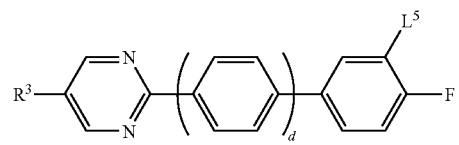

(7)

in which $R^2$ and $R^3$ each independently is alkyl of 1 to 10 carbon atoms; in the alkyl, arbitrary —$CH_2$— may be replaced by —O—, arbitrary —$(CH_2)_2$— may be replaced by —CH=CH—, and arbitrary hydrogen may be replaced by fluorine; $X^2$ is —CN or —C≡C—CN; G is 1,4-cyclohexylene, 1,4-phenylene, 1,3-dioxane-2,5-diyl, or pyrimidine-2,5-diyl; J is 1,4-cyclohexylene, 1,4-phenylene, pyrimidine-2,5-diyl, or 1,4-phenylene in which at least one hydrogen is replaced by fluorine; $Z^6$ is —$(CH_2)_2$—, —COO—, —$CF_2O$—, —$OCF_2$— or a single bond; $L^3$, $L^4$ and $L^5$ each independently is hydrogen or fluorine; and b, c and d each independently is 0 or 1.

[42] The liquid crystal composition described in the item [37], which further contains at least one compound selected from the group consisting of the compounds represented by Formula (13), Formula (14) and Formula (15), respectively:

(13)

(14)

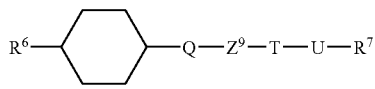

(15)

in which $R^6$ and $R^7$ each independently is alkyl of 1 to 10 carbon atoms; in the alkyl, arbitrary —$CH_2$— may be replaced by —O—, arbitrary —$(CH_2)_2$— may be replaced by —CH=CH—, and arbitrary hydrogen may be replaced by fluorine; Q, T and U each independently is 1,4-cyclohexylene, 1,4-phenylene, pyrimidine-2,5-diyl, or 1,4-phenylene in which at least one hydrogen is replaced by fluorine; and $Z^9$ and $Z^{10}$ each independently is —C≡C—, —COO—, —$(CH_2)_2$—, —CH=CH—, —$CH_2O$—, or a single bond.

[43] The liquid crystal composition described in the item [38], which further contains at least one compound selected from the group consisting of the compounds represented by Formula (13), Formula (14) and Formula (15), respectively:

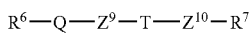

(13)

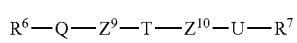

(14)

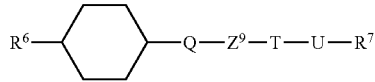

(15)

in which $R^6$ and $R^7$ each independently is alkyl of 1 to 10 carbon atoms; in the alkyl, arbitrary —$CH_2$— may be replaced by —O—, arbitrary —$(CH_2)_2$— may be replaced by —CH=CH—, and arbitrary hydrogen may be replaced by fluorine; Q, T and U each independently is 1,4-cyclohexylene, 1,4-phenylene, pyrimidine-2,5-yl, or 1,4-phenylene in which at least one hydrogen is replaced by fluorine; and $Z^9$ and $Z^{10}$ each independently is —C≡C—, —COO—, —$(CH_2)_2$—, —CH=CH—, —$CH_2O$—, or a single bond.

[44] The liquid crystal composition described in the item [39], which further contains at least one compound selected from the group consisting of the compounds represented by Formula (13), Formula (14) and Formula (15), respectively:

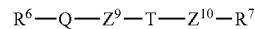

(13)

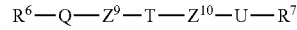

(14)

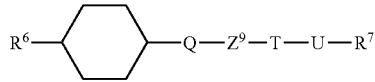

(15)

in which $R^6$ and $R^7$ each independently is alkyl of 1 to 10 carbon atoms; in the alkyl, arbitrary —$CH_2$— may be replaced by —O—, arbitrary —$(CH_2)_2$— may be replaced by —CH=CH—, and arbitrary hydrogen may be replaced by fluorine; Q, T and U each independently is 1,4-cyclohexylene, 1,4-phenylene, pyrimidine-2,5-diyl, or 1,4-phenylene in which at least one hydrogen is replaced by fluorine; and $Z^9$ and $Z^{10}$ each independently is —C≡C—, —COO—, —$(CH_2)_2$—, —CH=CH—, —$CH_2O$—, or a single bond.

[45] Use of the liquid crystal composition described in any one of the items [36] to [44] for producing a liquid crystal display device.

[46] A liquid crystal display device containing the liquid crystal composition described in any one of the items [36] to [44].

Effect of the Invention

The compound of the present invention has general physical property necessary for the liquid crystalline compound, stability to heat and light, appropriate optical anisotropy, appropriate dielectric anisotropy, and excellent compatibility with other liquid crystalline compounds. The liquid crystal composition of the invention contains at least one of the compounds, and has a high upper limit temperature of the nematic phase, a low limit temperature of the nematic phase, a low viscosity, an appropriate optical anisotropy, and a low threshold voltage. The liquid crystal display device of the invention contains the composition and has a wide usable temperature range, a quick response, high contrast ratio, and a low driving voltage.

BEST MODE FOR PRACTICING THE INVENTION

The compound of the present invention is represented by either Formula (1) or Formula (2).

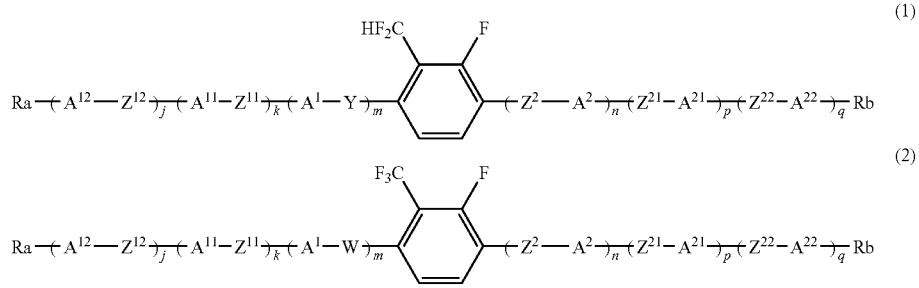

Ra and Rb in Formula (1) and Formula (2) each independently is hydrogen or alkyl of 1 to 20 carbon atoms. In the alkyl, arbitrary —$CH_2$— may be replaced by —O—, —S—, —CO— or —$SiH_2$—, arbitrary —$(CH_2)_2$— may be replaced by —CH=CH—, and arbitrary hydrogen may be replaced by halogen. Examples for Ra or Rb are hydrogen, alkyl, alkoxy, alkoxyalkyl, alkoxyalkoxy, alkylthio, alkylthioalkoxy, acyl, acylalkyl, acyloxy, acyloxyalkyl, alkoxycarbonyl, alkoxycarbonylalkyl, alkenyl, alkenyloxy, alkenyloxyalkyl, alkoxyalkenyl, alkynyl, alkynyloxy, sila alkyl, and disila alkyl. The groups described above in which at least one hydrogen is replaced by halogen, are also preferred. Preferred halogen is fluorine or chlorine. Furthermore preferred halogen is fluorine. In the groups, linear group is more preferred than the branched group. Ra and Rb are preferred even when they are branched groups in a case where they are optically active.

Preferred examples for Ra and Rb are alkyl of 1 to 10 carbon atoms, alkoxy of 1 to 10 carbon atoms, alkoxyalkyl of 2 to 10 carbon atoms, alkenyl of 2 to 10 carbon atoms, alkenyloxy of 2 to 10 carbon atoms, perfluoroalkyl of 1 to 10 carbon atoms, and perfluoroalkoxy of 1 to 10 carbon atoms. More preferred examples are alkyl of 1 to 10 carbon atoms, alkoxy of 1 to 10 carbon atoms, alkoxyalkyl of 2 to 10 carbon atoms, and alkenyl of 2 to 10 carbon atoms. Furthermore preferred Ra is alkyl of 1 to 10 carbon atoms or alkenyl of 2 to 10 carbon atoms, and particularly preferred Rb is alkoxy of 1 to 10 carbon atoms.

Preferred configuration of —CH=CH— in the alkenyl depends on the position of the double bond. A trans configuration is preferred in the alkenyl having a double bond at the odd number position such as —CH=$CHCH_3$, —CH=$CHC_2H_5$, —CH=$CHC_3H_7$, —CH=$CHC_4H_9$, —$C_2H_4$CH=$CHCH_3$, and —$C_2H_4$CH=$CHC_2H_5$. A cis-configuration is preferred in the alkenyl having a double bond at the even number position such as —$CH_2$CH=$CHCH_3$, —$CH_2$CH=$CHC_2H_5$, and —$CH_2$CH=$CHC_3H_7$.

Specific examples of the alkyl are —$CH_3$, —$C_2H_5$, —$C_3H_7$, —$C_4H_9$, —$C_5H_{10}$, —$C_6H_{13}$, —$C_7H_{15}$, and —$C_8H_{17}$. Specific examples of the alkoxy are —$OCH_3$, —$OC_2H_5$, —$OC_3H_7$, —$OC_4H_9$, —$OC_5H_{10}$, —$OC_6H_{13}$, and —$OC_7H_{15}$. Specific examples of the alkoxyalkyl are —$CH_2OCH_3$, —$CH_2OC_2H_5$, —$CH_2OC_3H_7$, —$(CH_2)_2OCH_3$, —$(CH_2)_2OC_2H_5$, —$(CH_2)_2OC_3H_7$, —$(CH_2)_3OCH_3$, —$(CH_2)_4OCH_3$, and —$(CH_2)_5OCH_3$.

Specific examples of the alkenyl are —CH=$CH_2$, —CH=$CHCH_3$, —$CH_2$CH=$CH_2$, —CH=$CHC_2H_5$, —$CH_2$CH=$CHCH_3$, —$(CH_2)_2$CH=$CH_2$, —CH=$CHC_3H_7$, —$CH_2$CH=$CHC_2H_5$, —$(CH_2)_2$CH=$CHCH_3$, and —$(CH_2)_3$CH=$CH_2$. Specific examples of the alkenyloxy are —$OCH_2$CH=$CH_2$, —$OCH_2$CH=$CHCH_3$, and —$OCH_2$CH=$CHC_2H_5$.

Specific examples of the alkyl in which at least one hydrogen is replaced by halogen are —$(CH_2)_2$F, —$CF_2CH_2$F, —$CF_2CHF_2$, —$CH_2CF_3$, —$CF_2CF_3$, —$(CH_2)_3$F, —$(CF_2)_2CF_3$, —$CF_2CHFCF_3$, and —$CHFCF_2CF_3$. Specific examples of the alkoxy, in which at least one hydrogen is replaced by halogen, are —$O(CH_2)_2$F, —$OCF_2CH_2$F, —$OCF_2CHF_2$, —$OCH_2CF_3$, —$OCF_2CF_3$, —$O(CH_2)_3$F, —$O(CF_2)_2CF_3$, —$OCF_2CHFCF_3$, and —$OCHFCF_2CF_3$. Specific examples of the alkenyl, in which at least one hydrogen is replaced by halogen, are —CH=CHF, —CH=$CF_2$, —CF=CHF, —CH=$CHCH_2$F, —CH=$CHCF_3$ and —$(CH_2)_2$CH=$CF_2$ Preferred specific examples of Ra or Rb are —$CH_3$, —$C_2H_5$, —$C_3H_7$, —$C_4H_9$, —$C_5H_{11}$, —$OCH_3$, —$OC_2H_5$, —$OC_3H_7$, —$OC_4H_9$, —$OC_5H_{11}$, —$CH_2OCH_3$, —$(CH_2)_2OCH_3$, —$(CH_2)_3OCH_3$, —CH=$CH_2$, —CH=$CHCH_3$, —$CH_2$CH=$CH_2$, —CH=$CHC_2H_5$, —$CH_2$CH=$CHCH_3$, —$(CH_2)_2$CH=$CH_2$, —CH=$CHC_3H_7$, —$CH_2$CH=$CHC_2H_5$, —$(CH_2)_2$CH=$CHCH_3$, —$(CH_2)_3$CH=$CH_2$, —$OCH_2$CH=$CH_2$, —$OCH_2$CH=$CHCH_3$, —$OCH_2$CH=$CHC_2H_5$, —$CF_2CF_3$, —$CF_2CHF_2$, —$CF_2CH_2$F, —$(CF_2)_2CF_3$, —$CF_2CHFCF_3$, —$CHFCF_2CF_3$, —$OCF_2CF_3$, —$OCF_2CHF_2$, —$OCF_2CH_2$F, —$OCF_2CF_2CF_3$, —$OCF_2CHFCF_3$, and —$OCHFCF_2CF_3$.

More preferred specific examples of Ra or Rb are —$CH_3$, —$C_2H_5$, —$C_3H_7$, —$C_4H_9$, —$C_5H_{11}$, —$OCH_3$, —$OC_2H_5$, —$OC_3H_7$, —$OC_4H_9$, —$OC_5H_{11}$, —$CH_2OCH_3$, —CH=$CH_2$, —CH=$CHCH_3$, —$CH_2$CH=$CH_2$, —CH=$CHC_2H_5$, —$CH_2$CH=$CHCH_3$, —$(CH_2)_2$CH=$CH_2$, —CH=$CHC_3H_7$, —$CH_2$CH=$CHC_2H_5$, —$(CH_2)_2$CH=$CHCH_3$, and —$(CH_2)_3$CH=$CH_2$.

Furthermore preferred specific examples of Ra are —$CH_3$, —$C_2H_5$, —$C_3H_7$, —$C_4H_9$, —$C_5H_{11}$, —CH=$CH_2$, —CH=$CHCH_3$, —$(CH_2)_2$CH=$CH_2$, and —$(CH_2)_2$CH=$CHCH_3$. Furthermore preferred specific examples of Rb are —$OCH_3$, —$OC_2H_5$ and —$OC_3H_7$.

$A^1, A^{11}, A^{12}, A^2, A^{21}$ and $A^{22}$ in Formula (1) and Formula (2) each independently is 1,4-cyclohexylene, 1,4-phenylene, decahydronaphthalene-2,6-diyl, 1,2,3,4-tetrahydronaphthalene-2,6-diyl, and naphthalene-2,6-diyl. In the rings, one or not-adjacent two —CH$_2$— may be replaced by —O—, —S—, —CO—, or —SiH$_2$—, and arbitrary hydrogen may be replaced by halogen.

Examples of the cyclic group in which one or not-adjacent two —CH$_2$— is replaced by —O—, —S—, —CO— or —SiH$_2$— are those groups represented by following Formula (16-1) to Formula (16-30). Among them, preferred examples are those of Formula (16-1), Formula (16-2), Formula (16-3), Formula (16-4), Formula (16-13), and Formula (16-21).

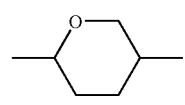 (16-1)

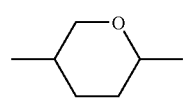 (16-2)

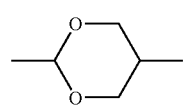 (16-3)

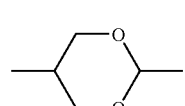 (16-4)

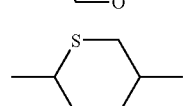 (16-5)

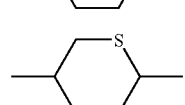 (16-6)

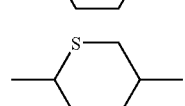 (16-7)

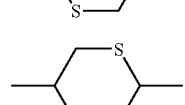 (16-8)

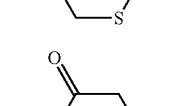 (16-9)

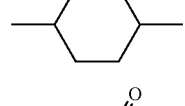 (16-10)

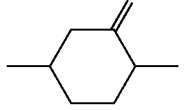 (16-11)

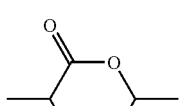 (16-12)

-continued

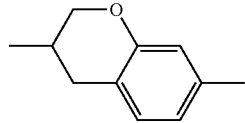 (16-13)

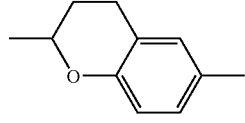 (16-14)

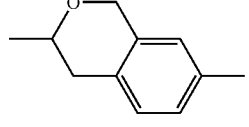 (16-15)

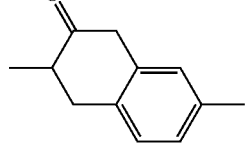 (16-16)

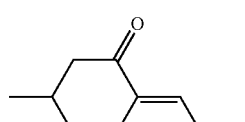 (16-17)

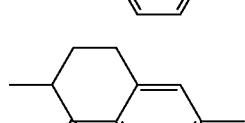 (16-18)

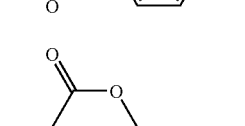 (16-19)

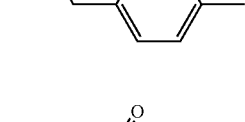 (16-20)

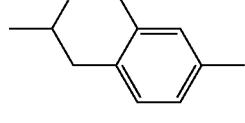 (16-21)

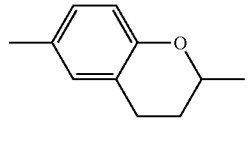 (16-22)

-continued
(16-23) 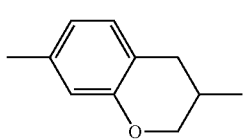
(16-24) 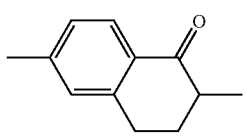
(16-25) 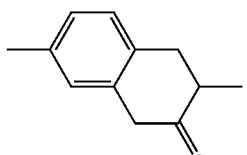
(16-26) 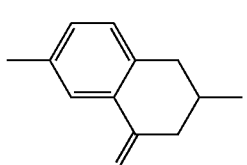
(16-27) 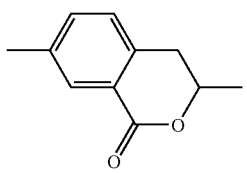
(16-28) 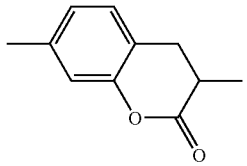
(16-29) 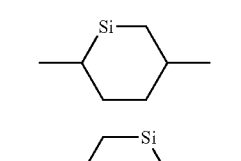
(16-30) 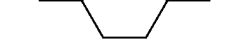
Examples of the cyclic group in which arbitrary hydrogen is replaced by halogen are cyclic groups represented by following Formula (17-1) to Formula (17-17). Among them, preferred examples are those of Formula (17-1), Formula (17-2), Formula (17-3), Formula (17-5), Formula (17-7), Formula (17-8), Formula (17-10), Formula (17-14), Formula (17-16), and Formula (17-17).
(17-1) 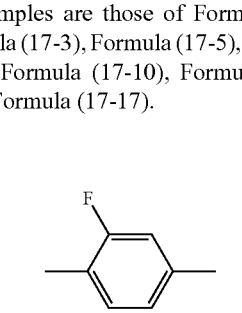
-continued
(17-2) 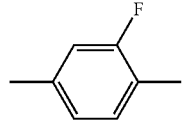
(17-3) 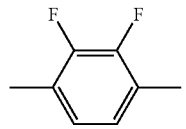
(17-4) 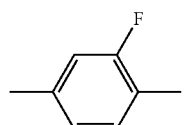
(17-5) 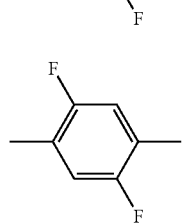
(17-6) 
(17-7) 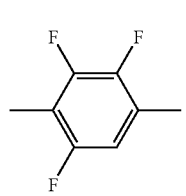
(17-8) 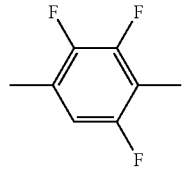
(17-9) 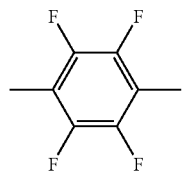
(17-10) 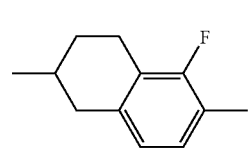

-continued

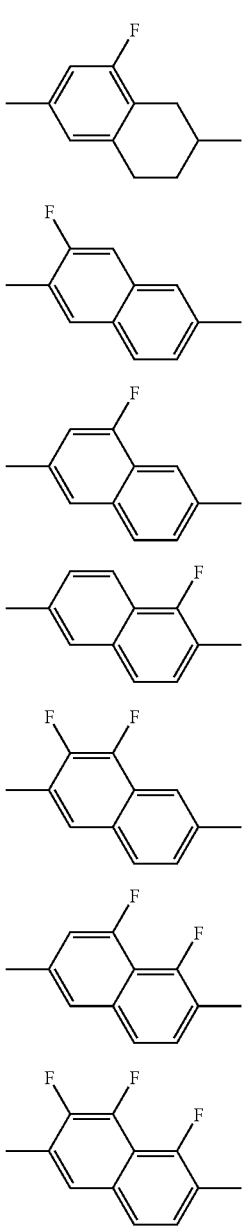

(17-11)
(17-12)
(17-13)
(17-14)
(17-15)
(17-16)
(17-17)

Preferred examples of $A^1$, $A^{11}$, $A^{12}$, $A^2$, $A^{21}$, or $A^{22}$ are 1,4-cyclohexylene, 1,3-dioxane-2,5-diyl, 4,6-dioxane-2,5-diyl, 1,4-phenylene, 2-fluoro-1,4-phenylene, 3-fluoro-1,4-phenylene, 2,3-difluoro-1,4-phenylene, decahydronaphthalene-2,6-diyl, 1,2,3,4-tetrahydronaphthalene-2,6-diyl, and naphthalene-2,6-diyl. More preferred examples are 1,4-cyclohexylene, 1,4-phenylene, 2-fluoro-1,4-phenylene, 3-fluoro-1,4-phenylene, or 2,3-difluoro-1,4-phenyle. Furthermore preferred examples are 1,4-cyclohexylene, 1,4-phenylene, 2-fluoro-1,4-phenylene, and 3-fluoro-1,4-phenylene. Then, particularly preferred examples of $A^1$ or $A^2$ are 1,4-cyclohexylene and 1,4-phenylene.

Y, W, $Z^{11}$, $Z^{12}$, $Z^2$, $Z^{21}$ and $Z^{22}$ in Formula (1) and Formula (2) are bonding groups. Y represents a single bond, —(CH$_2$)$_2$—, —COO—, —OCO—, —CF$_2$O—, —OCF$_2$—, —CH═CH—, —CF═CF—, —CH$_2$CO—, —COCH$_2$—, —CH$_2$SiH$_2$—, —SiH$_2$CH$_2$—, —(CH$_2$)$_4$—, —CH═CH—(CH$_2$)$_2$—, —(CH$_2$)$_2$—CH═CH—, —(CH$_2$)$_2$CF$_2$O—, or —OCF$_2$(CH$_2$)$_2$—. W represents —(CH$_2$)$_2$—, —CH═CH—, —CF═CF—, —CH$_2$O—, —OCH$_2$—, —CF$_2$O—, —OCF$_2$—, —CH$_2$CO—, —COCH$_2$—, —CH$_2$SiH$_2$—, —SiH$_2$CH$_2$—, —(CH$_2$)$_4$—, —(CH$_2$)$_3$O—, —O—(CH$_2$)$_3$—, —CH═CH—(CH$_2$)$_2$—, —(CH$_2$)$_2$—CH═CH—, —(CH$_2$)$_2$CF$_2$O—, or OCF$_2$(CH$_2$)$_2$—. $Z^2$, $Z^{11}$, $Z^{12}$, $Z^{21}$ and $Z^{22}$ each independently is a single bond, —(CH$_2$)$_2$—, —COO—, —OCO—, —CH$_2$O—, —OCH$_2$—, —CF$_2$O—, —OCF$_2$—, —CH═CH—, —CF═CF—, —CH$_2$CO—, —COCH$_2$—, —CH$_2$SiH$_2$—, —SiH$_2$CH$_2$—, —(CH$_2$)$_4$—, —(CH$_2$)$_3$O—, —O—(CH$_2$)$_3$—, —CH═CH—(CH$_2$)$_2$—, —(CH$_2$)$_2$—CH═CH—, —(CH$_2$)$_2$CF$_2$O— or —OCF$_2$(CH$_2$)$_2$.

Preferred examples of Y are a single bond, —(CH$_2$)$_2$—, —COO—, —OCO—, —CF$_2$O—, —OCF$_2$—, —CH═CH—, —(CH$_2$)$_4$—, —CH═CH—(CH$_2$)—, —(CH$_2$)—CH═CH—, —(CH$_2$)$_2$CF$_2$O—, and —OCF$_2$(CH$_2$)$_2$—. More preferred examples are a single bond, —(CH$_2$)$_2$—, —CF$_2$O—, —OCF$_2$—, —CH═CH—, —(CH$_2$)$_4$—, —CH═CH—(CH$_2$)$_2$—, —(CH$_2$)$_2$—CH═CH—, —(CH$_2$)$_2$CF$_2$O—, and —OCF$_2$(CH$_2$)$_2$—. Particularly preferred examples of Y are a single bond and —(CH$_2$)$_2$—. Trans-configuration is more preferred than the cis-configuration regarding the double bond of the bonding group such as —CH═CH—, —CH═CH—(CH$_2$)$_2$—, and —(CH$_2$)$_2$—CH═CH—.

Preferred examples of W are —(CH$_2$)$_2$—, —CH═CH—, —CF═CF—, —CH$_2$O—, —OCH$_2$—, —CF$_2$O—, —OCF$_2$—, —(CH$_2$)$_4$—, —(CH$_2$)$_3$—O—, —O—(CH$_2$)$_3$—, —CH═CH—(CH$_2$)$_2$—, —(CH$_2$)$_2$—CH═CH—, —(CH$_2$)$_2$CF$_2$O—, and —OCF$_2$(CH$_2$)$_2$—. More preferred examples are —(CH$_2$)$_2$—, —CH═CH—, —CH$_2$O—, —OCH$_2$—, —CF$_2$O—, —OCF$_2$—, —(CH$_2$)$_4$—, —CH═CH—(CH$_2$)$_2$—, —(CH$_2$)$_2$—CH═CH—, —(CH$_2$)$_2$CF$_2$O— and OCF$_2$(CH$_2$)$_2$—. Then, particularly preferred examples of W are —(CH$_2$)$_2$— and —CH$_2$O—. Trans-configuration is more preferred than cis-configuration regarding the double bond of the bonding group such as —CH═CH—, —CH═CH—(CH$_2$)$_2$, and —(CH$_2$)$_2$—CH═CH—.

Preferred examples of $Z^2$, $Z^{11}$, $Z^{12}$, $Z^{21}$ or $Z^{22}$ are a single bond, —(CH$_2$)$_2$—, —COO—, —OCO—, —CH$_2$O—, —OCH$_2$—, —CF$_2$O—, —OCF$_2$—, —CH═CH—, —CF═CF—, —(CH$_2$)$_4$—, —(CH$_2$)$_3$—O—, —O—(CH$_2$)$_3$—, —CH═CH—(CH$_2$)$_2$—, —(CH$_2$)$_2$—CH═CH—, —(CH$_2$)$_2$CF$_2$O—, and —OCF$_2$(CH$_2$)$_2$—. More preferred examples are a single bond, —(CH$_2$)$_2$—, —CH$_2$O—, —OCH$_2$—, —CF$_2$O—, —OCF$_2$—, —CH═CH—, —(CH$_2$)$_2$CF$_2$O—, and —OCF$_2$(CH$_2$)$_2$—. Then, particularly preferred examples of $Z^2$, $Z^{11}$, $Z^{12}$, $Z^{21}$ or $Z^{22}$ are a single bond, —CH$_2$O—, —OCH$_2$—, —CF$_2$O— and —OCF$_2$—. Then, trans-configuration is more preferred than cis-configuration regarding the double bond of the bonding group such as —CH═CH—, —CH═CH—(CH$_2$)$_2$, and (CH$_2$)$_2$—CH═CH—.

In Formula (1) and Formula (2), j, k, m, n, p and q each independently is 0 or 1 and the sum of them is 1, 2 or 3. That is, Compound (1) and Compound (2) are compounds having 2 to 4 rings. In a case where m is 0, each of j and k is 0, Ra in Formula (1) is none of hydrogen, alkoxy and alkoxymethyl, and Ra in Formula (2) is 1-alkenyl. It is preferred that the sum of j, k and m is 1 or 2, and it is preferred that also the sum for p and q is 1 or 2.

As described above, particularly preferred examples of $A^1$ or $A^2$ are 1,4-phenylene and 1,4-cyclohexylene. Accordingly, particularly preferred examples of Formula (1) and Formula (2) are a case where any of $A^1$ and $A^2$ is 1,4-phenylene, a case where $A^1$ is 1,4-phenylene and $A^2$ is 1,4-cyclohexylene, a case where $A^1$ is 1,4-cyclohexylene and $A^2$ is 1,4-phenylene, and a case where any of $A^1$ and $A^2$ is 1,4-cyclohexylene.

As described above, particularly preferred examples of Y are a single bond, —(CH$_2$)$_2$—, —CF$_2$O—, and —CH═CH—. Particularly preferred examples of $Z^2$ are a single bond, —CH$_2$O—, —OCH$_2$—, —CF$_2$O—, and —OCF$_2$—. That is, it is one of preferred examples of Compound (1) that at least one of Y and $Z^2$ in Formula (1) is a single bond.

In Formula (1), in a case where m is 0 and the sum of n, p and q is 1, 2 or 3, it is preferred that $Z^2$ is —CH$_2$O—, —OCH$_2$—, —CF$_2$O—, or —OCF$_2$—.

In Formula (1), in a case where m and k each is 1, and j and n each is 0, it is preferred that Ra is alkyl or alkenyl, Rb is alkoxy, $A^1$ and $A^{11}$ each independently is 1,4-phenylene or 1,4-cyclohexylene, and any of Y and $Z^{11}$ is a single bond.

In Formula (1), in a case where m is 1, and j, k, n, p and q each is 0, it is preferred that Ra is alkyl or alkenyl, Rb is alkoxy, $A^1$ is 1,4-cyclohexylene, and Y is a single bond or —(CH$_2$)$_2$—. In this case, it is more preferred that Y is —(CH$_2$)$_2$—.

In Formula (1), in a case where m and k each is 1, and j, n, p and q each is 0, it is preferred that Ra is alkyl or alkenyl, Rb is alkoxy, any of $A^1$ and $A^{11}$ is 1,4-cyclohexylene, Y is —(CH$_2$)$_2$—, and $Z^{11}$ is a single bond.

In Formula (1), in a case where m is 0, n is 1 and any of p and q is 0, it is preferred that Ra is alkyl, Rb is alkyl or alkenyl, $A^2$ is 1,4-cyclohexylene, and $Z^2$ is —OCH$_2$—.

In Formula (1), in a case where m and q each is 0, and n and p each is 1, it is preferred that Ra is alkyl, Rb is alkyl or alkenyl, any of $A^1$ and $A^{21}$ is 1,4-cyclohexylene, $Z^2$ is —OCH$_2$—, and $Z^{21}$ is a single bond.

In Formula (1), in a case where m and n each is 1, and each of j, k, p and q is 0, it is preferred that Ra and Rb each independently is alkyl or alkenyl, any of $A^1$ and $A^2$ is 1,4-phenylene, and any of Y and $Z^2$ is a single bond.

In Formula (1), in a case where each of m and n is 1, and each of j, k, p and q is 0, it is preferred that Ra and Rb each independently is alkyl or alkenyl, $A^1$ is 1,4-cyclohexylene, $A^2$ is 1,4-phenylene, and any of Y and $Z^2$ is a single bond.

In Formula (1), in a case where each of m and n is 1, and each of j, k, p and q is 0, it is preferred that Ra and Rb each independently is alkyl or alkenyl, $A^1$ is 1,4-phenylene, $A^2$ is 1,4-cyclohexylene, and any of Y and $Z^2$ is a single bond.

In Formula (2), in a case where m is 0, $Z^2$ is preferably a single bond.

In Formula (2), where m is 1 and the sum of n, p and q is 1 or 2, it is preferred that W is —(CH$_2$)$_2$— or —CH$_2$O—, and $Z^2$ is a single bond. It is more preferred that W is —CH$_2$O—.

In Formula (2), where m is 1, $A^1$ is preferably 1,4-cyclohexylene.

In Formula (2), in a case where m is 1 and each of j, k, n, p and q is 0, it is preferred that Ra is alkyl or alkenyl, Rb is alkoxy, $A^1$ is 1,4-cyclohexylene, and W is —(CH$_2$)$_2$—.

In Formula (2), in a case where each of m and k is 1, and each of j, n, p and q is 0, it is preferred that any of $A^1$ and $A^{11}$ is 1,4-cyclohexylene, W is —(CH$_2$)$_2$—, and $Z^{11}$ is a single bond.

In Formula (2), where all of m, j and k are 1, and each of n, p and q is 0, it is preferred that all of $A^1$, $A^{11}$ and $A^{12}$ are 1,4-cyclohexylene, Y is —(CH$_2$)$_2$—, and any of $Z^{11}$ and $Z^{12}$ is a single bond.

Compound (1) and Compound (2) may contain an isotope such as $^2$H (deuterium), $^{13}$C, etc. in an amount more than the amount of natural abundance ratio. Even in this case, the physical properties of the compound are not very different.

Preferred examples of Formula (1) are those of Formula (1-1) to Formula (1-9) and preferred examples of Formula (2) are Formula (2-1) to Formula (2-9).

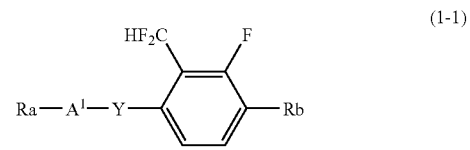

(1-1)

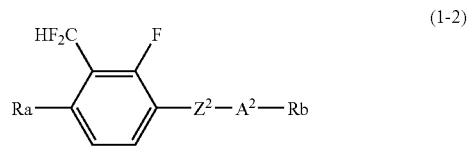

(1-2)

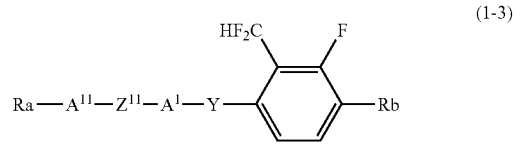

(1-3)

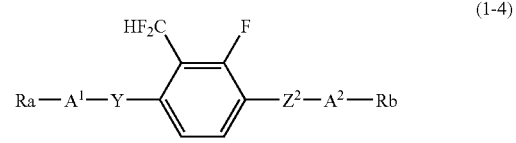

(1-4)

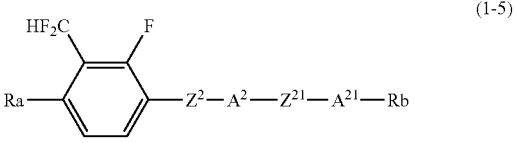

(1-5)

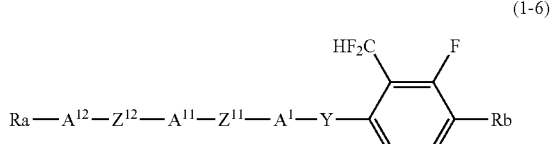

(1-6)

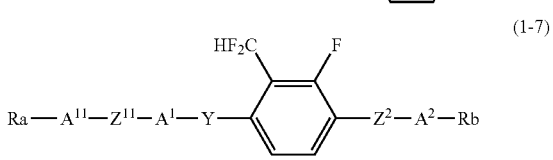

(1-7)

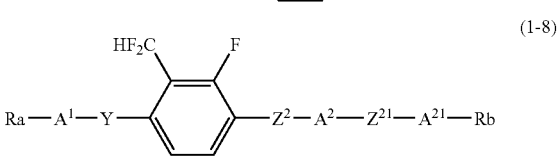

(1-8)

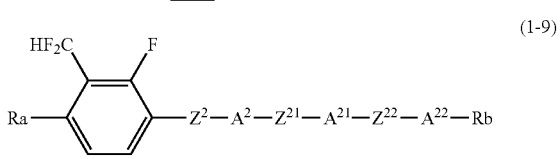

(1-9)

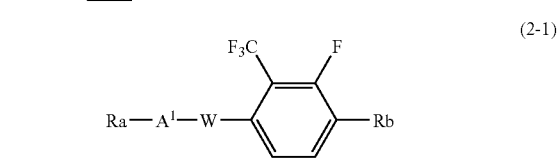

(2-1)

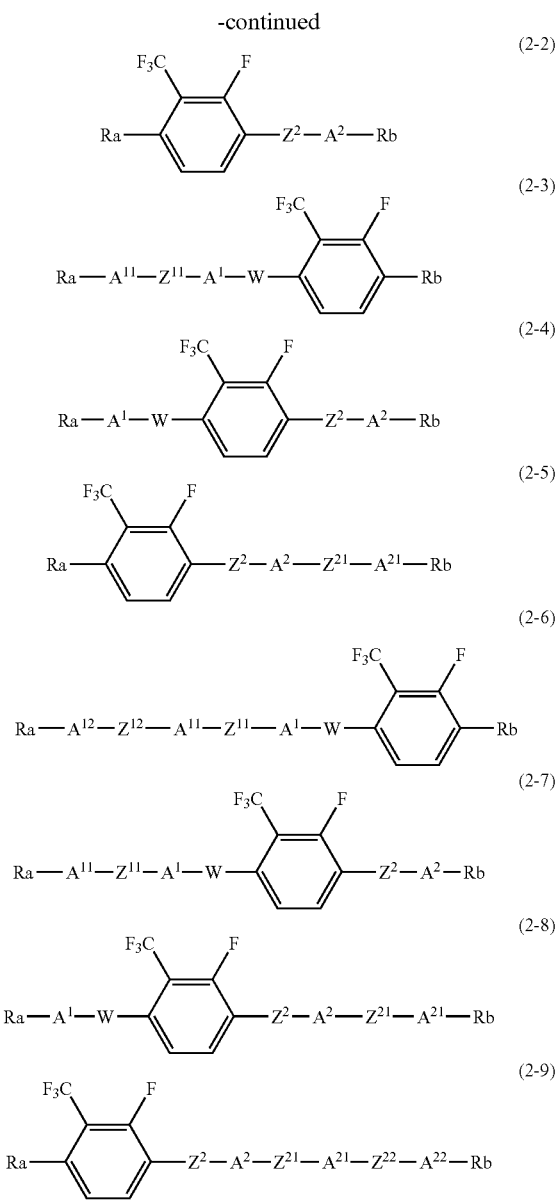

Symbols in the formulae have the same meanings as the respective symbols in Formula (1) and Formula (2) and preferred examples thereof are also identical.

In Formula (1-1) to Formula (1-9), it is particularly preferred that at least one of Y and $Z^2$ is a single bond. In Formula (2-1) to Formula (2-9), it is particularly preferred that $Z^2$ is a single bond.

In Formula (1-1), it is preferred that Ra is alkyl of 1 to 10 carbon atoms or alkenyl of 2 to 10 carbon atoms, Rb is alkoxy of 1 to 10 carbon atoms, $A^1$ is 1,4-cyclohexylene and Y is a single bond or —(CH$_2$)$_2$—.

In Formula (1-2), it is preferred that Ra is alkyl of 1 to 10 carbon atoms, Rb is alkyl of 1 to 10 carbon atoms, or alkenyl of 2 to 10 carbon atoms, $A^2$ is 1,4-cyclohexylene and $Z^2$ is —OCH$_2$—.

In Formula (1-2), Formula (1-4), Formula (1-5), Formula (1-7), Formula (1-8), and Formula (1-9), it is preferred that $Z^2$ is —CH$_2$O—, —OCH$_2$—, —CF$_2$O—, or —OCF$_2$—.

In Formula (1-3), it is preferred that Ra is alkyl of 1 to 10 carbon atoms or alkenyl of 2 to 10 carbon atoms, Rb is alkoxy of 1 to 10 carbon atoms, any of $A^1$ and $A^{11}$ is 1,4-cyclohexylene, and any of Y and $Z^{11}$ is a single bond.

In Formula (1-3), it is preferred that Ra is alkyl of 1 to 10 carbon atoms or alkenyl of 2 to 10 carbon atoms, Rb is alkoxy of 1 to 10 carbon atoms, any of $A^1$ and $A^{11}$ is 1,4-cyclohexylene, Y is —(CH$_2$)$_2$—, and $Z^{11}$ is a single bond.

In Formula (1-3), it is preferred that Ra is alkyl of 1 to 10 carbon atoms or alkenyl of 2 to 10 carbon atoms, Rb is alkoxy of 1 to 10 carbon atoms, $A^1$ is 1,4-phenylene, $A^{11}$ is 1,4-cyclohexylene, and any of Y and $Z^{11}$ is a single bond.

In Formula (1-3), it is preferred that Ra is alkyl of 1 to 10 carbon atoms or alkenyl of 2 to 10 carbon atoms, Rb is alkoxy of 1 to 10 carbon atoms and any of $A^1$ and $A^{11}$ is 1,4-phenylene, and any of Y and $Z^{11}$ is a single bond.

In Formula (1-4), it is preferred that Ra and Rb each independently is alkyl of 1 to 10 carbon atoms or alkenyl of 2 to 10 carbon atoms, any of $A^1$ and $A^2$ is 1,4-phenylene, and any of Y and $Z^2$ is a single bond.

In Formula (1-4), it is preferred that Ra and Rb each independently is alkyl of 1 to 10 carbon atoms or alkenyl of 2 to 10 carbon atoms, $A^1$ is 1,4-cyclohexylene, $A^2$ is 1,4-phenylene, and any of Y and $Z^2$ is a single bond.

In Formula (1-4), it is preferred that Ra and Rb each independently is alkyl of 1 to 10 carbon atoms or alkenyl of 2 to 10 carbon atoms, $A^1$ is 1,4-phenylene, $A^2$ is 1,4-cyclohexylene, and any of Y and $Z^2$ is a single bond.

In Formula (1-5), it is preferred that Ra is alkyl of 1 to 10 carbon atoms, Rb is alkyl of 1 to 10 carbon atoms or alkenyl of 2 to 10 carbon atoms, any of $A^2$ and $A^{21}$ is 1,4-cyclohexylene, $Z^2$ is —OCH$_2$—, and $Z^{21}$ is a single bond.

In Formula (2-1), Formula (2-3), Formula (2-5), and Formula (2-5) to Formula (2-7), $A^1$ is preferably 1,4-cyclohexylene.

In Formula (2-1), it is preferred that Ra is alkyl of 1 to 10 carbon atoms or alkenyl of 2 to 10 carbon atoms, Rb is alkoxy of 1 to 10 carbon atoms, W is —(CH$_2$)$_2$— or —CH$_2$O—, and $A^1$ is 1,4-cyclohexylene.

In Formula (2-3), it is preferred that any of $A^1$ and $A^{11}$ is 1,4-cyclohexylene, and $Z^{11}$ is a single bond.

In Formula (2-3), it is preferred that Ra is alkyl of 1 to 10 carbon atoms or alkenyl of 2 to 10 carbon atoms, Rb is alkoxy of 1 to 10 carbon atoms, W is —(CH$_2$)$_2$— or —CH$_2$O—, and any of $A^1$ and $A^{11}$ is 1,4-cyclohexylene, and $Z^{11}$ is a single bond.

In Formula (2-6), all of $A^1$, $A^{11}$ and $A^{12}$ are 1,4-cyclohexylene, W is —(CH$_2$)$_2$— or —CH$_2$O—, and any of $Z^{11}$ and $Z^{12}$ is a single bond.

The liquid crystal composition of the invention is to be described.

The liquid crystal composition of the invention is a composition which contains at least one of Compound (1) and Compound (2) and may also contain at least one optically active compound. The composition of the invention can contain other liquid crystalline compounds than Compound (1) and Compound (2). Preferred liquid crystalline compounds other than Compound (1) and Compound (2) are compounds selected from the group consisting of compounds represented by following Formula (3) to Formula (15), respectively.

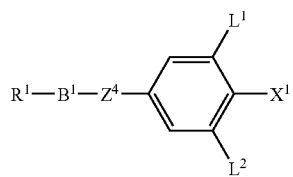
(3)

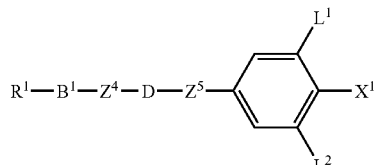
(4)

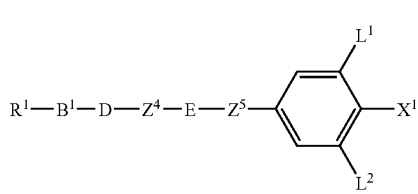
(5)

In the formulae, $R^1$ is alkyl of 1 to 10 carbon atoms. In the alkyl, arbitrary —$CH_2$— not positioned on the terminal may be replaced by —O—, arbitrary —$(CH_2)_2$— may be replaced by —CH=CH—, and arbitrary hydrogen may be replaced by fluorine. $X^1$ is fluorine, chlorine, —$OCF_3$—, —$OCHF_2$, —$CF_3$, —$CHF_2$, —$CH_2F$, —$OCF_2CHF_2$, or —$OCF_2CHFCF_3$. $B^1$ and D each independently is 1,4-cyclohexylene, 1,4-phenylene, 1,3-dioxane-2,5-diyl, or 1,4-phenylene in which at least one hydrogen is replaced by fluorine. E is 1,4-cyclohexylene, 1,4-phenylene, or 1,4-phenylene in which at least one hydrogen is replaced by fluorine. $Z^4$ and $Z^5$ each independently is —$(CH_2)_2$—, —$(CH_2)_4$—, —COO—, —$CF_2O$—, —$OCF_2$—CH=CH—, or a single bond. Then, $L^1$ and $L^2$ each independently is hydrogen or fluorine.

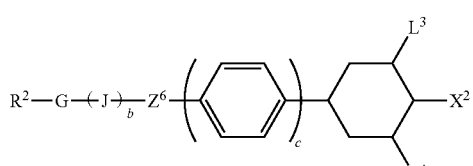
(6-1)

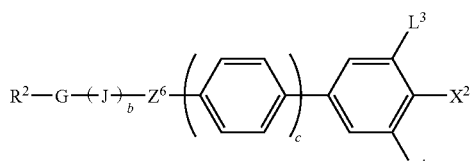
(6-2)

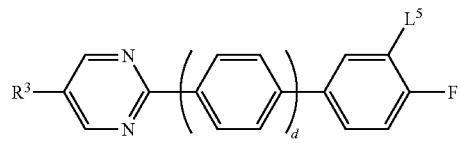
(7)

In the formulae, $R^2$ and $R^3$ each independently is alkyl of 1 to 10 carbon atoms. In the alkyl, arbitrary —$CH_2$— may be replaced by —O—, arbitrary —$(CH_2)_2$— may be replaced by —CH=CH—, and arbitrary hydrogen may be replaced by fluorine. $X^2$ is —CN or —C≡C—CN. G is 1,4-cyclohexylene, 1,4-phenylene, 1,3-dioxane-2,5-diyl, or pyrimidine-2,5-diyl. J is 1,4-cyclohexylene, 1,4-phenylene, pyrimidine-2,5-diyl, or 1,4-phenylene in which at least one hydrogen is replaced by fluorine. $Z^6$ is —$(CH_2)_2$—, —COO—, —$CF_2O$—, —$OCF_2$—, or a single bond. $L^3$, $L^4$, and $L^5$ each independently is hydrogen or fluorine. Then, b, c, and d each independently is 0 or 1.

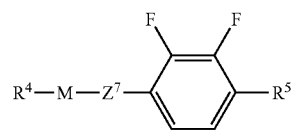
(8)

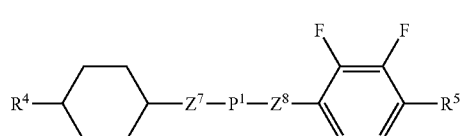
(9)

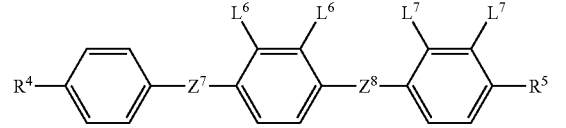
(10)

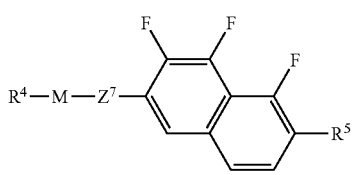
(11)

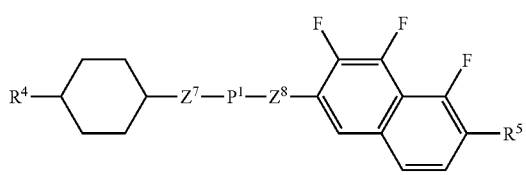
(12)

In the formulae, $R^4$ is alkyl of 1 to 10 carbon atoms, and $R^5$ is fluorine or alkyl of 1 to 10 carbon atoms. In the alkyl, arbitrary —$CH_2$— not positioned on the terminal may be replaced by —O—, arbitrary —$(CH_2)_2$— may be replaced by —CH=CH—, and arbitrary hydrogen may be replaced by fluorine. M and $P^1$ each independently is 1,4-cyclohexylene, 1,4-phenylene, or decahydro-2,6-naphthylene. $Z^7$ and $Z^8$ each independently is —$(CH_2)_2$—, —COO—, or a single bond. $L^6$ and
$L^7$ each independently is hydrogen or fluorine, and at least one of $L^6$ and $L^7$ is fluorine.

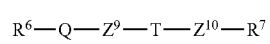
(13)

(14)

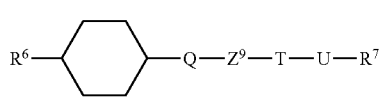
(15)

In the formulae, $R^6$ and $R^7$ each independently is alkyl of 1 to 10 carbon atoms. In the alkyl, arbitrary —$CH_2$— not positioned on the terminal may be replaced by —O—, arbitrary —(CH$_2$)$_2$— may be replaced by —CH=CH— and arbitrary hydrogen may be replaced by fluorine. Q, T, and U each independently is 1,4-cyclohexylene, 1,4-phenylene, pyrimidine-2,5-diyl, or 1,4-phenylene in which at least one hydrogen is replaced by fluorine. Then, $Z^9$ and $Z^{10}$ each independently is —C≡C—, —COO—, —(CH$_2$)$_2$—, —CH=CH—, —CH$_2$O—, or a single bond.

A first example of the liquid crystal composition in the invention is a composition which contains at least one compound selected from the group consisting of Compound (1) and Compound (2) and at least one compound selected from the group consisting of Compound (3), Compound (4), and Compound (5) and may also contain at least one optically active compound.

A second example of the liquid crystal composition in the invention is a composition which contains at least one compound selected from the group consisting of Compound (1) and Compound (2) and at least one compound selected from the group consisting of Compound (6-1), Compound (6-2), and Compound (7) and may also contain at least one optically active compound.

A third example of the liquid crystal composition in the invention is a composition which contains at least one compound selected from the group consisting of Compound (1) and Compound (2) and at least one compound selected from the group consisting of the compounds represented by Formula (8) to Formula (12), respectively, and may also contain at least one optically active compound.

A fourth example of the liquid crystal composition in the invention is a composition which contains at least one compound selected from the group consisting of Compound (1) and Compound (2) and at least one compound selected from the group consisting of Compound (13), Compound (14), and Compound (15) and may also contain at least one optically active compound.

The fifth example of the liquid crystal composition in the invention is a composition which further contains at least one compound selected from the group consisting of Compound (6-1), Compound (6-2), and Compound (7) in addition to the combination of the compounds shown in the first example. That is, this is a composition which contains at least one compound selected from the group consisting of Compound (1) and Compound (2), at least one compound selected from the group consisting of Compound (3), Compound (4), and Compound (5), as well as at least one compound selected from the group consisting of Compound (6-1), Compound (6-2), and Compound (7), and may also contain at least one optically active compound.

The sixth example of the liquid crystal composition in the invention is a composition which further contains at least one compound selected from the group consisting of the compound (13), the compound (14), and the compound (15) in addition to the combination of the compounds shown in the first example. That is, this is a composition which contains at least one compound selected from the group consisting of Compound (1) and Compound (2), at least one compound selected from the group consisting of Compound (3), Compound (4), and Compound (5), as well as at least one compound selected from the group consisting of Compound (13), Compound (14), and Compound (15), and may also contain at least one optically active compound.

The seventh example of the liquid crystal composition in the invention is a composition which further contains at least one compound selected from the group consisting of Compound (13), Compound (14), and Compound (15) in addition to the combination of the compounds shown in the second example. That is, this is a composition which contains at least one compound selected from the group consisting of Compound (1) and Compound (2), at least one compound selected from the group consisting of Compound (6-1), Compound (6-2) and Compound (7), as well as at least one compound selected from the group consisting of Compound (13), Compound (14), and Compound (15), and may also contain at least one optically active compound.

In Formula (3) to Formula (15), identical symbols used for a plurality of formulae may have identical meanings or different meanings. An example where the identical symbol has a different meaning is a case where $R^1$ in Formula (3) is alkyl and $R^1$ in Formula (4) is alkenyl.

The compound of the invention is to be described further. The compound of the invention is a bicyclic, tricyclic, or tetracyclic compound having 2-difluoromethyl-3-fluoro-1,4-phenylene or 2-trifluoromethyl-3-fluoro-1,4-phenylene. The compound of the invention is extremely stable physically and chemically under the conditions where the device is usually used, and is highly compatible with other liquid crystalline compounds. The composition containing the compound of the invention is stable under the condition where the device is used usually. Even when the composition is stored at a low temperature, the compound is not precipitated as crystals (or smectic phase). The compound of the invention has general physical properties necessary for the liquid crystal material, appropriate optical anisotropy, and appropriate dielectric anisotropy.

The physical properties of the compound according to the invention such as optical anisotropy and dielectric anisotropy can be optionally controlled by properly selecting the terminal group, the ring and the bonding group. The effect that the kind of the terminal group, the ring, and the bonding group on the physical property of the compound of the invention is to be described below.

The compound of the invention has a negative dielectric anisotropy. The compound of the invention shows a large negative dielectric anisotropy when the substituents and the bonding groups are properly selected. The compound having the large negative dielectric anisotropy is an ingredient useful for lowering the threshold voltage of a composition for IPS or VA use.

In a case where Ra or Rb is a linear group, the liquid crystal phase has a wide temperature range and a low viscosity. In a case where Ra or Rb is a branched group, it has a good compatibility with other liquid crystalline compounds. The compound in which Ra or Rb is an optically active group is useful as a chiral dopant. By the addition of the compound to the composition, reverse twisted domain generated in the device can be prevented. A compound in which Ra or Rb is not an optically active group is useful as the ingredient for the composition. In a case where Ra or Rb is alkenyl, a preferred configuration depends on the position of the double bond. An alkenyl compound having a preferred configuration has a high upper limit temperature or a wide temperature range of the liquid crystal phase.

In a case where at least two of $A^1, A^{11}, A^{12}, A^2, A^{21}$, and $A^{22}$ are 1,4-cyclohexylene, the upper limit temperature is high, the optically anisotropy is small, and the viscosity is low. In a case where at least one ring is 1,4-phenylene, the optical anisotropy is relatively large, and the orientational order parameter is large. In a case where at least two rings are 1,4-phenylene, the optical anisotropy is large, the temperature range of the liquid crystal phase is wide, and the upper limit temperature is high.

In a case where at least one of Y, $Z^{11}, Z^{12}, Z^2, Z^{21}$, and $Z^{22}$ is a single bond, —(CH$_2$)$_2$—, —CF$_2$O—, —OCF$_2$—, —CH=CH—, or —CF=CF—, the viscosity is low. In a case where the bonding group is a single bond, —OCF$_2$—, —CF$_2$O—, —(CH$_2$)$_2$—, or —CH=CH—, the viscosity is further lower. In a case where the bonding group is —CH=CH—, the temperature range of the liquid crystal phase is wide, and the elastic constant ratio K$_{33}$/K$_{11}$ (K$_{33}$: bend elastic constant, K$_{11}$: spray elastic constant) is large.

In a case where W is —(CH$_2$)$_2$—, —CH$_2$O—, —OCH$_2$—, —CF$_2$O—, —OCF$_2$—, —CH=CH—, or —CF=CF—, the viscosity is low. In a case where the bonding group is —(CH$_2$)$_2$—, —CH$_2$O—, —OCH$_2$—, —OCF$_2$—, —CF$_2$O—, or —CH=CH—, the viscosity is further lower. In a case where the bonding group —CH=CH—, the temperature range of the liquid crystal phase is wide and the elastic constant ratio K$_{33}$/K$_{11}$ (K$_{33}$: bent elastic constant, K$_{11}$: spray elastic constant) is large. In a case where the bonding group is —CH$_2$O—, the dielectric anisotropy is negative and further large.

A compound in which at least one of A$^1$ and A$^2$ is 1,4-phenylene which may be replaced by fluorine, and a bonding group Z$^1$ and Z$^2$ in direct bonding with the ring is a single bond has further larger negative dielectric anisotropy and also has a large optical anisotropy.

Compound (1-1) to Compound (1-5), and Compound (2-1) to Compound (2-5), which are 2-rings or 3-rings compounds, have low viscosity. Compound (1-3) to Compound (1-9), and Compound (1-3) to Compound (1-9), which are 3-rings or 4-rings, have high upper limit temperature. As described above, a compound having aimed physical property can be obtained by properly selecting the kind of the terminal group, the ring and the bonding group, and the number of rings. Accordingly, the compound of the invention, particularly, Compound (1-1) to Compound (1-9) and Compound (2-1) to Compound (2-9) are useful as the ingredient of the composition used for the device for IPS or VA use.

In Compound (1-1), Compound (1-3), Compound (1-4), and Compound (1-6) to Compound (1-8), a compound in which Z is —(CH$_2$)$_2$— or —CH=CH— shows large negative dielectric anisotropy and shows particularly excellent balance of the physical property as the liquid crystal material such as a wide temperature range of the liquid crystal phase and a low viscosity.

The compound of the invention can be synthesized by properly combining the methods in the organic synthesis chemistry. The methods of introducing an aimed terminal group, a ring, and a bonding group to the starting material are described (for example, in Organic Synthesis, John Wiley & Sons, Inc., Organic Reactions, John, Wiley & Sons, Inc. Comprehensive Organic Synthesis, Pergamon Press, and New Experimental Chemical Course (Maruzen)).

For an example of the method of forming the bonding group, a scheme is at first shown and then the scheme is explained in the paragraph (I) to paragraph (XI). In the scheme, MSG$^1$ or MSG$^2$ is a monovalent organic group having at least one ring. A plurality of MSG$^1$ (or MSG$^2$) used in the scheme may be identical or different with each other. The compound (1A) to the compound (1K) correspond to Compound (1), Compound (2), Compound (1-1) to Compound (1-9) or Compound (2-1) to Compound (2-9).

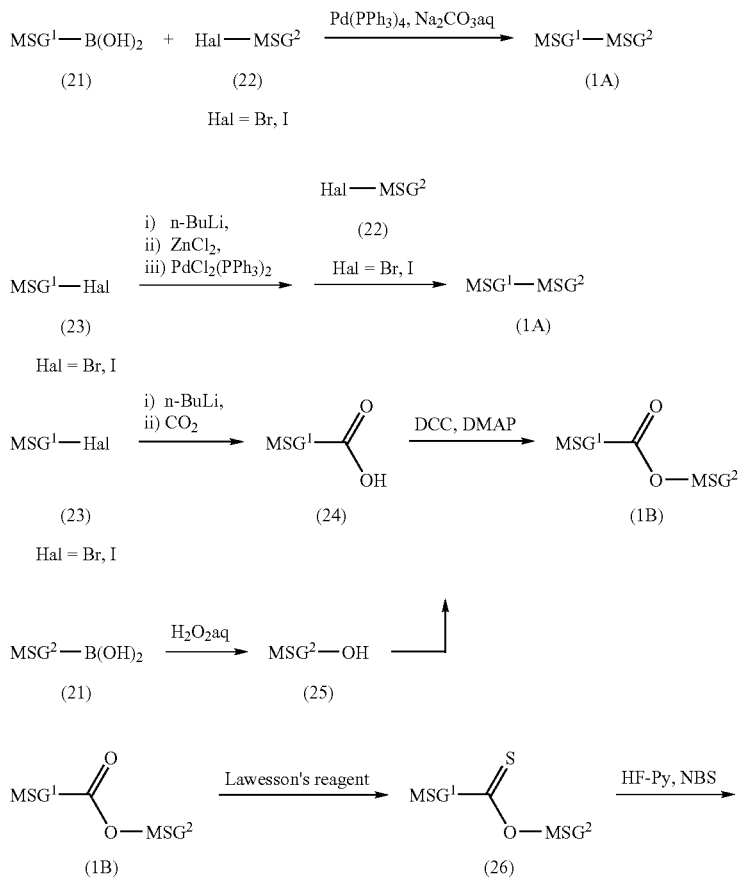

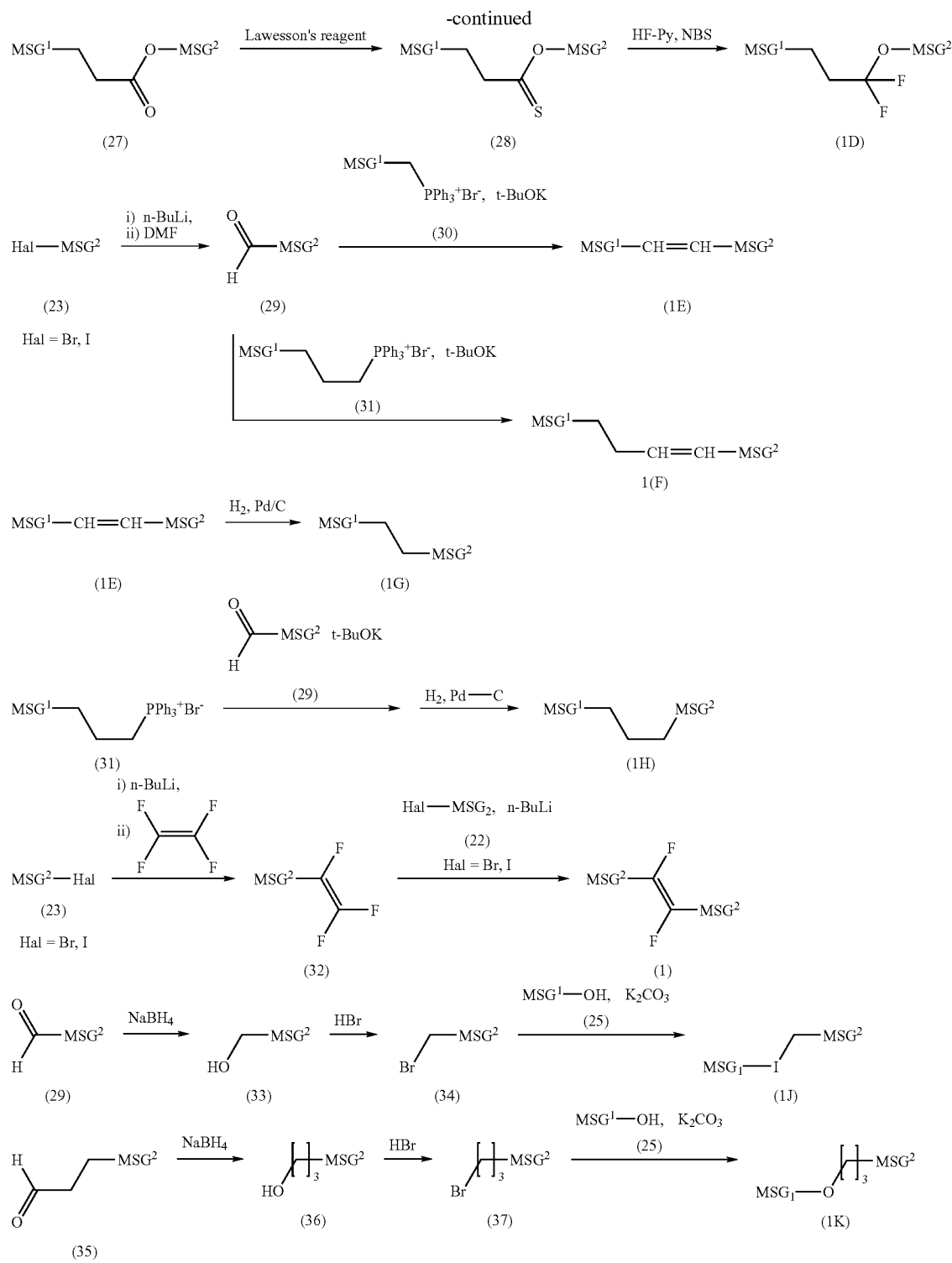

(I) Formation of Single Bond

Aryl boronic acid (21) and a compound (22) synthesized by a known method are reacted under the presence of an aqueous carbonate solution and a catalyst such as tetrakis(triphenylphosphine) palladium to synthesize the compound (1A). The compound (1A) is also synthesized by reacting a compound (23) synthesized by a known method with n-butyl lithium, then with zinc chloride and reacting a compound (22) under the presence of a catalyst such as dichlorobis(triphenylphosphine)palladium.

(II) Formation of —COO— and —OCO—

The compound (23) is reacted with n-butyl lithium and successively with carbon dioxide to obtain a carboxylic acid (24). The compound (24) and phenol (25) synthesized by a known method are dehydrated under the presence of DDC (1,3-dicyclohexylcarbodiimide) and DMAP (4-dimethylaminopyridine) to synthesize the compound (1B) having —COO—. A compound having —OCO— is also synthesized by the method.

(III) Formation of —CF$_2$O— and —OCF$_2$—

The compound (1B) is treated with a sulfurizing agent such as a Rawsson's reagent to obtain a compound (26). The compound (26) is fluorinated with a pyridine hydrogen fluoride complex and NBS (N-bromosuccine imide) to synthesize a compound having —CF$_2$O— (1C) (refer to M. Kuroboshi, et al., Chem. Lett. 1992, 827). The compound (1C) is synthesized also by fluorinating the compound (26) with (diethylamino)sulfur trifluoride (DAST) (refer to W. H. Bunnelle, et al., J. Org. Chem. 1990, 55, 768). A compound having —OCF$_2$— is also synthesized by the method. The bonding groups can also be formed by the method as described in Peer, Kirsch, et al., Anbew. Chem. Int. Ed. 2001, 40, 1480.

(IV) Formation of —(CH$_2$)$_2$CF$_2$O— and —OCF$_2$(CH$_2$)$_2$—

The compound (1D) is synthesized in accordance with the method in paragraph (III) by using the propionic ester derivative (27) synthesized by the methods described in U.S. Pat. No. 4,834,905 and U.S. Pat. No. 4,627,933 instead of the compound (1B). A compound having —OCF$_2$—(CH$_2$)$_2$— is also synthesized by the method.

(V) Formation of —CH=CH—

After treating the compound (23) with n-butyl lithium, it is reacted with formamide such as N,N-dimethylformamide (DMF) to obtain an aldehyde (29). The compound (1E) is synthesized by treating a phosphonium salt (30) synthesized by a known method with a base such as potassium tert-butoxide to generate phosphonium ylide, which is reacted with the aldehyde (29). Since a cis-form is formed depending on the reaction condition, the cis-form is isomerized into a transform optionally by a known method.

(VI) Formation of —(CH$_2$)$_2$—CH=CH— and —CH=CH—(CH$_2$)$_2$—

The compound (1F) is synthesized in accordance with the method in paragraph (V) using the phosphonium salt (31) instead of the phosphonium salt (30). Since a cis-form is formed depending on the reaction condition, the cis-form is optionally isomerized into a trans-form in accordance with a known method. A compound having —CH=CH—(CH$_2$)$_2$— is also synthesized by the method.

(VII) Formation of —(CH$_2$)$_2$—

The compound (1G) is synthesized by hydrogenating the compound (1E) under the presence of a catalyst such as palladium/carbon.

(VIII) Formation of —(CH$_2$)$_4$—

A compound (1H) is synthesized by catalytically hydrogenating the compound (1F) under the presence of a catalyst such as palladium carbon.

(IX) Formation of —CF=CF—

After treating a compound (23) with n-butyl lithium, a tetrafluoroethylene is reacted to obtain the compound (32). After treating the compound (22) with n-butyl lithium, it is reacted with a compound (32) to obtain a compound (1I).

(IX) Formation of —CH$_2$O— or —OCH$_2$—

The compound (29) is reduced with a reducing agent such as sodium borohydrate to obtain the compound (33). This is halogenated, for example, with a hydrobromic acid to obtain a compound (34). The compound (34) is reacted with the compound (25) under the presence of potassium carbonate or the like to synthesize the compound (1J).

(X) Formation of —(CH$_2$)$_3$O— or —O(CH$_2$)$_3$—

The compound (1K) is synthesized in accordance with the method in paragraph (IX) by using the compound (37) instead of the compound (34).

Then, an example of synthesizing a compound in which X is difluoromethyl in Formula (1) is shown in the following scheme.

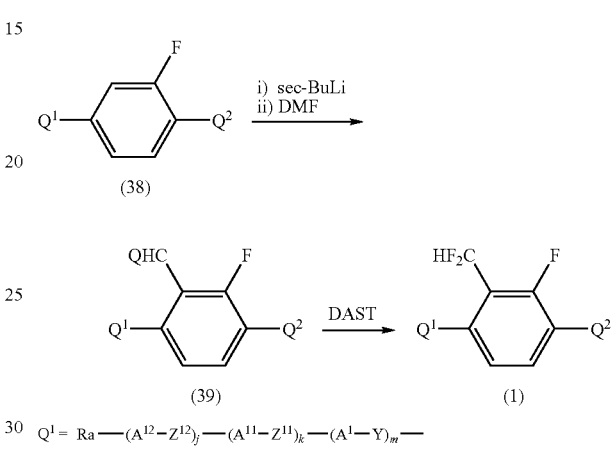

The symbols in the formulae have the same meanings as the symbols in Formula (1). This is also identical in the schemes shown below.

For example, the compound (39) is synthesized by reacting 3-fluorobenzene derivatives (38) synthesized by the methods disclosed in JP-S58-126823A, JP-S58-121225A, JP-S59-016840A, or JP-S59-042329A with sec-butyl lithium and then with dimethylformamide or formyl piperidine. The reactions are conducted, preferably, in a solvent such as etheric hydrocarbons, for example, diethyl ether or tetrahydrofuran at a temperature from −100° C. to a room temperature. Compound (1) is synthesized by reacting the compound (39) with a fluorinating agent such as DAST. The reaction is conducted in a solvent such as a halogenated hydrocarbon, for example, dichloromethane at a temperature from −100° C. to the boiling point of the solvent.

Then, an example of a synthesis method regarding the compound (45) is shown in which all of n, p, and q are 0 and Rb is alkoxy.

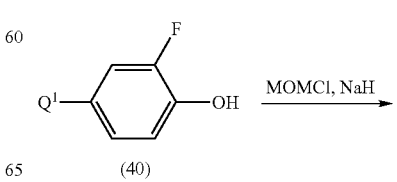

-continued

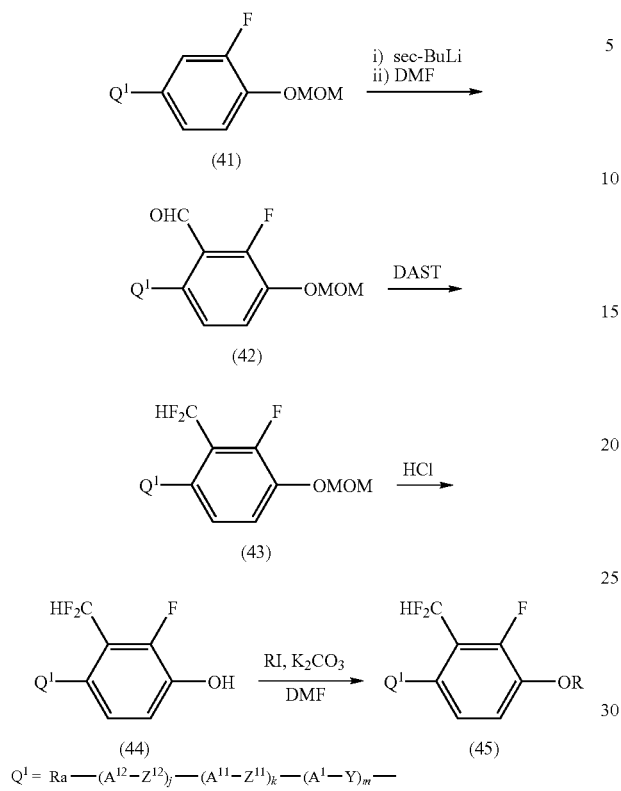

$Q^1 = Ra-(A^{12}-Z^{12})_j-(A^{11}-Z^{11})_k-(A^1-Y)_m-$

In the formulae, R is alkyl of 1 to 19 carbon atoms.

The compound (41) is synthesized by reacting the compound (40) with sodium hydride and chloromethyl methyl ether (MOMCl) successively. The reactions are preferably conducted in a solvent such as tetrahydrofuran at a temperature from −20° C. to the boiling point of the solvent. The reactions are preferably conducted in a solvent such as an etheric hydrocarbon, for example, diethyl ether or tetrahydrofuran at a temperature from −100° C. to a room temperature. The compound (43) is synthesized by reacting the compound (42) with a fluorinating agent such as DAST. The reaction is conducted in a solvent such as a halogenated hydrocarbon, for example, dichloromethane at a temperature from −100° C. to the boiling point of the solvent. The compound (44) is synthesized by deprotection of the compound (43). The reaction is conducted in an alcohol such as ethanol by reacting a diluted hydrochloric acid, for example, 2M hydrochloric acid at a temperature from a room temperature to the boiling point of the solvent. The compound (45) is synthesized by etherifying reaction of the compound (44). The reaction is conducted under the presence of a base such as sodium carbonate in a solvent such as dimethylformamide, by reacting the compound (44) with a halogenated alkyl such as an alkyl iodide at a temperature from a room temperature to the boiling point of the solvent.

Then, an example of a synthesis method regarding the compound (46) to the compound (50) in which the sum of n, p and q is 1 or greater, and $Z^2$ is —OCO—, —OCF$_2$—, —OCF$_2$(CH$_2$)$_2$—, —OCH$_2$— or O(CH$_2$)$_3$— is shown.

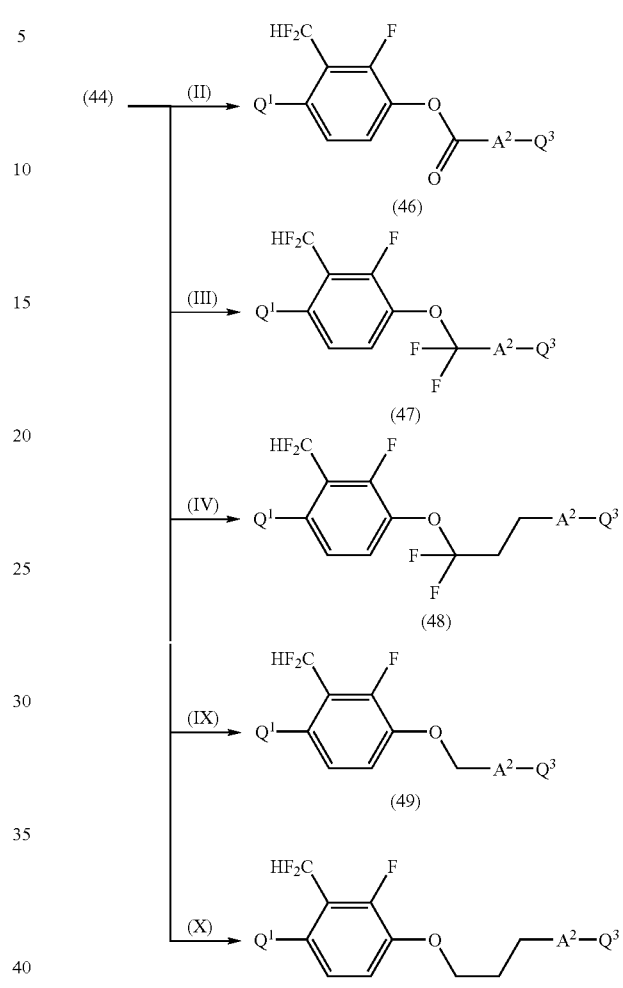

$Q^1 = Ra-(A^{12}-Z^{12})_j-(A^{11}-Z^{11})_k-(A^1-Y)_m-$
$Q^3 = -(Z^{21}-A^{21})_p-(Z^{22}-A^{22})_q-Rb$

The compounds (46) to (50) are synthesized respectively by using the compound (44) instead of the alcohol (phenol) intermediate product in the method of forming the bonding group described above.

The compounds (60) and (63) in which y, $Z^1$, $Z^{12}$, $Z^2$, $Z^{21}$, or $Z^{22}$ is a single bond and the directly bonded ring A A$^{11}$, A$^{12}$, A$^2$, A$^{21}$, or A$^{22}$ is 1,4-phenyle can also be synthesized by the following methods other than the synthesis methods described above.

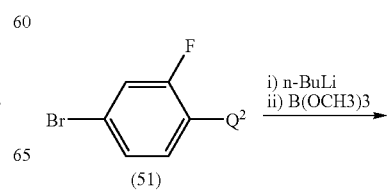

-continued (HO)₂B—[Ar(F)]—Q² →(H₂O₂)→

(52)

HO—[Ar(F)]—Q² →(MOMCl, NaH)→

(53)

MOMO—[Ar(F)]—Q² →(i) sec-BuLi; ii) DMF)→

(54)

MOMO—[Ar(F)(CHO)]—Q² →(DAST)→

(55)

MOMO—[Ar(F)(CHF₂)]—OR →(HCl)→

(56)

HO—[Ar(F)(CHF₂)]—Q² →((Tf)₂O, Pyridine)→

(57)

TfO—[Ar(F)(CHF₂)]—OR + Q⁴—[Ar]—B(OH)₂ →(KBr, K₃PO₄ cat.)→

(58)  (59)

Q⁴—[Ar]—[Ar(F)(CHF₂)]—Q²

(60)

Q¹—[Ar(F)(CHF₂)]—OH →((Tf)₂O, Pyridine)→

(44)

Q¹—[Ar(F)(CHF₂)]—OTf + (HO)₂B—[Ar]—Q³ →

(61)  (62)

-continued

Q¹—[Ar(F)(CHF₂)]—[Ar]—Q³

(63)

$Q^1 = Ra-(A^{12}-Z^{12})_j-(A^{11}-Z^{11})_k-(A^1-Y)_m-$ $Q^2 = -(Z^2-A^2)_n-(Z^{21}-A^{21})_p-(Z^{22}-A^{22})_q-Rb$ $Q^3 = -(Z^{21}-A^{21})_p-(Z^{22}-A^{22})_q-Rb$ $Q^4 = Ra-(A^{12}-Z^{12})_j-(A^{11}-Z^{11})_k-$

The compound (52) is synthesized by lithiating the compound (51) using n-butyl lithium, then reacting the same with a borate ester such as trimethyl borate and, further, hydrolyzing the same with hydrochloric acid or sulfuric acid. The reactions are preferably conducted in a solvent such as an etheric hydrocarbon, for example, diethyl ether or tetrahydrofuran at a temperature from −100° C. to a room temperature. The compound (53) is synthesized by acting a peroxide such as aqueous hydrogen peroxide or peracetic acid on the compound (52) and oxidizing the same. The reactions are preferably conducted in an etheric hydrocarbon, for example, diethyl ether or tetrahydrofuran, or a carboxylic acid, for example, formic acid or acetic acid at a temperature from −20° C. to the boiling point of the solvent. The compound (57) is synthesized in the reaction route of synthesizing the compound (44) from the compound (40) explained above by using the compound (53) instead of the compound (40) and applying identical reaction procedures. The compound (58) is synthesized by reacting the compound (57) with trifluoromethane sulfonic acid anhydride ((Tf)₂O) under the presence of a base, for example, pyridine or triethylamine. The reactions are preferably conducted in a solvent such as a halogenated hydrocarbon, for example, dichloromethane at a temperature from −20° C. to a room temperature. The compound (60) is synthesized by reacting the compound (58) and the boronic acid compound (59). The reactions are preferably conducted in a solvent, for example, an aromatic hydrocarbon such as toluene, an etheric hydrocarbon such as dioxane, ethylene glycol, and dimethyl ether, under the presence of a base such as potassium phosphate or potassium carbonate, by using a metal catalyst at a temperature from room temperature to the boiling point of the solvent. As the metal catalyst, tetrakis (triphenylphosphine) palladium, dichlorobis(triphenylphosphine) palladium, palladium carbon, etc. are used.

The compound (63) is synthesized in the reaction route of synthesizing the compound (60) from the compound (57) explained above, by using the compound (44) and compound (62) instead of the compound (57) and the compound (59) and applying identical reaction procedures.

Then, an example of a method of synthesizing a compound in which X is trifluoromethyl in Formula (2) is shown in the following scheme.

Q¹—[Ar(F)]—Q² →(i) sec-BuLi; iii) I₂)→

(38)

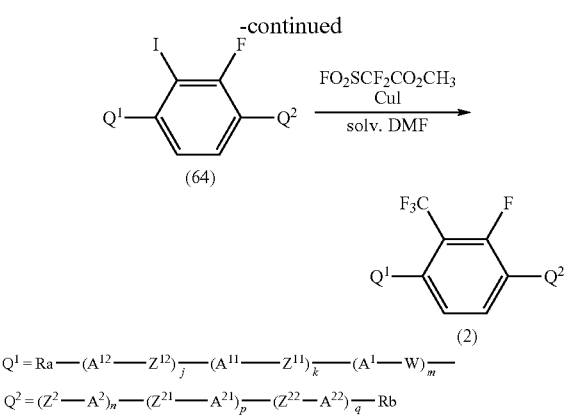

For example, the compound (64) is synthesized by reacting 3-fluorobenzene derivatives (38) synthesized by the methods disclosed in JP-S58-126823A, JP-S58-121225A, JP-S59-016840A, or JP-S59-042329A, with sec-butyl lithium and then with iodine. The reactions are preferably conducted in a solvent such as an etheric hydrocarbon, for example, diethyl ether or tetrahydrofuran at a temperature from −100° C. to a room temperature. Compound (1) is synthesized in accordance with the method by Qing-Yun Chen, et al described in J. Chem. Soc., Chem. Commun., 1989, 705, by reacting the compound (64) with methyl fluoro sulfonyl difluoro acetate under the presence of cuprous iodide. The reaction is conducted in an aprotic polar solvent such as dimethyl formamide or dimethyl sulfoxide at a temperature from 60° C. to the boiling point of the solvent.

An example of a synthesis method for the compound (69) in which n, p, and q each is 0, Rb is alkoxy and W is —CH═CH— and a compound (70) in which W is —(CH$_2$)$_2$— in Formula (2) is shown in the following scheme. The compound (69) and the compound (70) correspond to Formula (2-1), Formula (2-3), and Formula (2-6).

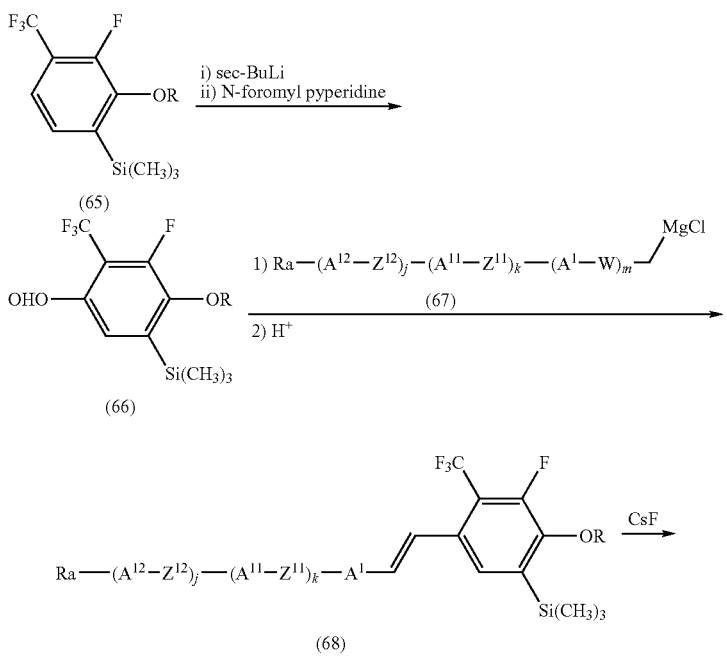

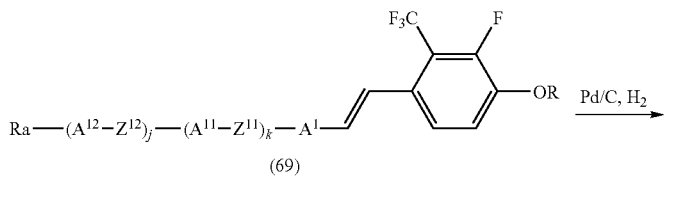

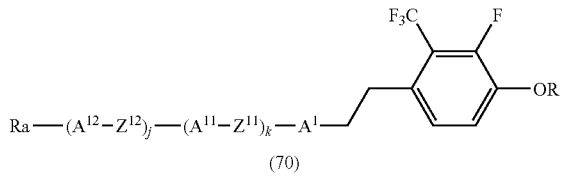

R in the formulae is alkyl of 1 to 19 carbon atoms.

For example, the compound (66) is synthesized by reacting the compound (65) described in Synlett 1999, No. 4, 389-396 with sec-butyl lithium and then with N-formyl piperidine. The reactions are preferably conducted in a solvent such as an etheric hydrocarbon, for example, diethyl ether or tetrahydrofuran at a temperature from −100° C. to a room temperature. The compound (68) is synthesized by treating the Grignard reagent (67) to the compound (66) and then subjecting the obtained alcohol form to a dehydrating reaction under the presence of an acid catalyst such as p-toluene sulfonic acid. Further, the compound (69) is synthesized by treating a THF solution of cesium fluoride or tetrabutyl ammonium fluoride to (68) in N,N-dimethyl formamide. The compound (70) can be synthesized by adding hydrogen to the compound (69) under the presence of a catalyst such as Pd/C.

An example of a synthesis method of the compound (76), in which n, p and q each is 0, Rb is alkoxy and W is —CH$_2$O— in Formula (2), is shown in the following scheme. The compound (76) corresponds to that of Formula (2-1), Formula (2-3), and Formula (2-6).

with sec-butyl lithium and then with bromine. The reactions are preferably conducted in a solvent such as an etheric hydrocarbon, for example, diethyl ether or tetrahydrofuran at a temperature from −100° C. to a room temperature. Further, the compound (72) is synthesized by treating a THF solution of cesium fluoride or tetrabutyl ammonium fluoride to the compound (71) in N,N-dimethyl formamide. The compound (73) is synthesized by reacting the compound (72) with n-butyl lithium and then with a borate ester such as dimethyl borate. The compound (74) is synthesized by treating hydrogen peroxide to the compound (73). The compound (76) can be synthesized by treating a halide such as the compound (75) to the compound (74) under a basic condition.

Then, an example of a synthesis method for the compounds (77) to (80) in which n, p, and q each is 0, Rb is alkoxy, and W is —COO—, —CF$_2$O—, —(CH$_2$)$_2$CF$_2$O—, or —(CH$_2$)$_3$O— in Formula (2) is shown. The compounds (77) to the compound (80) correspond to those of Formula (2-1), Formula (2-3), and Formula (2-6).

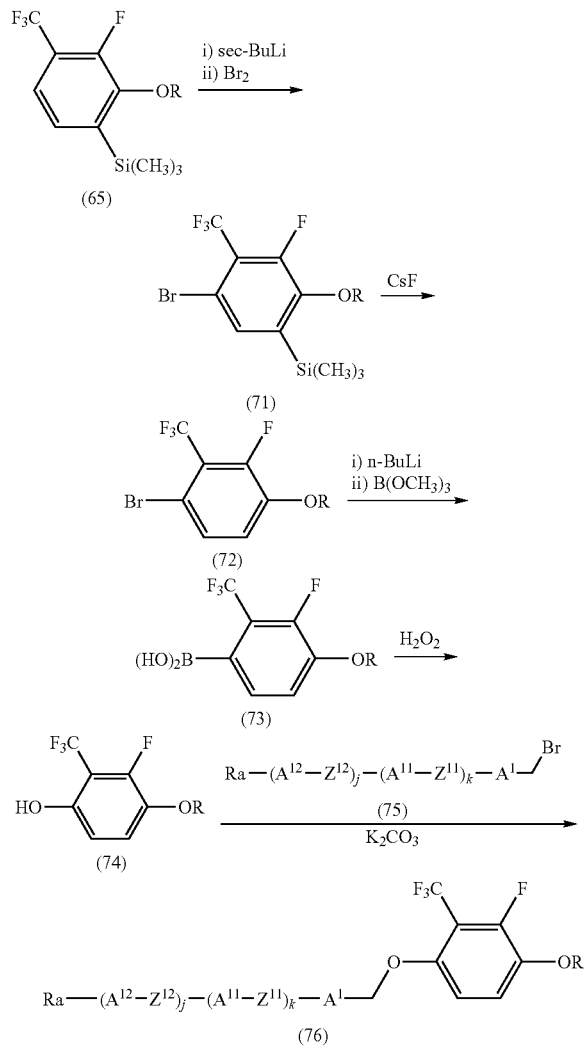

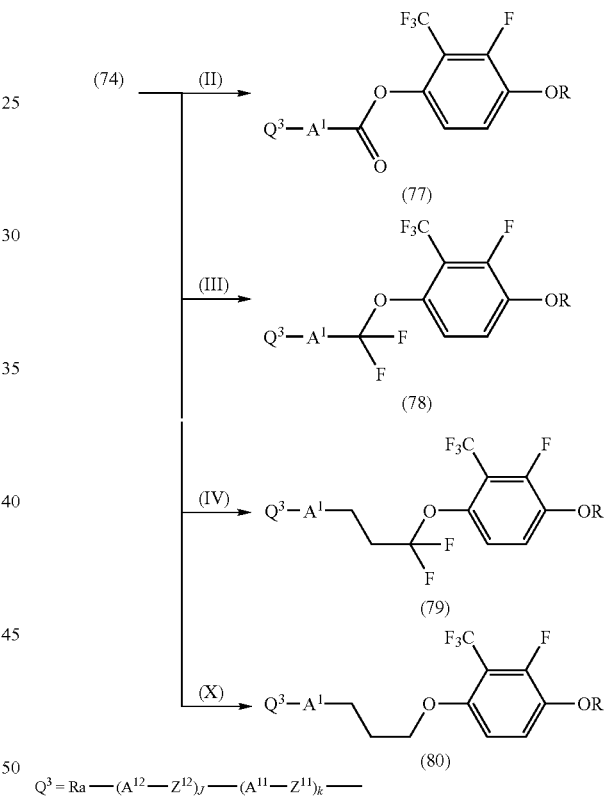

R in the formulae is alkyl of 1 to 19 carbon atoms.

The compounds (77) to (80) are synthesized respectively by using the compound (74) instead of the alcohol (phenol) intermediate product in the method of forming the bonding group described above.

Then, the composition of the invention is to be described more specifically. The ingredients of the composition may consist only of Compound (1) and Compound (2) and, preferably, a plurality of compounds selected from Compound (1-1) to Compound (1-9) and Compound (2-1) to Compound (2-9). A preferred composition contains at least one compound selected from Compound (1-1) to Compound (1-9) and Compound (2-1) to Compound (2-9) at a ratio of from 1 to 99%. The compound also includes an ingredient selected R in the formulae is alkyl of 1 to 19 carbon atoms.

For example, the compound (71) is synthesized by reacting the compound (65) described in Synlett 1999, No. 4, 389-396 from the group consisting of Compound (3) to Compound (15). When the composition is prepared, the ingredients are selected while considering the level of the dielectric anisotropy of Compound (1) and Compound (2).

A preferred composition containing compounds selected from Compound (1) and Compound (2) showing the dielectric anisotropy of a value which is negative and at about a medium level is as follows. The preferred composition contains at least one compound selected from the group consisting of Compound (3), Compound (4), and Compound (5). Another preferred composition contains at least one compound selected from the group consisting of Compound (6-1), Compound (6-2), and Compound (7). A further preferred composition contains at least two compounds selected from the two groups respectively. The compositions may further contain at least one compound selected from the group consisting of Compound (13), Compound (14), and Compound (15), with an aim of controlling the temperature range of the liquid crystal phase, viscosity, optical anisotropy, dielectric anisotropy, threshold voltage, etc. The compositions may further contain at least one compound selected from the group consisting of Compound (8) to Compound (12) with an aim of further controlling the physical property. The compositions may further contain other liquid crystalline compounds, compounds such as additives with an aim of conforming to AM-TN devices, STN devices, etc.

A further preferred composition contains at least one compound selected from the group consisting of Compound (13), Compound (14), and Compound (15). The composition may further contain at least one compound selected from the group consisting of Compound (8) to Compound (12) with an aim of further controlling the physical property. The composition may further contain compounds such as other liquid crystalline compounds, and additives with an aim of conforming to AM-TN devices, STN devices, etc.

A preferred composition containing compounds selected from Compound (1) and Compound (2) showing the dielectric anisotropy of negative and large value is as follows. The preferred composition contains at least one compound selected from the group consisting of Compound (8) to Compound (13). The compound may further contain at least one compound selected from the group consisting of Compound (13), Compound (14), and Compound (15). The composition may further contain at least one compound selected from the group consisting of Compound (3) to Compound (7) with an aim of further controlling the physical property. The compositions may further contain compounds such as other liquid crystalline compounds, additives with an aim of conforming to VA devices, etc.

A further preferred composition contains at least one compound selected from the group consisting of Compound (13), Compound (14), and Compound (15). The composition may further contain at least one compound selected from the group consisting of Compound (8) to Compound (12). The composition may further contain at least one compound selected from the group consisting of Compound (3) to Compound (7). The composition may further contain compounds such as other liquid crystalline compounds and additives.

A preferred composition containing the compounds selected from Compound (1) and Compound (2) with a negative and small dielectric anisotropy value is as follows. A preferred composition contains at least one compound selected from the group consisting of Compound (3), Compound (4), and Compound (5). Another preferred composition contains at least one compound selected from the group consisting of Compound (6-1), Compound (6-2), and Compound (7). A further preferred composition contains at least two compounds selected from the two groups respectively. The compounds may further contain at least one compound selected from the group consisting of Compound (13), Compound (14), and Compound (15) with an aim of controlling the temperature range of the liquid crystal phase, viscosity, optical anisotropy, dielectric anisotropy, the threshold voltage, etc. The composition may further contain at least one compound selected from the group consisting of Compound (8) to Compound (12) with an aim of further controlling the physical property. The compositions may further contain compounds such as other liquid crystalline compounds and additives with an aim of conforming to AM-TN devices, STN devices, etc.

A further preferred composition contains at least one compound selected from the compound consisting of Compound (8) to Compound (12). The composition may further contain at least one compound selected from the group consisting of Compound (13), Compound (14), and Compound (15). The composition may further contain at least one compound selected from the group consisting of Compound (3) to Compound (7) with an aim of further controlling the physical property. The compositions may further contain compounds such as other liquid crystalline compound, and additives with an aim of conforming to VA devices, etc.

Since Compound (3), Compound (4), and Compound (5) have positive and large dielectric anisotropy, they are mainly used as the composition for use in AM-TN device. In the composition, the amount of the compounds is from 1 to 99%. A preferred amount is from 10 to 97%. A further preferred amount is from 40 to 95%. In a case of further adding Compound (13), Compound (14), or Compound (15) to the composition, a preferred amount of the compound is 60% or less. A more preferred amount is 40% or less.

Since Compound (6-1), Compound (6-2), and Compound (7) have positive and extremely large dielectric anisotropy, they are mainly used as the composition for use in STN devices. In the composition, the amount of the compound is from 1 to 99%. A preferred amount is from 10 to 97%. A more preferred amount is from 40 to 95%. In a case of further adding Compound (13), Compound (14), or Compound (15) to the composition, a preferred amount of the compound is 60% or less. A more preferred amount is 40% or less.

Since Compound (8) to Compound (12) have negative dielectric anisotropy, it is mainly used as the composition for use in VA devices. A preferred amount of the compounds is 80% or less. A more preferred amount is from 40 to 80%. In a case of further adding Compound (13), Compound (14), or Compound (15) to the composition, a preferred amount of the compound is 60% or less. A more preferred amount is 40% or less.

The dielectric anisotropy of Compound (13), Compound (14), and Compound (15) is small. Compound (13) is mainly used with an aim of controlling the viscosity or the optical anisotropy. Compound (14) and Compound (15) increase the upper limit temperature to extend the temperature range of the liquid crystal phase. Alternatively, they are used with an aim of controlling the optical anisotropy. In a case of increasing the amount of Compound (13), Compound (14), and Compound (15), the threshold voltage of the composition increases and the viscosity is lowered. Accordingly, it may be used in a great amount so long as the required value for the threshold voltage of the composition can be satisfied.

Preferred examples of Compound (3) to Compound (15) are Compound (3-1) to Compound (3-9), Compound (4-1) to Compound (4-97), Compound (5-1) to Compound (5-33), Compound (6-1) to Compound (6-56), Compound (7-1) to Compound (7-3), Compound (8-1) to Compound (8-4), Compound (9-1) to Compound (9-6), Compound (10-1) to Compound (10-4), Compound (11-1), Compound (12-1), Compound (13-1) to Compound (13-14), Compound (14-1) to Compound (14-31), and Compound (15-1) to Compound (15-6). Symbols in the compound have the same meanings as the respective symbols in Compound (3) to Compound (15).
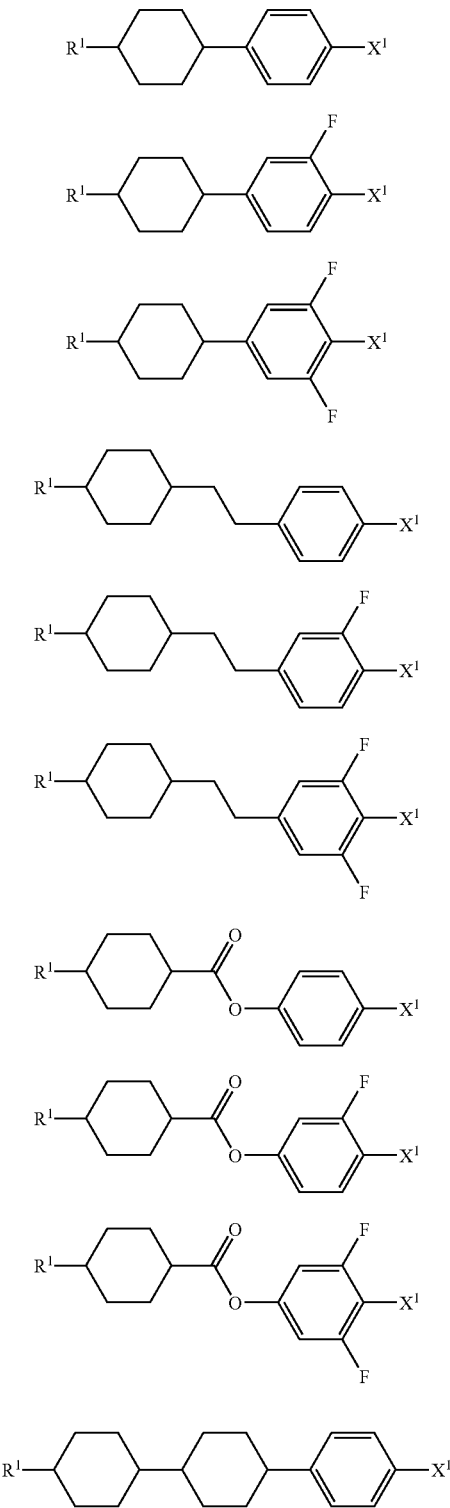
-continued
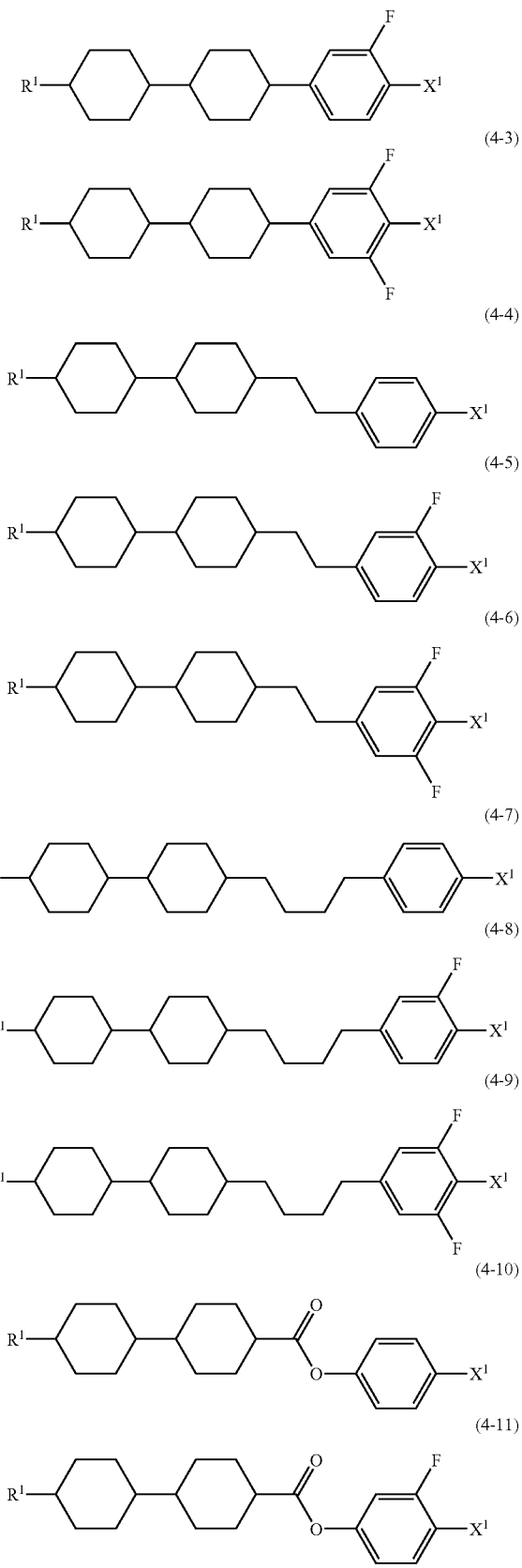

-continued (4-12)
(4-13)
(4-14)
(4-15)
(4-16)
(4-17)
(4-18)
(4-19)
(4-20)

-continued (4-21)
(4-22)
(4-23)
(4-24)
(4-25)
(4-26)
(4-27)
(4-28)
(4-29)
(4-30)

-continued

-continued
(4-49)
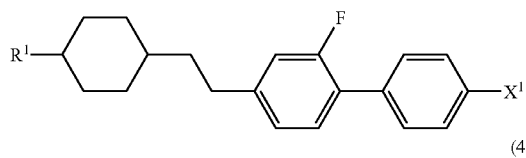
(4-50)
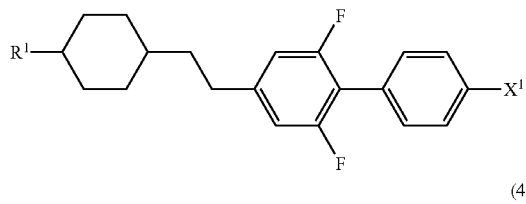
(4-51)
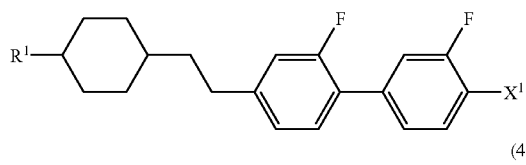
(4-52)
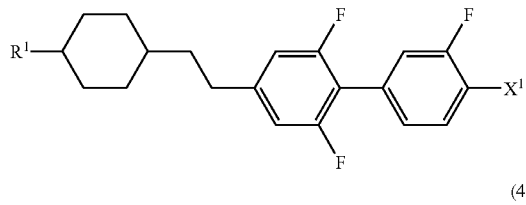
(4-53)
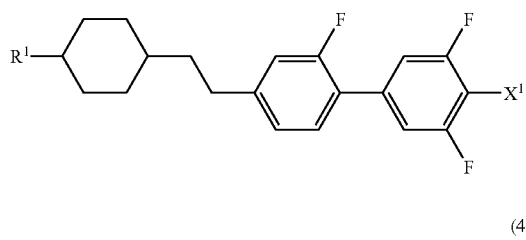
(4-54)
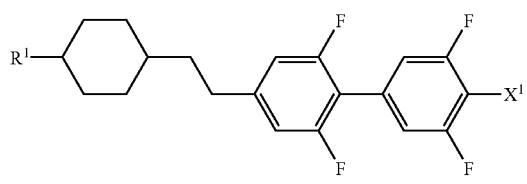
(4-55)
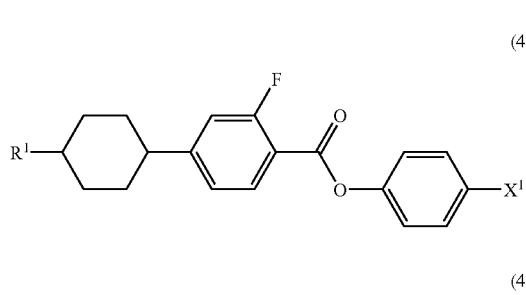
(4-56)
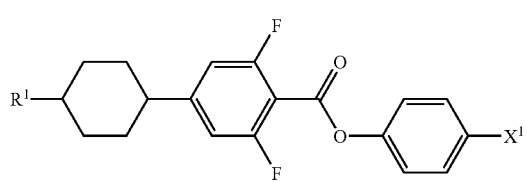
-continued
(4-57)
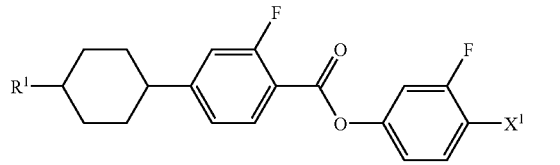
(4-57)
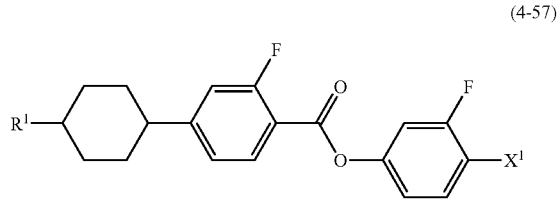
(4-58)
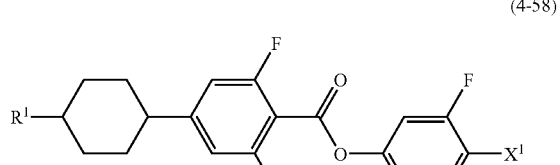
(4-59)
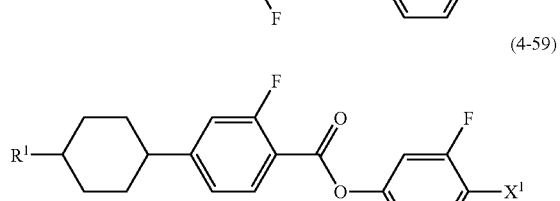
(4-60)
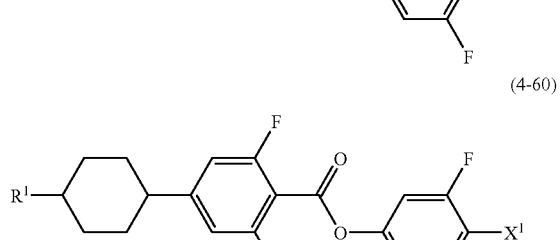
(4-61)
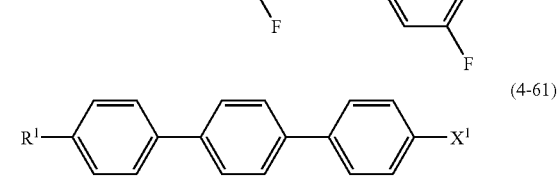
(4-62)
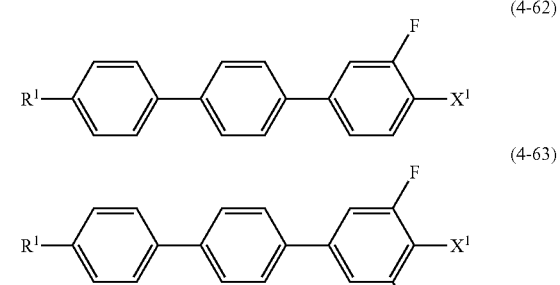
(4-63)
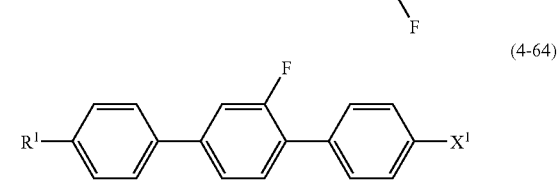
(4-64)

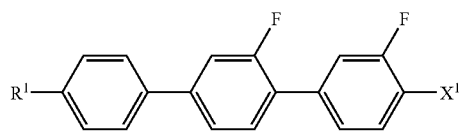 (4-65)
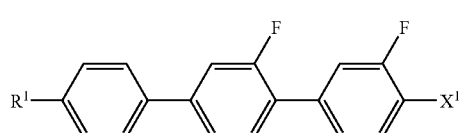 (4-66)
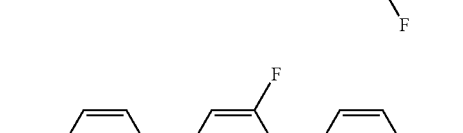 (4-67)
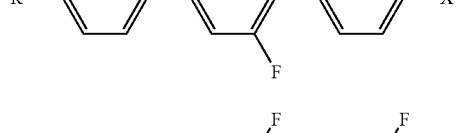 (4-68)
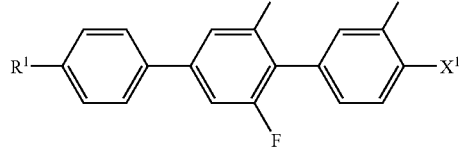 (4-69)
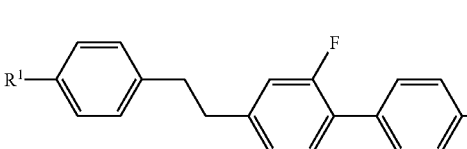 (4-70)
 (4-71)
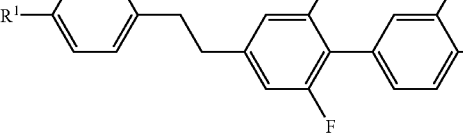 (4-72)
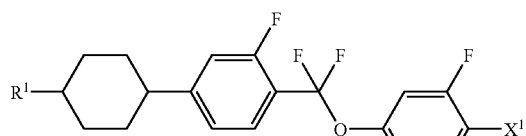 (4-73)
 (4-74)
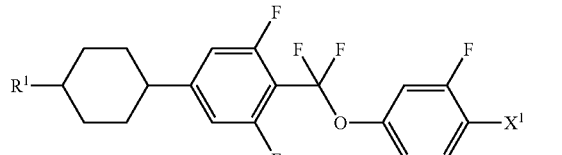 (4-75)
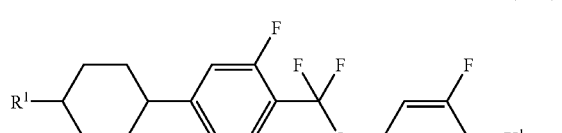 (4-76)
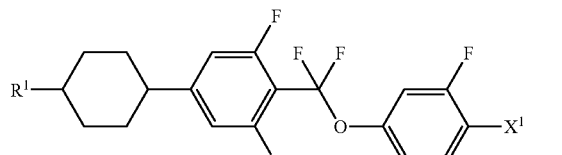 (4-77)
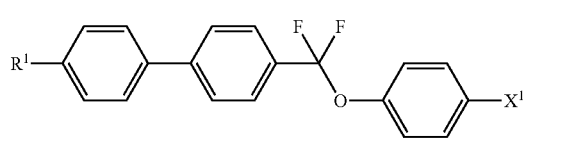 (4-78)
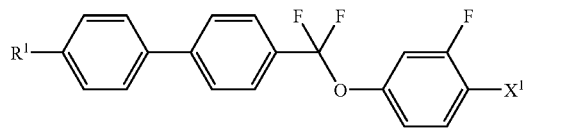 (4-79)
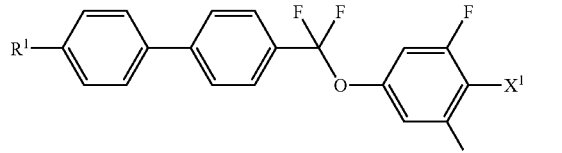 (4-80)

-continued
(4-81) 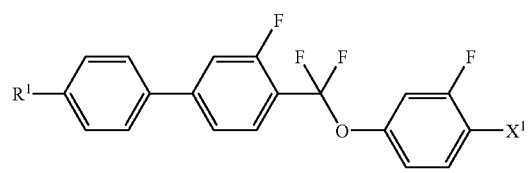
(4-82) 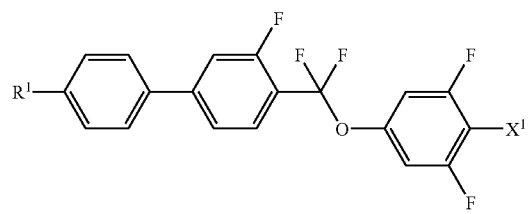
(4-83) 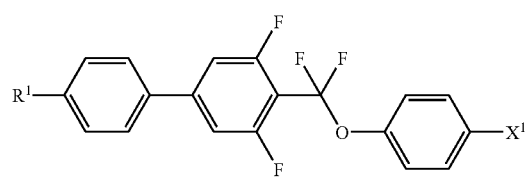
(4-84) 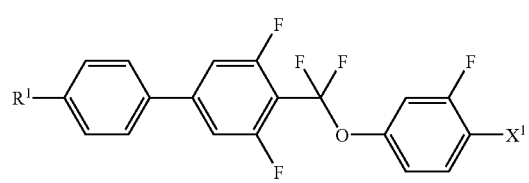
(4-85) 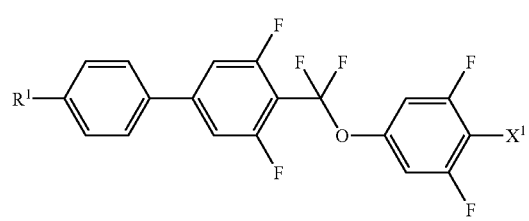
(4-86) 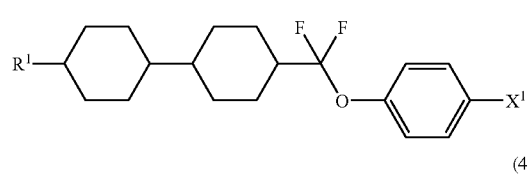
(4-87) 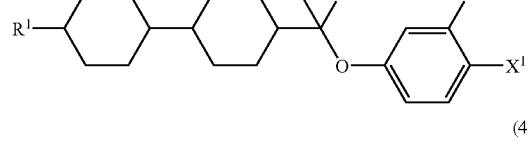
(4-88) 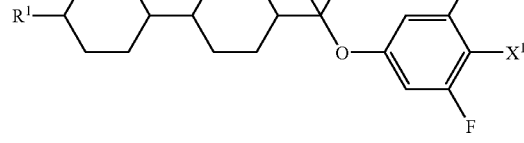
-continued
(4-89) 
(4-90) 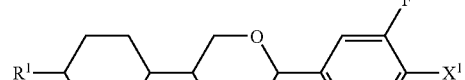
(4-91) 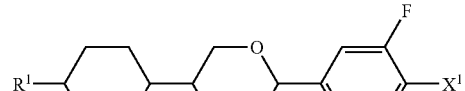
(4-92) 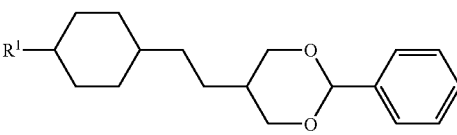
(4-93) 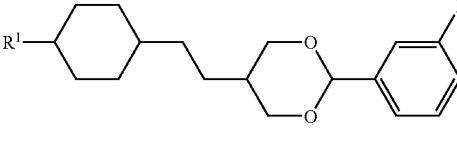
(4-94) 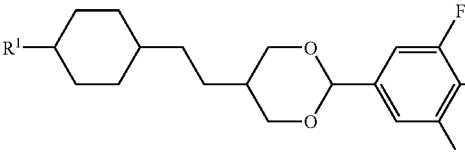
(4-95) 
(4-96) 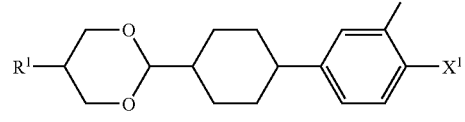
(4-97) 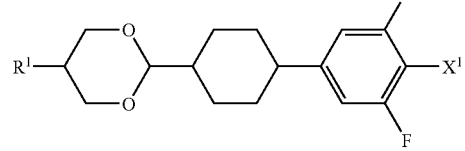
(5-1) 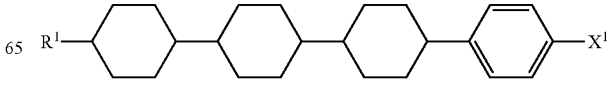

-continued
(5-2)
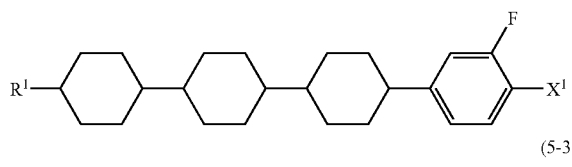
(5-3)
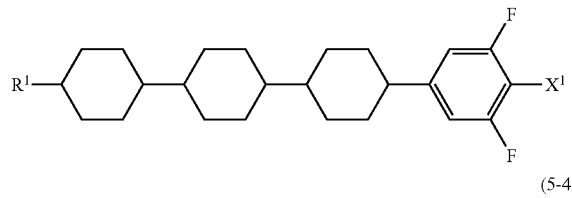
(5-4)
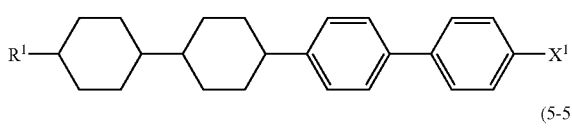
(5-5)
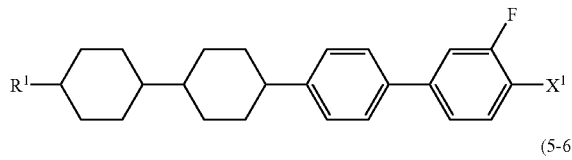
(5-6)
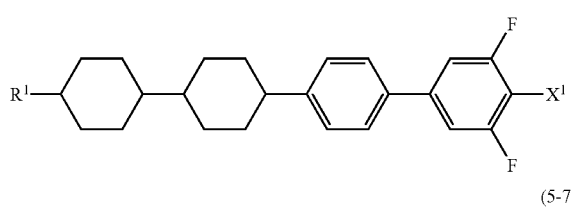
(5-7)
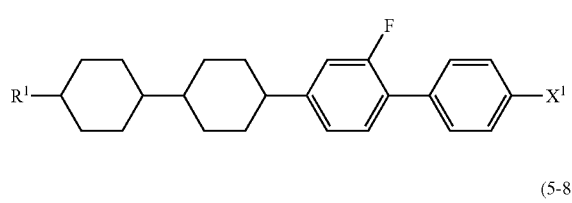
(5-8)
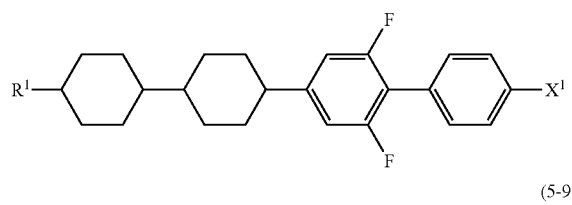
(5-9)
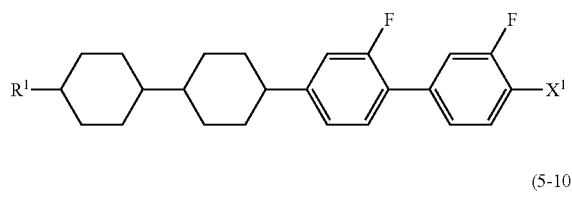
(5-10)
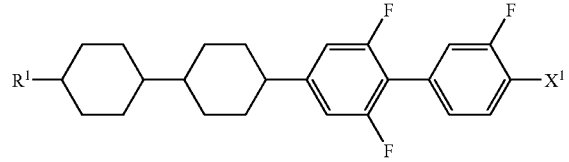
-continued
(5-11)
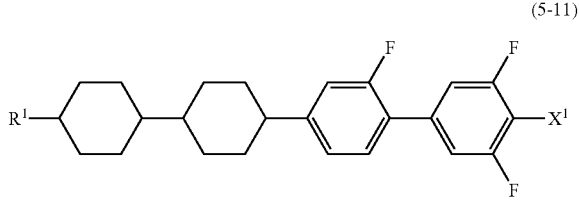
(5-12)
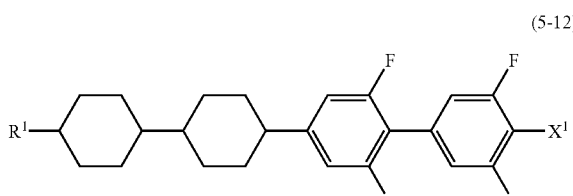
(5-13)
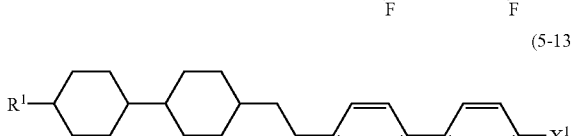
(5-14)
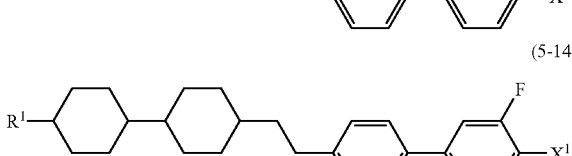
(5-15)
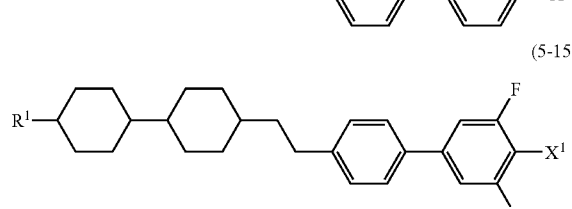
(5-16)
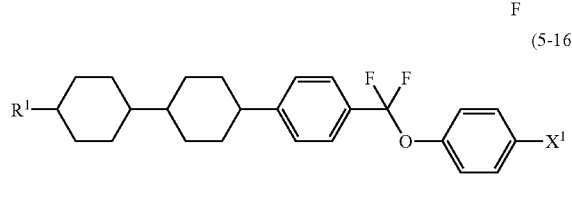
(5-17)
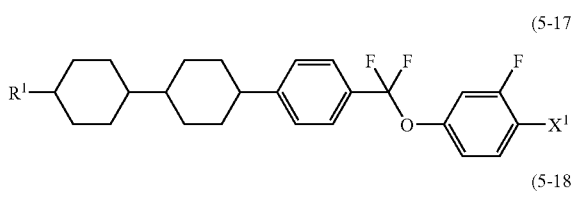
(5-18)
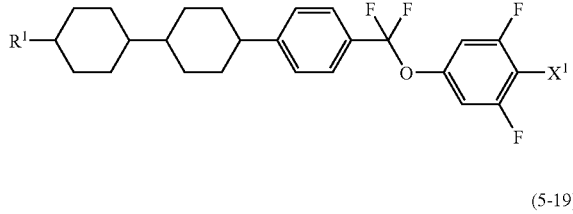
(5-19)
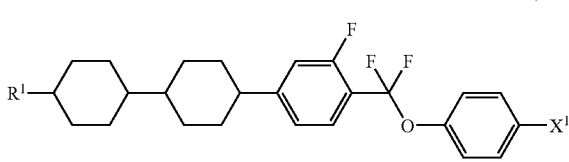

-continued
(5-20)
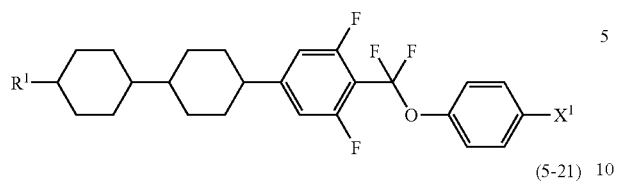
(5-21)
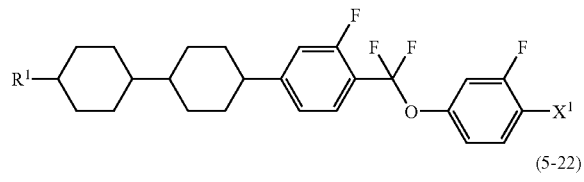
(5-22)
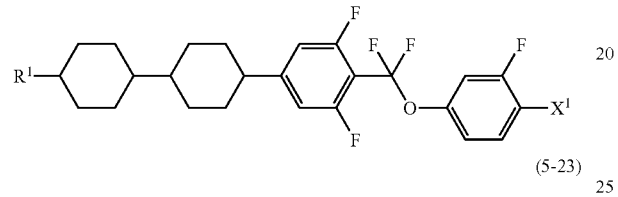
(5-23)
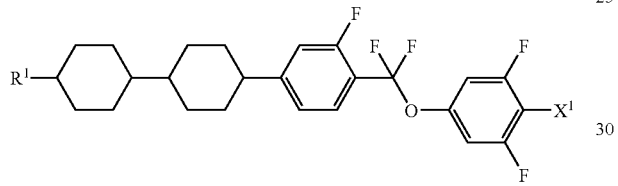
(5-24)
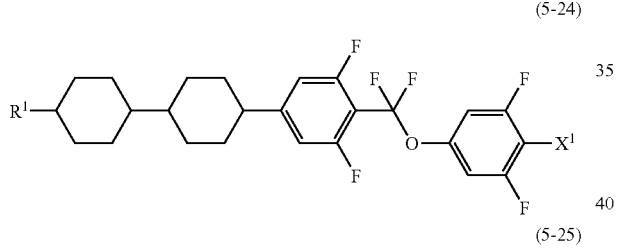
(5-25)
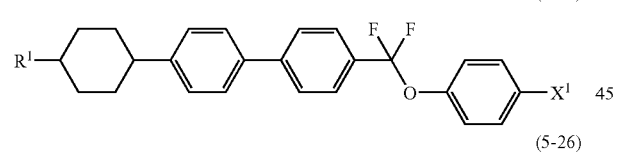
(5-26)
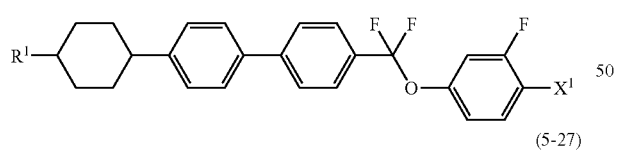
(5-27)
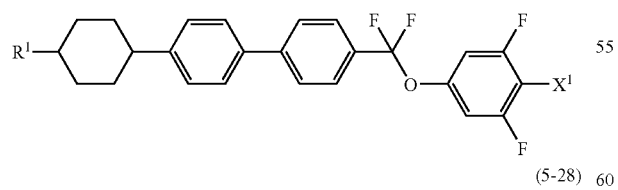
(5-28)
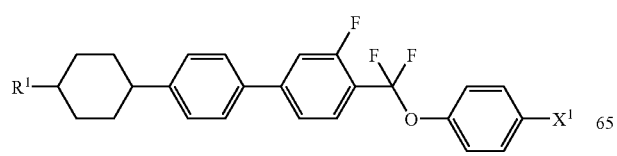
-continued
(5-29)
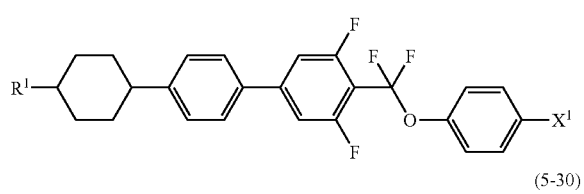
(5-30)
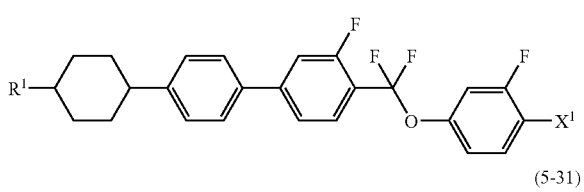
(5-31)
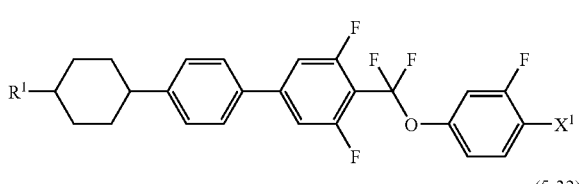
(5-32)
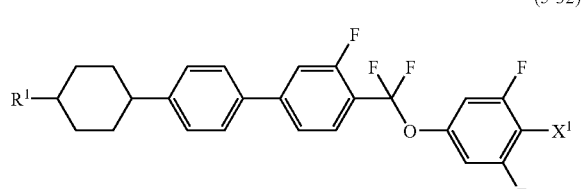
(5-33)
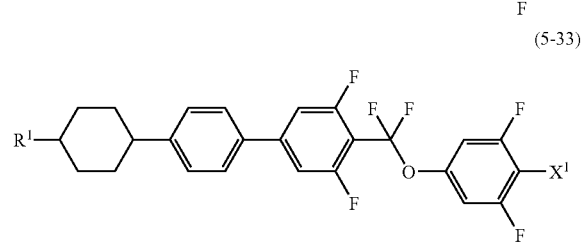
(6-1)
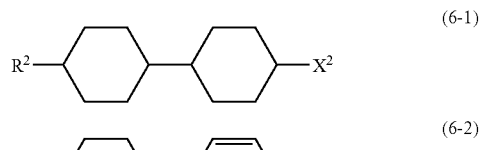
(6-2)
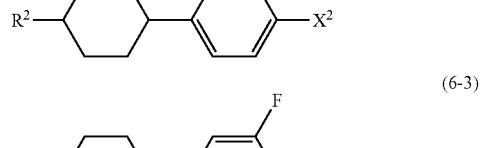
(6-3)
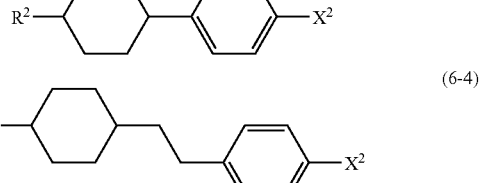
(6-4)
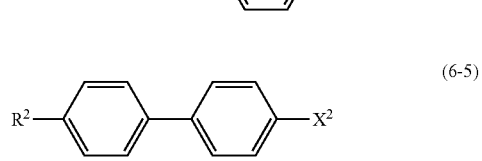
(6-5)

-continued
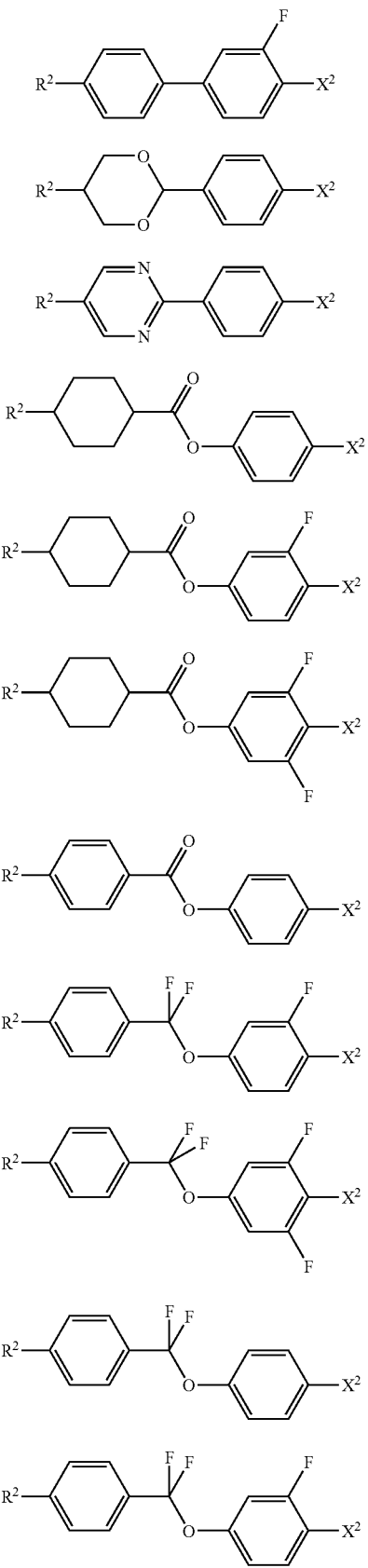
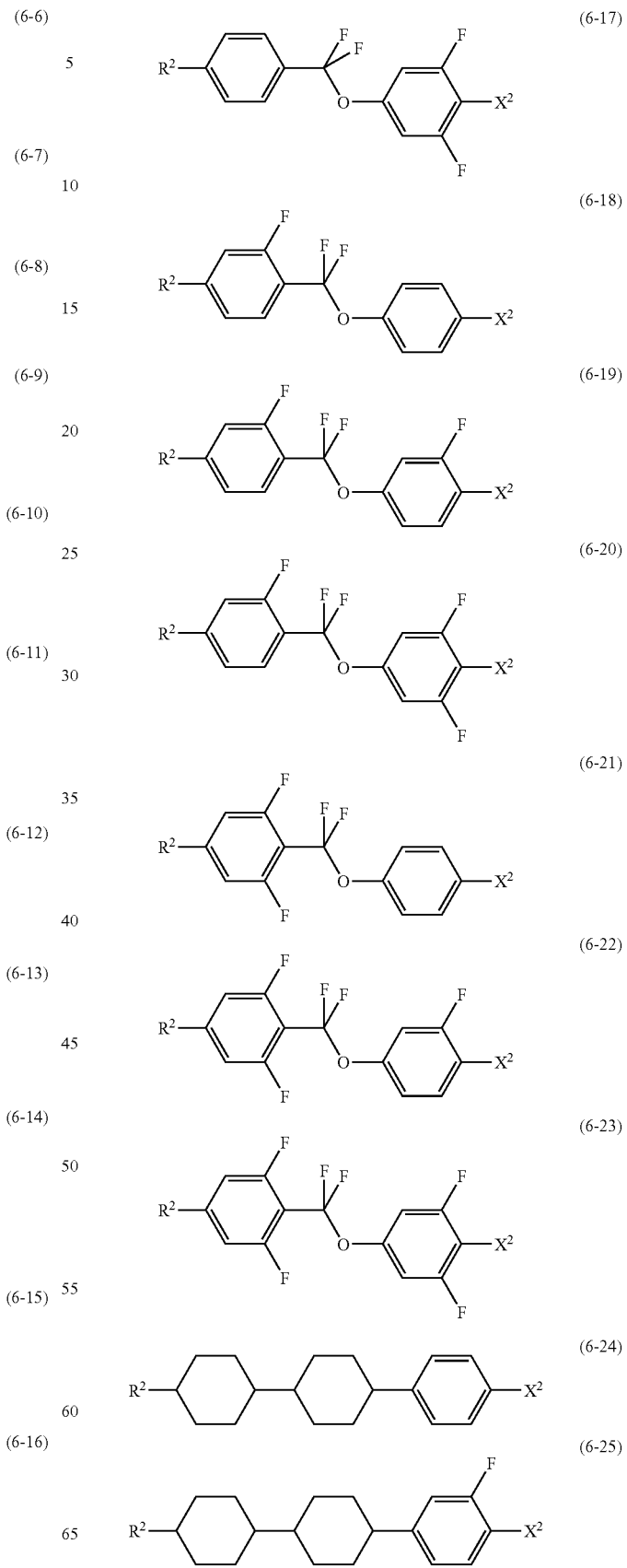

(6-26) 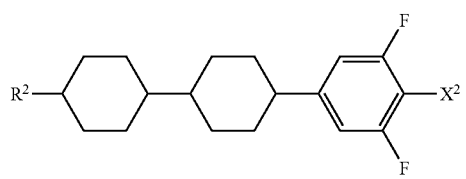
(6-27) 
(6-28) 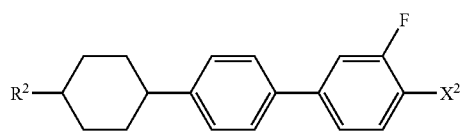
(6-29) 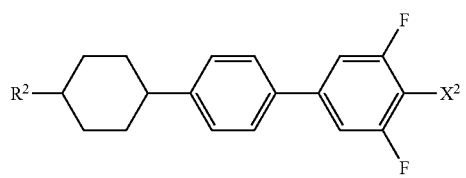
(6-30) 
(6-31) 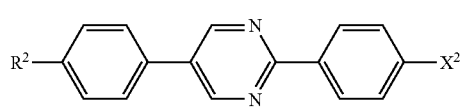
(6-32) 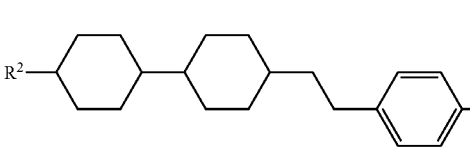
(6-33) 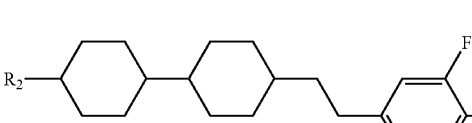
(6-34) 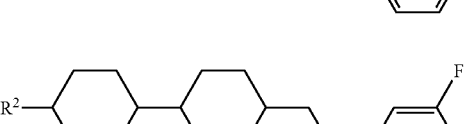
(6-35) 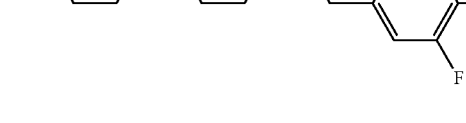
(6-36) 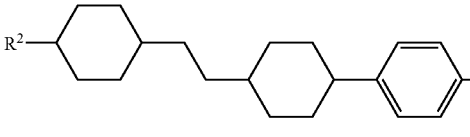
(6-37) 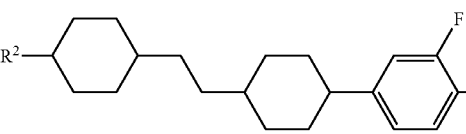
(6-37) 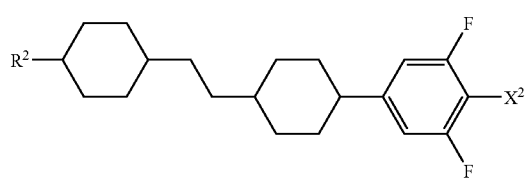
(6-38) 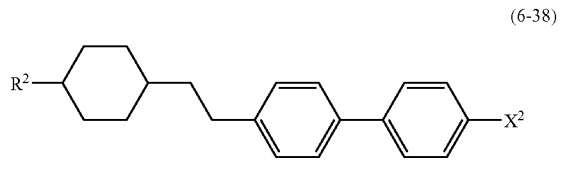
(6-39) 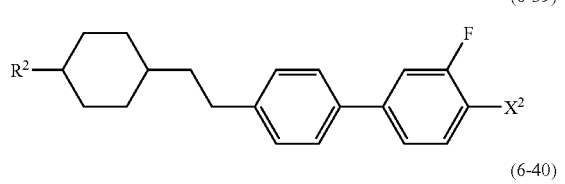
(6-40) 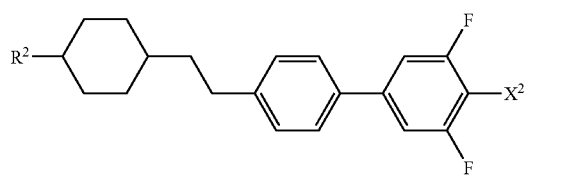
(6-41) 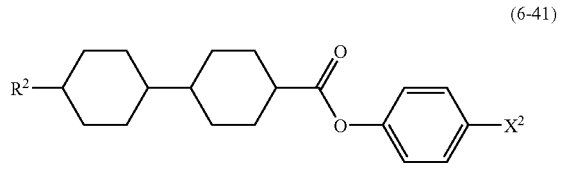
(6-42) 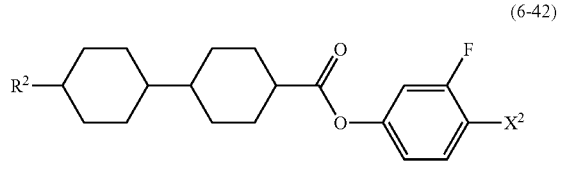
(6-43) 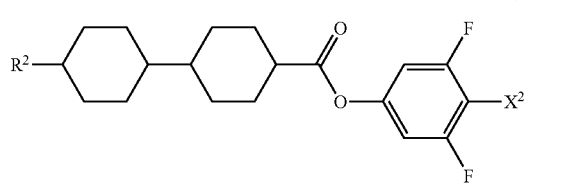
(6-44) 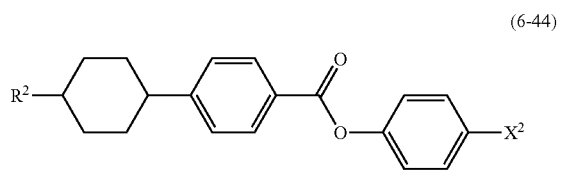
(6-45) 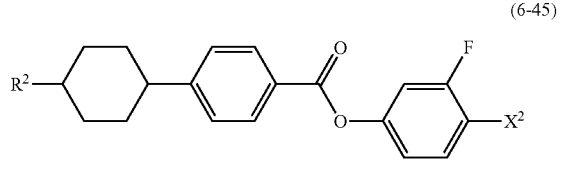

-continued
(6-46) 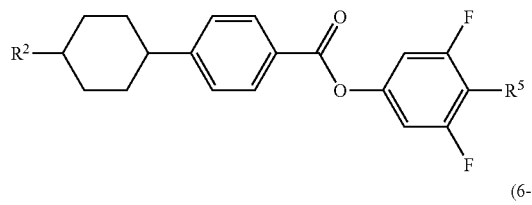
(6-47) 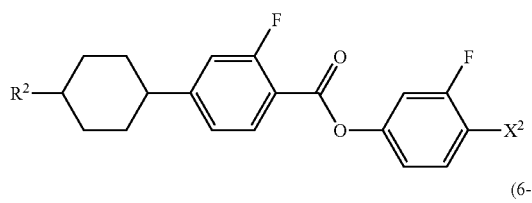
(6-48) 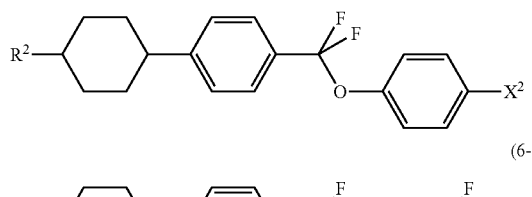
(6-49) 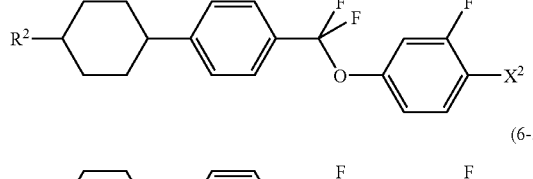
(6-50) 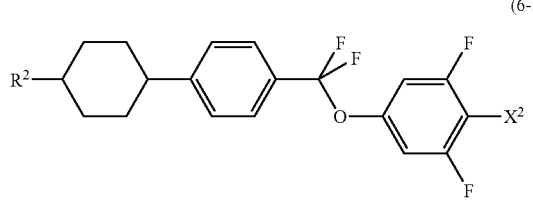
(6-51) 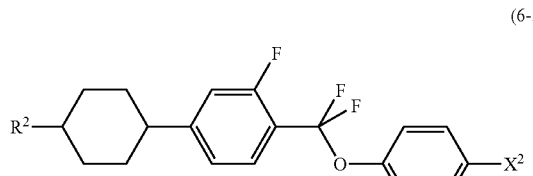
(6-52) 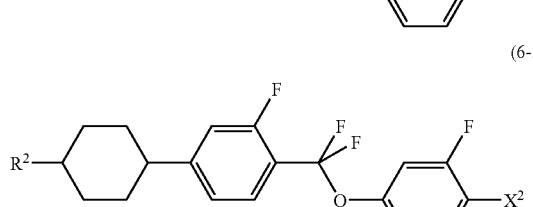
(6-53) 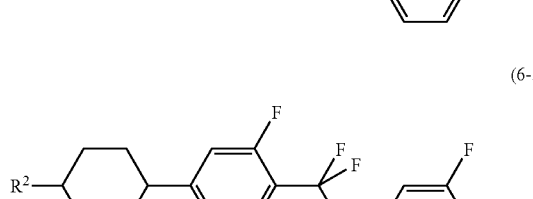
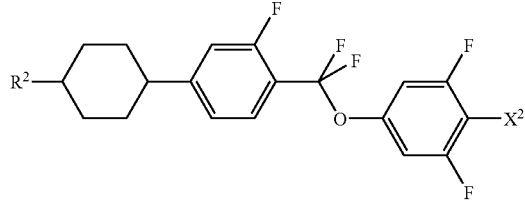
-continued
(6-54) 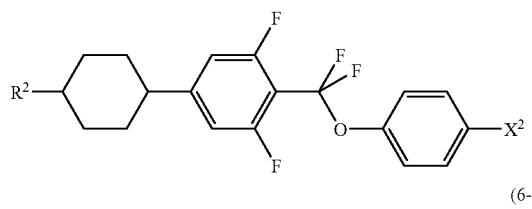
(6-55) 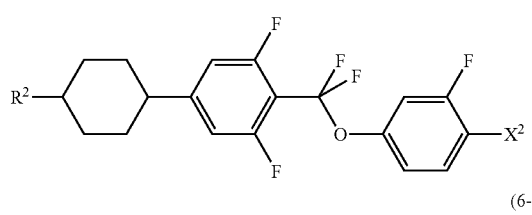
(6-56) 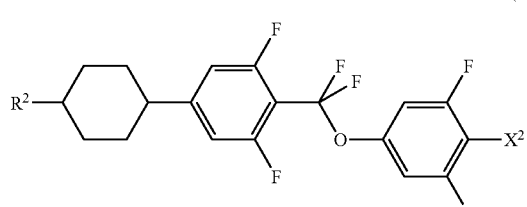
(7-1) 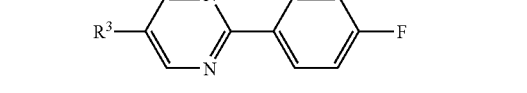
(7-2) 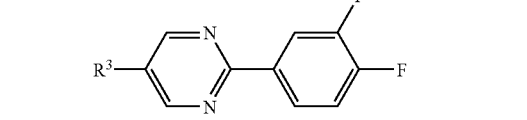
(7-3) 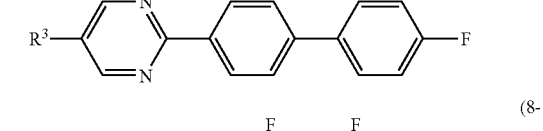
(8-1) 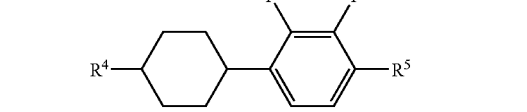
(8-2) 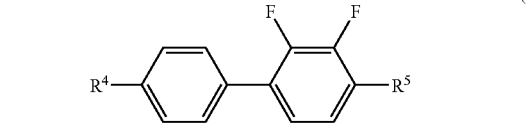
(8-3) 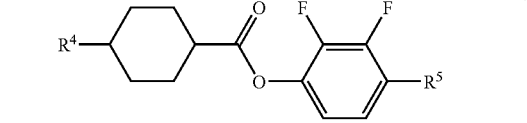
(8-4) 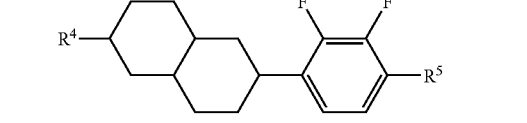

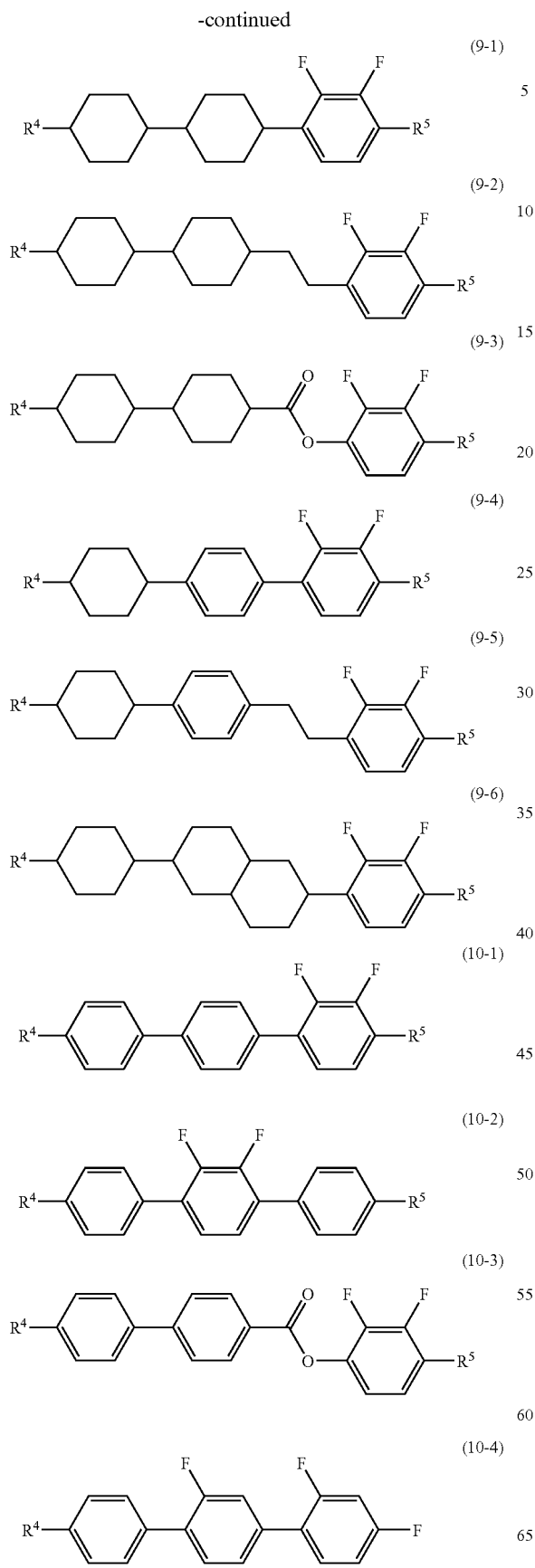
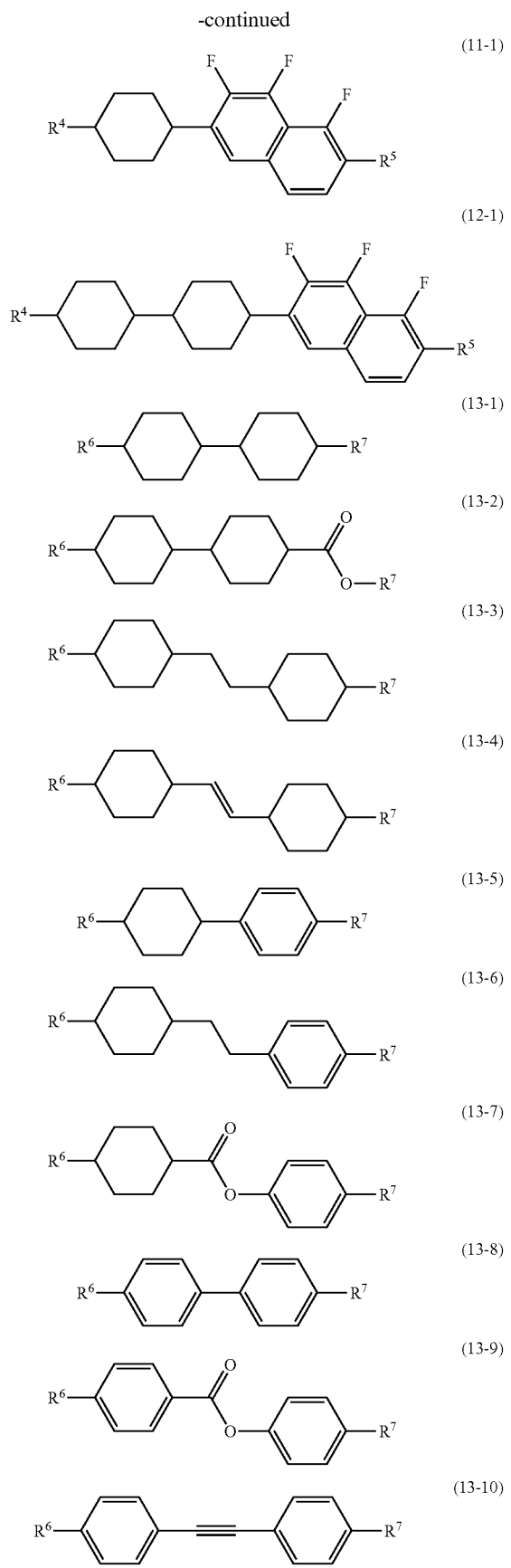

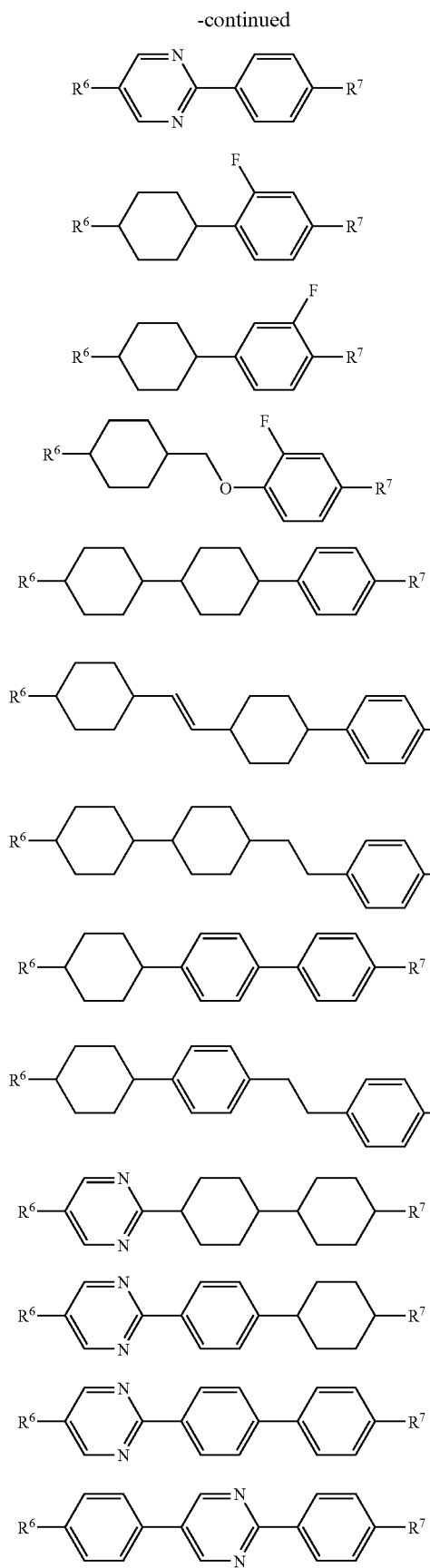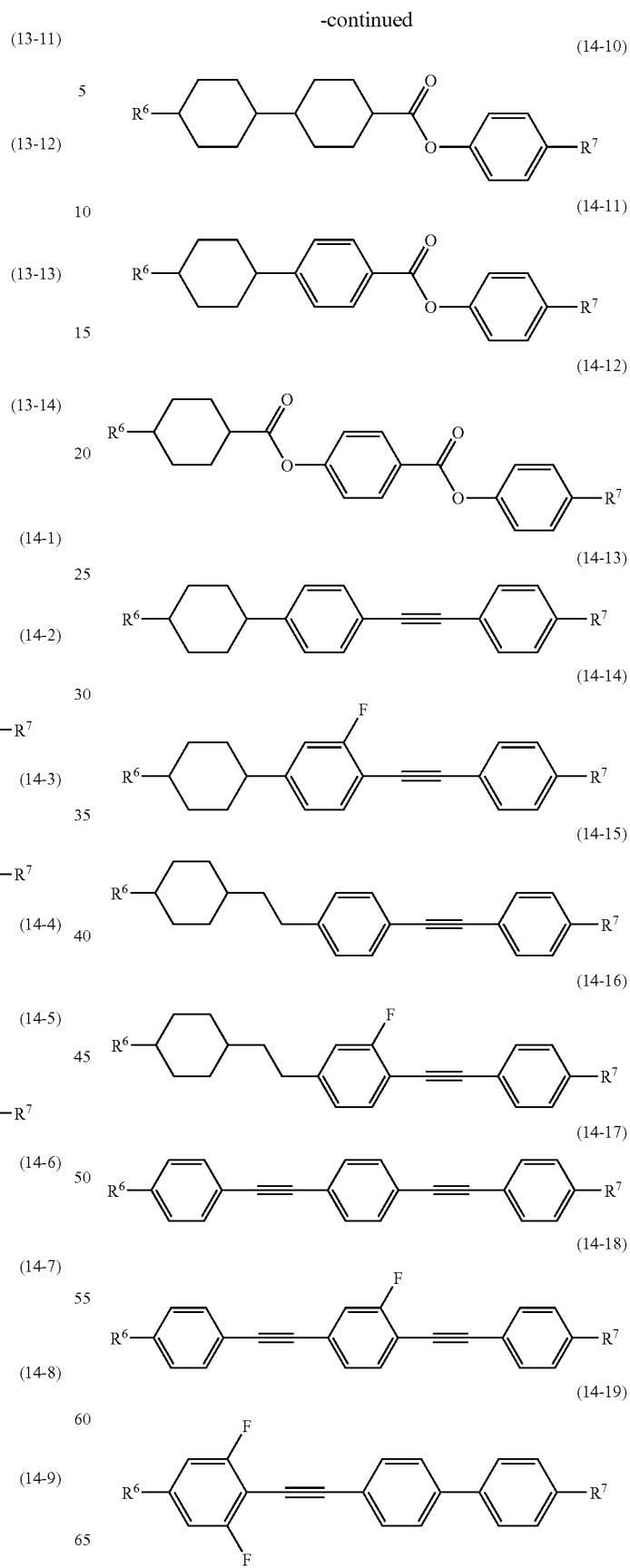

-continued (14-20) 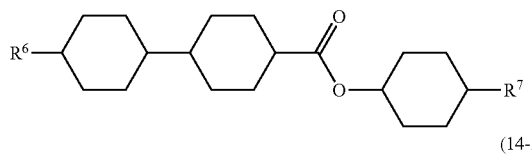

(14-21) 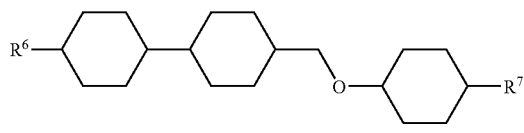

(14-22) 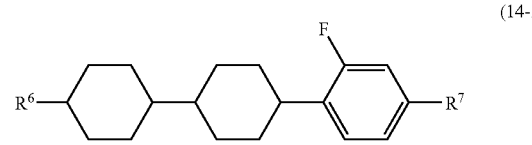

(14-23) 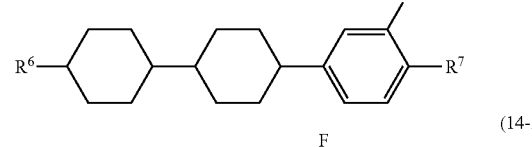

(14-24) 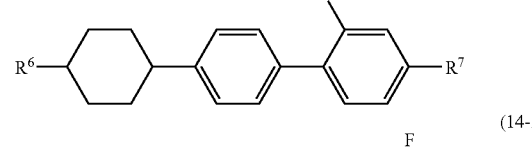

(14-25) 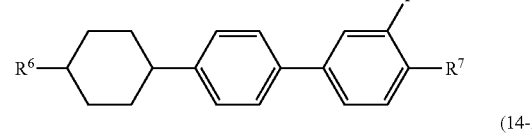

(14-26) 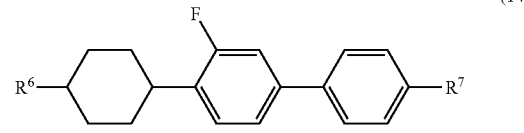

(14-27) 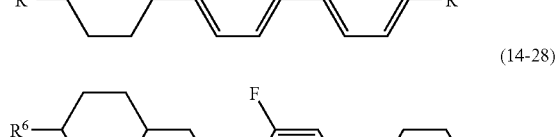

(14-28) 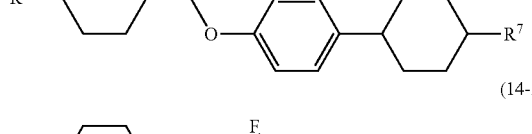

(14-29) 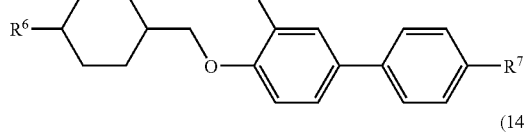

(14-30) 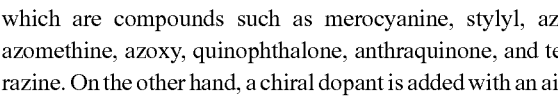

-continued (14-31) 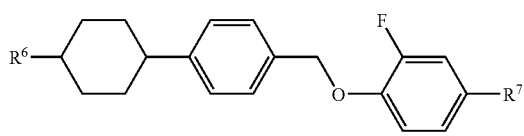

(15-1) 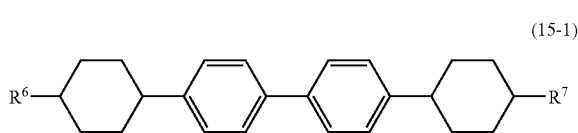

(15-2) 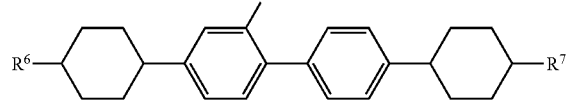

(15-3) 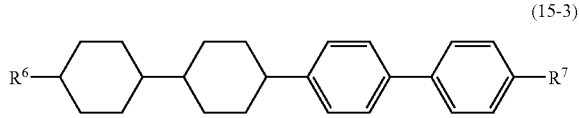

(15-4) 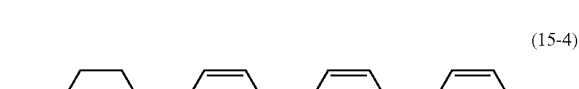

(15-5) 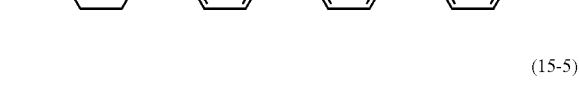

(15-6) 

The composition of the invention can be prepared by known methods. For example, compounds as ingredients are mixed and dissolved to each other by heating. An appropriate additive may be added to the composition to control the physical property of the composition. Such additives are well-known to those skilled in the art. A composition for use in GH devices may be prepared by adding dichroic dyes which are compounds such as merocyanine, styryl, azo, azomethine, azoxy, quinophthalone, anthraquinone, and tetrazine. On the other hand, a chiral dopant is added with an aim of inducing the helical structure of the liquid crystal to provide a necessary twisting angle. Examples of the chiral dopant are the following optically active compounds (Op-1) to (Op-13).

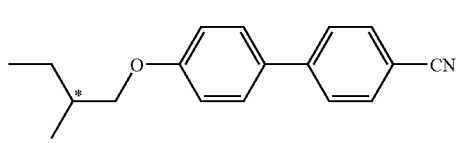 (Op-1)
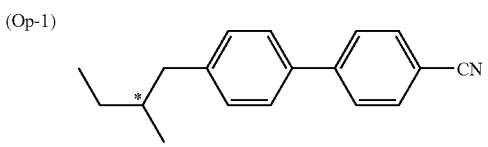 (Op-2)
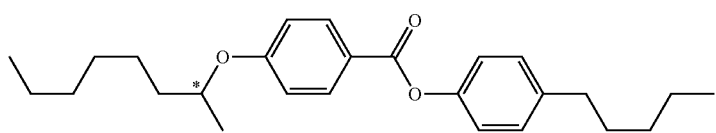 (Op-3)
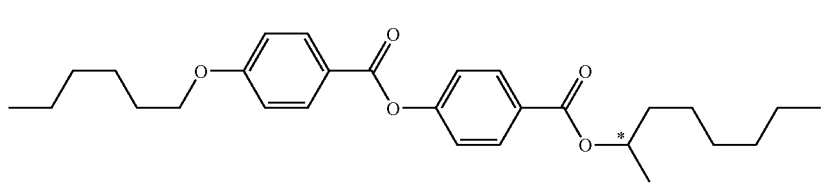 (Op-4)
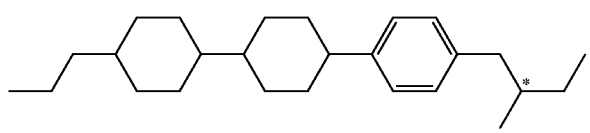 (Op-5)
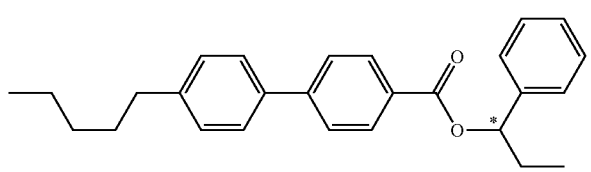 (Op-6)
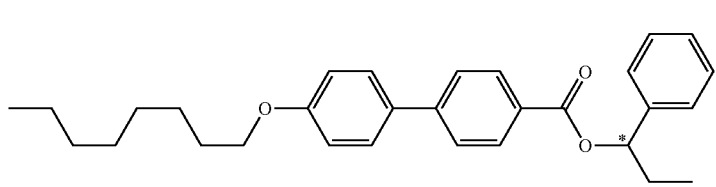 (Op-7)
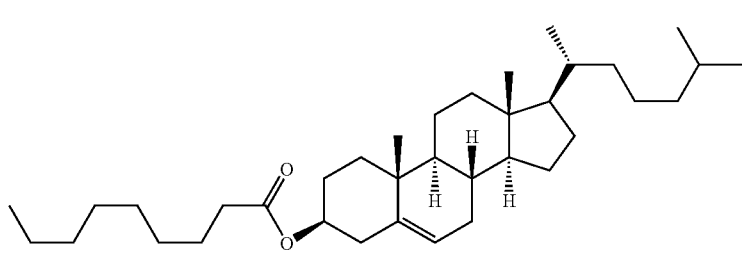 (Op-8)
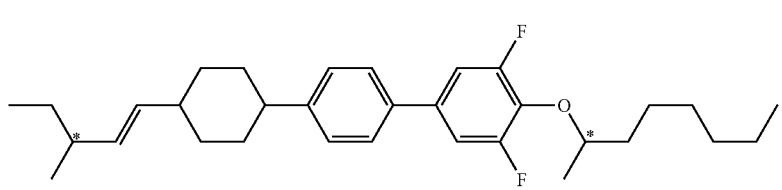 (Op-9)
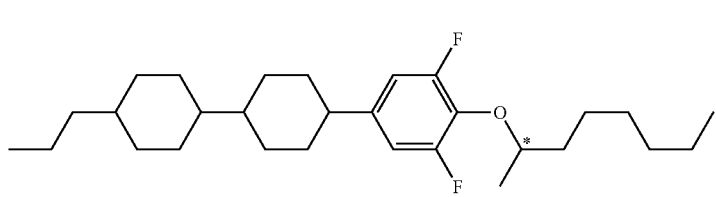 (Op-10)

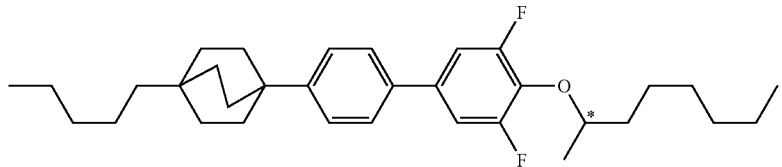 (Op-11)

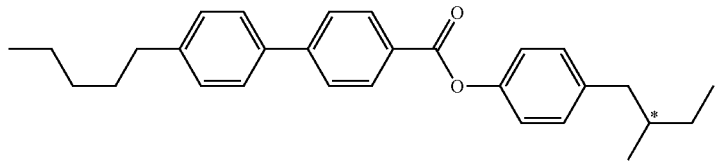 (Op-12)

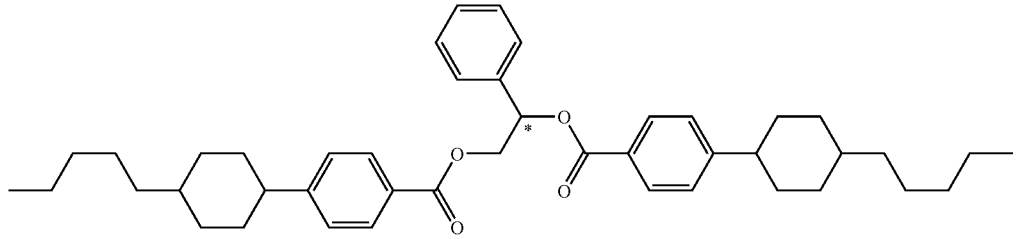 (Op-13)

When a chiral dopant is added to a composition to control the pitch of twist, a preferred pitch for use in TN devices and TN-TFT devices is within a range from 40 to 200 μm; a preferred pitch for use in STN devices is within a range from 6 to 20 μm; a preferred pitch for use in BTN devices is within a range from 1.5 to 4 μm. The chiral dopant is added in a relatively great amount to the composition for use in PC devices. At least two chiral dopants may be added with an aim of controlling the temperature dependence of the pitch.

The composition of the invention can be used for devices such as PC, TN, STN, BTN, ECB, OCB, IPS, and VA. The driving system for the devices may be PM or AM. It can be used also for NCAP (nematic curvilinear aligned phase) devices prepared by microcapsulating the composition, or PD (polymer dispersed) devices in which a three-dimensional network polymer is formed in the composition, for example, PN (polymer network) devices.

The, the invention is to be described more specifically. The invention is not restricted to the examples. The compound No. such as No. 1 corresponds to that of the compound indicated in the table in Example 10. The obtained compounds are identified by nuclear magnetic resonance spectroscopy, mass spectroscopy or the like. In the nuclear magnetic resonance spectroscopy, s is singlet, d is doublet, t is triplet, q is quartet, and m is multiplet. The amount of the compound (percentage) is weight percent on the basis of the entire weight of the composition. Measurement for physical values are in accordance with Standard of Electronic Industries Association of Japan, a method described in EIAJ•ED-2521A, or a modified method thereof.

The ratio (percentage) of the ingredient or the liquid crystalline compound is a weight percent (wt %) based on the entire weight of the liquid crystalline compound. The composition is prepared by mixing after measuring weight of the ingredient such as the liquid crystalline compound. Accordingly, it is easy to calculate the weight % for the ingredients. However, it is not easy to accurately calculate the ratio of the ingredients by gas chromatographic analysis of the composition. This is because the correction coefficient depends on the kind of the liquid crystalline compounds. Fortunately, the correction coefficient is approximately 1. Further, difference of 1 wt % in the ingredient compound gives less effect on the characteristic of the composition. Accordingly, in the invention, the area ratio of ingredient peak in the gas chromatograph can be regarded as weight % of the ingredient compound. That is, the result of the gas chromatographic analysis (peak area ratio) can be considered to be equivalent with the weight % of the liquid crystalline compound without correction.

Measurement of the characteristic values include three methods, that is, a case of using a compound alone as it is for the specimen, a case of mixing the compound with a mother liquid crystal and using them for the specimen, and a case of using a composition alone as it is for the specimen. In the case of mixing the compound with the mother liquid crystal, the following method is adopted. A specimen was prepared by mixing 15% by weight of a compound and 85% by weight of a mother liquid crystal. A characteristic value of the compound was calculated based a value obtained by measurement by an extrapolation method. Extrapolation value=(measured value for specimen−0.85×measured value for mother liquid crystal)/0.15. In a case where the smectic phase (or crystal) was precipitated by the ratio at 25° C., the ratio between the compound and the mother liquid crystal was changed in the order of the 10 wt %: 90 wt %, 5 wt %: 95 wt %, and 1 wt %: 99 wt %.

Among the values obtained by the measurement, the values obtained by using the compound alone as it is for the specimen and the values obtained by using the composition alone as it is for the specimen are described as experimental data with the values as they are. For the values obtained by mixing the compound with the mother liquid crystal and using the same as the specimen, the obtained values are sometimes described as they are as the experimental data, or the values obtained by the extrapolation method are sometimes described.

In a case of mixing the compound with the mother liquid crystal and using them as the specimen, a plurality of mother liquid crystals are present. An example of the mother liquid crystal is a mother liquid crystal A. The composition of the mother liquid crystal A is as described below.

Mother liquid crystal A:

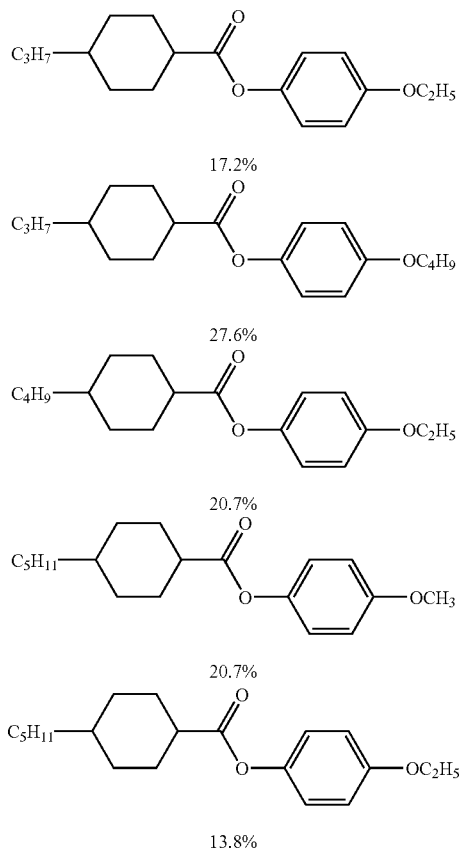

[Transition Temperature of Liquid Crystal Phase (° C.)]
It was measured by any one of the following methods.
1) A specimen was placed on a hot plate (FP-52 model Hot Stage manufactured by Mettler Co.) of a melting point measuring apparatus equipped with a polarization microscope and heated at a rate of 1° C./min. The temperature when the specimen showed phase change was measured.
2) It was measured by using a differential scanning calorimeter DSC-7 system manufactured by Perkin Elmer Co. at a rate of 3° C./min.

[Identification of the Liquid Crystal Phase and Indication of Phase Series]
Crystal was indicated as C. When the crystals could be distinguished, they were indicated as $C_1$ or $C_2$ respectively. The smectic phase was indicated as S. Liquid (isotropic) was indicated as Iso. The nematic phase was indicated as N. In the smectic phase, in a case where the smectic B phase, smectic C phase, or smectic A phase can be distinguished, they were indicated as $S_B$, $S_C$, or $S_A$ respectively. "C 92.9 N 196.9 Iso" as the indication of the transfer temperature shows that the transition temperature from crystal to nematic phase (CN) is 92.9° C. and the transition temperature from nematic phase to liquid (NI) is 196.9° C. Other indications are also identical.

[Upper Limit of Nematic Phase (NI; ° C.)]
A specimen was placed on a hot plate of a melting point measuring apparatus equipped with a polarization microscope and heated at a rate of 1° C./min. The temperature when a portion of the specimen changed from the nematic phase to isotropic liquid is measured. The upper limit temperature for the nematic phase is sometimes referred to simply as "upper limit temperature".

[Lower Limit of Nemactic Phase (Tc; ° C.)]
After storing a specimen having the nematic phase for 10 days in a freezer at −10° C., −20° C., −30° C., and −40° C., the liquid crystal phase is observed. For example, when the specimen was remained in the nematic phase as it was at −20° C., changed to crystals (or smectic phase) at −30° C., Tc was described as <−20° C. The lower limit temperature of the nematic phase is sometimes referred to simply as "lower limit temperature".

[Compatibility of Compound]
Several compounds having similar structures were mixed to prepare a mother liquid crystal having a nematic phase. A composition in which a compound to be measured and a mother liquid crystal were mixed was obtained. An example of the mixing ratio comprised 15% of the compound and 85% of the mother liquid crystal. The composition was stored for 30 days at a low temperature as −20° C., −30° C. It was observed whether a portion of the composition changed to crystals (or smectic phase) or not. The mixing ratio and the storing temperature were changed optionally. Based on the result of the measurement described above, the condition for depositing the crystals (or smectic phase) and condition not for depositing the crystals (or smectic phase) were determined. The conditions are parameters for the solubility.

[Viscosity (η: Measured at 20° C.: mPa·s)]
E-viscometer was used for the measurement of viscosity.

[Optical Anisotropy (Refractive Index Anisotropy: Δn: Measured at 25° C.)]
Measurement was conducted by an Abbe's refractometer in which a polarizing plate was attached to an eyepiece using a light at a wavelength of 589 nm. After rubbing the surface of a main prism in one direction, the specimen was dripped on the main prism. Refractive index n∥ was measured when the direction of polarization was in parallel with the rubbing direction. Refractive index n⊥ was measured when the polarizing direction was vertical to the rubbing direction. The value for the optical anisotropy was calculated according to the equation: Δn=n∥−n⊥.

[Dielectric anisotropy (Δ∈; measured at 25° C.)]
1) Specimen Having Positive Dielectric Anisotropy:
A specimen was placed in a TN device with a distance (cell gap) between two sheets of glass substrates of 9 µm and a twist angle of 80°. A sine wave (10 V, 1 kHz) was applied to the device, and the dielectric constant in the direction of the major axis of the liquid crystal molecule (∈∥) was measured 2 sec after. A sine wave (0.5 V, 1 KHz) was applied to the device and the dielectric constant in the direction of the minor axis of the liquid crystal molecule (∈⊥) was measured 2 sec after. The value for the dielectric anisotropy was calculated according to Formula: Δ∈=∈∥−∈⊥.
2) Specimen Having Negative Dielectric Anisotropy:
A specimen was placed in a VA device with a distance (cell gap) between two sheets of glass substrates of 20 µm. A sine wave (0.5 V, 1 kHz) was applied to the device, and the dielectric constant in the direction of the major axis of the liquid crystal molecule (∈∥) was measured 2 sec after. The specimen was placed in a TN device with a distance (cell gap) between two sheets of glass substrates of 9 µm and a twist angle of 80°. A sine wave (0.5 V, 1 KHz) was applied to the device and the dielectric constant in the direction of the minor axis of the liquid crystal molecule (∈⊥) was measured 2 sec after. The value for the dielectric anisotropy was calculated according to Formula: Δ∈=∈∥−∈⊥.

[Threshold Value (Vth; Measured at 25° C.; V)]
(1) Composition of Positive Dielectric Anisotropy
A specimen was placed in a liquid crystal display device of a normally white mode having a distance (gap) between two sheets of glass substrates of (0.5/Δn) μm and a twist angle of 80°. Δn is a value for optical anisotropy measured by the method described above. A rectangular wave at a frequency of 32 Hz was applied to the device. The voltage of the rectangular wave was increased and the value of voltage when the transmittance of light passing through the device was 90%.
(2) Composition of Negative Dielectric Anisotropy
A specimen was placed in a liquid crystal display device of a normally black mode having a distance (gap) between two sheets of glass substrates of about 9 μm treated to homeotropic alignment. A rectangular wave at a frequency of 32 Hz was applied to the device. The voltage of the rectangular wave was increased and the value of voltage when the transmittance of light passing the device was 10%.

[Proton NMR Analysis Method ($^1$H-NMR)]
DRX-500 (manufactured by Bruker Biospin) was used for measurement. A solution in which a sample soluble to a dueteriated solvent such as CDCl$_3$ was dissolved was measured at a room temperature by using an NMR apparatus.

Tetramethyl silane (TMS) was used as a reference material for the zero point of δ value.

[Gas Chromatogram (GC) Analysis]
GC-14B model gas chromatograph manufactured by Shimazu Seisakusho was used for measurement. A carrier gas was helium (2 mL/min). A specimen gasifying chamber was set to 280° C. and a detector (FID) was set to 300° C. For the separation of the ingredient compound, a capillary column DB-1 manufactured by Agilent Technologies Inc (30 m length, 0.32 inner diameter, 0.25 μm film thickness; dimethyl polysiloxane fixed liquid phase: non-polarity) was used. After storing the column at 200° C. for 2 min, it was elevated up to 280° C. at a rate of 5° C./sec. The specimen was prepared as an acetone solution (0.1 wt %) and 1 μL thereof was injected into the specimen gasifying chamber. The recording meter was C-R5A model Chromatopac manufactured by Shimazu Seisakusho or a product equivalent therewith. The obtained gas chromatogram showed a peak retention time and peak area corresponding to the ingredient compound.

As the solvent for diluting the specimen, chloroform, hexane or the like may be used. For separating the ingredient compound, the following capillary columns may be used. HP-1 manufactured by Agilent Technologies Inc. (30 m length, 0.32 mm inner diameter, 0.25 μm film thickness), Rtx-1 manufactured by Restek Corporation (30 m length, 0.32 mm inner diameter, 0.25 μm film thickness), and BP-1 manufactured by SGE International Pty. Ltd. (30 m length, 0.32 mm inner diameter, 0.25 μm film thickness).

Capillary column CBP1-M50-025 manufactured by Shimazu Seisakusho (50 m length, 0.25 mm inner diameter, 0.25 μm film thickness) may be used with an aim of preventing compound peaks from overlapping with each other. The area ratio of the peak in the gas chromatogram corresponds to the ratio of the ingredient compound. The weight % of the ingredient compound is not completely identical with the area ratio for the each of the peak. However in the invention, when the capillary column is used, the weight % of the ingredient compound may be regarded as identical with the area ratio of each peak. This because there is no significant difference for the correction coefficient in the ingredient compound.

EXAMPLE 1

Synthesis of 4-(4-propylcyclohexyl)cyclohexyl-2-fluoro-3-difluoromethyl-ethoxybenzene (Compound No. 1-3-1)

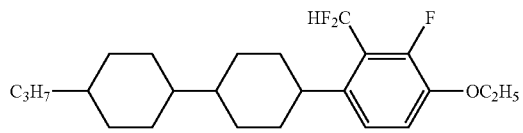

First Step
A THF solution of 2-fluoro-4-ethoxybromobenzene was dropped at 40 to 60° C. to dried turnings magnesium. A THF solution of 4-(propylcyclohexyl)cyclohexanone was dropped to the solution at 40 to 60° C. and further stirred for 2 hours. The reaction mixture was poured into aqueous saturated ammonium chloride and extracted with toluene. The organic layer was washed with water and then with an aqueous saturated sodium chloride solution successively and, after drying over anhydrous magnesium sulfate, concentrated under a reduced pressure. The obtained crude 1-hydroxy-4-(4-propylcyclohexyl)cyclohexyl-2-fluoroethoxybenzene was used without purification for a second step.

Second Step
The crude 1-hydroxy-4-(4-propylcyclohexyl)cyclohexyl-2-fluoroethoxybenzene obtained in the first step was dissolved in toluene. p-Toluene sulfonic acid monohydrate was added and refluxed while heating for two hours under dewatering by using a Dean-Stark apparatus. The reaction mixture was poured into an aqueous saturated sodium hydrogen carbonate solution and extracted with toluene. The organic layer was washed with water and then with an aqueous saturated sodium chloride solution successively and, after dying over anhydrous magnesium sulfate, concentrated under a reduced pressure. The residue was purified by silica gel column chromatography to obtain 4-(4-propylcyclohexyl)cyclohexenyl-2-fluoroethoxybenzene.

Third Step
4-(4-propylcyclohexyl)cyclohexenyl-2-fluoroethoxybenzene obtained in the second step was dissolved in a mixed toluene-solmix solvent. A Raney nickel catalyst was added to the solution in a nitrogen atmosphere to conduct hydrogenating reaction at ambient temperature and pressure for 2 days. After the completion of the reaction, the catalyst was removed by filtration. The filtrate was concentrated under a reduced pressure, and the residue was purified by silica gel column chromatography, to obtain 4-(4-propylcyclohexyl)cyclohexyl-2-fluoroethoxybenzene. This was further purified by repeating recrystallization, to obtain pure 4-(4-propylcyclohexyl)cyclohexyl-2-fluoroethoxybenzene.

Fourth Step
4-(4-propylcyclohexyl)cyclohexyl-2-fluoroethoxybenzene obtained in the third step was dissolved in tetrahydrofuran and cooled to −70° C. in a nitrogen atmosphere under acetone-dry ice coolant. Sec-butyl lithium (cyclohexane, n-hexane solution) was dropped in a nitrogen atmosphere to the solution and, stirred at −65° C. or lower for 2 hours after dropping. Then, dimethylformamide was dropped at −65° C.

and stirred for 2 hours after dropping. The reaction mixture was poured into an aqueous saturated ammonium chloride solution and extracted with hexane. The organic layer was washed with water and with an aqueous saturated sodium chloride solution successively and, after drying over anhydrous magnesium sulfate, concentrated under a reduced pressure, and the residue was purified by silica gel column chromatography, to obtain 4-(4-propylcyclohexyl)cyclohexyl-2-fluoro-3-formyl-ethoxybenzene.

Fifth Step 4-(4-propylcyclohexyl)cyclohexyl-2-fluoro-3-formyl-ethoxybenzene obtained in the 4th step was dissolved in dichloromethane and, after cooling to 0° C. in a nitrogen atmosphere, diethylaminosulfure trifluoride (DAST) was added and they were further stirred at a room temperature for 20 hours. The solution was poured into an aqueous sodium hydrogen carbonate solution and extracted with heptane. The organic layer was washed with water and then with an aqueous saturated sodium chloride solution successively and, after drying over anhydrous magnesium sulfate, it was concentrated under a reduced pressure and the residue was purified by silica gel column chromatography to obtain 4-(4-propylcyclohexyl)cyclohexyl-2-fluoro-3-difluoromethyl-ethoxybenzene. The product was purified by further repeating recrystallization to obtain pure 4-(4-propylcyclohexyl)cyclohexyl-2-fluoro-3-difluoromethyl-ethoxybenzene.

EXAMPLE 2

Synthesis of 4-(4-propylcyclohexyl)phenyl-2-fluoro-3-difluoromethyl-ethoxybenzene (Compound No. 1-3-5)

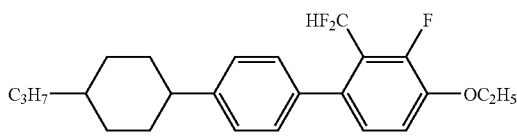

First Step 100 ml of a THF solution of 22.8 g (104 mmol) of 3-fluoro-4-ethoxybromobenzene was dropped, while stirring, at 40 to 60° C. to 3.03 g (124.8 mmol) of dried turnings magnesium, and refluxed under heating after dropping for one hour. The solution was cooled by a coolant to −70° C. and, a THF solution of 16 ml (132.5 mmol) of trimethyl borate (THF: 70 ml) was dropped under stirring. After stirring at −70° C. for 3 hours, and further stirring at a room temperature for 20 hours, the reaction solution was cooled to 5° C., and 50 ml of 6M hydrochloric acid was added. After separating the organic layer, the aqueous layer was extracted with 100 ml of ethyl acetate. After mixing the organic layer, it was washed with water and then with an aqueous saturated sodium chloride solution successively and, after drying over anhydrous magnesium sulfate, concentrated under a reduced pressure, to obtain 22.3 g of crude 3-fluoro-4-ethoxyphenyl boronic acid. The obtained crude boronic acid derivative was used without purification for a second step.

22.3 g of the crude 3-fluoro-4-ethoxyphenyl boronic acid obtained in the first step was dissolved in 200 ml of tetrahydrofuran, and 23.6 g (208 mmol) of aqueous 30% hydrogen peroxide was added while being kept at about 35° C. in a warm bath. After addition and after stirring the reaction solution at a room temperature for 24 hours, the reaction solution was poured into 300 ml of water, then sodium hydrogen sulfite was added and stirred at a room temperature for one hour. The reaction solution was extracted with 300 ml of ethyl acetate and the extracted layer was washed with water and then with an aqueous saturated sodium chloride solution successively and, after dying over anhydrous magnesium sulfate, concentrated under a reduced pressure. The concentrated residue was purified by silica gel column chromatography using a ethyl acetate/heptane mixed solvent as an eluent to obtain 17.6 g (113 mmol) of 3-fluoro-4-ethoxyphenol.

Third Step

In a nitrogen atmosphere, 17.1 g (109 mmol) of 3-fluoro-4-ethoxyphenol obtained in the second step was dropped to a THF suspension (170 ml) of 5.2 g (130.8 mmol) of sodium hydride at 5 to 10° C. in a nitrogen atmosphere and stirred at that temperature for 30 min. Then, a THF (10 ml) solution of 9.9 ml (130.8 mmol) of chloromethyl ether was dropped at 5 to 10° C. and stirred after dropping at a room temperature for 2 hours. After pouring the reaction solution into iced water, it was extracted with 30 ml of heptane, the extracted layer was washed with water and then with an aqueous saturated sodium chloride solution successively and, after drying over anhydrous magnesium sulfate, concentrated under a reduced pressure. The concentrated residue was purified by silica gel column chromatography by using a mixed ethyl acetate/heptane solvent as an eluent to obtain 16.5 g of 3-fluoro-4-ethoxyphenyl methoxymethyl ether.

Fourth Step 16 g (79.9 mmol) of 3-fluoro-4-ethoxyphenyl methoxymethyl ether obtained in the third step was dissolved in 160 ml of tetrahydrofuran and cooled to −70° C. in a nitrogen atmosphere by acetone-dry ice coolant. 89 ml (87.9 mmol) of sec-butyl lithium (0.99M, cyclohexane, n-hexane solution) was dropped to the solution and, stirred at −70° C. for one hour after dropping. Then, 6.8 ml (87.9 mmol) of dimethylformamide was dropped at −70° C. and stirred at that temperature for 2 hours after dropping. The reaction mixture was poured into an aqueous saturated ammonium chloride and extracted with 300 ml of hexane. The organic layer was washed with water and then with an aqueous saturated sodium chloride solution successively and, after drying over anhydrous magnesium sulfate, concentrated under a reduced pressure. The obtained residue was purified by silica gel column chromatography using a mixed ethyl acetate/heptane solvent as an eluent to obtain 16.5 g of 2-formyl-3-fluoro-4-ethoxyphenyl methoxymethyl ether.

Fifth Step 8 g (35 mmol) of 2-formyl-3-fluoro-4-ethoxyphenyl methoxy methyl ether obtained in the 4th step was dissolved in 80 mmol of dichloromethane and, after cooling to 0° C. in a nitrogen atmosphere, 9.5 ml (71.8 mmol) of diethylaminosulfure trifluoride (DAST) was added and further stirred at a room temperature for 20 hours. The solution was poured into an aqueous sodium hydrogen carbonate solution and extracted with 200 ml of heptane. The organic layer was washed with water and then with an aqueous saturated sodium chloride solution successively and, after drying over anhydrous magnesium sulfate, concentrated under a reduced pressure and the residue was purified by silica gel column chromatography using a mixed ethyl acetate/heptane solvent as an eluent. The product was purified by further repeating recrystallization to obtain 7.6 g of 2-difluoromethyl-3-fluoro-4-ethoxyphenyl methoxymethyl ether.

Sixth Step 7.5 g (30 mmol) of 2-difluoromethyl-3-fluoro-4-ethoxyphenyl methoxymethyl ether obtained in the 5th step was dissolved in 30 ml of ethanol and, while stirring at a room temperature, 30 ml (60 mmol) of 2M hydrochloric acid was added and refluxed under heating for 2 hours after the addition. The reaction solution was poured into water and extracted with 150 ml of ethyl acetate. The organic layer was washed with water and then with an aqueous saturated sodium chloride solution successively and, after drying over anhydrous magnesium sulfate, concentrated under a reduced pressure. The residue was purified by silica gel column chromatography using a mixed ethyl acetate/heptane solvent as an eluent to obtain 6.0 g of 2-difluoromethyl-3-fluoro-4-ethoxyphenol.

Seventh Step 2.5 g (12 mmol) of 2-difluoromethyl-3-fluoro-4-ethoxyphenol obtained in the 6th step and 2 ml of pyridine were dissolved in 50 ml of dichloromethane, 2.6 ml (15.6 mmol) of trifluoromethane sulfonic acid anhydride was added at 5 to 10° C. in a nitrogen atmosphere and stirred at that temperature for 1.5 hours. The reaction mixture was poured into an aqueous sodium hydrogen carbonate solution and extracted with 100 ml of dichlormethane. The organic layer was washed with water and then with an aqueous saturated sodium chloride solution successively and, after drying over anhydrous magnesium sulfate, concentrated under a reduced pressure to obtain a crude triflate derivative. The obtained crude triflate derivative (5.5 g) was mixed with 3.2 g (13.2 mmol) of 4-(propylcyclohexyl)phenyl boronic acid, 1.6 g (13.2 mmol) of potassium bromide, 5.1 g (24 mmol) of potassium phosphate, 50 ml of dioxane, and 0.4 g (0.3 mmol) of tetrakis triphenyl phosphine palladium as a coupling catalyst and refluxed under heating for 5 hours. After pouring the reaction mixture into water and extracting with 100 ml of toluene, the organic layer was washed with water and then with an aqueous saturated sodium chloride solution successively and, after drying over anhydrous magnesium sulfate, concentrated under a reduced pressure. The concentrated residue was purified by silica gel column chromatography by using an ethyl acetate/heptane mixed solvent as an eluent and further purified by repeating recrystallization from a heptane/ethanol mixed solvent to obtain pure 4-(4-propylcyclohexyl)phenyl-2-fluoro-3-difluoromethyl-ethoxybenzene. The melting point of compound was 82.2° C.

EXAMPLE 3

Synthesis of 4-(4-propylcyclohexyl)methyl 2-fluoro-3-difluoromethyl-4-methylphenyl ether (Compound No. 1-2-8)

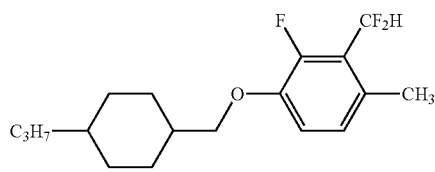

First Step

In a nitrogen atmosphere, 2-fluoro-4-methylphenole was dropped at about 5° C. to a THF suspension of sodium hydride and stirred at that temperature for 30 min. Then, a THF solution of chloromethyl methyl ether was dropped at about 5° C. and stirred after dropping at a room temperature for 2 hours. The reaction solution was poured into iced water and then extracted with heptane. The extracted layer was washed with water and then with an aqueous saturated sodium chloride solution successively and, after drying over anhydrous magnesium sulfate, concentrated under a reduced pressure. The obtained concentrated residue was purified by silica gel column chromatography, to obtain 2-fluoro-4-methylphenyl methoxy methyl ether.

Second Step 2-fluoro-4-methylphenyl methoxy methyl ether obtained in the first step was dissolved in tetrahydrofuran and cooled to −70° C. in a nitrogen atmosphere under acetone-dry ice coolant. Sec-butyl lithium was dropped in a nitrogen atmosphere to the solution and, stirred at −70° C. for 1 hours after dropping. Then, dimethylformamide was dropped at −70° C. and stirred at the same temperature for 2 hours after dropping. The reaction mixture was poured into an aqueous saturated ammonium chloride solution and extracted with hexane. The organic layer was washed with water and with an aqueous saturated sodium chloride solution successively and, after drying over anhydrous magnesium sulfate, concentrated under a reduced pressure. The resulting residue was purified by silica gel column chromatography, to obtain 2-fluoro-3-formyl-4-methylphenyl methoxymethyl ether.

Third Step 2-fluoro-3-formyl-4-methylphenylmethoxymethyl ether obtained in the second step was dissolved in dichloromethane and, after cooling to 0° C. in a nitrogen atmosphere, diethylamino sulfur trifluoride (DAST) was added and further stirred at a room temperature for 20 hours. The solution was poured into an aqueous sodium hydrogen carbonate solution and extracted with heptane. The organic layer was washed with water and then with an aqueous saturated sodium chloride solution successively and, after drying over anhydrous magnesium sulfate, concentrated under a reduced pressure. The concentrated residue was purified by silica gel column chromatography, to obtain 2-fluoro-3-difluoromethyl-4-methylphenyl methoxymethyl ether.

Fourth Step 2-fluoro-3-formyl-4-methylphenyl methoxymethyl ether obtained in the third step was dissolved in ethanol and, while stirring at a room temperature, 2M hydrochloric acid was added and refluxed under heating for 2 hours after the addition. The reaction solution was poured into water and extracted with ethyl acetate. The organic layer was washed with water and then with an aqueous saturated sodium chloride solution successively and, after drying over anhydrous magnesium sulfate, concentrated under a reduced pressure. The residue was purified by silica gel column chromatography, to obtain 2-fluoro-3-difluoromethyl-4-methylphenol.

Fifth Step 2-fluoro-3-difluoromethyl-4-methylphenol obtained in the 4th step was mixed in a nitrogen atmosphere with 4-propylcyclohexyl iodo methane and potassium carbonate in DMF and heated under stirring at 100° C. for 8 hours. The reaction mixture was poured in water and extracted with toluene. The organic layer was washed with water and then with an aqueous saturated sodium chloride solution successively and, after drying over anhydrous magnesium sulfate, concentrated under a reduced pressure. The concentrated residue was purified by silica gel column chromatography and further purified by repeating recrystallization, to obtain pure 4-(4-propylcyclohexyl)methyl 2-fluoro-3-difluoromethyl-4-methylphenyl ether.

EXAMPLE 4

Synthesis of 4-pentyl-2'-difluoromethyl-3'-fluoro-4"-ethyl terphenyl (Compound No. 1-4-6)

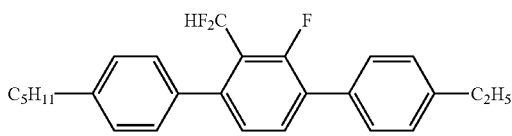

First Step 4-ethylphenyl boronic acid was mixed with 3-fluoro-4-iodoanysole, potassium carbonate, and tetrakistriphenyl phosphine palladium as a coupling catalyst in a toluene/ethanol mixed solvent and refluxed under heating for 8 hours. The reaction mixture was poured into water and extracted with 100 ml of toluene. The organic layer was washed with water and then with an aqueous saturated sodium chloride solution successively and, after drying over anhydrous magnesium sulfate, concentrated under a reduced pressure. The concentrated residue was purified by silica gel column chromatography and further purified by repeating recrystallization to obtain pure 3-fluoro-4-(4-ethylphenyl)anisole.

Second Step 3-fluoro-4-(4-ethylphenyl)anisole obtained in the first step was dissolved in dichloromethane and, after cooling by a coolant to −60° C., boron tribromide was dropped. After dropping, they were stirred at that temperature for 2 hours and, further stirred at a room temperature for 8 hours. The reaction mixture was poured into water to separate the dichlormethane layer. The dichloromethane layer was washed with water and then with an aqueous saturated sodium chloride solution successively and, after drying over anhydrous magnesium sulfate, concentrated under a reduced pressure. The concentrated residue was purified by silica gel column chromatography, to obtain 3-fluoro-4-(4-ethylphenyl)phenol.

Third Step

In a nitrogen atmosphere, 3-fluoro-4-(4-ethylphenyl) phenol obtained in the second step was dropped at about 5° C. to a THF suspension of sodium hydride, and stirred at that temperature for 30 min. Then, a THF solution of chloromethyl methyl ether was dropped at about 5° C., and stirred at a room temperature after the dropping for 2 hours. After pouring the reaction solution into iced water, it was extracted with heptane. The extracted layer was washed with water and with an aqueous saturated sodium chloride solution successively and, after drying over anhydrous magnesium sulfate, concentrated under a reduced pressure. The obtained concentrated residue was purified by silica gel column chromatography to obtain 3-fluoro-4-(4-ethylphenyl)phenyl methoxymethyl ether.

Fourth Step 3-fluoro-4-(4-ethylphenyl)phenyl methoxymethyl ether obtained in the third step was dissolved in tetrahydrofuran and cooled by acetone-dry ice coolant to −70° C. in a nitrogen atmosphere. Sec-butyl lithium was dropped to the solution in a nitrogen atmosphere and stirred after dropping at −70° C. for one hour. Then, dimethylformamide was dropped at −70° C. and stirred at the temperature for 2 hours after dropping. The reaction mixture was poured into an aqueous saturated ammonium chloride and extracted with hexane. The organic layer was washed with water and then with an aqueous saturated ammonium chloride solution successively and, after drying over anhydrous magnesium sulfate, concentrated under a reduced pressure. The obtained residue was purified by silica gel column chromatography, to obtain 2-formyl-3-fluoro-4-(4-ethylphenyl)phenyl methoxymethyl ether.

Fifth Step 2-formyl-3-fluoro-4-(4-ethylphenyl)phenyl methoxymethyl ether obtained in the 4th step was dissolved in dichloromethane and, after cooling to 0° C. in a nitrogen atmosphere, diethylamino sulfur trifluoride (DAST) was added and further stirred at a room temperature for 20 hours. The solution was poured into an aqueous sodium hydrogen carbonate solution and extracted with heptane. The organic layer was washed with water and then with an aqueous saturated sodium chloride solution successively and, after drying over anhydrous magnesium sulfate, concentrated under a reduced pressure. The concentrated residue was purified by silica gel column chromatography, to obtain 2-difluoromethyl-3-fluoro-4-(4-ethylphenyl)phenyl methoxymethyl ether.

Sixth Step 2-difluoromethyl-3-fluoro-4-(4-ethylphenyl)phenyl methoxymethyl ether obtained in the 5th step was dissolved in ethanol, 2M hydrochloric acid was added while stirring at a room temperature and refluxed under heating for 2 hours after the addition. The reaction solution was poured into water and extracted with ethyl acetate. The organic layer was washed with water and then with an aqueous saturated sodium chloride solution successively and, after drying over anhydrous magnesium sulfate, concentrated under a reduced pressure. The residue was purified by silica gel column chromatography, to obtain 2-difluoromethyl-3-fluoro-4-(4-ethylphenyl)phenol.

Seventh Step 2-difluoromethyl-3-fluoro-4-(4-ethylphenyl)phenol obtained in the 6th step and pyridine were dissolved in dichloromethane, trifluoromethane sulfonic acid anhydride was added at about 5° C. in a nitrogen atmosphere and stirred at that temperature for 2 hours. The reaction mixture was poured into an aqueous sodium hydrogen carbonate solution and extracted with dichloromethane. The organic layer was washed with water and then with an aqueous saturated sodium chloride solution successively and, after drying over anhydrous magnesium sulfate, concentrated under a reduced pressure, to obtain a crude triflate derivative. The obtained crude triflate derivative was mixed with 4-pentylphenyl boronic acid, potassium bromide, and potassium phosphate in dioxane and, further, tetrakistriphenyl phosphine palladium was added as a coupling catalyst and refluxed under heating for 8 hours. The reaction mixture was poured into water and extracted with toluene. The organic layer was washed with water and then with an aqueous saturated sodium chloride solution successively and, after drying over anhydrous magnesium sulfate, concentrated under a reduced pressure. The concentrated residue was purified by silica gel column chromatography, and further purified by repeating recrystallization to obtain pure 4-pentyl-2'-difluoromethyl-3'-fluoro-4"-ethyl terphenyl.

EXAMPLE 5

Synthesis of β-(4-(4-propylcyclohexyl)cyclohexyl)-2-difluoro methyl-3-fluoro-4-ethoxy styrene (Compound No. 1-3-15)

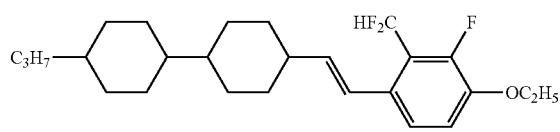

First Step 30 ml of a THF solution of 15.0 g (68.5 mmol) of 3-fluoro-4-ethoxybromobenzene was dropped under stirring to 1.8 g (75.4 mmol) of dried turnings magnesium at 40 to 60° C. Then, 100 ml of a THF solution of 22.3 g (89.1 mmol) of (4-(4-propylcyclohexyl)cyclohexyl)acetoaldehyde was dropped to the solution and stirred for 2 hours. The reaction mixture was poured into 100 ml of an aqueous saturated ammonium chloride solution and extracted with 200 ml of toluene. The organic layer was washed with 100 ml of water and then with 100 ml of aqueous saturated sodium chloride solution successively and, after drying over anhydrous magnesium sulfate, concentrated under a reduced pressure to obtain 25.9 g of crude 1-hydroxy-1-(3-fluoro-4-ethoxyphenyl)-2-(4-(4-propylcyclohexyl)cyclohexyl)ethane.

Second Step 25.9 g of crude 1-hydroxy-1-(3-fluoro-4-ethoxyphenyl)-2-(4-(4-propylcyclohexyl)cyclohexyl)ethane obtained in the first step was dissolved in toluene. 0.8 g (4 mmol) of p-toluene sulfonic acid monohydrate was added and refluxed under stirring for 2 hours while dewatering by using a Dean-Stark apparatus. The reaction mixture was poured into 200 ml of an aqueous saturated sodium hydrogen carbonate solution and extracted with 200 ml of toluene. The organic layer was washed with 200 ml of water and then with 100 ml of an aqueous saturated sodium chloride solution successively and, after drying over anhydrous magnesium sulfate, concentrated under a reduced pressure. The residue was purified by silica gel column chromatography (eluent: heptane/toluene=8/2) and further recrystallized from heptane to obtain 13.2 g of β-(4-(4-propylcyclohexyl)cyclohexyl)-3-fluoro-4-ethoxy styrene.

Third Step 13.2 g (35.4 mmol) of β-(4-(4-propylcyclohexyl)cyclohexyl)-3-fluoro-4-ethoxy styrene obtained in the second step was dissolved in 150 ml of THF and cooled in a nitrogen atmosphere to −70° C. by an acetone-dry ice coolant. 46 ml (46 mmol) of sec-butyl lithium (cyclohexane, 1M n-hexane solution) was dropped to the solution in a nitrogen atmosphere and stirred after dropping for 2 hours at −65° C. or lower. Then, 7.8 g (106.2 mmol) of dimethyl formamide was dropped at −65° C. and further stirred for 2 hours after dropping. The reaction mixture was poured into 200 ml of aqueous saturated ammonium chloride solution and extracted with 200 ml of heptane. The organic layer was washed with 300 ml of water and then with 100 ml of an aqueous saturated sodium chloride solution successively and, after drying over anhydrous magnesium sulfate, concentrated under a reduced pressure, and the residue was purified by silica gel column chromatography (eluent: heptane/toluene=7/3), to obtain 5.5 g of β-4-(4-propylcyclohexyl)cyclohexyl)-2-formyl-3-fluoro-4-ethoxy styrene.

Fourth Step 5.5 g (13.7 mmol) of β-(4-(4-propylcyclohexyl)cyclohexyl)-2-formyl-3-fluoro-4-ethoxy styrene obtained in the third step was dissolved in 100 ml of dichloromethane and, after cooling in a nitrogen atmosphere to 0° C., 6.6 g (41.1 mmol) of diethylamino sulfur trifluoride (DAST) was added and further stirred at a room temperature for 20 hours. The solution was poured into 300 ml of an aqueous saturated sodium hydrogen carbonate solution and extracted with 200 ml of heptane. The organic layer was washed with 300 ml of water and then with 200 ml of an aqueous saturated sodium chloride solution successively and, after drying over anhydrous magnesium sulfate, concentrated under a reduced pressure. The residue was purified by silica gel column chromatography (eluent: heptane/toluene=9/1), and further recrystallized twice from a heptane/ethanol mixed solvent to obtain 2.1 g of pure β-(4-(4-propylcyclohexyl)cyclohexyl)-2-difluoromethyl-3-fluoro-4-ethoxy styrene. The compound showed a liquid crystal phase and the transition point thereof was as shown below.

C 69.0 N 168.7 Iso $^1$H-NMR(CDCl$_3$): δ(ppm); 7.23(d,1H), 7.02(t,1H), 6.97 (T, 1H), 6.71(d, 1H), 6.00(dd, 1H), 4.10(q, 2H), 2.09-2.04(m, 1H), 1.86-1.70(m, 8H), 1.44(t, 3H), 1.34-1.27(m, 2H), 1.17-0.94(m, 11H), 0.87(t, 3H), 0.89-0.81(m, 2H)

EXAMPLE 6

Synthesis of 1-(2-difluoromethyl-3-fluoro-4-ethoxyphenyl)-2-(4-(4-propylcyclohexyl)cyclohexyl) ethane (Compound No. 1-3-13)

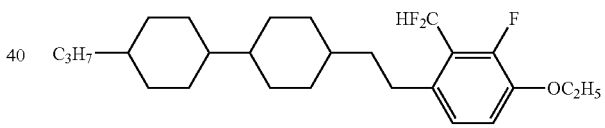

1.6 g of β-(4-(4-propylcyclohexyl)cyclohexyl)-2-difluoromethyl-3-fluoro-4-ethoxy styrene obtained in Example 5 was dissolved in 25 ml of a mixed toluene-solmix solvent. A palladium carbon catalyst was added to the solution in a nitrogen atmosphere and a hydrogenation reaction was conducted at ambient temperature and pressure for 2 days. After the completion of the reaction, the catalyst was removed by filtration. The filtrate was concentrated under a reduced pressure and the residue was purified by silica gel column chromatography (eluent: heptane/toluene=9/1) to obtain 1-(2-difluoromethyl-3-fluoro-4-ethoxyphenyl)-2-(4-(4-propylcyclohexyl)cyclohexyl)ethane. This was further recrystallized twice from a heptane/ethanol mixed solvent to obtain pure 1-2-difluoromethyl-3-fluoro-4-ethoxyphenyl)-2-(4-(4-propylcyclohexyl)cyclohexyl)ethane. The compound showed a liquid crystal phase and the transition point was as described below.

C 76.6 (5 mA 49.1) N 120.4 Iso $^1$H NMR(CDCl$_3$): δ(ppm); 7.02(t, 1H), 7.00(d,1H), 6.96(t, 1H), 4.11(g, 2H), 1.86-1.71(m, 8H), 1.46(t, 3H), 1.37-1.15 (m, 6H), 1.04-0.93(m, 8H), 0.90(t, 3H), 0.91-0.83(m, 2H).

EXAMPLE 7

Synthesis of β-(4-(4-propylcyclohexyl)cyclohexyl)-2-trifluoromethyl-3-fluoro-4-ethoxystyrene (Compound No. 2-3-3)

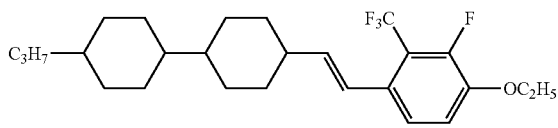

First Step

In a nitrogen atmosphere, (1.0 mol/L) 42.4 mL of sec-butyl lithium was dropped at −78° C. to 10.0 g (35.7 mmol) of 2-fluoro-2-trifluoromethyl-6-trimethylsylilethoxy benzene dissolved in 60 ml of THF and stirred at that temperature for 2 hours. Then, 22 ml of a THF solution of 10.7 g (42.8 mmol) of (4-(4-propylcyclohexyl)cyclohexyl)acetoaldehyde was dropped to the solution and, after stirring at that temperature for one hour, temperature was elevated to a room temperature and stirring was conducted overnight. The reaction mixture was poured into 100 ml of an aqueous saturated ammonium chloride solution and extracted with 200 ml of toluene. The organic layer was washed with 100 ml of water and then with 100 ml of an aqueous saturated sodium chloride solution successively and, after drying over anhydrous magnesium sulfate, concentrated under a reduced pressure to obtain 20.7 g of a crude 1-hydroxy-1-(2-trifluoromethyl-3-fluoro-4-ethoxy-5-trimethylsilylphenyl)-2-(4-(4-propylcyclohexyl)cyclohexyl)ethane.

Second Step 20.7 g of the crude 1-hydroxy-1-(2-trifluoromethyl-3-fluoro-4-ethoxy-5-trimethylsilylphenyl)-2-(4-(4-propylcyclohexyl)cyclohexyl)ethane obtained in the first step was dissolved in toluene. 0.68 g (3.57 mmol) of p-toluene sulfonic acid monohydrate was added and refluxed under heating for 2 hours while dewatering by using a Dean Stark apparatus. The reaction mixture was poured into 200 ml of an aqueous sodium hydrogen chloride solution and extracted with 200 ml of toluene. The organic layer was washed with 200 ml of water and then with 100 ml of an aqueous saturated sodium chloride solution successively and, after drying over anhydrous magnesium sulfate, it was concentrated under a reduced pressure to obtain 16.03 g of a crude β-(4-(4-propylcyclohexyl)cyclohexyl)-2-trifluoromethyl-3-fluoro-4-ethoxy-5-trimethylsilyl styrene.

Third Step 16.03 g of crude of β-(4-(4-propylcyclohexyl)cyclohexyl)-2-trifluoromethyl-3-fluoro-4-ethoxy-5-trimethylsilyl styrene was dissolved in 35 mL of THF, to which 23.4 mL of tetrabutyl ammonium fluoride/THF solution (1 mol/L) was dropped and stirred for 2 hours. The reaction solution was poured into 100 ml of water and extracted with 200 ml of toluene. The organic layer was washed with 100 ml of an aqueous saturated sodium chloride solution and dried over anhydrous magnesium sulfate. The residue was purified by silica gel column chromatography (eluent: heptane/toluene=8/2) and further recrystallized twice from a heptane/ethanol mixed solvent to obtain 7.89 g of β-(4-(4-propylcyclohexyl)cyclohexyl)-2-trifluoromethyl-3-fluoro-4-ethoxy styrene. The compound showed a liquid crystal phase and the transition points were as shown below.

C 83.0 N 149.3 Iso
$^1$H NMR(CDCl$_3$): δ(ppm); 7.17(d, 1H), 7.01(t, 1H), 6.59 (d, 1H), 5.91(dd, 1H), 4.09(q, 2H), 2.07-2.01(m, 1H), 1.85-1.70(m, 8H), 1.44(t, 3H), 1.34-1.27(m, 2H), 1.15-0.93(m, 11H), 0.87(t, 3H), 0.89-0.81(m, 2H).

EXAMPLE 8

Synthesis of 1-(2-trifluoromethyl-3-fluoro-4-ethoxyphenyl)-2-(4-(4-propylcyclohexyl)cyclohexyl) ethane (Compound No. 2-3-12)

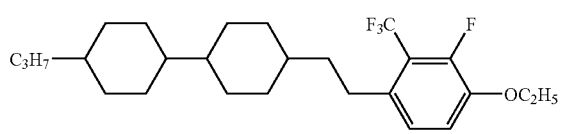

7.89 g of β-(4-(4-propylcyclohexyl)cyclohexyl)-2-trifluoromethyl-3-fluoro-4-ethoxy styrene obtained in Example 7 was dissolved in 200 ml of a mixed toluene-solmix solvent. A palladium carbon catalyst was added to the solution in a nitrogen atmosphere and a hydrogenation reaction was conducted at ambient temperature and pressure for 2 hours. After the completion of the reaction, the catalyst was removed by filtration. The filtrate was concentrated under a reduced pressure and the residue was purified by silica gel column chromatography (eluent: heptane:toluene=4:1) to obtained 1-(2-trifluoromethyl-3-fluoro-4-ethoxyphenyl)-2-(4-(4-propylcyclohexyl)cyclohexyl)ethane. This was further recrystallized twice from a heptane/ethanol mixed solvent to obtain 5.35 g of pure 1-(2-trifluoromethyl-3-fluoro-4-ethoxyphenyl)-2-(4-(4-propylcyclohexyl)cyclohexyl)ethane. The compound showed a liquid crystal phase and the transition point was as described below.

C 68.0 (SmA 44.9) N 112.8 Iso
$^1$H NMR(CDCl$_3$): δ(ppm); 7.01(t, 1H), 6.92(d, 1H), 4.08 (q, 2H), 2.69(m, 2H), 1.81-1.68(m, 8H), 1.43(t, 3H), 1.45-1.39(m, 2H), 1.33-1.12(m, 6H), 1.00-0.92(m, 8H), 0.87(t, 3H), 0.90-0.80(m, 2H)

EXAMPLE 9

Synthesis of (4-(4-(4-propylcyclohexyl)cyclohexyl) methoxy-3-trifluoromethyl-2-fluoroethoxybenzene (Compound No. 2-3-13)

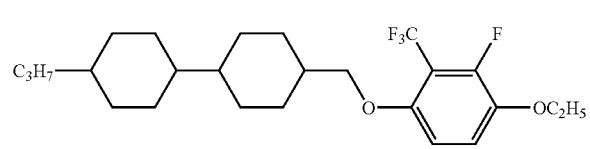

First Step

In a nitrogen atmosphere, 85.7 mL of sec-butyl lithium (1.0 mol/L) was dropped at −78° C. to 20.0 g (71.4 mmol) of 2-fluoro-2-trifluoromethyl-6-trimethylsilylethoxy benzene dissolved in 60 mL of THF and stirred at that temperature for 2 hours. Then, 13.7 g (85.7 mmol) of bromine was dropped to the solution and after stirring at that temperature for one hour, the temperature was elevated to a room temperature and stirring was conducted overnight. The reaction mixture was poured into 100 ml of water and extracted with 200 ml of toluene. The organic layer was washed with 100 ml of water and then with 100 ml of an aqueous saturated sodium chloride solution successively and, after drying over anhydrous magnesium sulfate, concentrated under a reduced pressure to obtain 27.8 g of crude 2-trifluoromethyl-3-fluoro-4-ethoxy-5-trimethylsilylbromo benzene.

Second Step 27.8 g of crude 2-trifluoromethyl-3-fluoro-4-ethoxy-5-trimethylsilylbromo benzene obtained in the first step was dissolved in 100 ml of THF. Then, 100 mL of a THF solution of tetrabutyl ammonium fluoride (1.0 mol/L) was dropped and stirred overnight. The reaction mixture was poured into 200 ml of water and extracted with 200 mol of toluene. The organic layer was washed with 200 ml of water and then with 100 ml of an aqueous saturated sodium chloride solution successively and, after drying over an hydrous magnesium sulfate, concentrated under a reduced pressure. The residue was purified by silica gel column chromatography (eluent: heptane) to obtain 15.0 g of 2-trifluoromethyl-3-fluoro-4-ethoxybromobenzene.

Third Step 15.0 g of 2-trifluoromethyl-3-fluoro-4-ethoxybromobenzene obtained in the second step was dissolved in 50 ml of THF and cooled in a nitrogen atmosphere to −70° C. by acetone-dry ice coolant. 40 ml (62.6 mmol) of n-butyl lithium (1.56 mol/L; n-hexane solution) was dropped to the solution and stirred at −65° C. or lower for 2 hours after dropping. Then, 13.0 g (125.2 mmol) of trimethyl borate dissolved in 30 ml of THF was dropped at −65° C. and further stirred for one hour after dropping. Then, temperature was elevated to a room temperature and stirring was conducted overnight. The reaction mixture was poured into 200 ml of 3N-hydrochloric acid and extracted with 200 ml of ethyl acetate. The organic layer was washed with 300 ml of water and then with 100 ml of an aqueous saturated sodium chloride solution and after drying over anhydrous magnesium sulfate, concentrated under a reduced pressure, to obtain 13.8 g of crude 2-trifluoromethyl-3-fluoro-4-ethoxyphenyl boronic acid.

Fourth Step 16.2 g (104.4 mmol) of an aqueous 30% hydrogen peroxide was dropped to 13.8 g (52.2 mmol) of the crude 2-trifluoromethyl-3-fluoro-4-ethoxyphenyl boronic acid obtained in the third step dissolved in 100 ml of THF, and further stirred at a room temperature for 2 hours. The solution was poured into 300 ml of an aqueous saturated sodium hydrogen sulfite solution and extracted with 200 ml of ethyl acetate. The organic layer was washed with 300 ml of an aqueous saturated sodium hydrogen sulfite solution, with 300 ml of water, and then with 200 ml an aqueous saturated sodium chloride solution successively and, after drying over anhydrous magnesium sulfate, concentrated under a reduced pressure. The residue was purified by distillation and further recrystallized twice from a heptane/ethanol mixed solvent to obtain 5.67 g of pure 2-trifluoromethyl-3-fluoro-4-ethoxyphenol.

Fifth Step 3.0 g (13.4 mmol) of 2-trifluoromethyl-3-fluoro-4-ethoxyphenol obtained in the 4th step was dissolved in 70 ml of N,N-dimethylformamide, to which 4.44 g (14.7 mmol) of 4-(4-propylcyclohexyl)cyclohexyl bromomethane, 2.03 g (14.7 mmol) of potassium carbonate and 0.22 g (0.67 mmol) of tetrabutyl ammonium bromide were added and refluxed under heating for three hours. After cooling to a room temperature, the solution was poured into 300 ml of water and extracted with 200 ml of toluene. The organic layer was washed with 300 ml of water and then with 200 ml of an aqueous saturated sodium chloride solution successively and, after dying over anhydrous magnesium sulfate, concentrated under a reduced pressure. The residue was purified by silica gel column chromatography (eluent: heptane:toluene=7:1) and further recrystallized twice from a heptane/ethanol mixed solvent to obtain 3.01 g of pure 4-(4-(4-propylcyclohexyl)cyclohexyl)methoxy-3-trifluoromethyl-2-fluoroethoxy benzene (Compound No. 2-3-13). The compound showed a liquid crystal phase.

$^1$H NMR(CDCl$_3$): δ(ppm); 6.69(d, 1H), 6.59(t, 1H), 4.12 (q, 2H), 3.73(d, 2H), 1.97-1.91(m, 2H), 1.80-1.70(m, 7H), 1.37(t, 3H), 1.34-1.27(m, 2H), 1.15-0.94(m, 11H), 0.87(t, 3H), 0.89-0.81(m, 2H)

EXAMPLE 10

The following compounds No 1-1-1 to No. 2-9-9 were synthesized by applying the synthesis methods and Examples 1 to 9 described above.

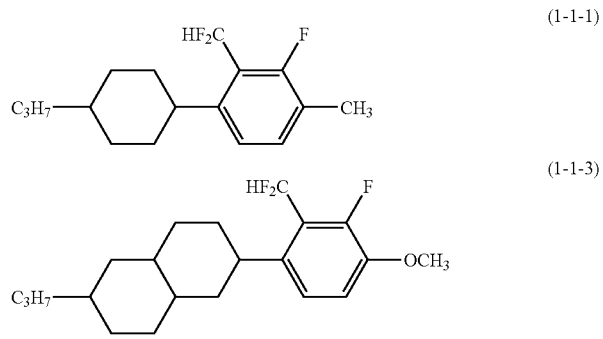

(1-1-1)

(1-1-3)

(1-1-5)

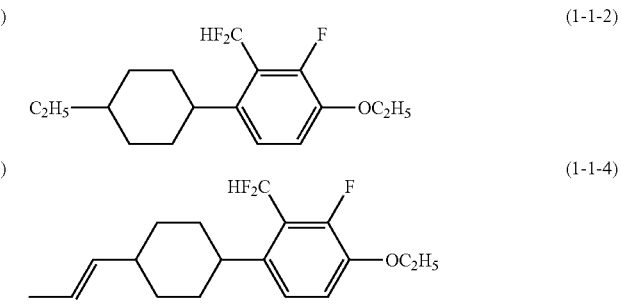

(1-1-2)

(1-1-4)

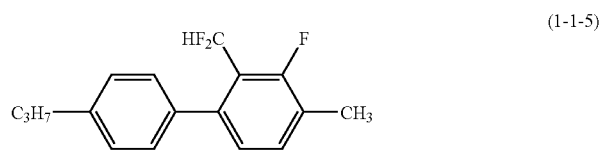

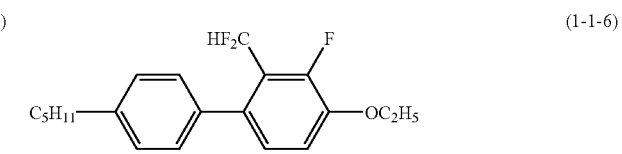

(1-1-6)

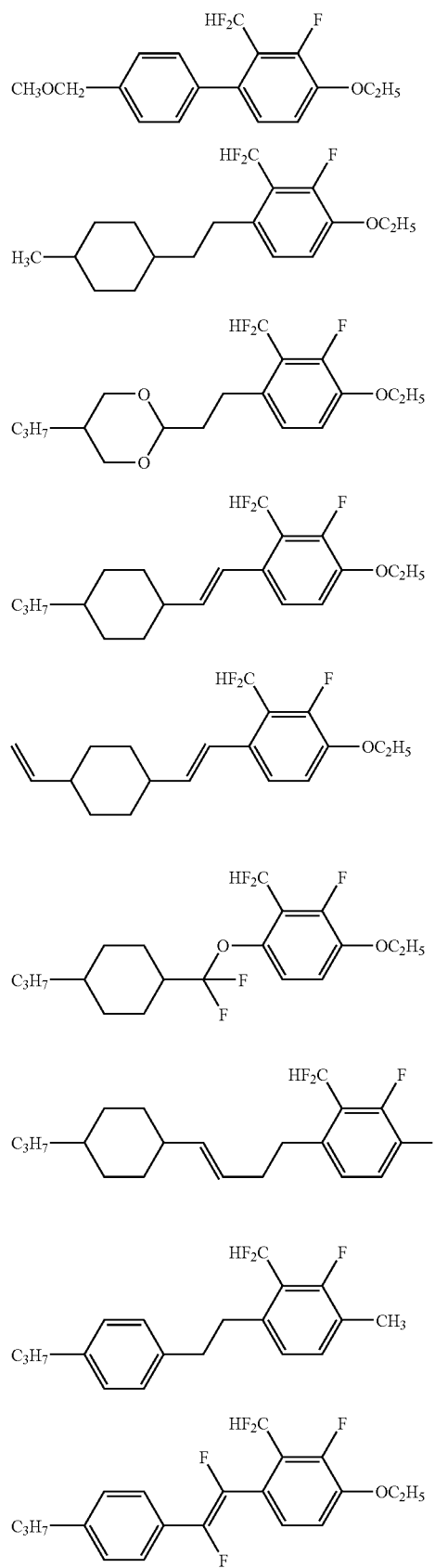
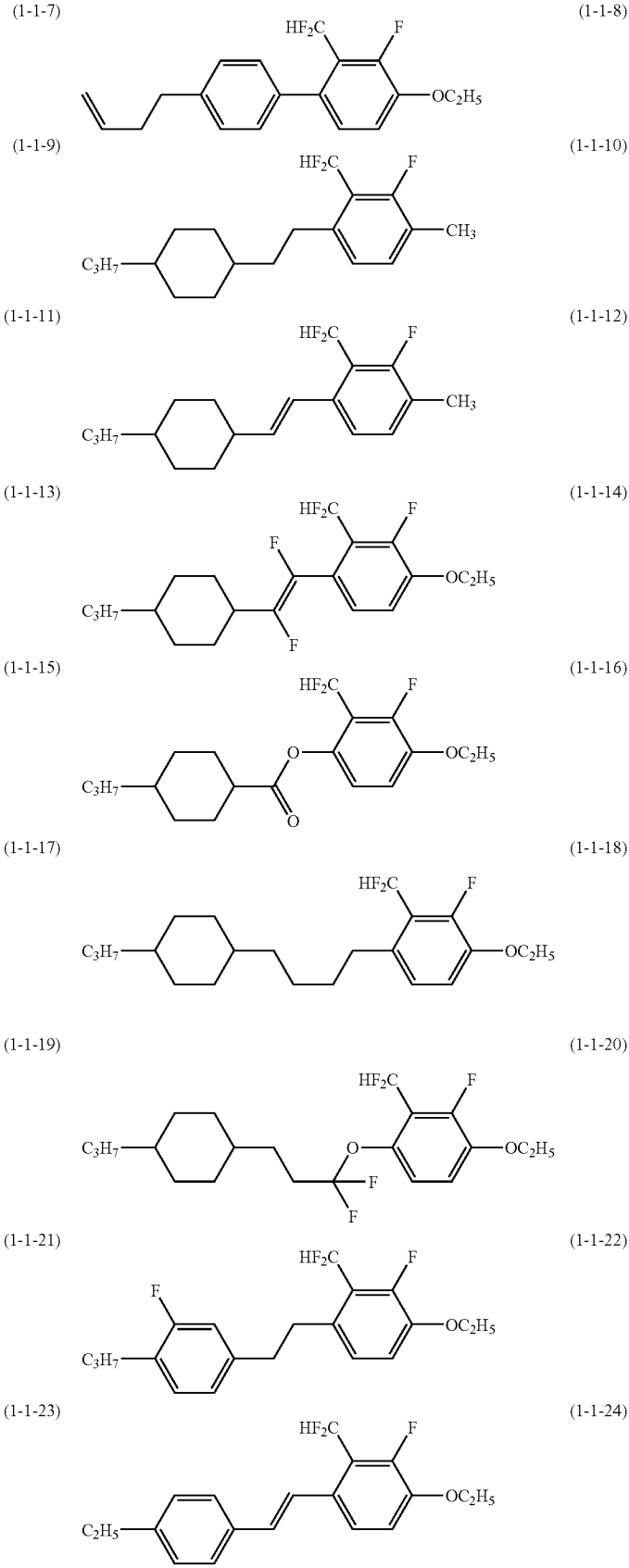

-continued
(1-1-25) 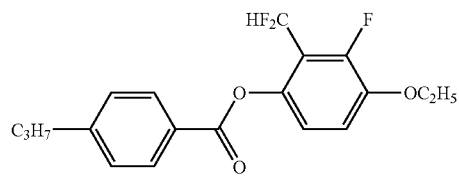
(1-1-26) 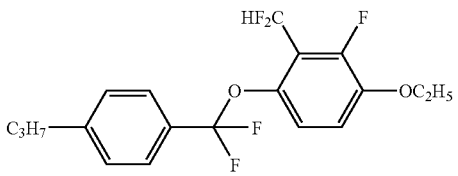
(1-1-27) 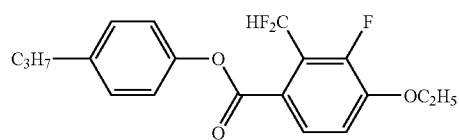
(1-1-28) 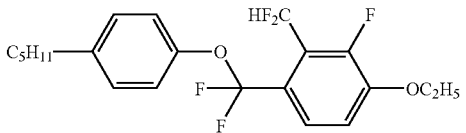
(1-1-29) 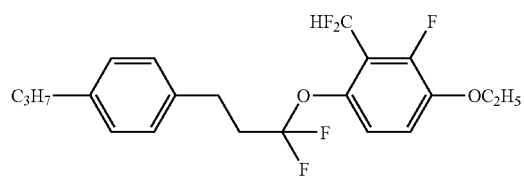
(1-1-30) 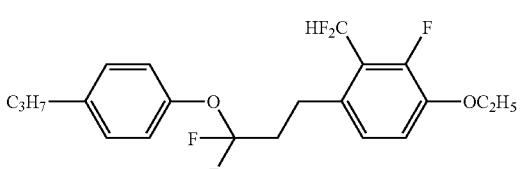
(1-2-1) 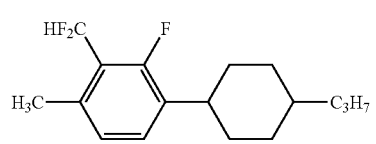
(1-2-2) 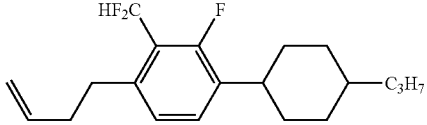
(1-2-3) 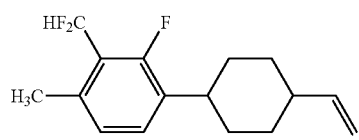
(1-2-4) 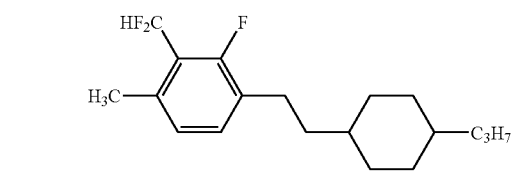
(1-2-5) 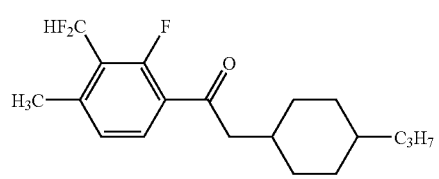
(1-2-6) 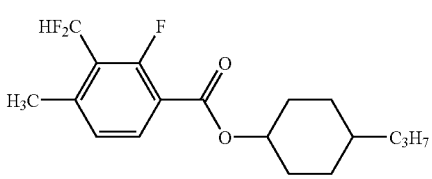
(1-2-7) 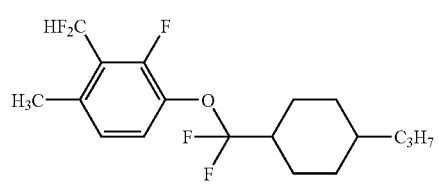
(1-2-8) 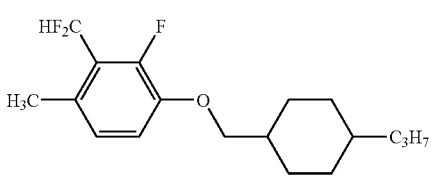
(1-2-9) 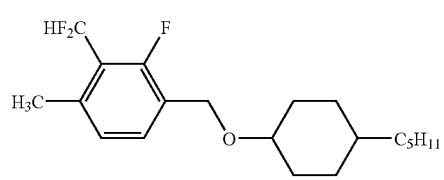
(1-2-10) 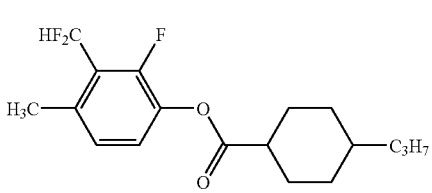
(1-2-11) 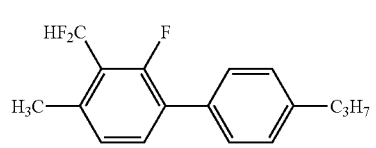
(1-2-12) 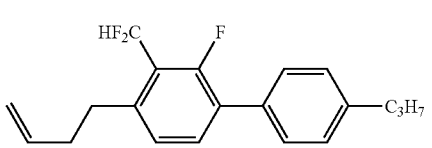

-continued (1-2-13) (1-2-14) (1-2-15) (1-2-16) (1-2-17) (1-2-18) (1-2-19) (1-2-20) (1-2-21) (1-2-22) (1-2-23) (1-2-24)

(1-3-1) (1-3-2) (1-3-3) (1-3-4) (1-3-5) (1-3-6)

C 82.2 Iso
$T_{NI}$: 49.3° C. Δε: -5.90 Δn: 0.124

-continued
(1-3-7)
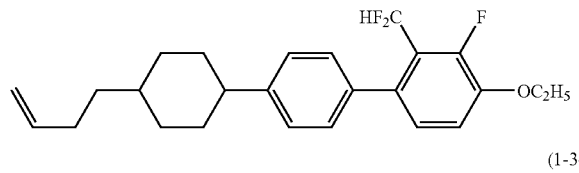
(1-3-8)
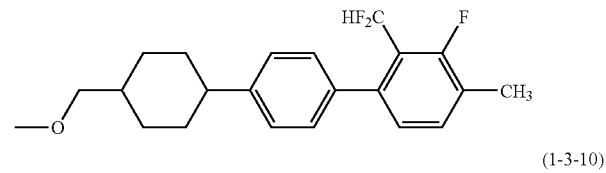
(1-3-9)
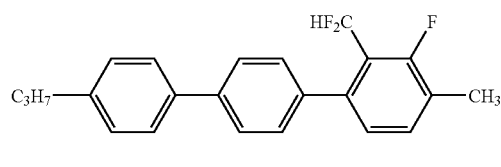
(1-3-10)
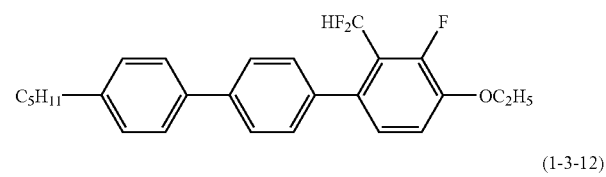
(1-3-11)
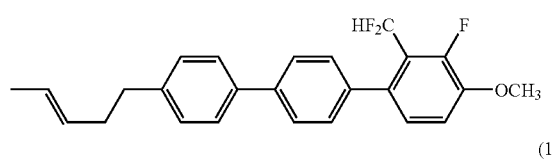
(1-3-12)
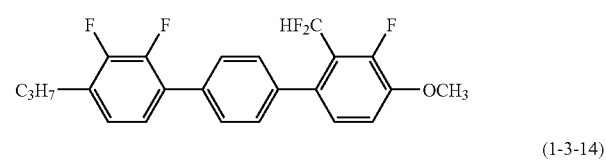
(1-3-13)
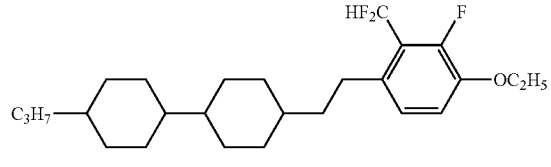
(1-3-14)
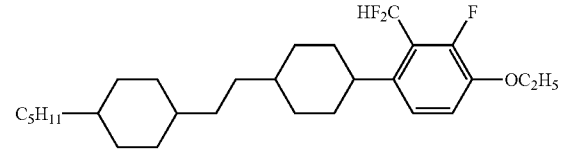
C 76.6 (SmA 49.1) N 120.4 Iso
$T_{NI}$: 107.3 °C. Δε: -4.18 Δn: 0.084
(1-3-15)
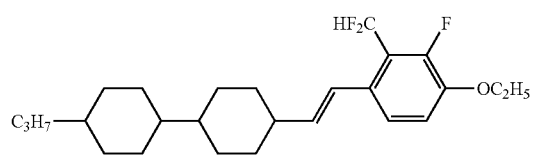
(1-3-16)
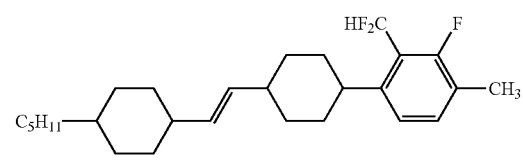
C 69.0 N 168.7 Iso
$T_{NI}$: 139.9 °C. Δε: -4.23 Δn: 0.126
(1-3-17)
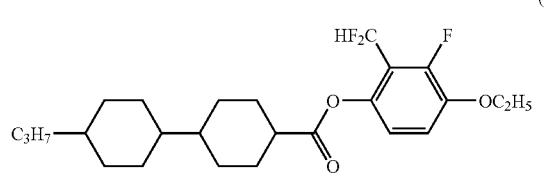
(1-3-18)
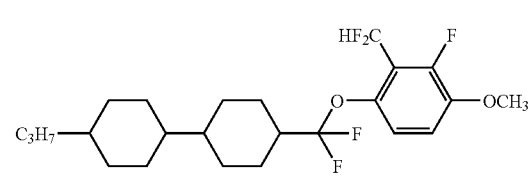
(1-3-19)
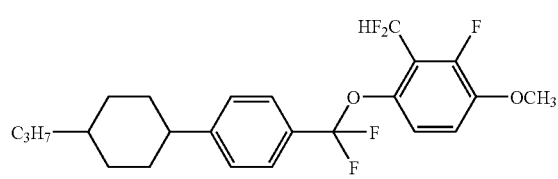
(1-3-20)
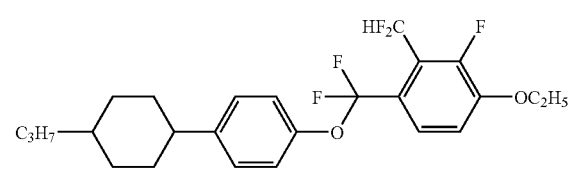
(1-3-21)
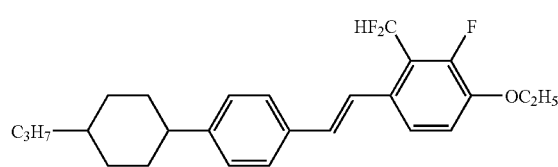
(1-3-22)
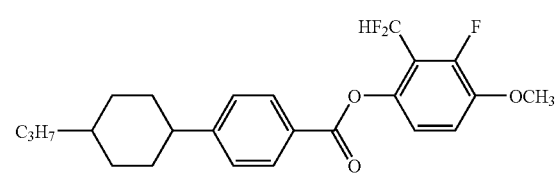

-continued
(1-3-23)
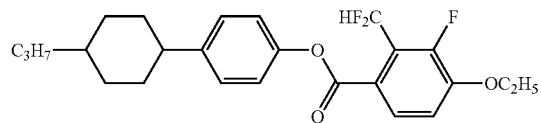
(1-3-24)
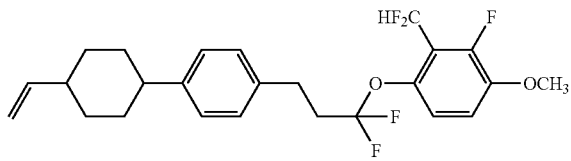
(1-3-25)
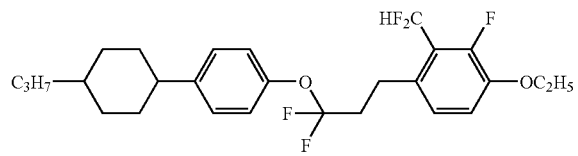
(1-3-26)
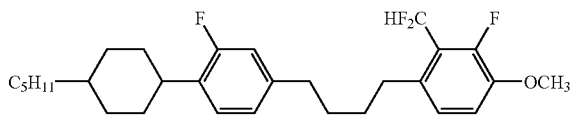
(1-3-27)
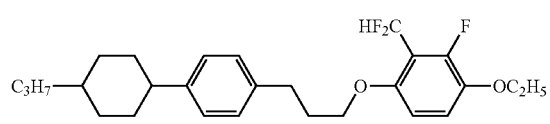
(1-3-28)
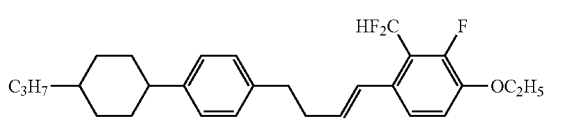
(1-3-29)
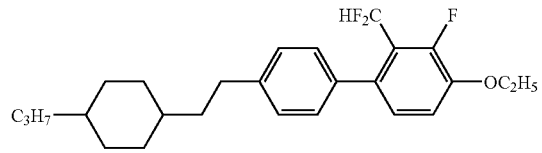
(1-3-30)
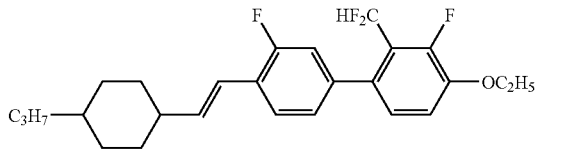
(1-3-31)
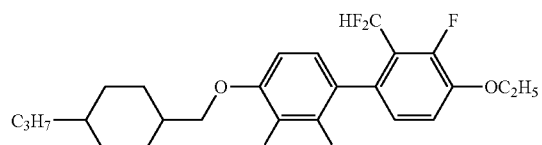
(1-3-32)
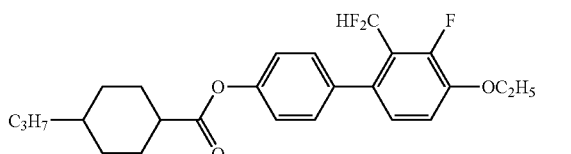
(1-3-33)
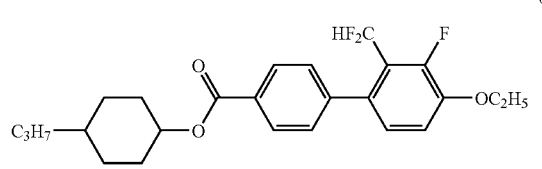
(1-3-34)
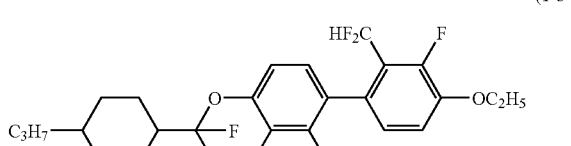
(1-3-35)
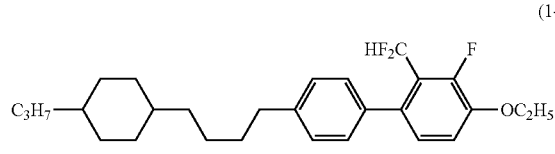
(1-3-36)
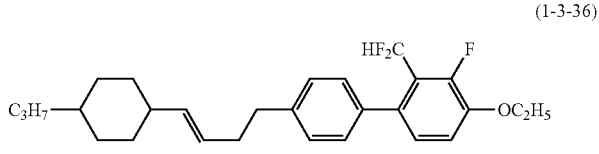
(1-3-37)
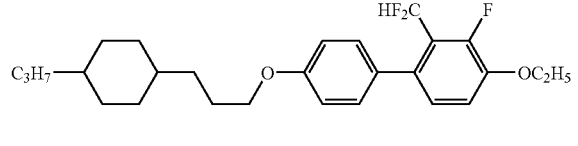
(1-3-38)
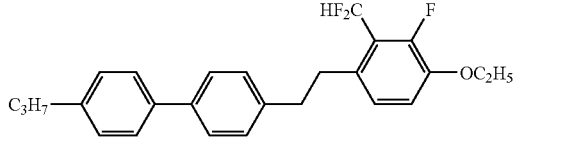
(1-3-39)
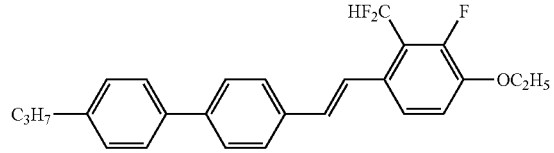
(1-3-40)
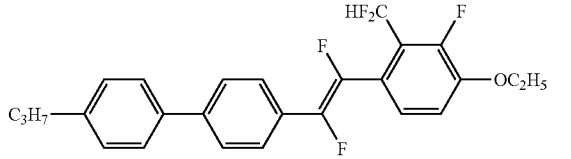

-continued
(1-3-41)
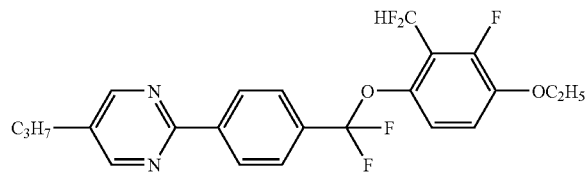
(1-3-42)
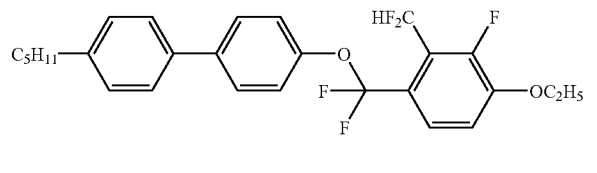
(1-3-43)
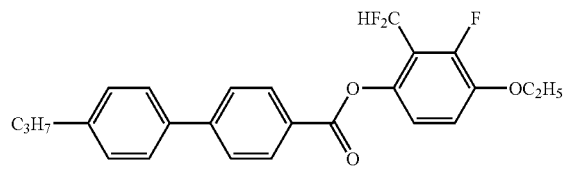
(1-3-44)
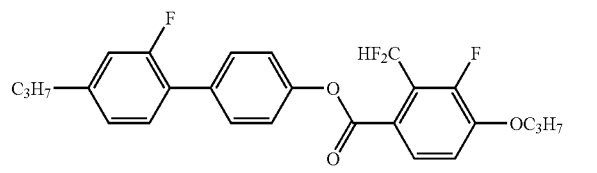
(1-3-45)
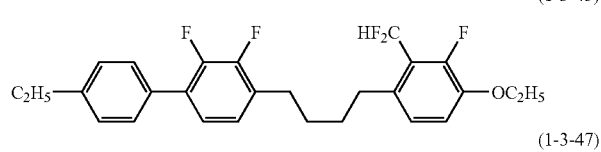
(1-3-46)
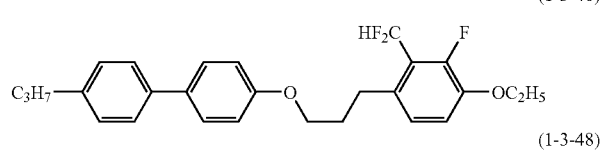
(1-3-47)
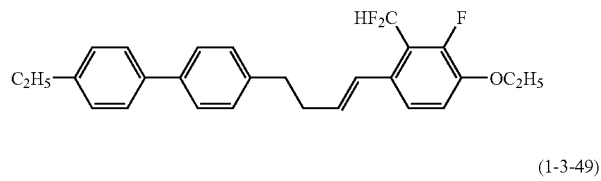
(1-3-48)
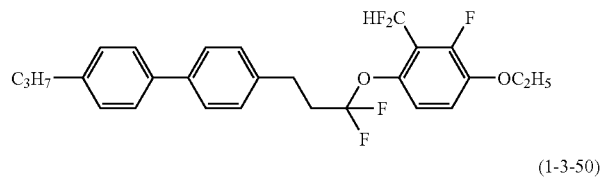
(1-3-49)
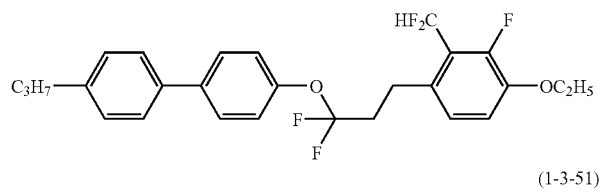
(1-3-50)
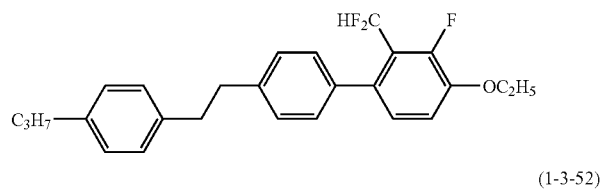
(1-3-51)
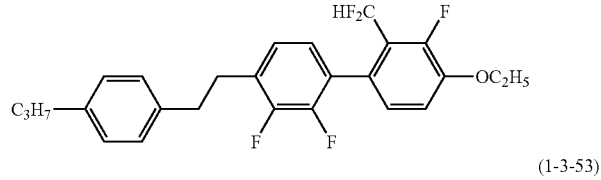
(1-3-52)
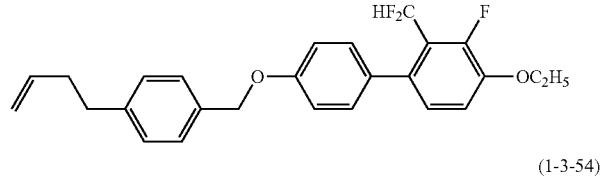
(1-3-53)
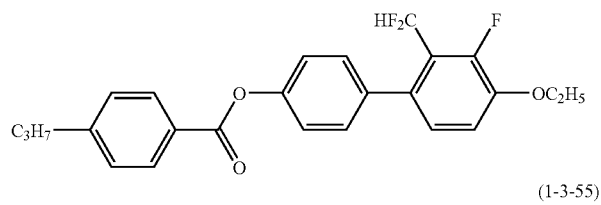
(1-3-54)
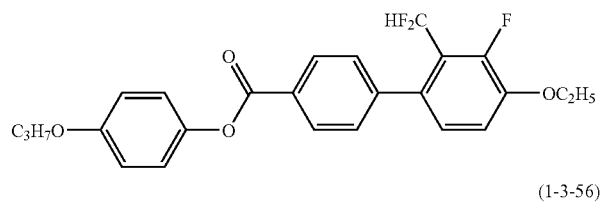
(1-3-55)
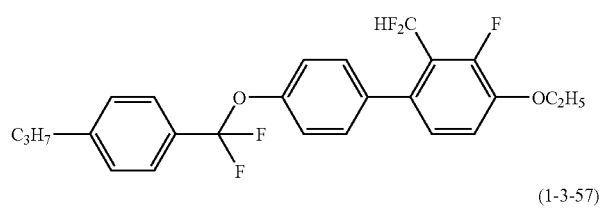
(1-3-56)
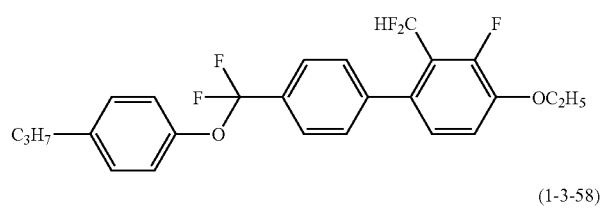
(1-3-57)
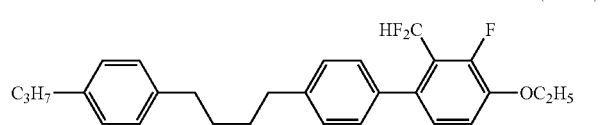
(1-3-58)
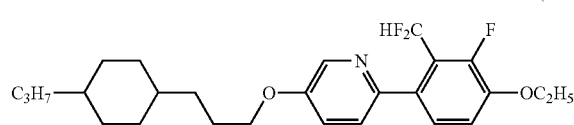

(1-3-59) 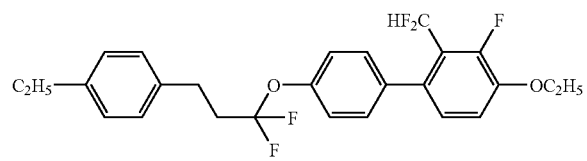
(1-3-60) 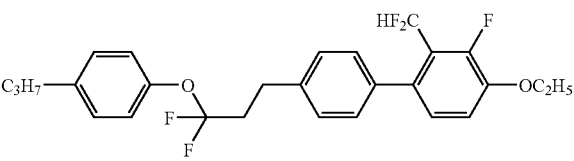
(1-3-61) 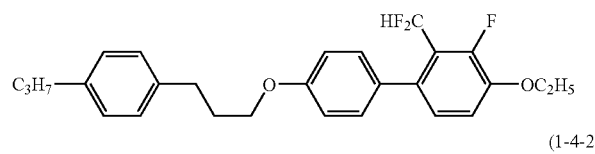
(1-4-1) 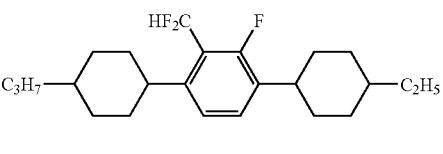
(1-4-2) 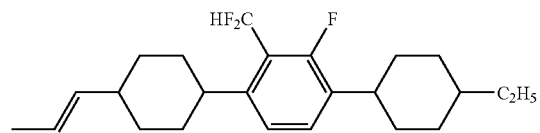
(1-4-3) 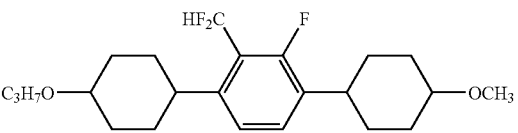
(1-4-4) 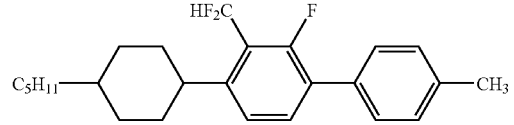
(1-4-5) 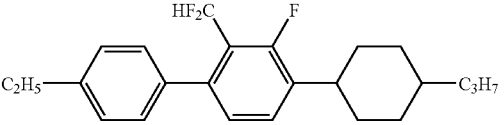
C 58.6 Iso
$T_{NI}$: -8.1° C. $\Delta\epsilon$: -2.8 $\Delta n$: 0.087
(1-4-6) 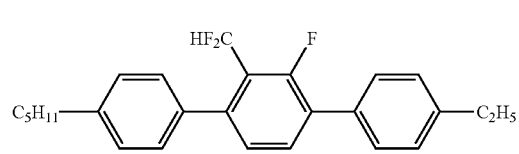
(1-4-7) 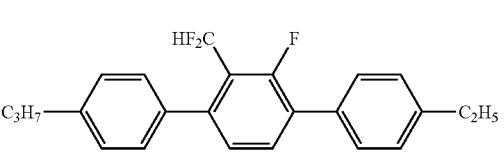
C 36.1 Iso
$T_{NI}$: -13.4° C. $\Delta\epsilon$: -1.9 $\Delta n$: 0.160
(1-4-8) 
(1-4-9) 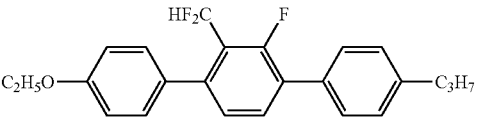
(1-4-10) 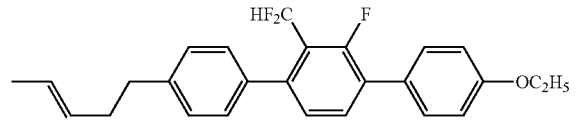
(1-4-11) 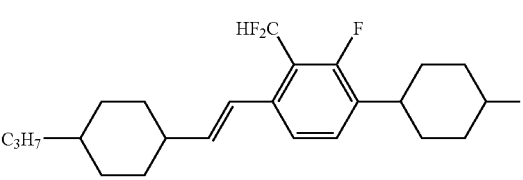
(1-4-12) 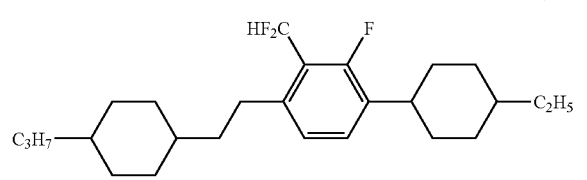
(1-4-13) 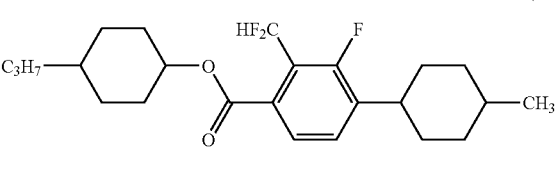
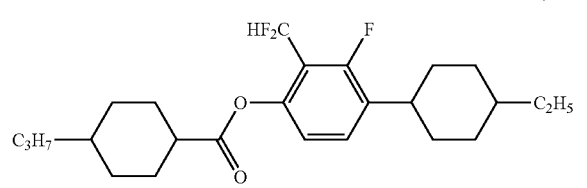

-continued
(1-4-14)
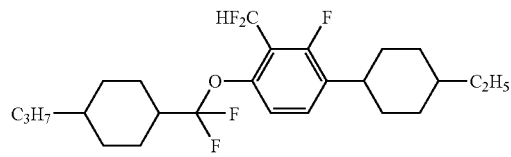
(1-4-15)
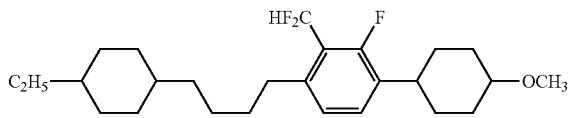
(1-4-16)
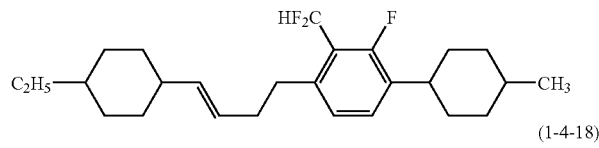
(1-4-17)
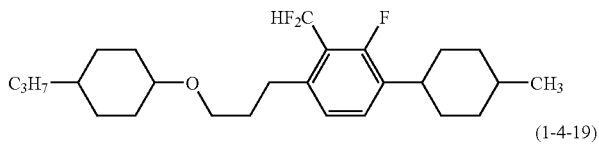
(1-4-18)
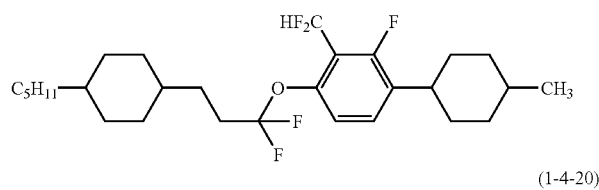
(1-4-19)
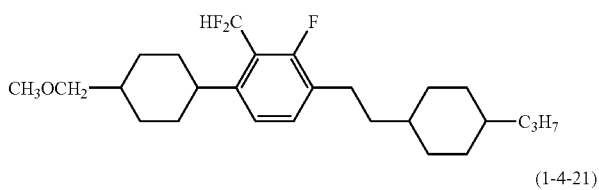
(1-4-20)
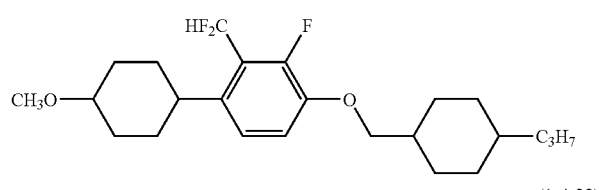
(1-4-21)
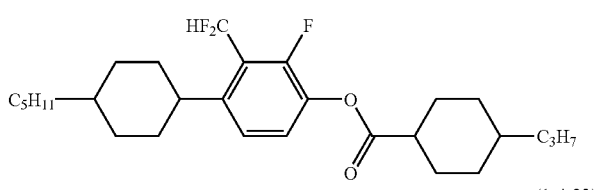
(1-4-22)
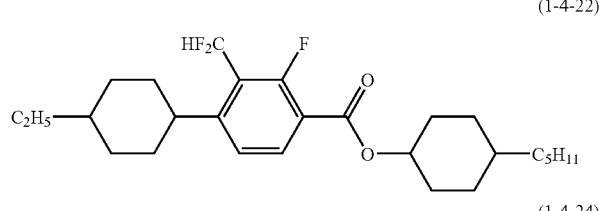
(1-4-23)
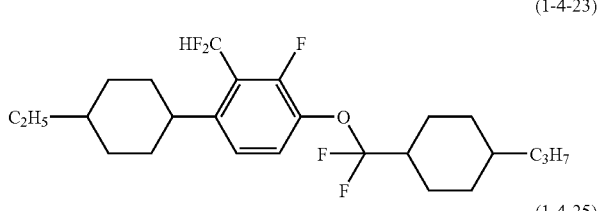
(1-4-24)
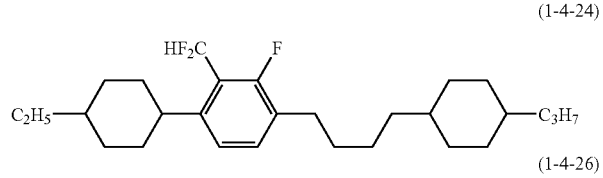
(1-4-25)
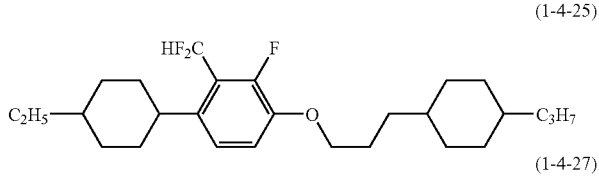
(1-4-26)
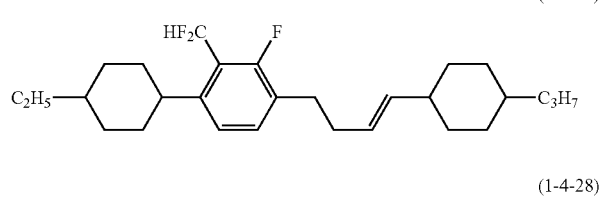
(1-4-27)
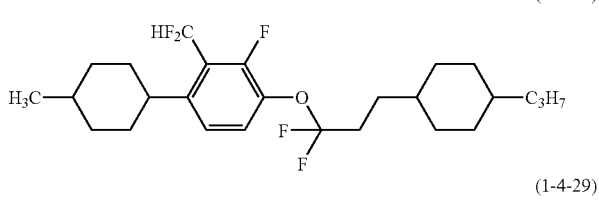
(1-4-28)
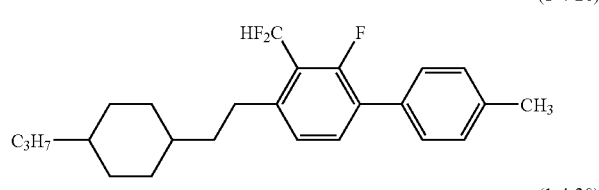
(1-4-29)
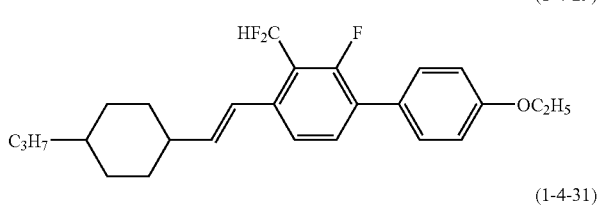
(1-4-30)
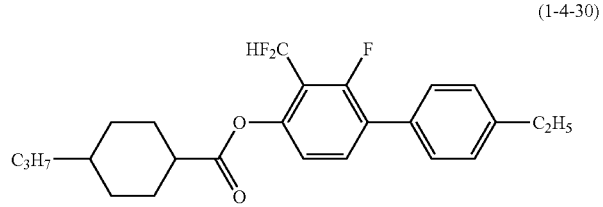

-continued

-continued
(1-4-48)
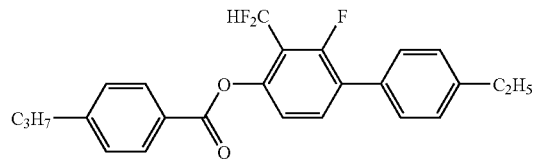
(1-4-49)
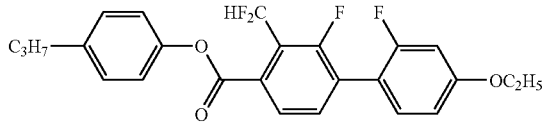
(1-4-50)
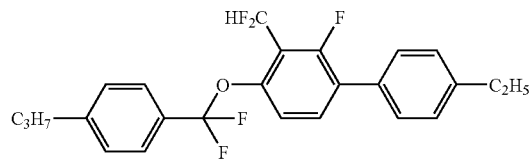
(1-4-51)
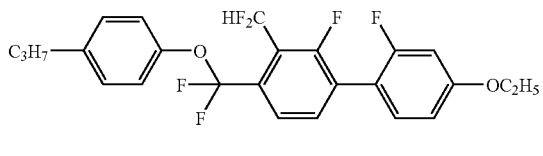
(1-4-52)
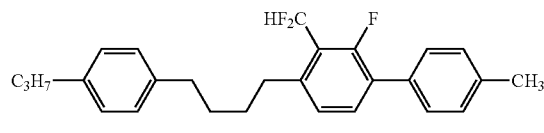
(1-4-53)
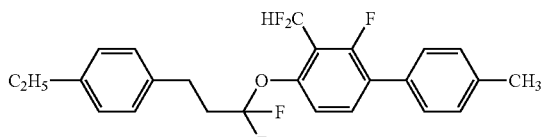
(1-4-54)
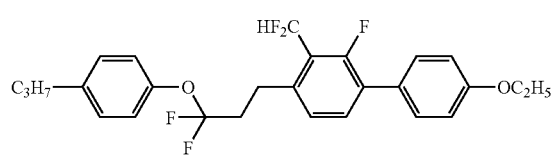
(1-4-55)
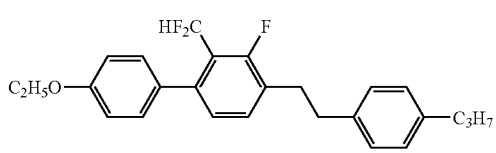
(1-4-56)
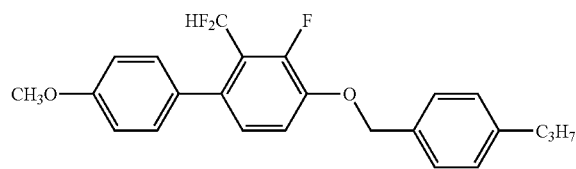
(1-4-57)
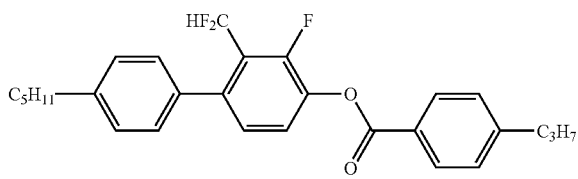
(1-4-58)
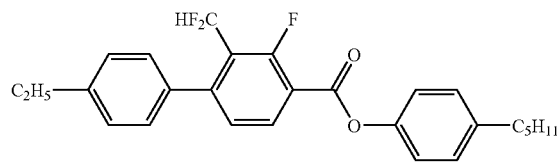
(1-4-59)
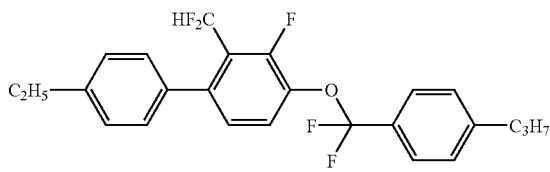
(1-4-60)
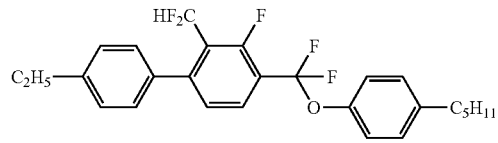
(1-4-61)
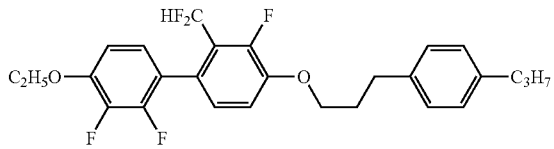
(1-4-62)
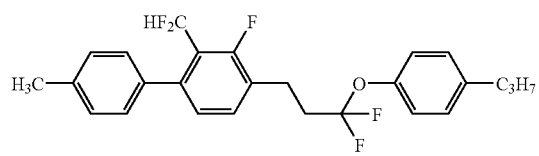
(1-4-63)
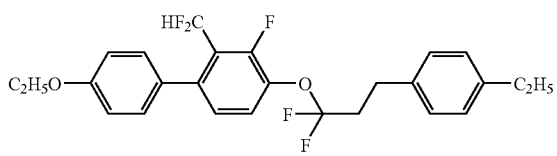

-continued
(1-4-64)
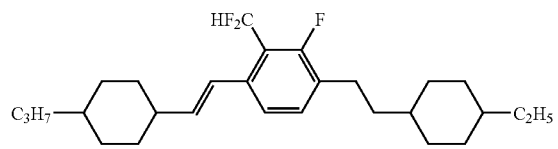
(1-4-65)
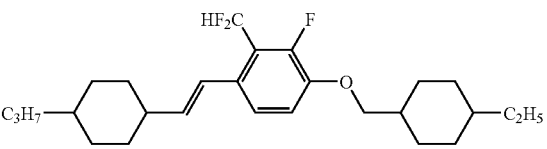
(1-4-66)
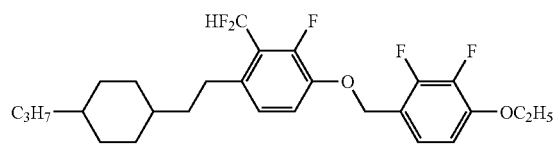
(1-4-67)
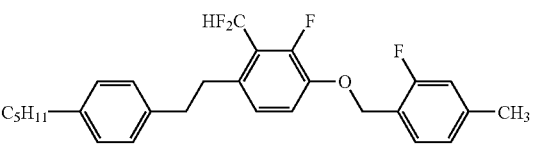
(1-5-1)
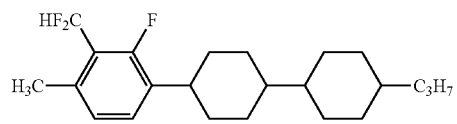
(1-5-2)
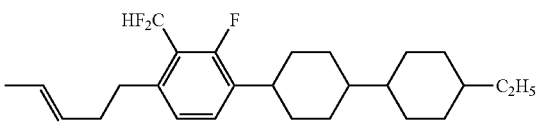
(1-5-3)
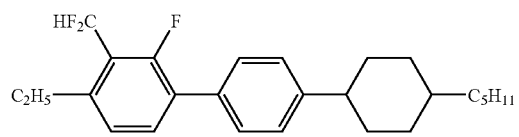
(1-5-4)
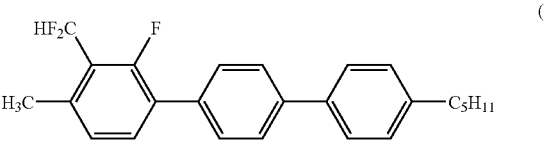
(1-5-5)
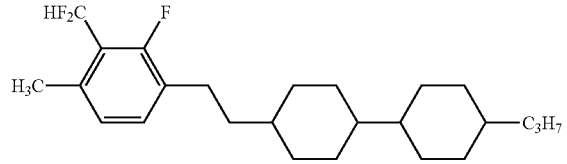
(1-5-6)
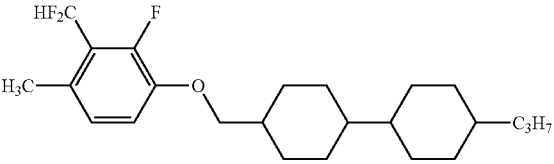
(1-5-7)
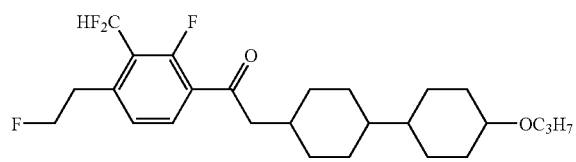
(1-5-8)
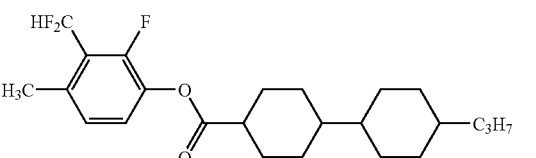
(1-5-9)
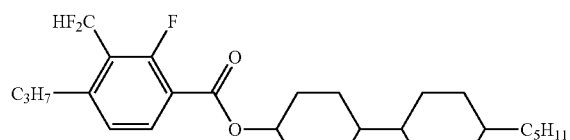
(1-5-10)
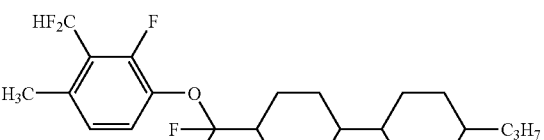
(1-5-11)
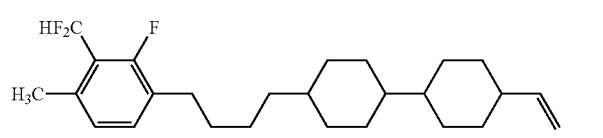
(1-5-12)
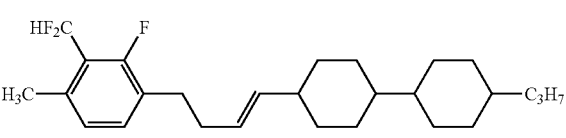
(1-5-13)
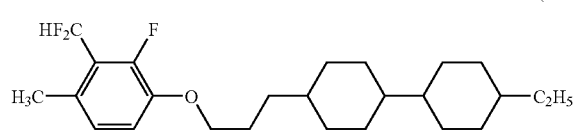
(1-5-14)
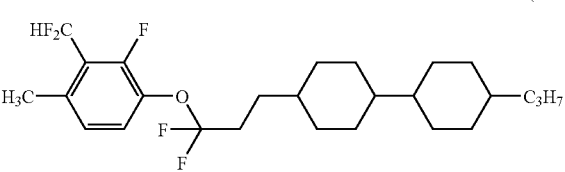

-continued
(1-5-15) 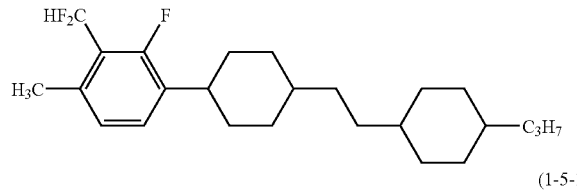
(1-5-16) 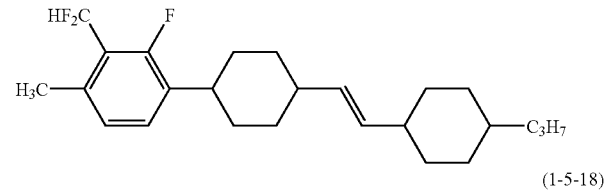
(1-5-17) 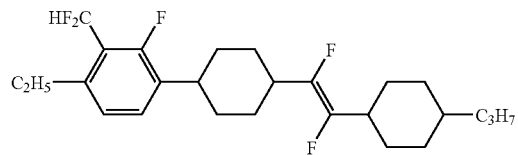
(1-5-18) 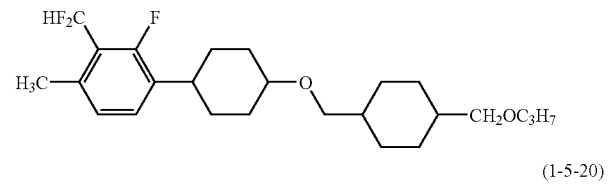
(1-5-19) 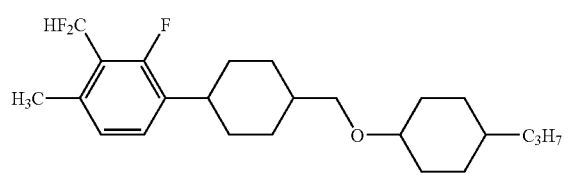
(1-5-20) 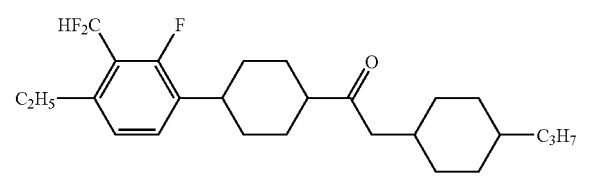
(1-5-21) 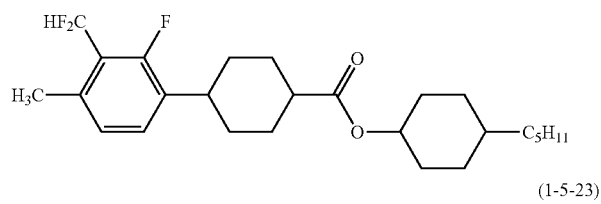
(1-5-22) 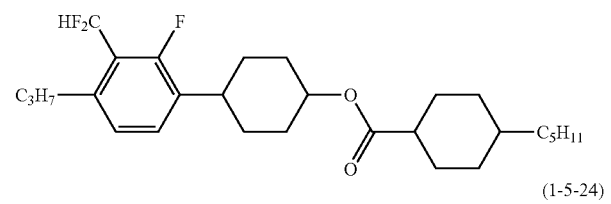
(1-5-23) 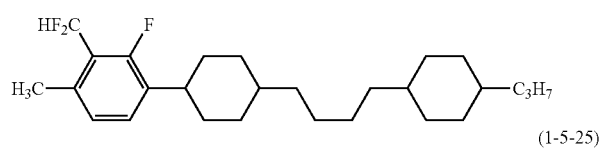
(1-5-24) 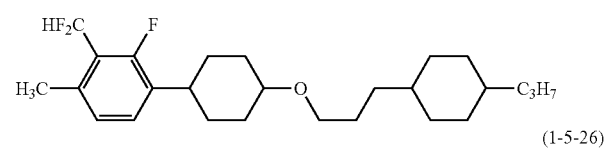
(1-5-25) 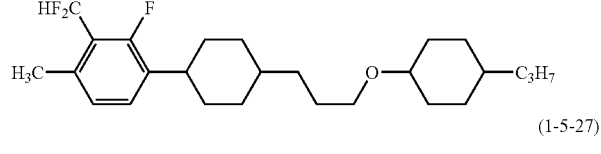
(1-5-26) 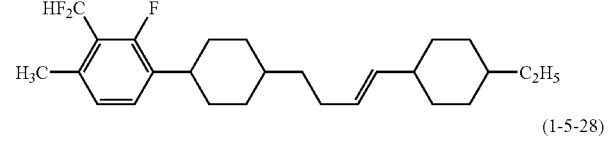
(1-5-27) 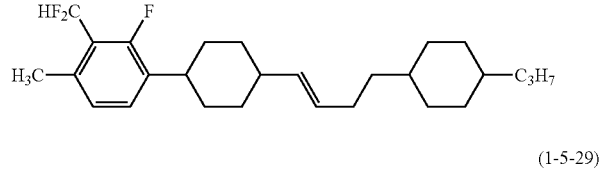
(1-5-28) 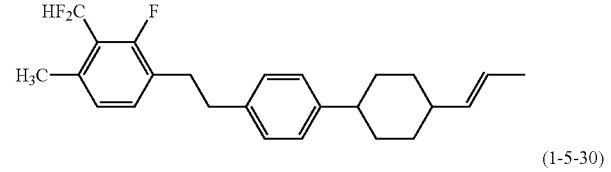
(1-5-29) 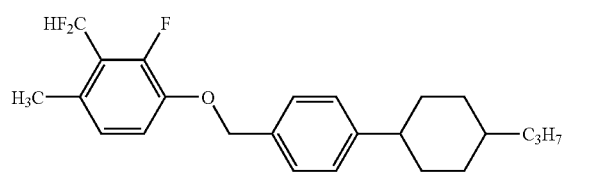
(1-5-30) 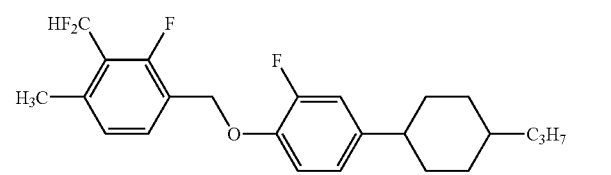
(1-5-31) 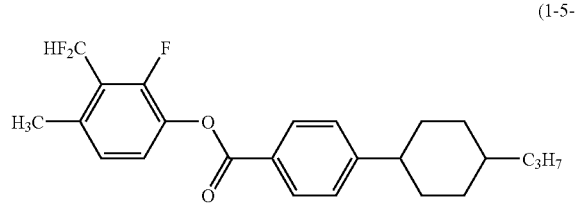
(1-5-32) 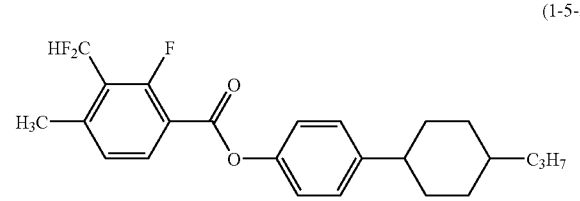

-continued
(1-5-33)
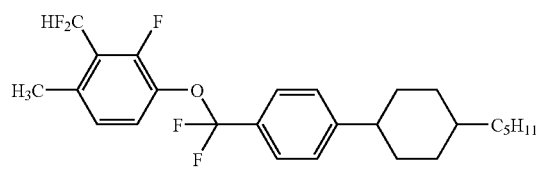
(1-5-34)
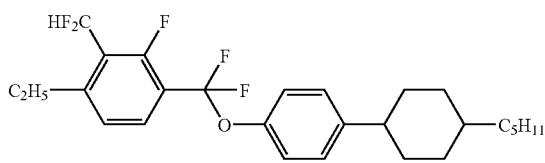
(1-5-35)
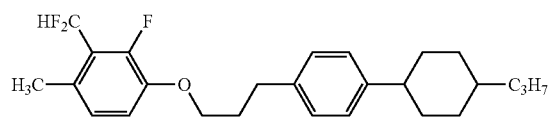
(1-5-36)
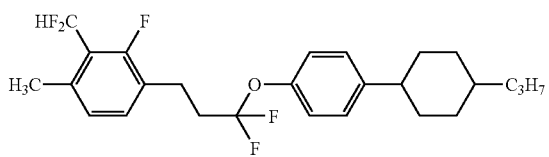
(1-5-37)
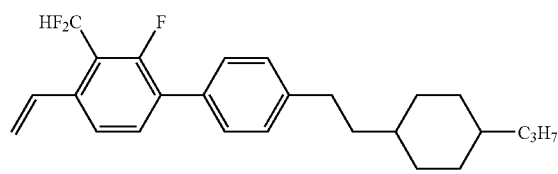
(1-5-38)
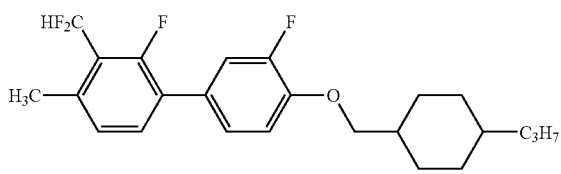
(1-5-39)
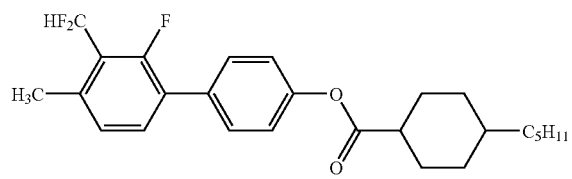
(1-5-40)
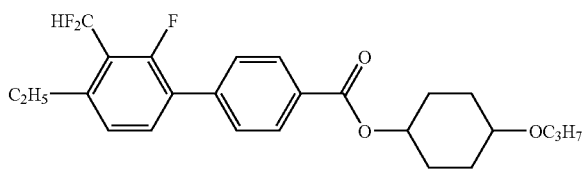
(1-5-41)
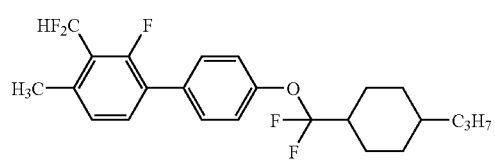
(1-5-42)
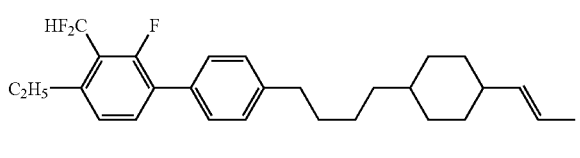
(1-5-43)
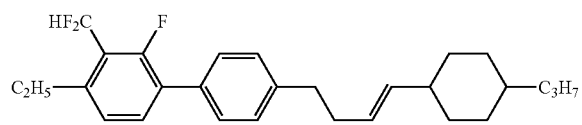
(1-5-44)
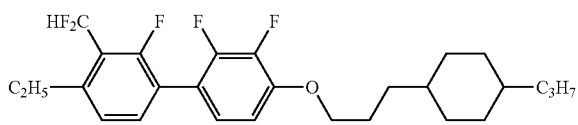
(1-5-45)
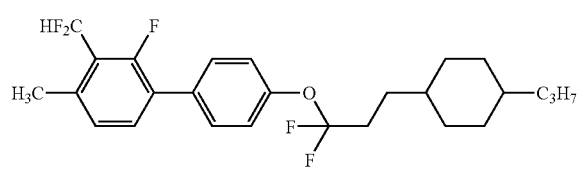
(1-5-46)
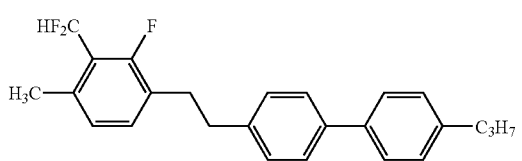
(1-5-47)
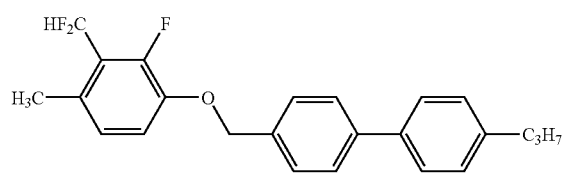
(1-5-48)
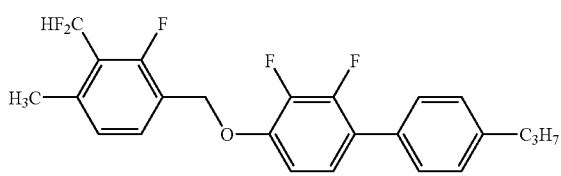

-continued (1-5-49)
(1-5-50)
(1-5-51)
(1-5-52)
(1-5-53)
(1-5-54)
(1-5-55)
(1-5-56)
(1-5-57)
(1-5-58)
(1-5-59)
(1-5-60)
(1-5-61)
(1-5-62)
(1-5-63)
(1-5-64)

-continued
(1-5-65)
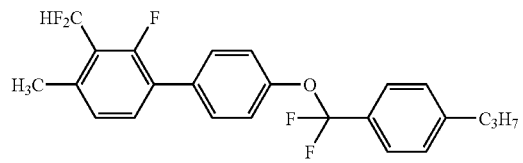
(1-5-66)
(1-5-67)
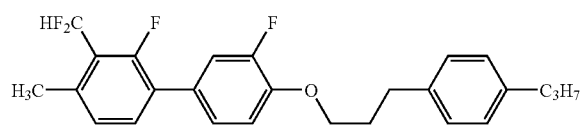
(1-5-68)
(1-5-69)
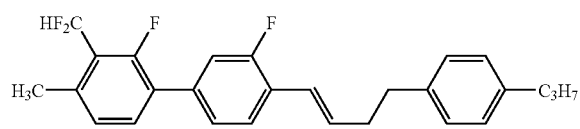
(1-5-70)
(1-5-71)
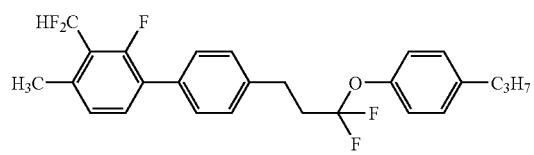
(1-5-72)
(1-6-1)
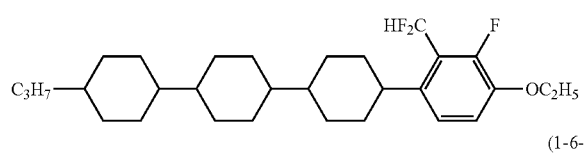
(1-6-2)
(1-6-3)
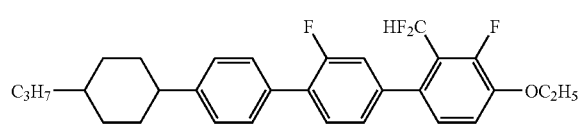
(1-6-4)
(1-6-5)
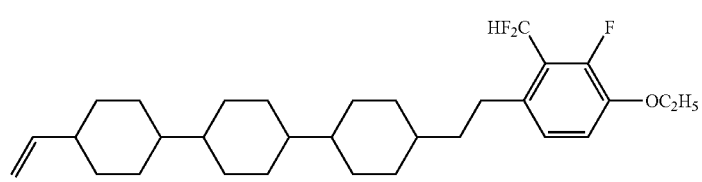
(1-6-6)
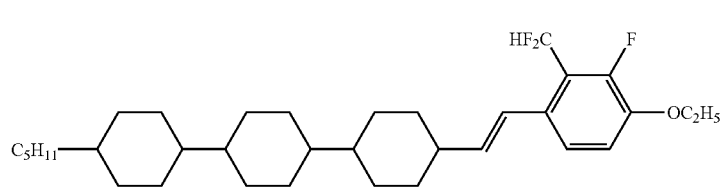
(1-6-7)
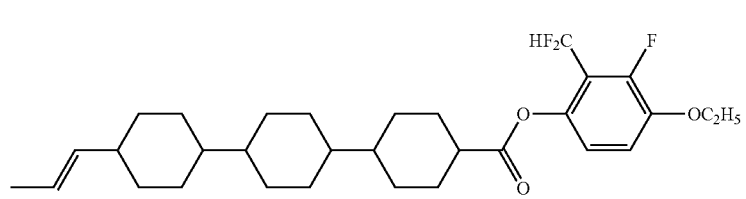

-continued
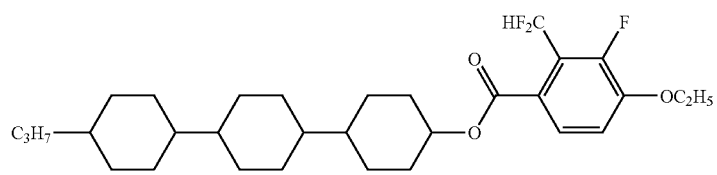
(1-6-8)
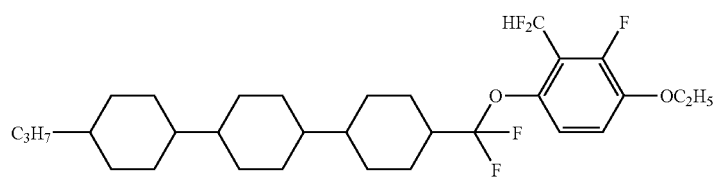
(1-6-9)
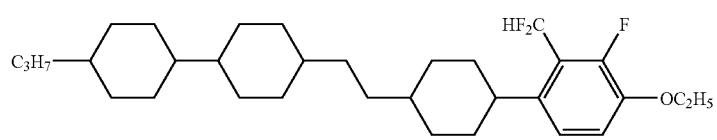
(1-6-10)
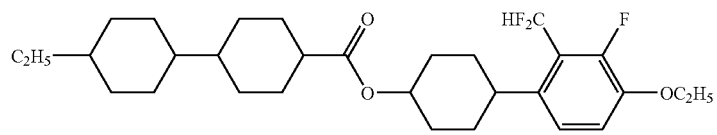
(1-6-11)
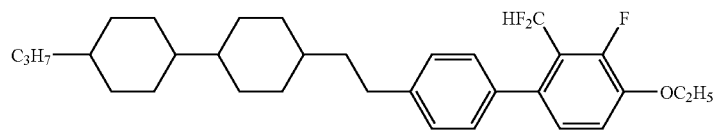
(1-6-12)
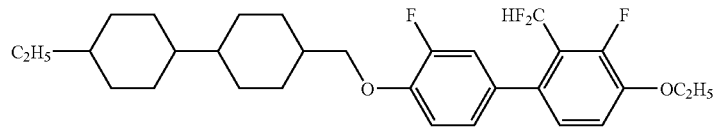
(1-6-13)
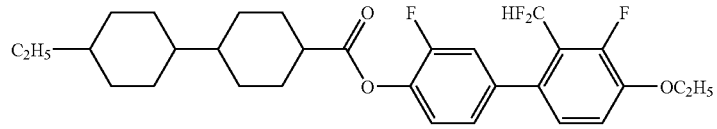
(1-6-14)
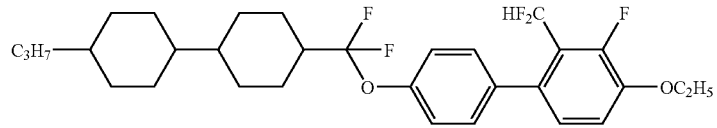
(1-6-15)
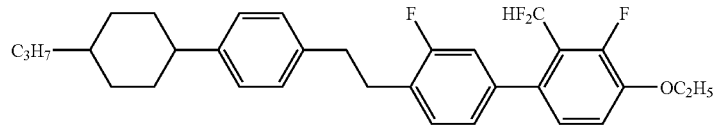
(1-6-16)
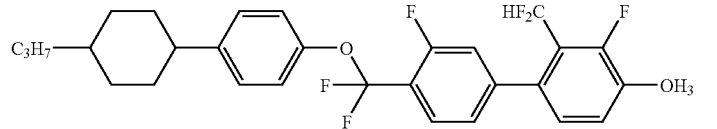
(1-6-17)
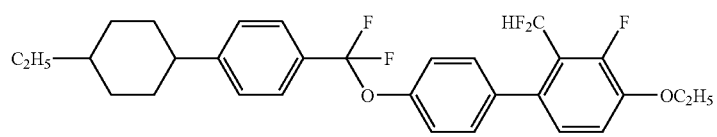
(1-6-18)

-continued
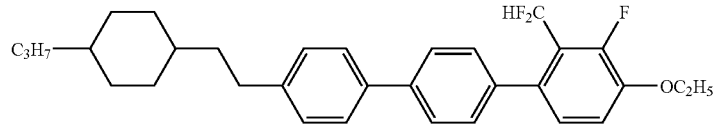
(1-6-19)
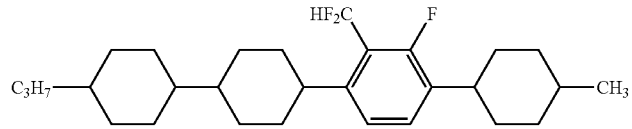
(1-7-1)
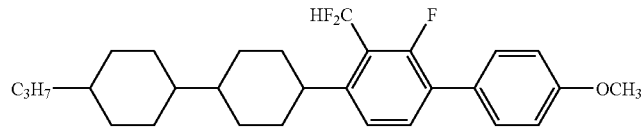
(1-7-2)
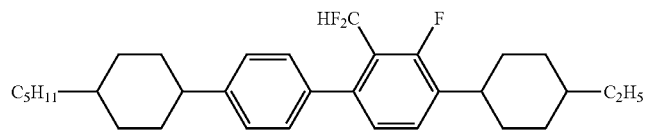
(1-7-3)
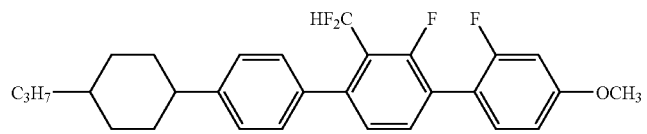
(1-7-4)
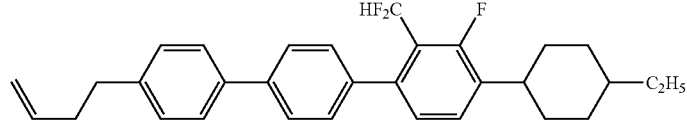
(1-7-5)
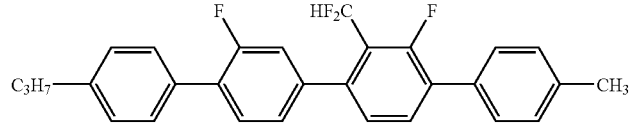
(1-7-6)
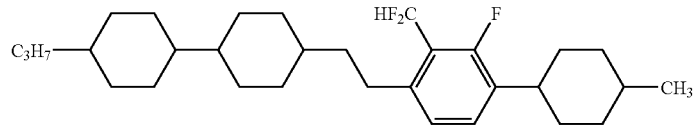
(1-7-7)
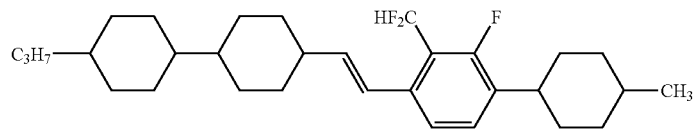
(1-7-8)
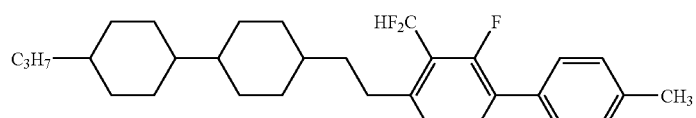
(1-7-9)
(1-7-10)

-continued
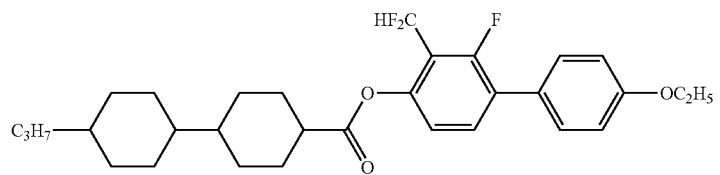
(1-7-11)
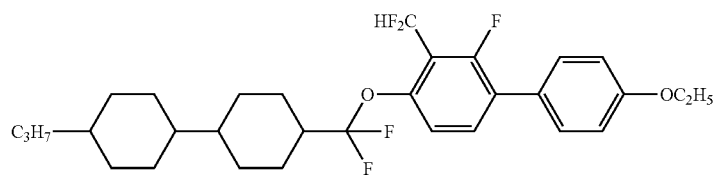
(1-7-12)
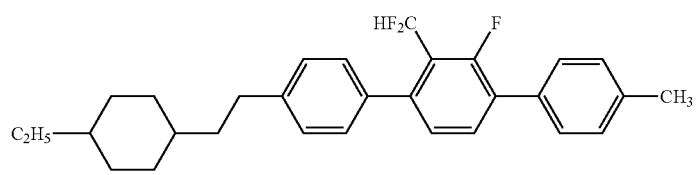
(1-7-13)
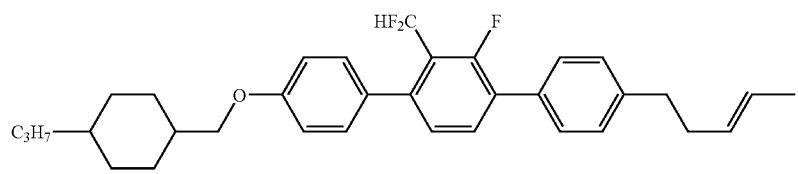
(1-7-14)
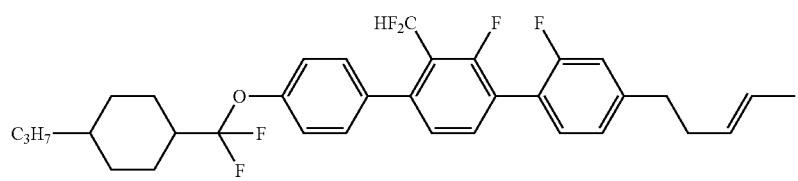
(1-7-15)
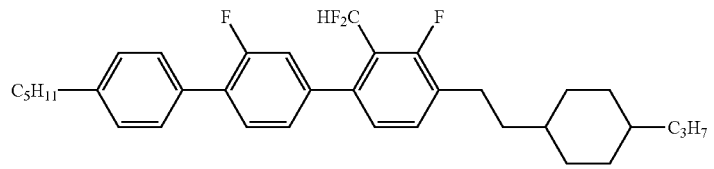
(1-7-16)
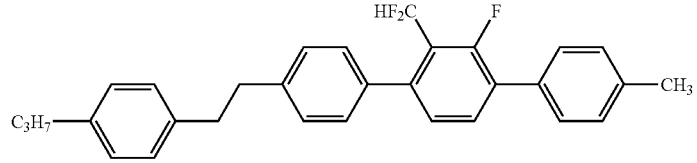
(1-7-17)
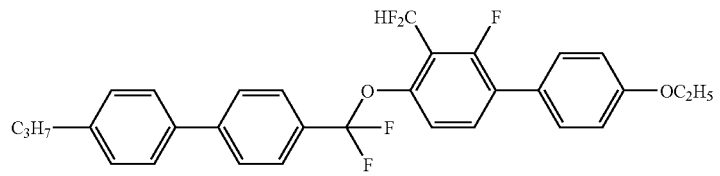
(1-7-18)
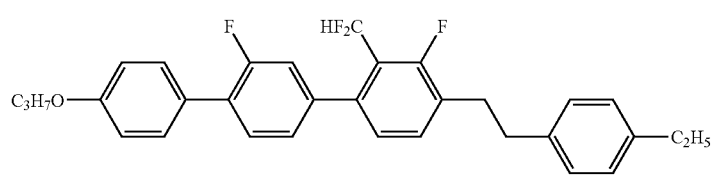
(1-7-19)

-continued
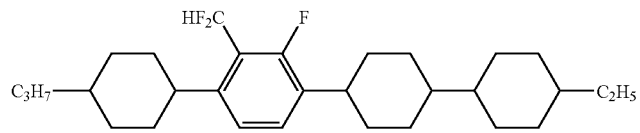
(1-8-1)
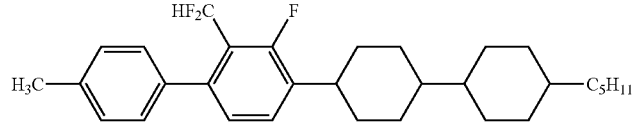
(1-8-2)
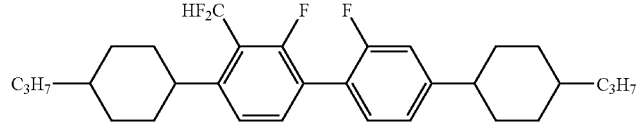
(1-8-3)
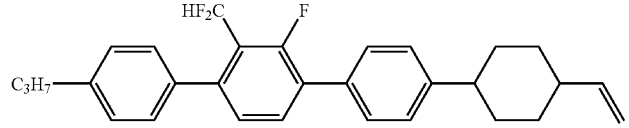
(1-8-4)
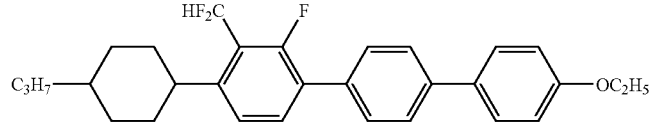
(1-8-5)
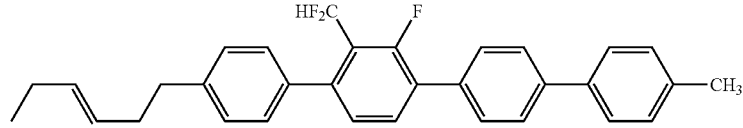
(1-8-6)
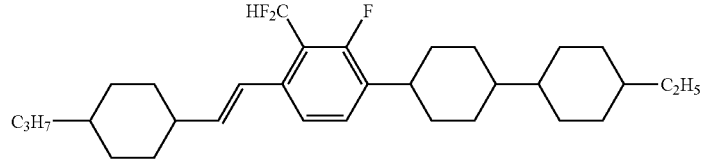
(1-8-7)
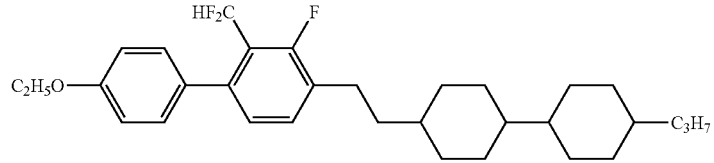
(1-8-8)
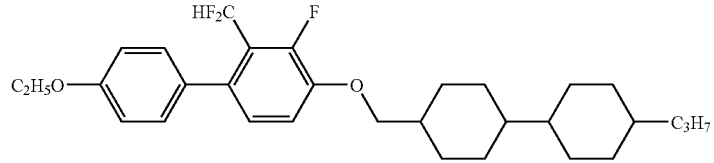
(1-8-9)
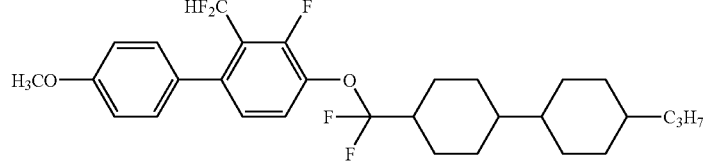
(1-8-10)

-continued
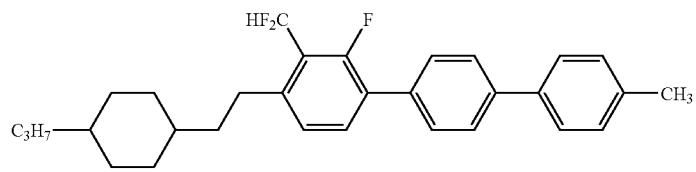
(1-8-11)
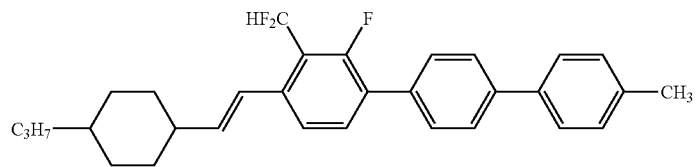
(1-8-12)
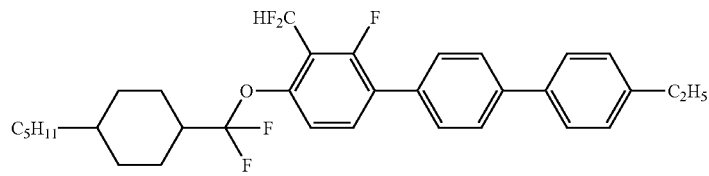
(1-8-13)
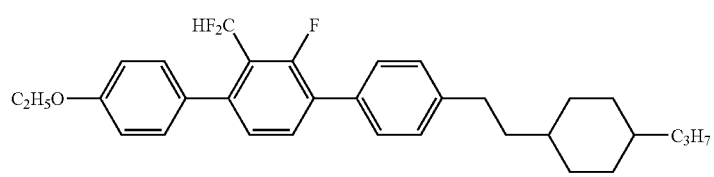
(1-8-14)
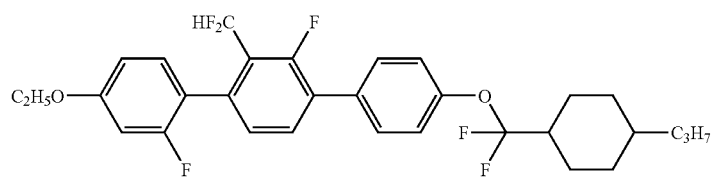
(1-8-15)
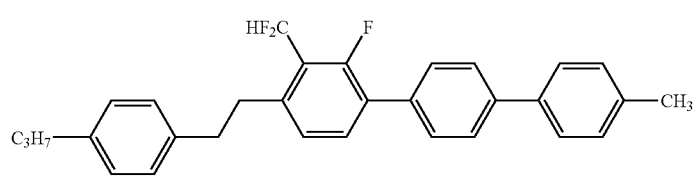
(1-8-16)
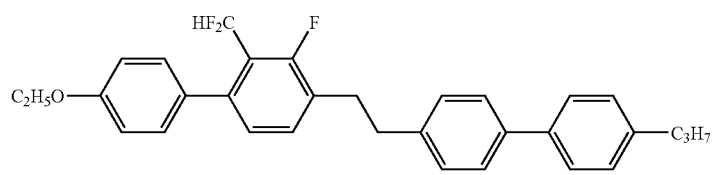
(1-8-17)
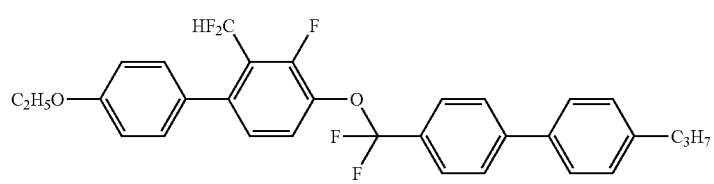
(1-8-18)
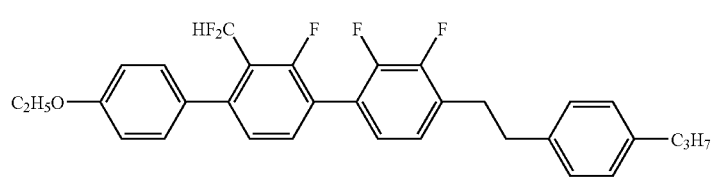
(1-8-19)

-continued
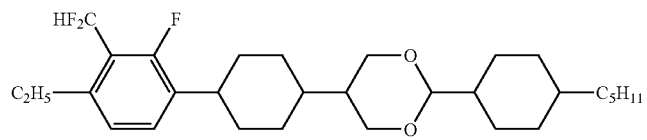
(1-9-1)
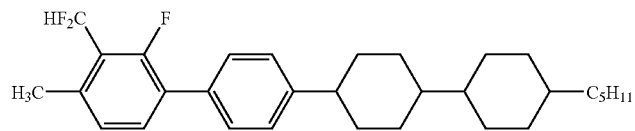
(1-9-2)
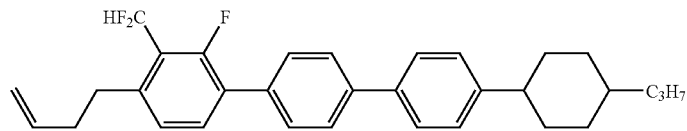
(1-9-3)
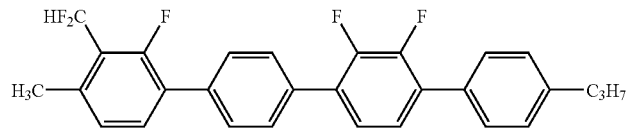
(1-9-4)
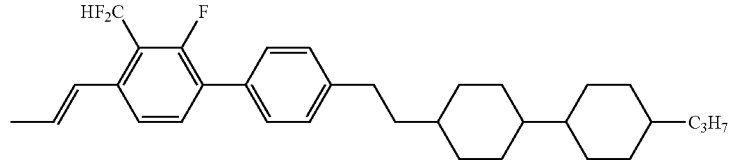
(1-9-5)
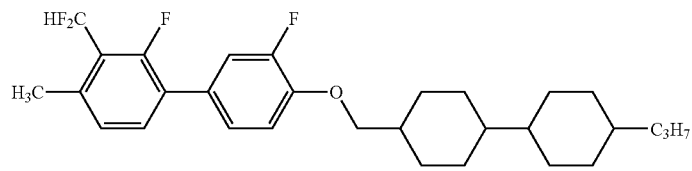
(1-9-6)
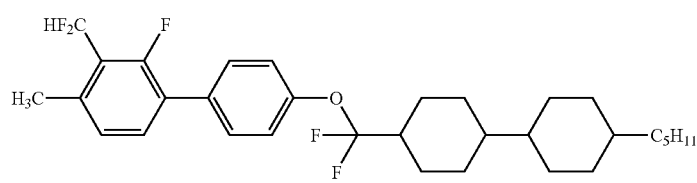
(1-9-7)
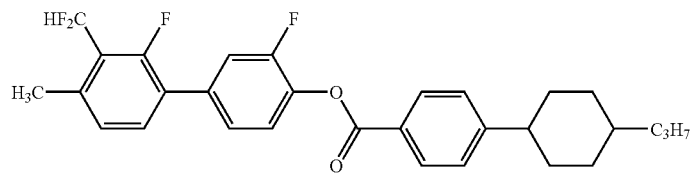
(1-9-8)
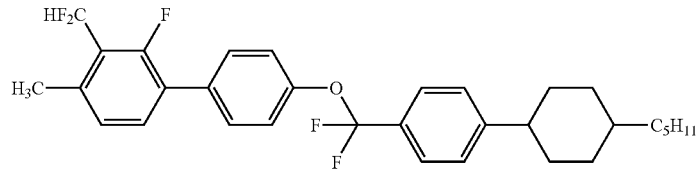
(1-9-9)
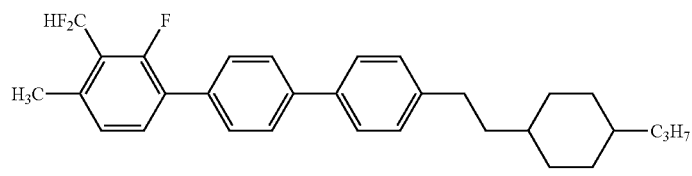
(1-9-10)

-continued
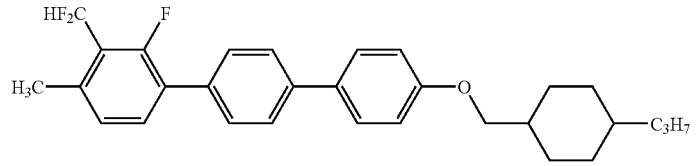
(1-9-11)
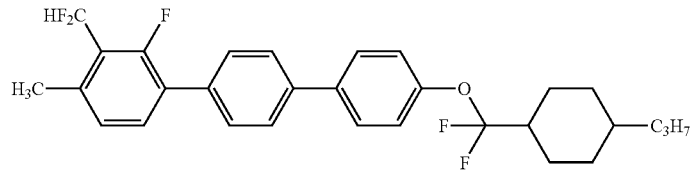
(1-9-12)
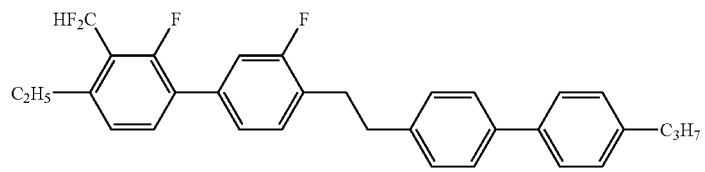
(1-9-13)
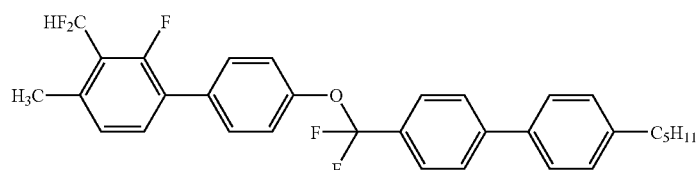
(1-9-14)
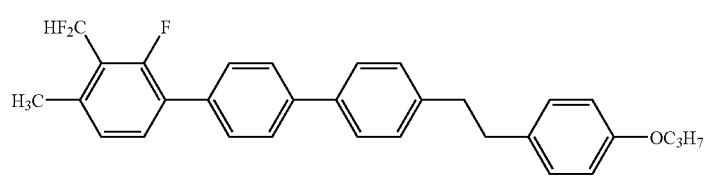
(1-9-15)
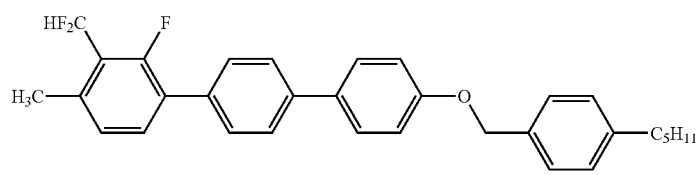
(1-19-16)
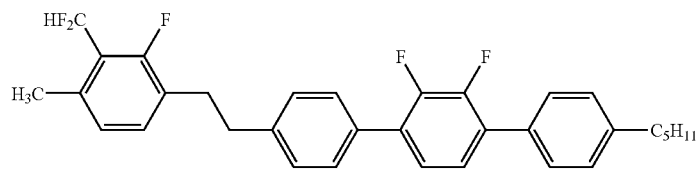
(1-9-17)
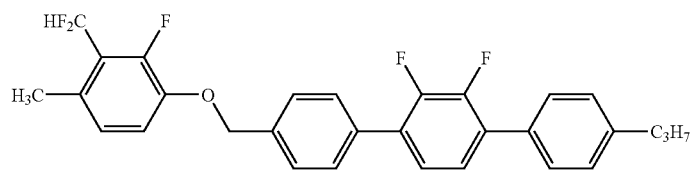
(1-9-18)
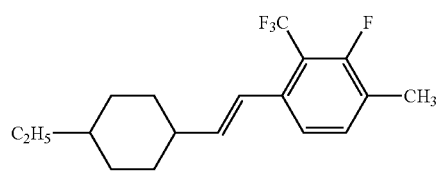
(2-1-1)
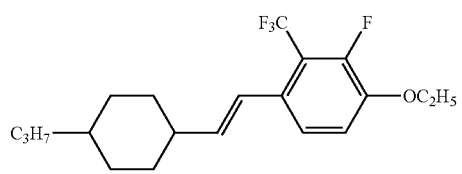
(2-1-2)

-continued
(2-1-3) 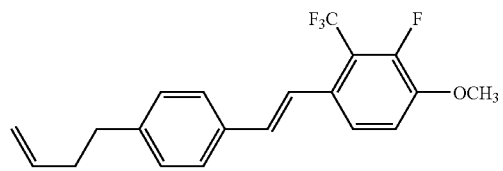
(2-1-4) 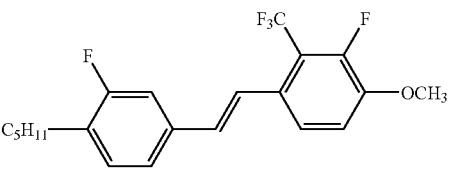
(2-2-1) 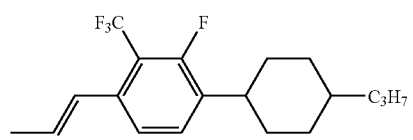
(2-2-2) 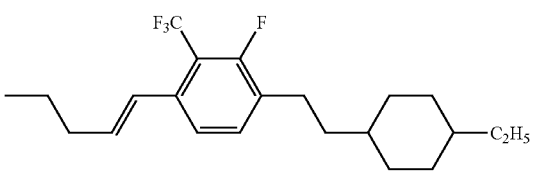
(2-2-3) 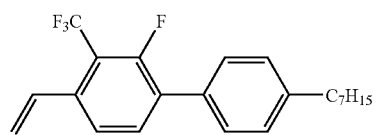
(2-3-1) 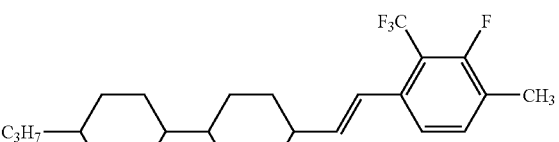
(2-3-2) 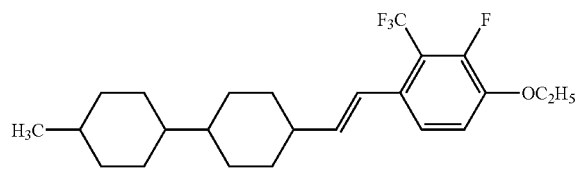
(2-3-3) 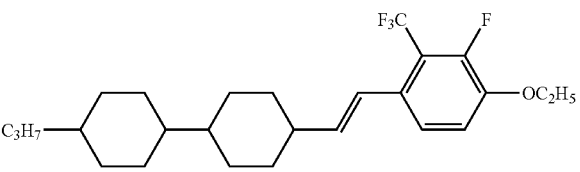
C 83.0 N 149.3I
T$_{NI}$: 132.6° C. Δε: -8.24 Δn: 0.114
(2-3-4) 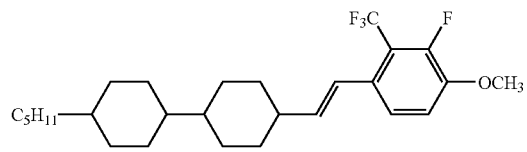
(2-3-5) 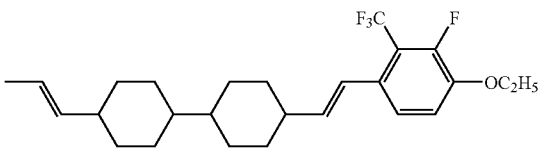
(2-3-6) 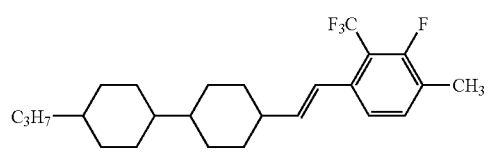
(2-3-7) 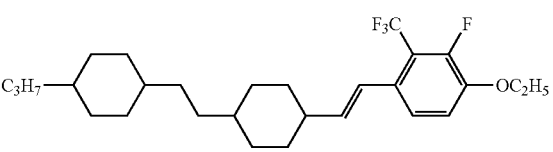
(2-3-8) 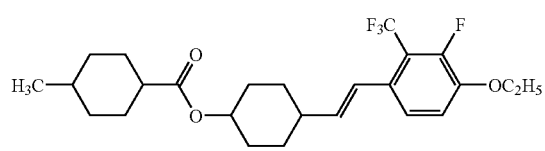
(2-3-9) 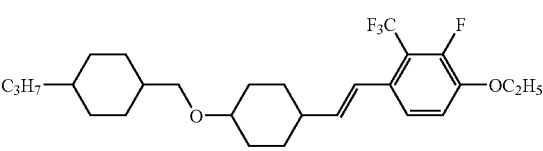
(2-4-1) 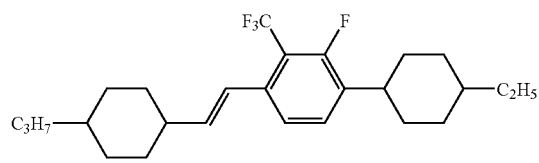
(2-4-2) 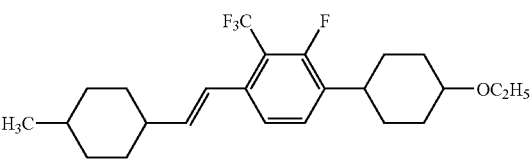

-continued
(2-4-3)
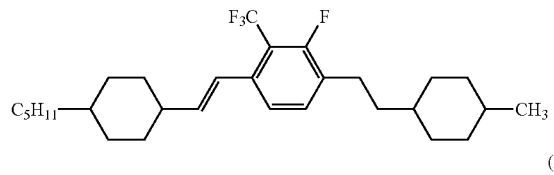
(2-4-4)
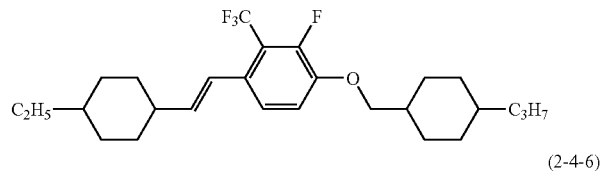
(2-4-5)
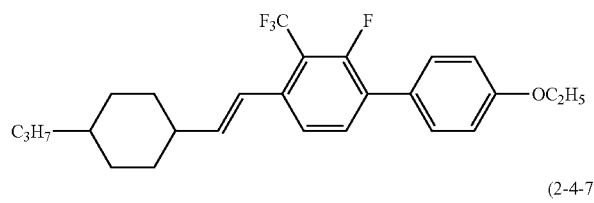
(2-4-6)
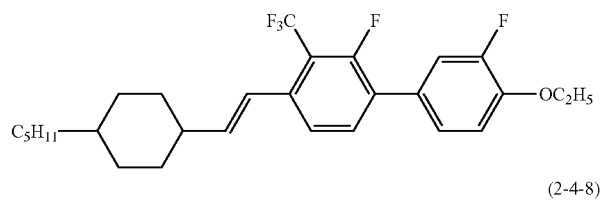
(2-4-7)
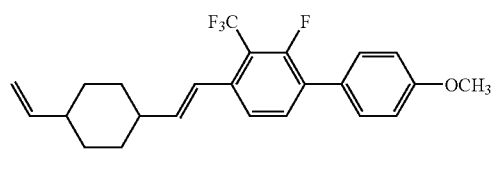
(2-4-8)
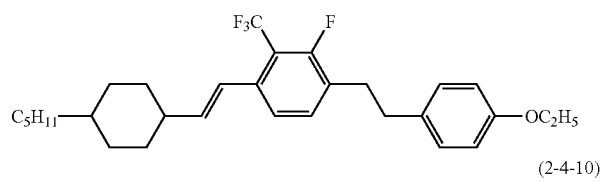
(2-4-9)
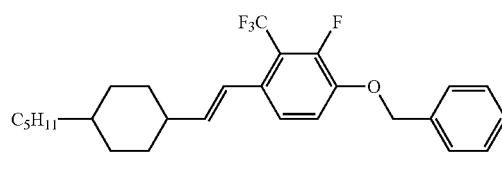
(2-4-10)
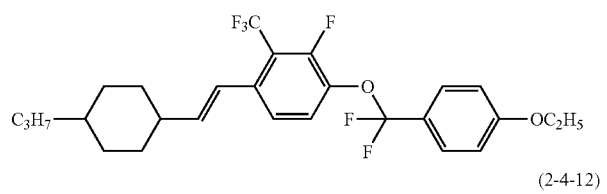
(2-4-11)
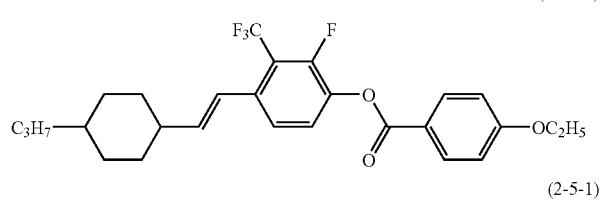
(2-4-12)
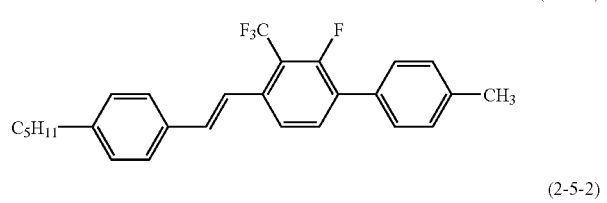
(2-5-1)
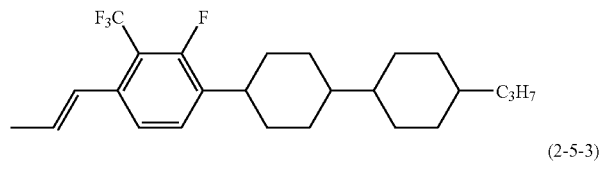
(2-5-2)
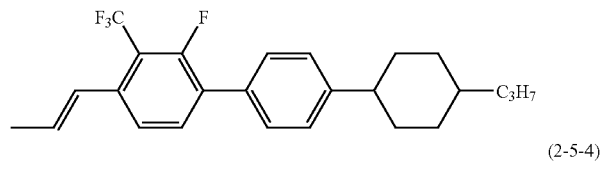
(2-5-3)
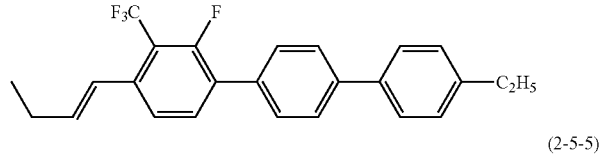
(2-5-4)
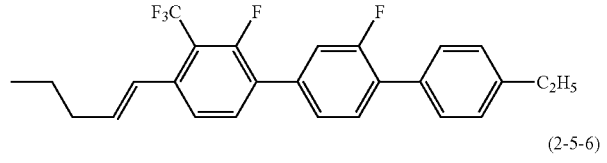
(2-5-5)
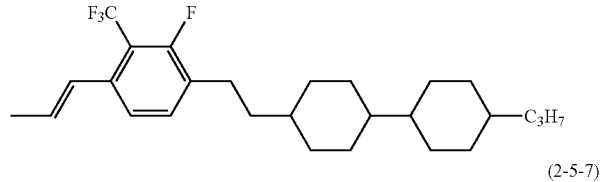
(2-5-6)
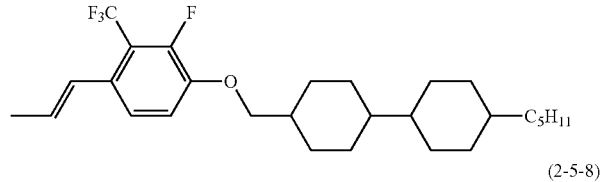
(2-5-7)
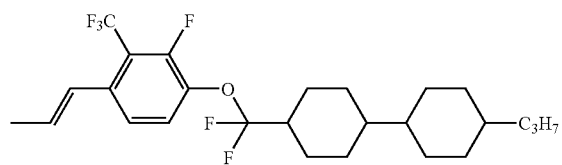
(2-5-8)
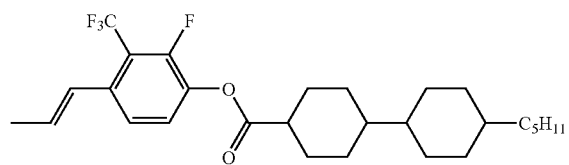

-continued
(2-5-9)
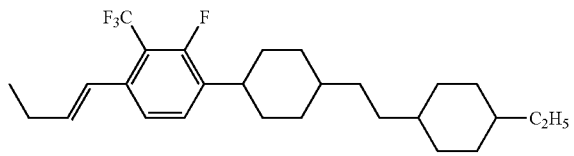
(2-5-10)
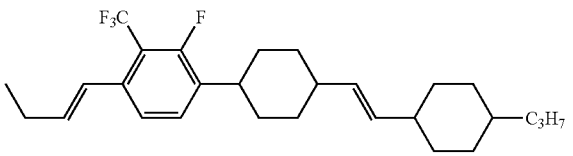
(2-5-11)
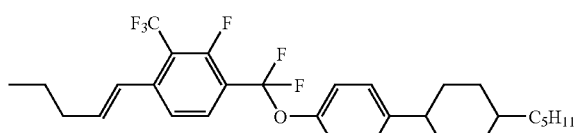
(2-5-12)
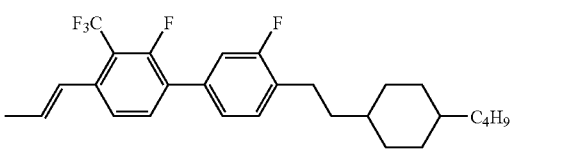
(2-5-13)
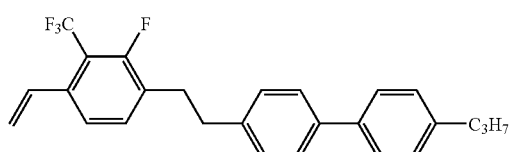
(2-5-14)
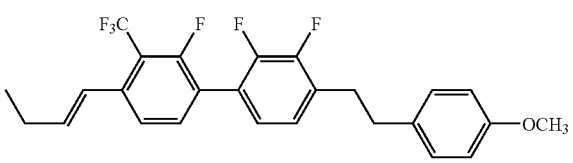
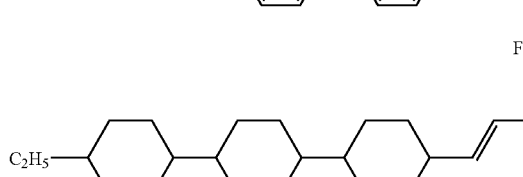
(2-6-1)
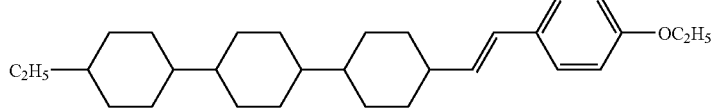
(2-6-2)
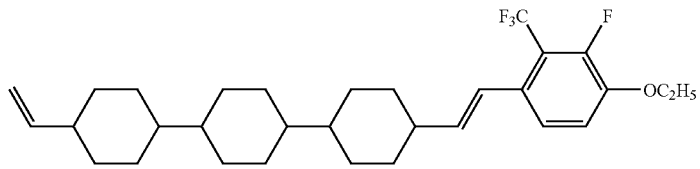
(2-6-3)
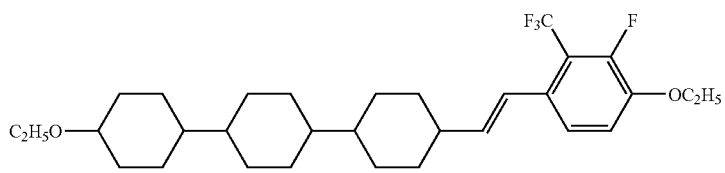
(2-6-4)
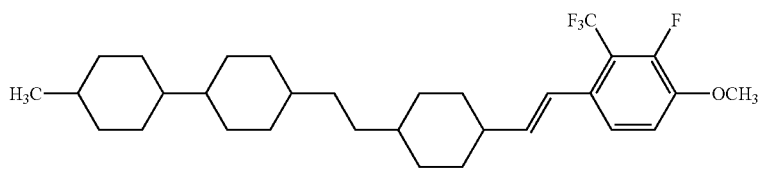
(2-6-5)
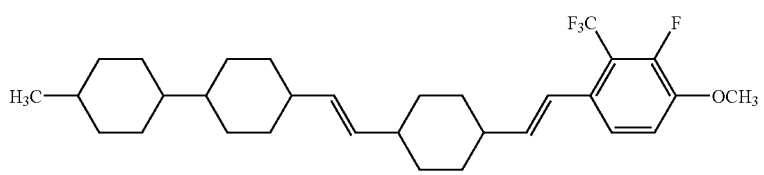
(2-6-6)
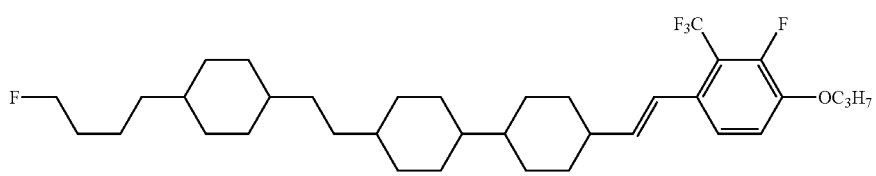

-continued
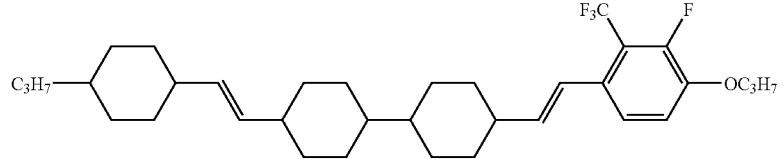 (2-6-7)
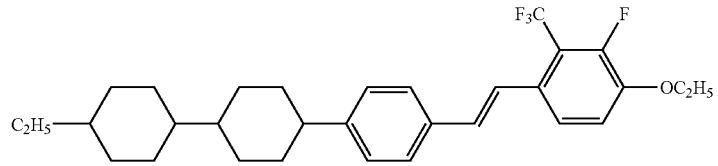 (2-6-8)
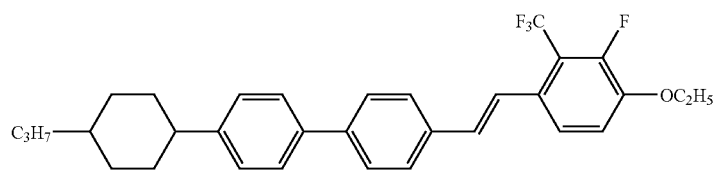 (2-6-9)
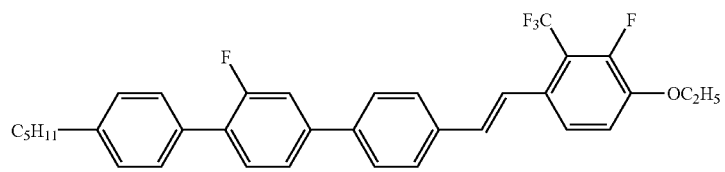 (2-6-10)
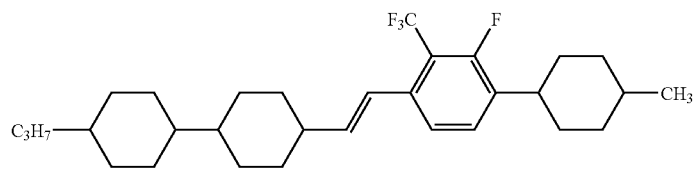 (2-7-1)
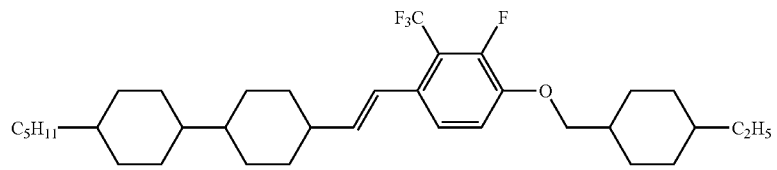 (2-7-2)
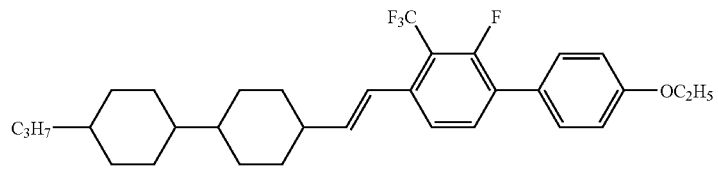 (2-7-3)
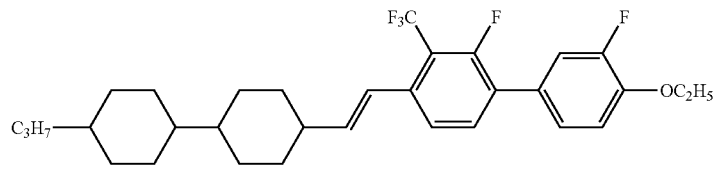 (2-7-4)
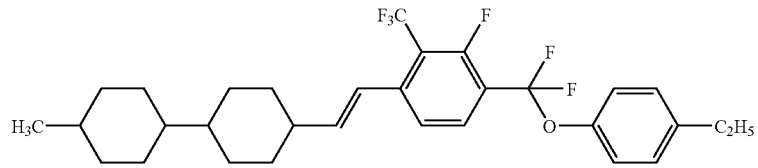 (2-7-5)

-continued
(2-7-6)
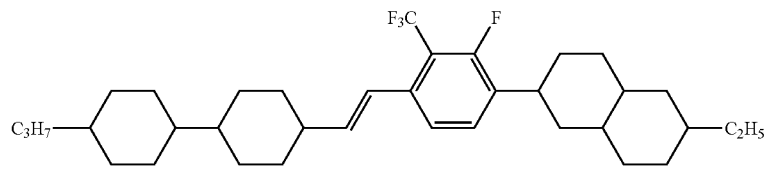
(2-7-7)
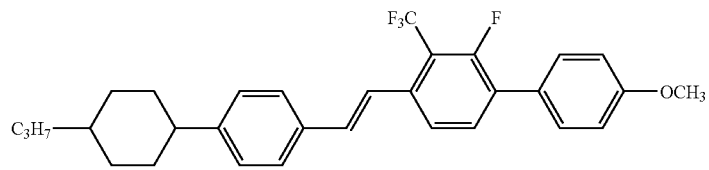
(2-7-8)
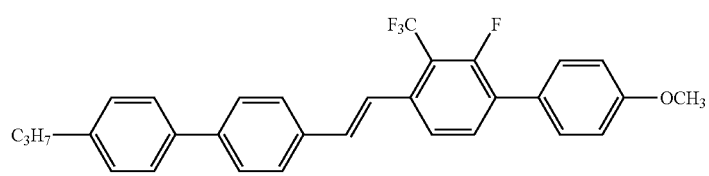
(2-7-9)
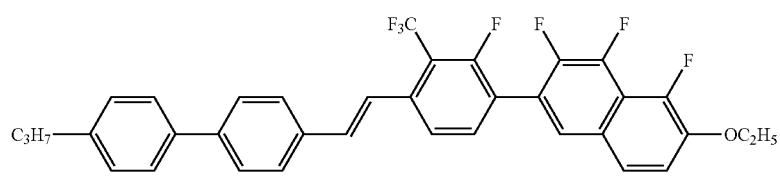
(2-8-1)
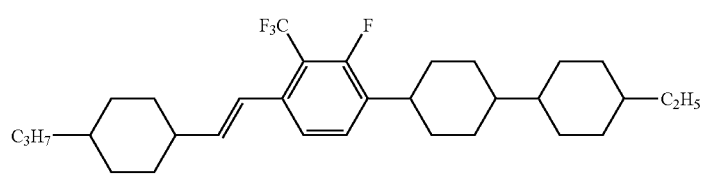
(2-8-2)
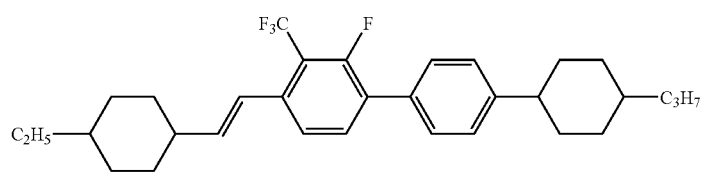
(2-8-3)
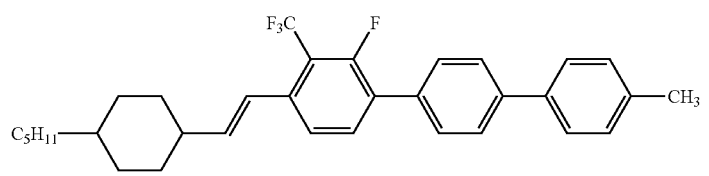
(2-8-4)
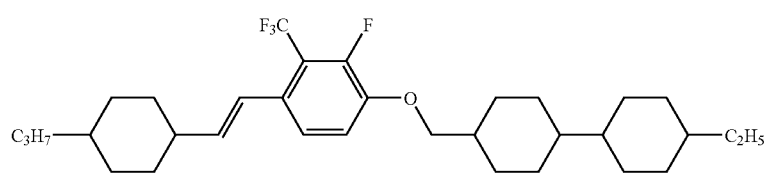
(2-8-5)
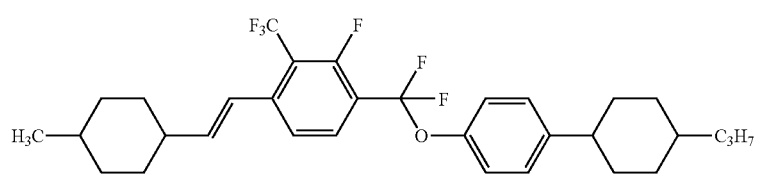

-continued
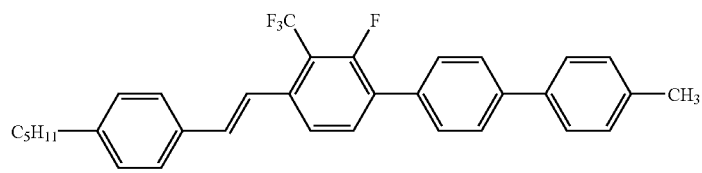 (2-8-6)
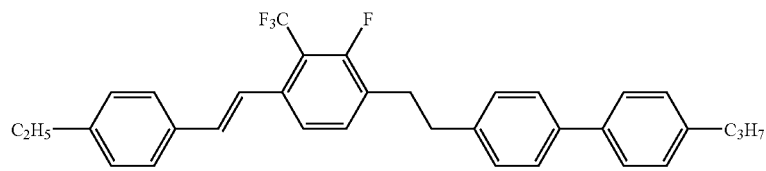 (2-8-7)
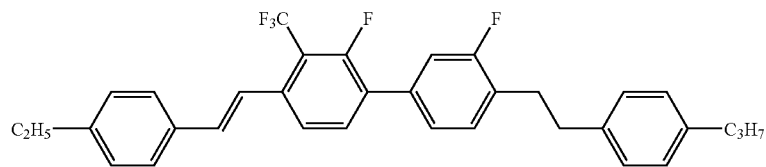 (2-8-8)
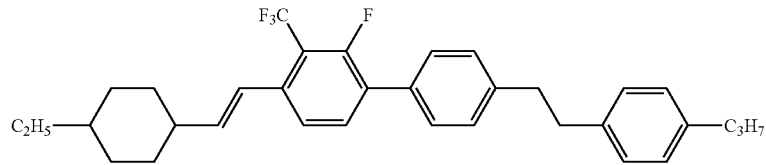 (2-8-9)
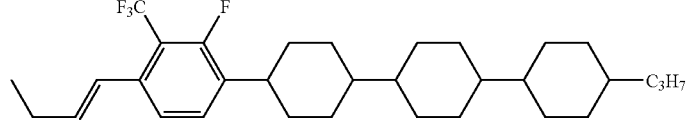 (2-9-1)
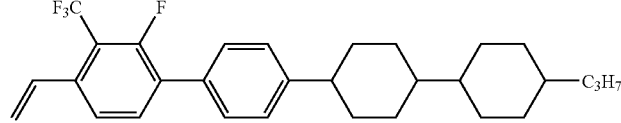 (2-9-2)
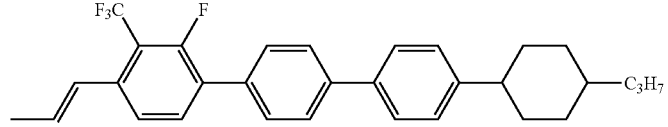 (2-9-3)
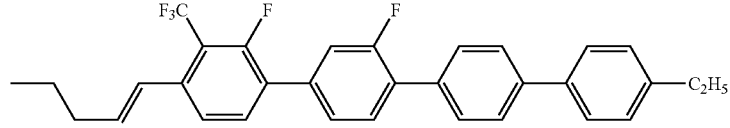 (2-9-4)
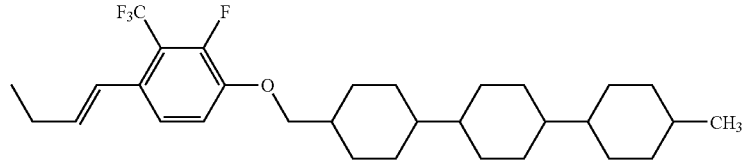 (2-9-5)
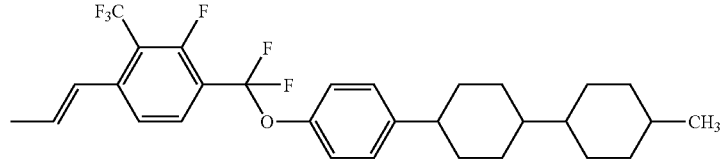 (2-9-6)

-continued
(2-9-7)
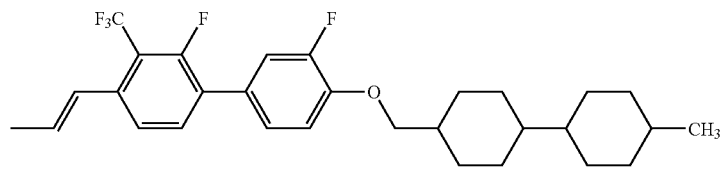
(2-9-8)
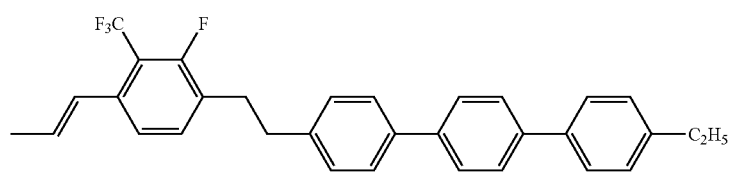
(2-9-9)
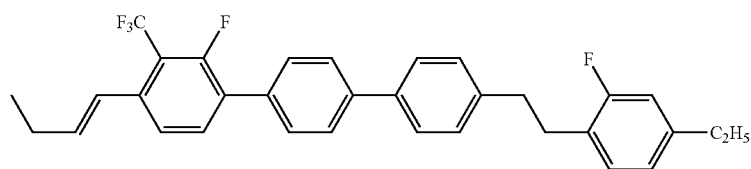
(2-1-5)
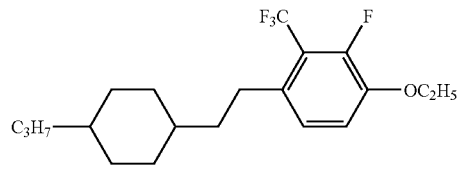
(2-1-6)
(2-1-7)
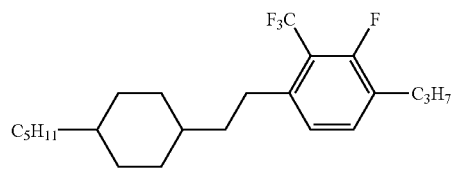
(2-1-8)
(2-1-9)
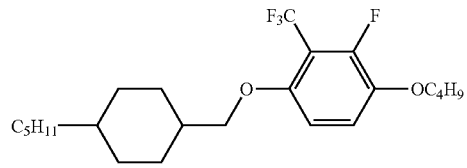
(2-1-10)
(2-1-11)
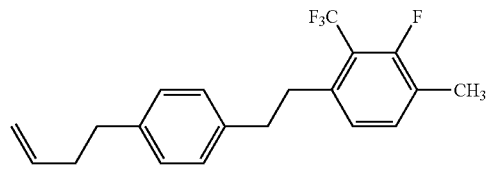
(2-1-12)
(2-1-13)
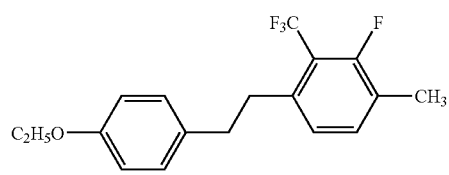
(2-1-14)
(2-3-10)
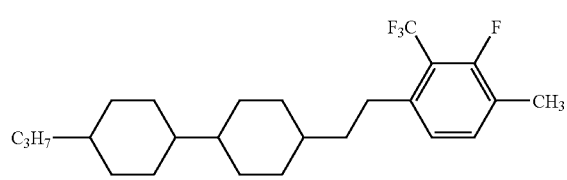
(2-3-11)
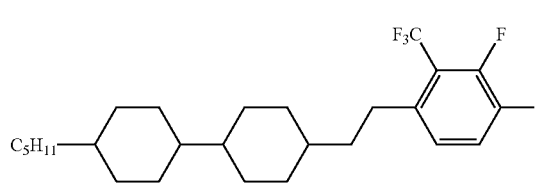

-continued
(2-3-12)
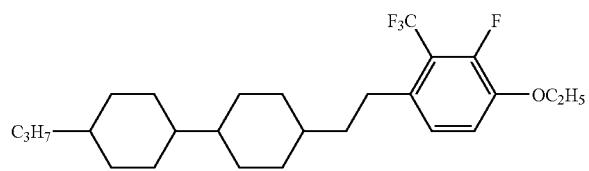
C 68.0 (SmA 44.9) N 112.8I
$T_{NI}$: 110.6° C. Δε: -6.86 Δn: 0.078
(2-3-13)
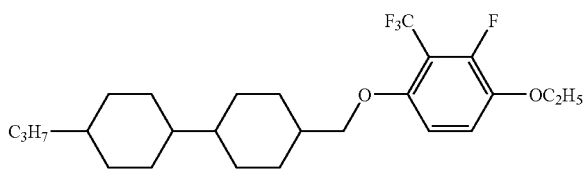
C 68.0 (SmA 44.9) N 112.8I
$T_{NI}$: 110.6° C. Δε: -6.86 Δn: 0.078
(2-3-14)
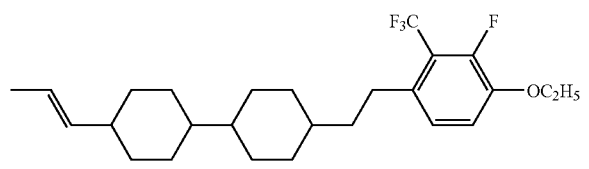
(2-3-15)
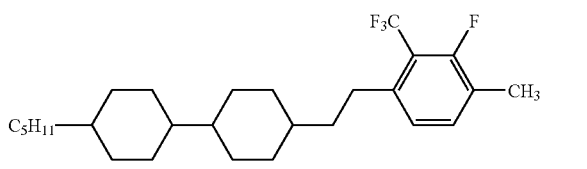
(2-3-16)
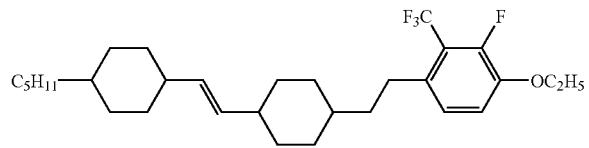
(2-3-17)
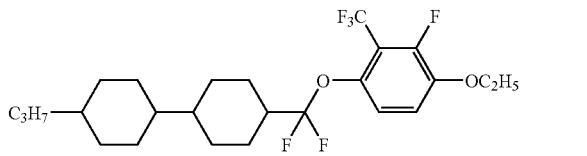
(2-3-18)
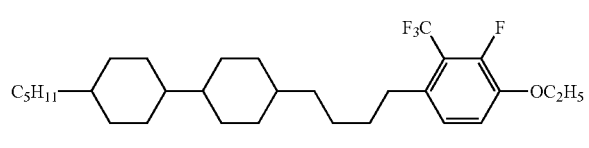
(2-3-19)
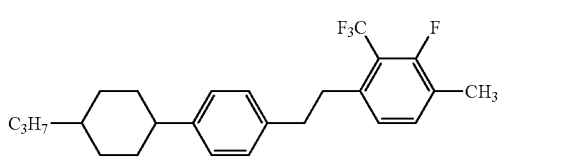
(2-3-20)
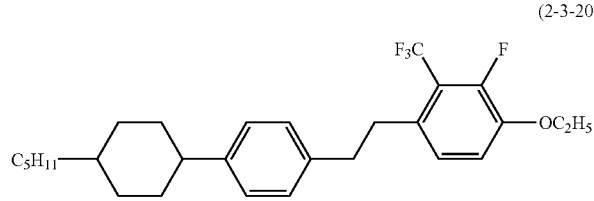
(2-3-21)
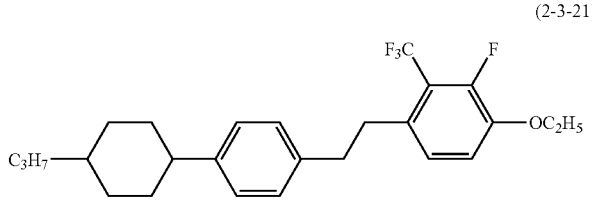
(2-3-22)
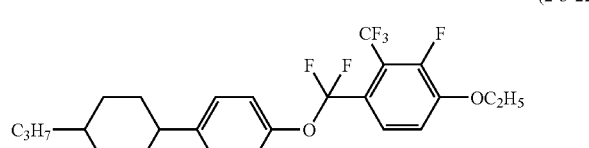
(2-3-23)
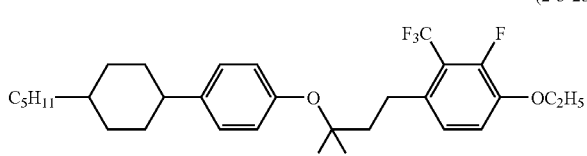
(2-3-24)
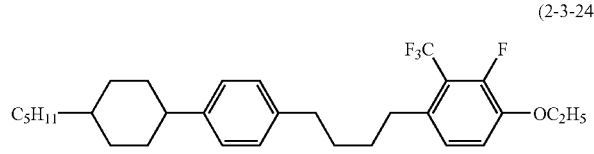
(2-3-25)
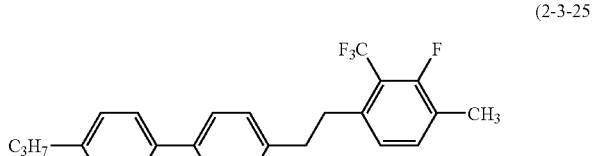
(2-3-26)
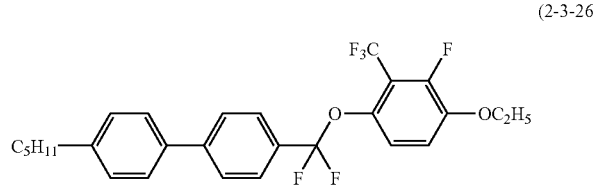
(2-3-27)
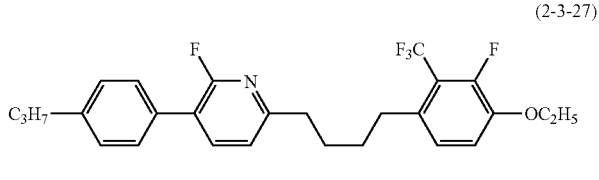

-continued
(2-3-28)
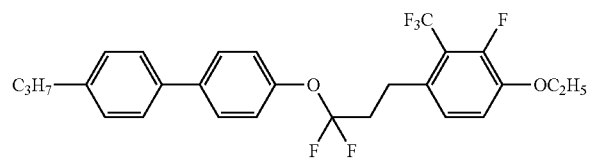
(2-4-13)
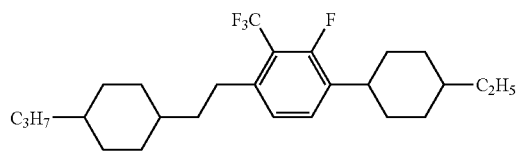
(2-4-14)
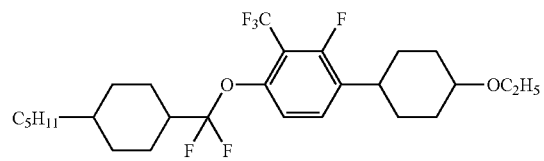
(2-4-15)
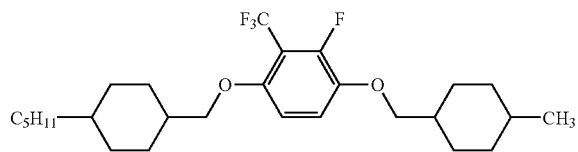
(2-4-16)
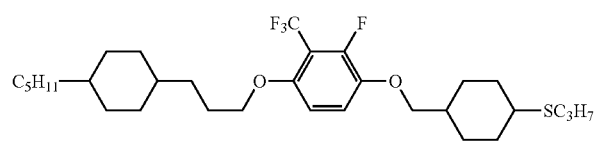
(2-4-17)
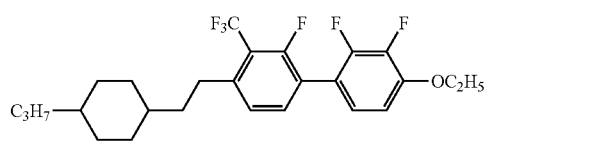
(2-4-18)
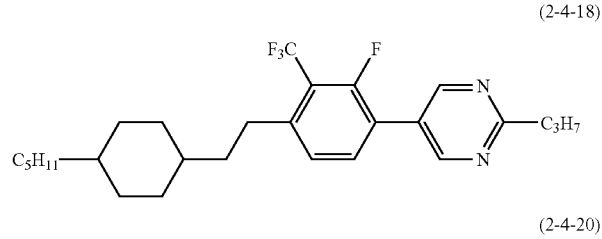
(2-4-19)
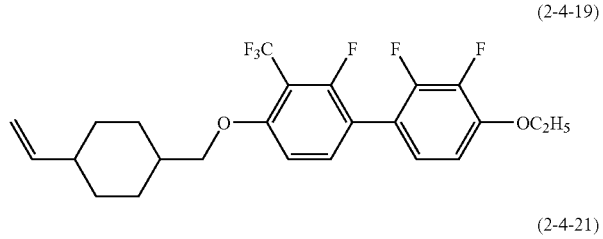
(2-4-20)
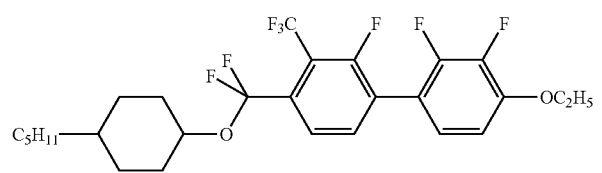
(2-4-21)
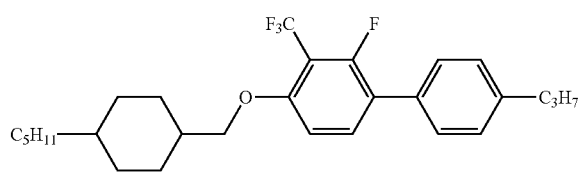
(2-4-22)
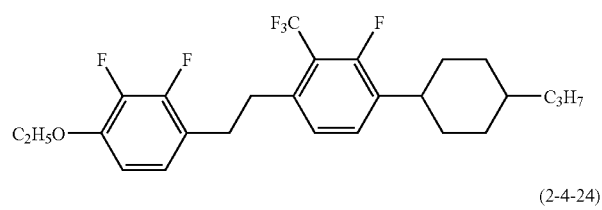
(2-4-23)
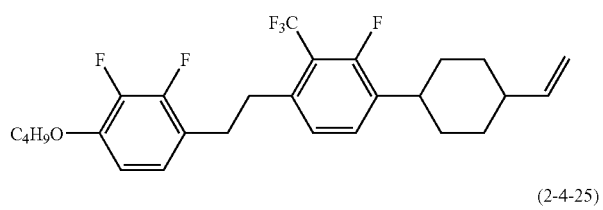
(2-4-24)
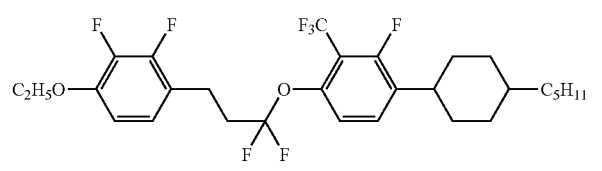
(2-4-25)
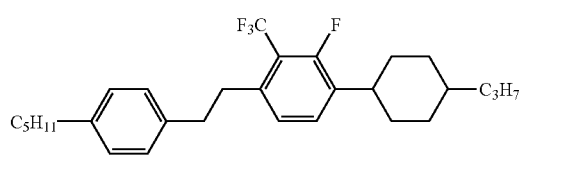
(2-4-26)
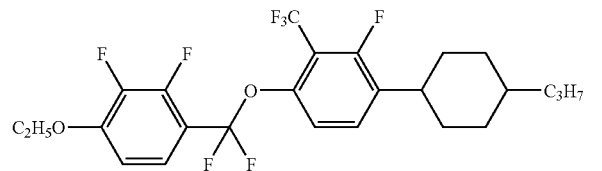
(2-4-27)
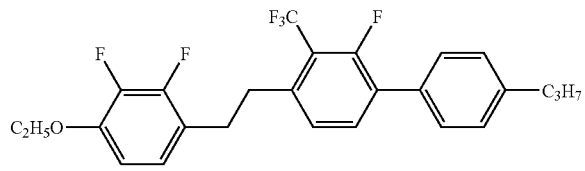

-continued
(2-4-28)
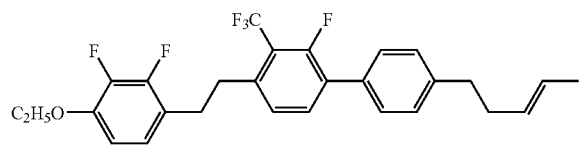
(2-4-29)
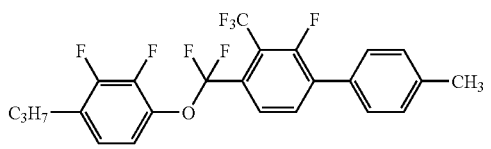
(2-4-30)
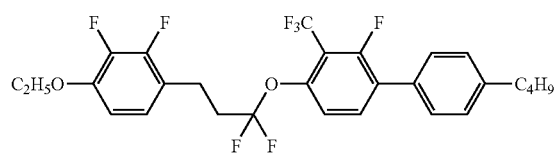
(2-4-31)
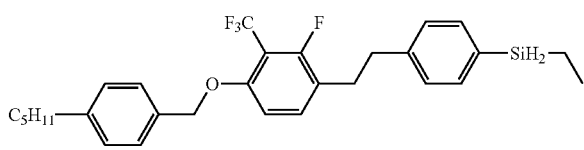
(2-6-11)
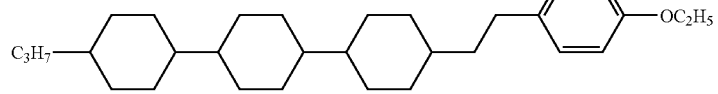
(2-6-12)
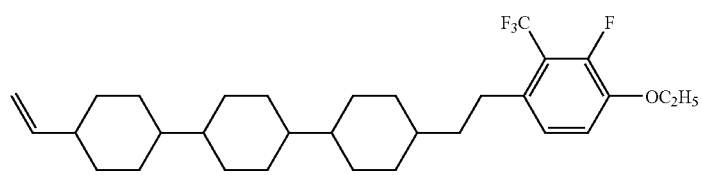
(2-6-13)
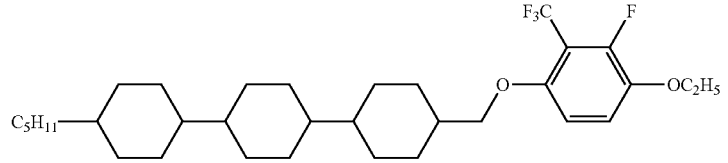
(2-6-14)
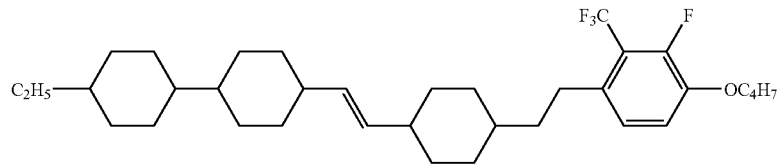
(2-6-15)
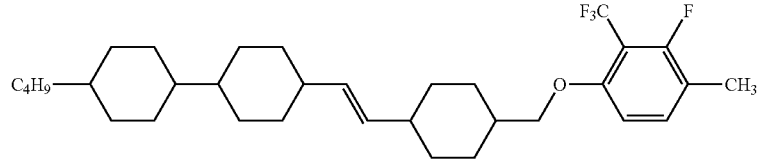
(2-6-16)
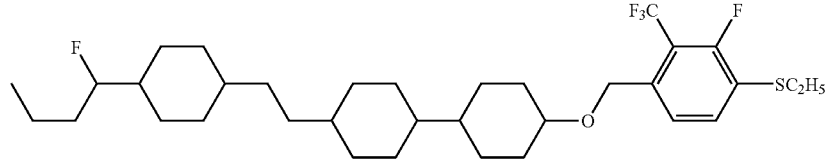
(2-6-17)
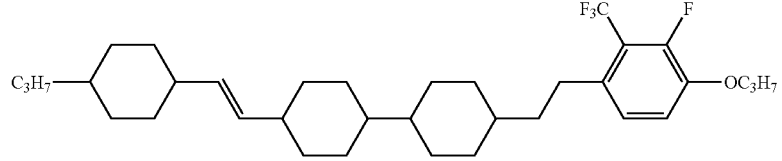

-continued
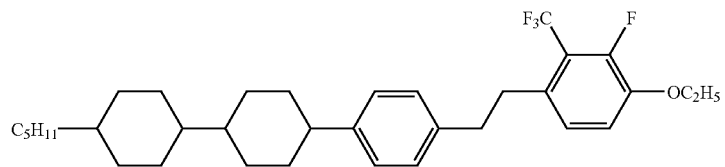
(2-6-18)
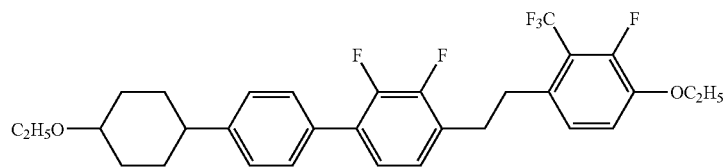
(2-6-19)
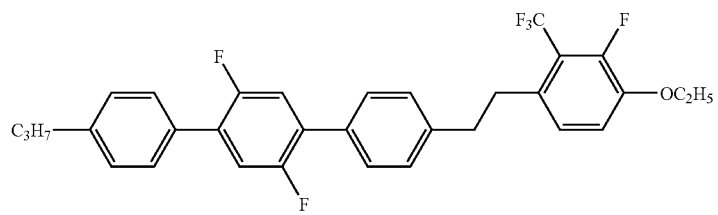
(2-6-20)
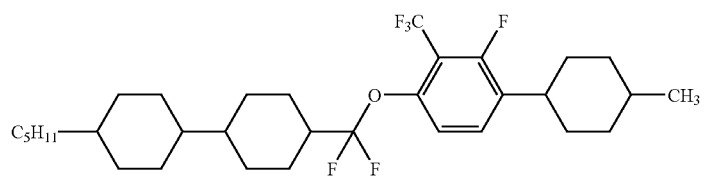
(2-7-10)
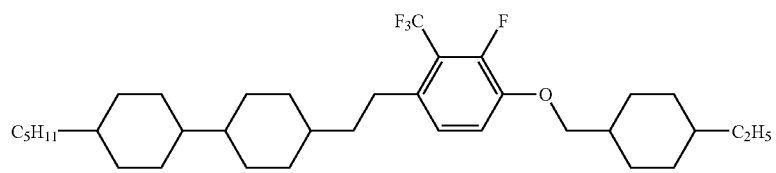
(2-7-11)
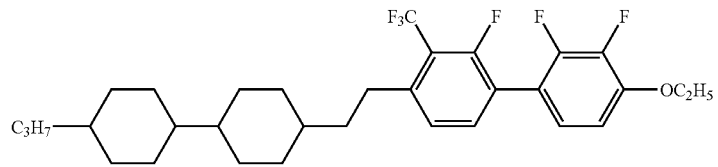
(2-7-12)
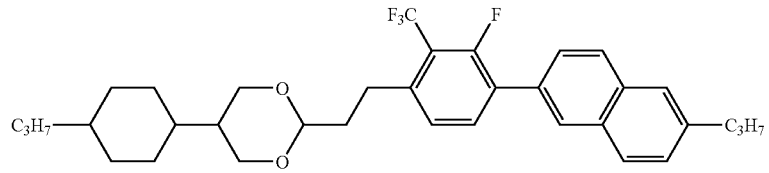
(2-7-13)
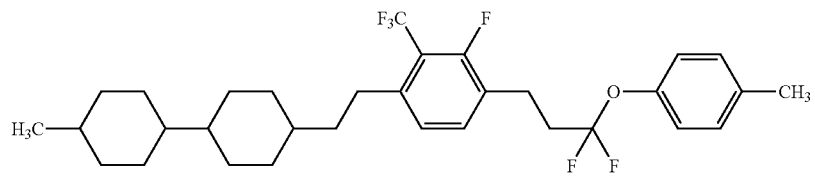
(2-7-14)

-continued
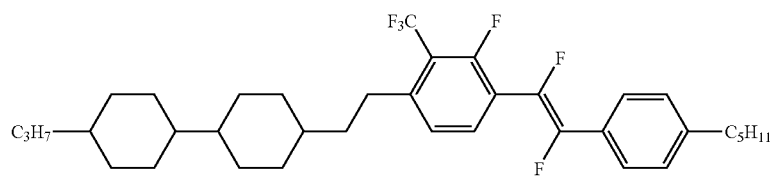
(2-7-15)
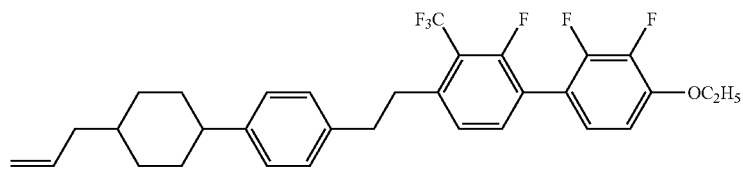
(2-7-16)
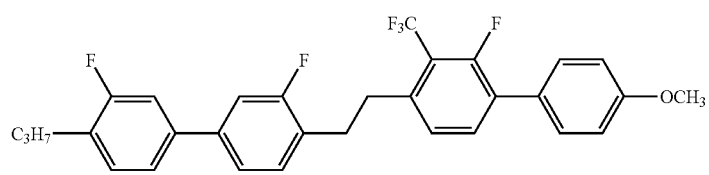
(2-7-17)
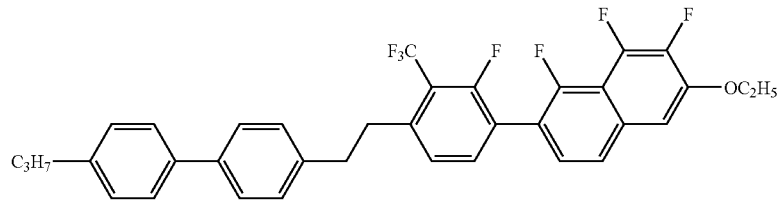
(2-7-18)
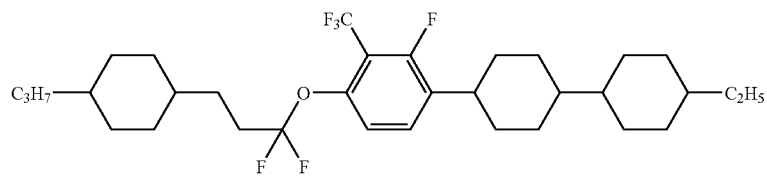
(2-8-10)
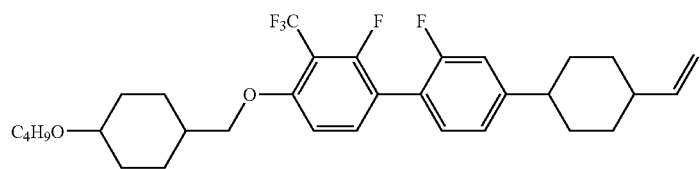
(2-8-11)
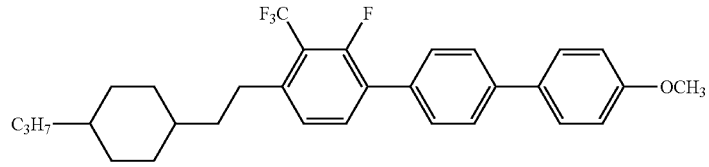
(2-8-12)
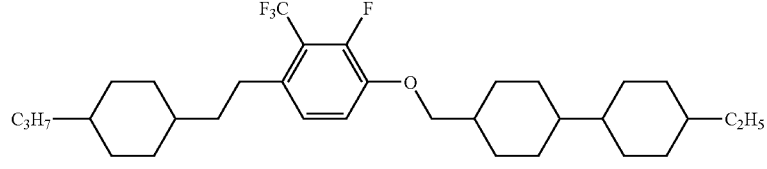
(2-8-13)
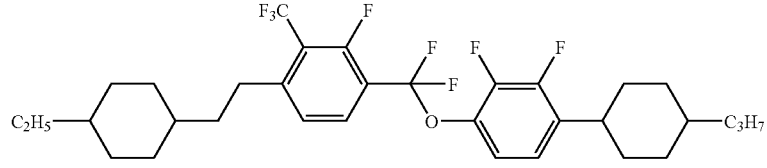
(2-8-14)

-continued

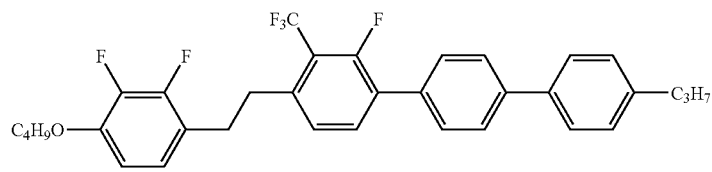
(2-8-15)

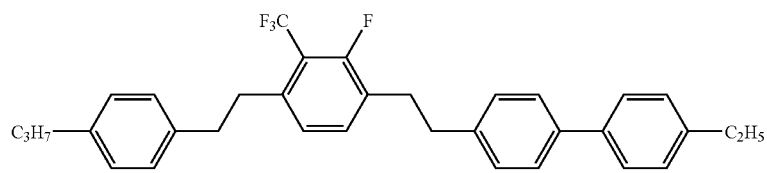
(2-8-16)

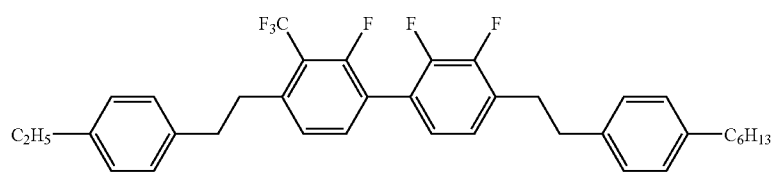
(2-8-17)

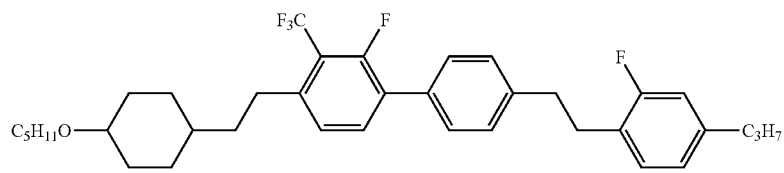
(2-8-18)

EXAMPLE 11

The following five compounds were mixed to prepare a composition having a nematic phase (mother liquid crystal A).

(Mother Liquid Crystal A)

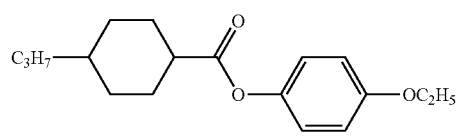

17.2%

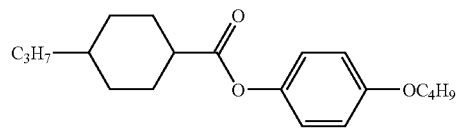

27.6%

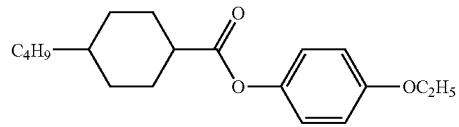

20.7%

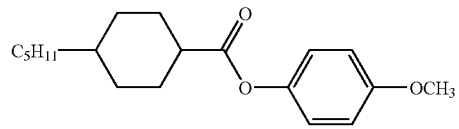

20.7%

-continued

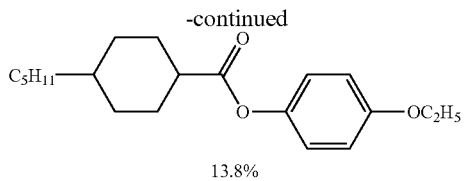

13.8%

The physical property of the mother liquid crystal A was as described below. Upper limit temperature (NI)=74.0° C.; viscosity ($\eta_{20}$)=18.9 mPa·s; optical anisotropy ($\Delta n$)=0.087; dielectric anisotropy ($\Delta \in$)=−1.3.

A composition B comprising 85% of the mother liquid crystal A and 15% of 4-(4-propylcyclohexyl)phenyl-2-fluoro-3-difluoromethyl-ethoxybenzene (Compound No. 1-3-5) obtained in Example 2 was prepared. The physical property values of the composition B were as shown below.

Optical anisotropy ($\Delta n$)=0.096; dielectric anisotropy ($\Delta \in$)=−2.4.

It was found that by applying the Compound No. 1-3-5, the dielectric anisotropy increased negatively and had a low driving voltage when formed into a liquid crystal display device.

EXAMPLE 12

A composition B comprising 85% of the mother liquid crystal A and 15% of 4-(4-propylcyclohexyl)cyclohexyl)ethyl)-2-fluoro-3-trifluoromethyl-ethoxybenzene (Compound No. 2-3-12) obtained in Example 8 was prepared. The physical property values of the composition B was as shown below.

Optical anisotropy ($\Delta n$)=0.086; dielectric anisotropy ($\Delta \in$)=−2.21.

It was found that by applying the Compound No. 2-3-12, the dielectric anisotropy increased negatively and had a low driving voltage when formed into a liquid crystal display device.

COMPARATIVE EXAMPLE 1

A composition D comprising 85% of the composition A described in Example 10 and 15% of 4-(4-propylcyclohexyl) phenyl-2-fluoro-3-difluoromethyl-ethoxybenzene described in the pamphlet of WO2000/03963 was prepared. The physical property of the composition D was as shown below.

Optical anisotropy ($\Delta n$)=0.096; dielectric anisotropy ($\Delta \in$)=−2.1.

Typical compositions of the invention are collectively shown in Working Examples 1 to 7. At first, compounds as the ingredient of the composition and the amounts thereof (wt %) are shown and then the physical property values of compositions are shown. In accordance with the definition in Table 1, the compounds are indicated by symbols for left terminal group, bonding group, cycle structure, and right terminal groups. Configuration of 1,4-cyclohexylene and 1,3-dioxane-2,5-diyl is trans. In a case with no symbols for the terminal groups, this means that the terminal groups are hydrogen.

TABLE 1

| Indication method for compound by using symbols<br>R—($A_1$)—$Z_1$- . . . -$Z_n$—($A_n$)—X | |
|---|---|
| 1) Left terminal group R— | Symbol |
| $C_nH_{2n+1}$— | n- |
| $C_nH_{2n+1}OC_mH_{2m}$— | nOm- |
| $CH_2$=CH— | V- |
| $C_nH_{2n+1}CH$=CH— | nV- |
| $CH_2$=CH$C_nH_{2n}$— | Vn- |
| $C_nH_{2n+1}CH$=CH$C_mH_{2m}$— | nVm- |
| $CF_2$=CH— | VFF- |
| $CF_2$=CH$C_nH_{2n}$— | VFFn- |
| 2) Ring structure —An— | Symbol |
|  | B |
| 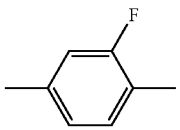 | B(F) |
| 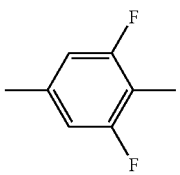 | B(F, F) |
| 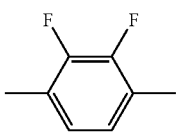 | B(2F, 3F) |
| 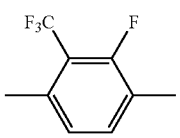 | B(2CF3, 3F) |
| 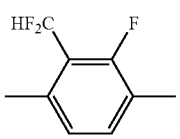 | B(2CF2H, 3F) |
| 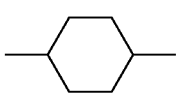 | H |

TABLE 1-continued

Indication method for compound by using symbols
R—(A$_1$)—Z$_1$- ... -Z$_n$—(A$_n$)—X

| 3) Connection group —Zn— | Symbol |
|---|---|
| —C$_2$H$_4$— | 2 |
| —C$_4$H$_8$— | 4 |
| —CH=CH— | V |
| —CH$_2$O— | 1O |
| —COO— | E |
| —C≡C— | T |
| —CF$_2$O— | X |
| —OCH$_2$— | O1 |

| 4) Right terminal group —X | Symbol |
|---|---|
| —F | —F |
| —Cl | —CL |
| —CN | —C |
| —OCF$_2$H | —OCF2H |
| —OCF$_3$ | —OCF3 |
| —CF$_3$ | —CF3 |
| —C$_n$H$_{2n+1}$ | -n |
| —OC$_n$H$_{2n+1}$ | —On |
| —CH=CH$_2$ | -V |
| —C$_n$H$_{2n}$CH=CH$_2$ | -nV |
| —C$_n$H$_{2n}$CH=CHC$_m$H$_{2m+1}$ | -nVm |
| —CH=CF$_2$ | -VFF |
| —COOCH$_3$ | -EMe |

5) Indication Example

Example 1  3-HVB(2CF3, 3F)—O2

Example 2  1O1-HBBH-5

Example 3  2-BB(2CF2H, 3F)H-3

WORKING EXAMPLE 1

| | | |
|---|---|---|
| 3-HBB (2CF2H, 3F) —O2 | (1-3-5) | 6% |
| 2-BB (2CF2H, 3F) H-3 | (1-4-5) | 3% |
| 2-BB (2CF2H, 3F) B-3 | (1-4-6) | 6% |
| 1V2-BEB (F, F) —C | | 6% |
| 3-HB—C | | 9% |
| 2-BTB-1 | | 10% |
| 5-HH-VFF | | 24% |
| 3-HHB-1 | | 4% |
| VFF-HHB-1 | | 8% |
| VFF2-HHB-1 | | 11% |
| 3-H2BTB-2 | | 5% |
| 3-H2BTB-3 | | 4% |
| 3-H2BTB-4 | | 4% |

NI = 76.5° C.; Δn = 0.136; η (20° C.) = 25.0 mPa·s; Δε = 4.8

WORKING EXAMPLE 2

| | | |
|---|---|---|
| 3-HBB (2CF2H, 3F) —O2 | (1-3-5) | 10% |
| 2-BB (2CF2H, 3F) H-3 | (1-4-5) | 5% |
| 3-HH-4 | | 8% |

-continued

| | |
|---|---|
| 3-HHB-1 | 6% |
| 3-HHB (F, F) —F | 10% |
| 3-H2HB (F, F) —F | 9% |
| 3-HBB (F, F) —F | 10% |
| 3-BB (F, F) XB (F, F) —F | 25% |
| 1O1-HBBH-5 | 7% |
| 2-HHBB (F, F) —F | 3% |
| 3-HHBB (F, F) —F | 3% |
| 3-HH2BB (F, F) —F | 4% |

NI = 83.0° C.; Δn = 0.115; η (20° C.) = 36.9 mPa · s; Δε = 8.2.

WORKING EXAMPLE 3

| | | |
|---|---|---|
| 3-HHVB (2CF2H, 3F) —O2 | (1-3-15) | 7% |
| 3-HHVB (2CF3, 3F) O2 | (2-3-3) | 6% |
| 1-B (2CF2H, 3F) O1H-3 | (1-2-8) | 5% |
| 3-HH-4 | | 5% |
| 3-HH-5 | | 5% |
| 3-HH—O1 | | 3% |
| 3-HH—O3 | | 3% |
| 3-HB—O1 | | 5% |
| 3-HB—O2 | | 5% |
| 3-HB (2F, 3F) —O2 | | 10% |
| 5-HB (2F, 3F) —O2 | | 10% |
| 3-HHEH-3 | | 2% |
| 3-HHEH-5 | | 2% |
| 4-HHEH-3 | | 2% |
| 2-HHB (2F, 3F) -1 | | 4% |
| 3-HHB (2F, 3F) -2 | | 4% |
| 3-HHB (2F, 3F) —O2 | | 12% |
| 5-HHB (2F, 3F) —O2 | | 10% |

WORKING EXAMPLE 4

| | | |
|---|---|---|
| 3-HVB (2CF2H, 3F) —O2 | (1-1-13) | 5% |
| 3-HVB (2CF3, 3F) —O2 | (2-1-2) | 5% |
| 3-HHB (2CF2H, 3F) —O2 | (1-3-1) | 5% |
| 3-HH-4 | | 5% |
| 3-HH-5 | | 5% |
| 3-HH—O1 | | 6% |
| 3-HH—O3 | | 6% |
| 3-HB—O1 | | 5% |
| 3-HB—O2 | | 5% |
| 3-HB (2F, 3F) —O2 | | 10% |
| 3-HHEH-3 | | 5% |
| 3-HHEH-5 | | 5% |
| 4-HHEH-3 | | 5% |
| 2-HHB (2F, 3F) -1 | | 4% |
| 3-HHB (2F, 3F) —O2 | | 12% |
| 5-HHB (2F, 3F) —O2 | | 12% |

WORKING EXAMPLE 5

| | | |
|---|---|---|
| 1V-HB (2CF2H, 3F) —O2 | (1-1-4) | 10% |
| 3-HHVB (2CF2H, 3F) —O2 | (1-3-15) | 5% |
| 3-HH-4 | | 5% |
| 3-HH-5 | | 5% |
| 3-HH—O1 | | 4% |
| 3-HH—O3 | | 4% |
| 3-HB—O1 | | 4% |
| 3-HB—O2 | | 3% |

-continued

| | |
|---|---|
| 3-HB (2F, 3F) —O2 | 10% |
| 5-HB (2F, 3F) —O2 | 5% |
| 3-HHEH-3 | 5% |
| 3-HHEH-5 | 5% |
| 4-HHEH-3 | 5% |
| 2-HHB (2F, 3F) -1 | 4% |
| 3-HHB (2F, 3F) -2 | 4% |
| 3-HHB (2F, 3F) —O2 | 12% |
| 5-HHB (2F, 3F) —O2 | 10% |

WORKING EXAMPLE 6

| | | |
|---|---|---|
| 3-HVB (2CF2H, 3F) —O2 | (1-1-13) | 7% |
| 2-BB (2CF2H, 3F) H-3 | (1-4-5) | 5% |
| 3-HH-4 | | 5% |
| 3-HH-5 | | 5% |
| 3-HH—O1 | | 6% |
| 3-HH—O3 | | 6% |
| 3-HB—O1 | | 5% |
| 3-HB—O2 | | 5% |
| 3-HB (2F, 3F) —O2 | | 10% |
| 5-HB (2F, 3F) —O2 | | 10% |
| 3-HHEH-3 | | 4% |
| 3-HHEH-5 | | 3% |
| 2-HHB (2F, 3F) -1 | | 4% |
| 3-HHB (2F, 3F) -2 | | 4% |
| 3-HHB (2F, 3F) —O2 | | 12% |
| 5-HHB (2F, 3F) —O2 | | 9% |

WORKING EXAMPLE 7

| | | |
|---|---|---|
| 3-HBB (2CF2H, 3F) —O2 | (1-3-5) | 10% |
| 2-BB (2CF2H, 3F) H-3 | (1-4-5) | 5% |
| 3-HH-4 | | 5% |
| 3-HH-5 | | 5% |
| 3-HH—O1 | | 3% |
| 3-HH—O3 | | 3% |
| 3-HB—O1 | | 4% |
| 3-HB—O2 | | 4% |
| 3-HB (2F, 3F) —O2 | | 10% |
| 5-HB (2F, 3F) —O2 | | 10% |
| 3-HHEH-3 | | 5% |
| 3-HHEH-5 | | 5% |
| 4-HHEH-3 | | 5% |
| 2-HHB (2F, 3F) -1 | | 4% |
| 3-HHB (2F, 3F) -2 | | 4% |
| 3-HHB (2F, 3F) —O2 | | 10% |
| 5-HHB (2F, 3F) —O2 | | 8% |

NI = 77.8° C.; Δn = 0.083; η (20° C.) = 39.1 mPa · s; Δε = −3.7

A pitch when (Op-5) was added by 0.25 parts to 100 parts of the composition was 58.5 μm.

INDUSTRIAL APPLICABILITY

The present invention provides a liquid crystalline compound showing a negative dielectric anisotropy, as well as having excellent balance for physical property such as having general physical property required for liquid crystalline compound, stability to heat, light, etc., appropriate optical anisotropy, appropriate dielectric anisotropy and excellent compatibility with other liquid crystalline compounds. A liquid crystal composition containing at least one of the liquid crystalline compounds has an appropriate nematic phase, low viscosity, appropriate optical anisotropy, and low threshold voltage. Then, by incorporation of the composition, a liquid crystal display device having a wide usable temperature range, a short response time, a high contrast ratio, a low driving voltage, etc. can be manufactured.

The invention claimed is:

1. A compound represented by Formula (1) or Formula (2):

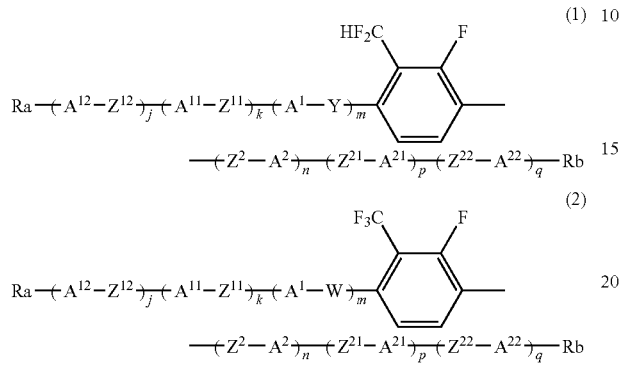

in which Ra and Rb each independently is hydrogen or alkyl of 1 to 20 carbon atoms; in the alkyl, arbitrary —$CH_2$— may be replaced by —O—, or —CO—, arbitrary —$(CH_2)_2$— may be replaced by —CH=CH—, and arbitrary hydrogen may be replaced by halogen;

$A^1$, $A^{11}$, $A^{12}$, $A^2$, $A^{21}$ and $A^{22}$ each independently is 1,4-cyclohexylene, 1,4-phenylene, decahydronaphthalene-2,6-diyl, 1,2,3,4-tetrahydronaphthalene-2,6-diyl, or naphthale-2,6-diyl; in the rings, one or not-adjacent two —$CH_2$— may be replaced by —O—, and arbitrary hydrogen may be replaced by halogen;

Y is a single bond, —$(CH_2)_2$—; —CH=CH—, —CF=CF—, —$(CH_2)_4$—, —CH=CH—$(CH_2)_2$—, or —$(CH_2)_2$—CH=CH—;

W is —CH=CH—, —$CH_2O$—, —$OCH_2$—, —$CF_2O$—, —$OCF_2$—, —$(CH_2)_4$—, —$(CH_2)_3$—O—, —O—$(CH_2)_3$—, —$(CH_2)_2CF_2O$—, or —$OCF_2(CH_2)_2$—;

$Z^{11}$, $Z^{12}$, $Z^2$, $Z^{21}$ and $Z^{22}$ each independently is a single bond, —$(CH_2)_2$—, —COO—, —OCO—, —$CH_2O$—, —$OCH_2$—, —$CF_2O$—, —$OCF_2$—, —CH=CH—, —CF=CF—, —$(CH_2)_4$—, —$(CH_2)_3$—O—, —O—$(CH_2)_3$—, —CH=CH—$(CH_2)_2$—, —$(CH_2)_2$—CH=CH—, —$(CH_2)_2CF_2O$—, or —$OCF_2(CH_2)_2$—;

j, k, m, n, p and q each independently is 0 or 1, and the sum of them is 1, 2 or 3;

each of j and k is 0 when m is 0, Ra in Formula (1) is none of hydrogen, alkoxy and alkoxymethyl when m is 0, and Ra in Formula (2) is 1-alkenyl when m is 0.

2. The compound according to claim 1, wherein the sum of j, k and m, and the sum of n, p and q each independently is 1 or 2.

3. The compound according to claim 1, which is represented by any one of Formula (1-1) to Formula (1-9) and Formula (2-1) to Formula (2-9),

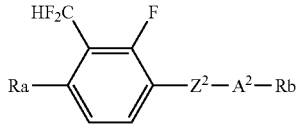

(1-1)

-continued

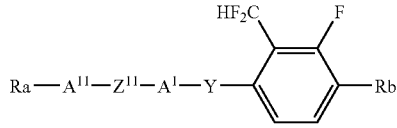

(1-2)

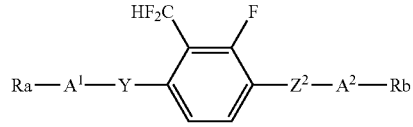

(1-3)

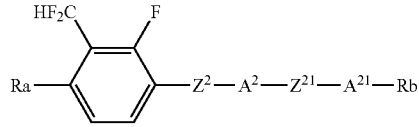

(1-4)

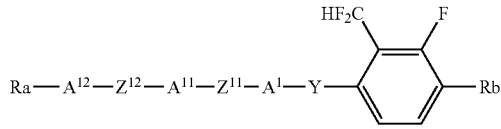

(1-5)

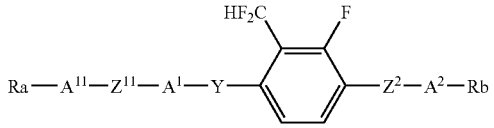

(1-6)

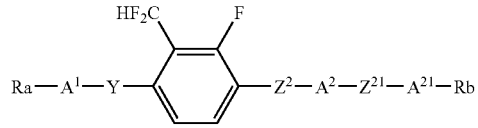

(1-7)

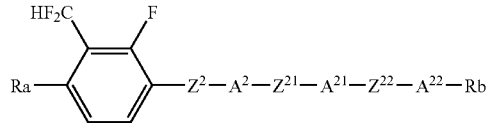

(1-8)

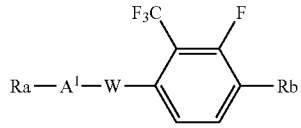

(1-9)

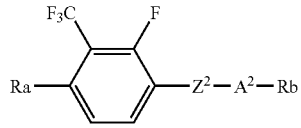

(2-1)

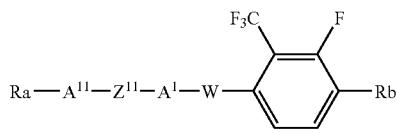

(2-2)

(2-3)

-continued

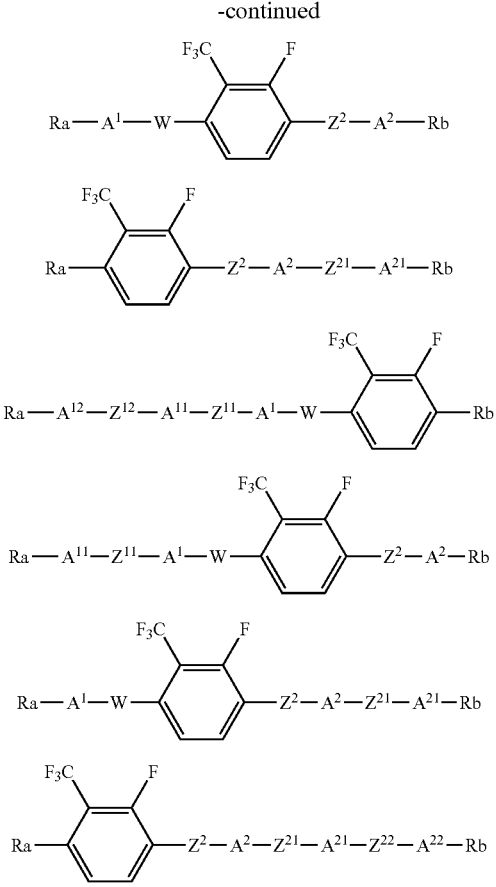

in which Ra and Rb each independently is hydrogen or alkyl of 1 to 20 carbon atoms; in the alkyl, arbitrary —$CH_2$— not situated on the terminal may be replaced by —O—, or —CO—, arbitrary —$(CH_2)_2$— may be replaced by —CH=CH—, and arbitrary hydrogen may be replaced by halogen;

$A^1$, $A^{11}$, $A^{12}$, $A^2$, $A^{21}$ and $A^{22}$ each independently is 1,4-cyclohexylene, 1,4-phenylene, decahydronaphthalene-2,6-diyl, 1,2,3,4-tetrahydronaphthalene-2,6-diyl, or naphthalene-2,6-diyl; and in the rings, one or not-adjacent two —$CH_2$— may be replaced by —O—, and arbitrary hydrogen may be replaced by halogen;

Y is a single bond, —$(CH_2)_2$—, —CH=CH—, —CF=CF—, —$(CH_2)_4$—, —CH=CH—$(CH_2)_2$—, or —$(CH_2)_2$—CH=CH—;

W is —CH=CH—, —$CH_2O$—, —$OCH_2$—, —$CF_2O$—, —$OCF_2$—, —$(CH_2)_4$—, —$(CH_2)_3$—O—, —O—$(CH_2)_3$—, —$(CH_2)_2CF_2O$—, or —$OCF_2(CH_2)_2$—;

$Z^{11}$, $Z^{12}$, $Z^2$, $Z^{21}$ and $Z^{22}$ each independently is a single bond, —$(CH_2)_2$—, —COO—, —OCO—, —$CH_2O$—, —$OCH_2$—, —$CF_2O$—, —$OCF_2$—, —CH=CH—, —CF=CF—, —$(CH_2)_4$—, —$(CH_2)_3$—O—, —O—$(CH_2)_3$—, —CH=CH—$(CH_2)_2$—, —$(CH_2)_2$—CH=CH—, —$(CH_2)_2CF_2O$—, or —$OCF_2(CH_2)_2$—;

Ra is none of hydrogen, alkoxy and alkoxymethyl in Formula (1—2), Formula (1-5) and formula (1-9); and Ra is 1-alkenyl in Formula (2-2), Formula (2-5) and Formula (2-9).

4. The compound according to claim 3, wherein Ra and Rb each independently is alkyl of 1 to 10 carbon atoms, alkoxy of 1 to 10 carbon atoms, alkoxyalkyl of 2 to 10 carbon atoms, alkenyl of 2 to 10 carbon atoms, alkenyloxy of 3 to 10 carbon atoms, perfluoroalkyl of 1 to 10 carbon atoms, or perfluoroalkoxy of 1 to 10 carbon atoms;

$A^1$, $A^{11}$, $A^{12}$, $A^2$, $A^{21}$ and $A^{22}$ each independently is 1,4-cyclohexylene, 1,3-dioxane-2,5-diyl, 4,6-dioxane-2,5-diyl, 1,4-phenylene, 2-fluoro-1,4-phenylene, 3-fluoro-1,4-phenylene, 2,3-difluoro-1,4-phenylene, decahydronaphthalene-2,6-diyl, 1,2,3,4-tetrahydronaphthalene-2,6-diyl, or naphthalene-2,6-diyl;

$Z^{11}$ and $Z^{12}$ each independently is a single bond, —$(CH_2)_2$—, —COO—, —OCO—, —$CF_2O$—, —$OCF_2$—, —CH=CH—, —$(CH_2)_4$—, —CH=CH—$(CH_2)_2$—, —$(CH_2)_2$—CH=CH—, —$(CH_2)_2CF_2O$—, or —$OCF_2(CH_2)_2$—;

$Z^2$, $Z^{21}$ and $Z^{22}$ each independently is a single bond, —$(CH_2)_2$—, —COO—, —OCO—, —$CH_2O$—, —$OCH_2$—, —$CF_2O$—, —$OCF_2$—, —CH=CH—, —CF=CF—, —$(CH_2)_4$—, —$(CH_2)_3$—O—, —O—$(CH_2)_3$—, —CH=CH—$(CH_2)_2$—, —$(CH_2)_2$—CH=CH—, —$(CH_2)_2CF_2O$—, or —$OCF_2(CH_2)_2$—;

Y is a single bond, —$(CH_2)_2$—, —CH=CH—, or —$(CH_2)_4$—; and

W is —$CH_2O$—, —$OCH_2$—, —$CF_2O$—, —$OCF_2$—, —CH=CH—, —$(CH_2)_4$—, —$(CH_2)_3$—O—, —O—$(CH_2)_3$—, —$(CH_2)_2CF_2O$—, or —$OCF_2(CH_2)_2$—.

5. The compound according to claim 3, wherein Ra and Rb each independently is alkyl of 1 to 10 carbon atoms, alkoxy of 1 to 10 carbon atoms, alkoxyalkyl of 2 to 10 carbon atoms, or alkenyl of 2 to 10 carbon atoms;

$A^1$, $A^{11}$, $A^{12}$, $A^2$, $A^{21}$ and $A^{22}$ each independently is 1,4-cyclohexylene, 1,4-phenylene, 2-fluoro-1,4-phenylene, 3-fluoro-1,4-phenylene, or 2,3-difluoro-1,4-phenylene;

$Z^{11}$ and $Z^{12}$ each independently is a single bond, —$(CH_2)_2$—, —$CF_2O$—, —$OCF_2$—, —CH=CH—, —$(CH_2)_4$—, —CH=CH—$(CH_2)_2$—, —$(CH_2)_2$—CH=CH—, —$(CH_2)_2CF_2O$—, or —$OCF_2(CH_2)_2$—;

$Z^2$, $Z^{21}$ and $Z^{22}$ each independently is a single bond, —$(CH_2)_2$—, —$CH_2O$—, —$OCH_2$—, —$CF_2O$—, —$OCF_2$—, —CH=CH—, —$(CH_2)_2CF_2O$—, or —$OCF_2(CH_2)_2$—;

Y is a single bond, —$(CH_2)_2$—, —CH=CH—, or —$(CH_2)_4$—; and

W is —$CH_2O$—, —$OCH_2$—, —$CF_2O$—, —$OCF_2$—, —CH=CH—, —$(CH_2)_4$—, —$(CH_2)_3$—O—, —O—($CH_2$)_3—, —$(CH_2)_2CF_2O$—, or —$OCF_2(CH_2)_2$—.

6. The compound according to claim 3, wherein Ra is alkyl of 1 to 10 carbon atoms or alkenyl of 2 to 10 carbon atoms, and Rb is alkoxy of 1 to 10 carbon atoms;

$A^1$, $A^{11}$, $A^{12}$, $A^2$, $A^{21}$ and $A^{22}$ each independently is 1,4-cyclohexylene, 1,4-phenylene, 2-fluoro-1,4-phenylene, or 3-fluoro-1,4-phenylene;

$Z^{11}$ and $Z^{12}$ each independently is a single bond, or —CH=CH—;

$Z^2$, $Z^{21}$ and $Z^{22}$ each independently is a single bond, —$CH_2O$—, —$OCH_2$—, —$CF_2O$—, —or $OCF_2$—,;

Y is a single bond, —$(CH_2)_2$—, —CH=CH—, or —$(CH_2)_4$—; and

W is —$CH_2O$—, —$OCH_2$—, —$CF_2O$—, —$OCF_2$—, —CH=CH—, —$(CH_2)_4$—, —$(CH_2)_3$—O—, —O—$(CH_2)_3$—, —$(CH_2)_2CF_2O$—, or —$OCF_2(CH_2)_2$—.

7. The compound according to claim 3, wherein $A^1$ or $A^2$ is 1,4-clohexylene.

8. The compound according to claim 3, wherein $A^1$ or $A^2$ is 1,4-phenylene.

9. The compound according to claim 3, wherein Y or $Z^2$ is a single bond in Formula (1-1) to Formula (1-9), and $Z^2$ is a single bond in Formula (2-1) to Formula (2-9).

10. The compound according to claim 3, wherein $A^1$ or $A^2$ is 1,4-cyclohexylene, Y or $Z^2$ is a single bond in Formula (1-1) to Formula (1-9), and $Z^2$ is a single bond in Formula (2-1) to Formula (2-9).

11. The compound according to claim 3, which is represented by any one of Formula (2-1), Formula (2-3), Formula (2-4), Formula (2,6), Formula (2-7) and Formula (2-8); in which $A^1$ is 1,4-cyclohexylene.

12. The compound according to claim 3, which is represented by Formula (2-1); in which $A^1$ is 1,4-cyclohexylene, and W is —$CH_2O$—, or —$CF_2O$—.

13. The compound according to claim 3, which is represented by Formula (2-3); in which any of $A^1$ and $A^{11}$ is 1,4-cyclohexylene, $Z^{11}$ is a single bond, and W is —$CH_2O$— or —$CF_2O$—.

14. The compound according to claim 3, which is represented by Formula (2-6); in which any of $A^1$, $A^{11}$ and $A^{12}$ is 1,4-cyclohexylene; any of $Z^{11}$ and $Z^{12}$ is a single bond; and W is —$CH_2$—O— or —$CF_2O$—.

15. The compound according to claim 3, which is represented by any one of Formula (1-2), Formula (1-4), Formula (1-5), Formula (1-7), Formula (1-8), and Formula (1-9); in which $Z^2$ is —$CH_2O$—, —$OCH_2$—, —$CF_2O$— or —$OCF_2$—.

16. The compound according to claim 3, which is represented by Formula (1-3); in which Ra is alkyl of 1 to 10 carbon atoms or alkenyl of 2 to 10 carbon atoms, Rb is alkoxy of 1 to 10 carbon atoms, any of $A^1$ and $A^{11}$ is 1,4-cyclohexylene, and any of Y and $Z^{11}$ is a single bond.

17. The compound according to claim 3, which is represented by Formula (1-3); in which Ra is alkyl of 1 to 10 carbon atoms or alkenyl of 2 to 10 carbon atoms, Rb is alkoxy of 1 to 10 carbon atoms, any of $A^1$ and $A^{11}$ is 1,4-cyclohexylene, Y is —$CH_2CH_2$—, and $Z^{11}$ is a single bond.

18. The compound according to claim 3, which is represented by Formula (1-3); in which Ra is alkyl of 1 to 10 carbon atoms or alkenyl of 2 to 10 carbon atoms, Rb is alkoxy of 1 to 10 carbon atoms, $A^1$ is 1,4-phenylene, $A^{11}$ is 1,4-cyclohexylene, and any of Y and $Z^1$ is a single bond.

19. The compound according to claim 3, which is represented by Formula (1-3); in which Ra is alkyl of 1 to 10 carbon atoms or alkenyl of 2 to 10 carbon atom, Rb is alkoxy of 1 to 10 carbon atoms, any of $A^1$ and $A^{11}$ is 1,4-phenylene, and any of Y and $Z^{11}$ is a single bond.

20. The compound according to claim 3, which is represented by Formula (1-1); in which Ra is alkyl of 1 to 10 carbon atoms or alkenyl of 2 to 10 carbon atoms, Rb is alkoxy of 1 to 10 carbon atoms, $A^1$ is 1,4-cyclohexylene, and Y is a single bond.

21. The compound according to claim 3, which is represented by Formula (1-1); in which Ra is alkyl of 1 to 10 carbon atoms or alkenyl of 2 to 10 carbon atoms, Rb is alkoxy of 1 to 10 carbon atoms, $A^1$ is 1,4-cyclohexylene, and Y is —$CH_2CH_2$.

22. The compound according to claim 3, which is represented by Formula (2-1); in which Ra is alkyl of 1 to 10 carbon atoms or alkenyl of 2 to 10 carbon atoms, Rb is alkoxy of 1 to 10 carbon atoms, $A^1$ is 1,4-cyclohexylene, and W is —$CH_2O$—.

23. The compound according to claim 3, which is represented by Formula (2-3); in which Ra is alkyl of 1 to 10 carbon atoms or alkenyl of 2 to 10 carbon atoms, Rb is alkoxy of 1 to 10 carbon atoms, any of $A^1$ and $A^{11}$ is 1,4-cyclohexylene, $Z^{11}$ is a single bond, and W is —$CH_2O$—.

24. The compound according to claim 3, which is represented by Formula (2-6); in which Ra is alkyl of 1 to 10 carbon atoms or alkenyl of 2 to 10 carbon atoms, Rb is alkoxy of 1 to 10 carbon atoms, any of $A^1$, $A^{11}$ and $A^{12}$ is 1,4-cyclohexylene; any of $Z^{11}$ and $Z^{12}$ is a single bond, and W is —$CH_2O$—.

25. The compound according to claim 3, which is represented by Formula (1-2); in which Ra is alkyl of 1 to 10 carbon atoms, Rb is alkyl of 1 to 10 carbon atoms or alkenyl of 2 to 10 carbon atoms, $A^2$ is 1,4-cyclohexylene, and $Z^2$ is —$OCH_2$—.

26. The compound according to claim 3, which is represented by Formula (1-5); in which Ra is alkyl of 1 to 10 carbon atoms, Rb is alkyl of 1 to 10 carbon atoms or alkenyl of 2 to 10 carbon atoms, any of $A^2$ and $A^{21}$ is 1,4-cyclohexylene, $Z^2$ is —$OCH_2$—, and $Z^{21}$ is a single bond.

27. The compound according to claim 3, which is represented by Formula (1-4); in which Ra and Rb each independently is alkyl of 1 to 10 carbon atoms or alkenyl of 2 to 10 carbon atoms, any of $A^1$ and $A^2$ is 1,4-phenylene, and any of Y and $Z^2$ is a single bond.

28. The compound according to claim 3, which is represented by Formula (1-4); in which Ra and Rb each independently is alkyl of 1 to 10 carbon atoms or alkenyl of 2 to 10 carbon atoms, $A^1$ is 1,4-cyclohexylene, $A^2$ is 1,4-phenylene, and any of Y and $Z^2$ is a single bond.

29. The compound according to claim 3, which is represented by Formula (1-4); in which Ra and Rb each independently is alkyl of 1 to 10 carbon atoms or alkenyl of 2 to 10 carbon atoms, $A^1$ is 1,4-phenylene, $A^2$ is 1,4-cyclohexylene, and any of Y and $Z^2$ is a single bond.

30. A liquid crystal composition which contains at least one of the compounds described in claim 1 and may contain at least one optically active compound.

31. A liquid crystal composition which contains at least one of the compounds described in claim 1 and at least one compound selected from the group consisting of compounds represented by Formula (3), Formula (4), and Formula (5) respectively, and may contain at least one optically active compound:

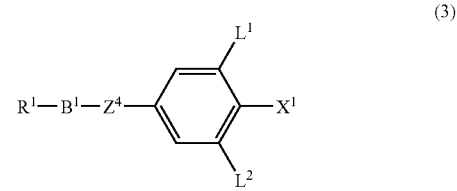

(3)

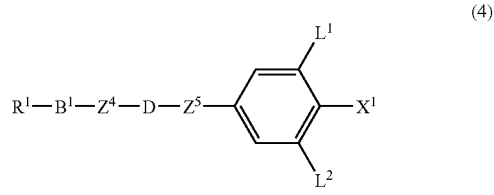

(4)

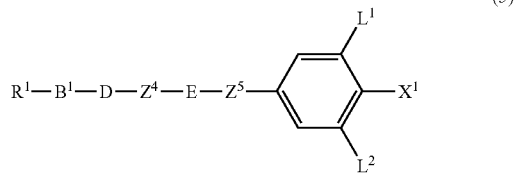

(5)

in which $R^1$ is alkyl of 1 to 10 carbon atoms; in the alkyl, arbitrary —$CH_2$— may be replaced by —O—, arbitrary —$(CH_2)_2$— may be replaced by —CH=CH—, and arbitrary hydrogen may be replaced by fluorine; $X^1$ is fluorine, chlorine, —$OCF_3$, —$OCHF_2$, —$CF_3$, —$CHF_2$, —$CH_2F$, —$OCF_2CHF_2$ or —$OCF_2CHFCF_3$; $B^1$ and D each independently is 1,4-cyclohexylene, 1,4-phenylene, 1,3-dioxane-2,5-diyl, or 1,4-phenylene in which at least one hydrogen is replaced by fluorine; E is 1,4-cyclohexylene, 1,4-phenylene, or 1,4-phenylene in which at least one hydrogen is replaced by fluorine; $Z^4$ and $Z^5$ each independently is —(CH$_2$)$_2$—, —(CH$_2$)$_4$—, —COO—, —CF$_2$O—, —OCF$_2$—, —CH=CH—, or a single bond; and $L^1$ and $L^2$ each independently is hydrogen or fluorine.

32. A liquid crystal composition which contains at least one of the compounds described in claim 1 and at least one compound selected from the group consisting of compounds represented by Formula (6-1), Formula (6-2), and Formula (7) respectively, and may contain at least one optically active compound:

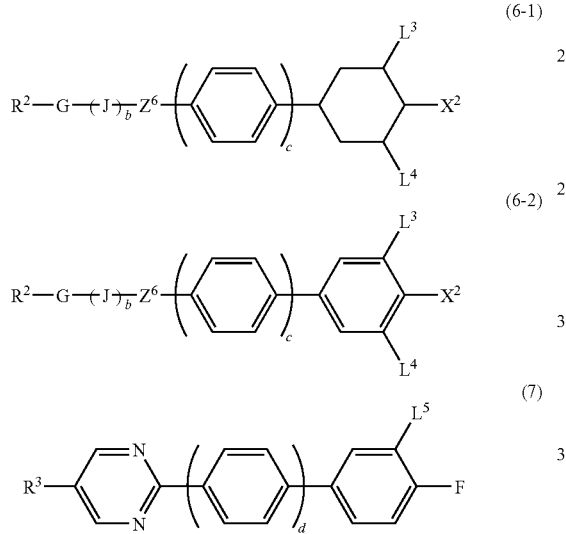

in which $R^2$ and $R^3$ each independently is alkyl of 1 to 10 carbon atoms; in the alkyl, arbitrary —CH$_2$— may be replaced by —O—, arbitrary —(CH$_2$)$_2$— may be replaced by —CH=CH—, and arbitrary hydrogen may be replaced by fluorine; $X^2$ is —CN or —C≡C—CN; G is 1,4-cyclohexylene, 1,4-phenylene, 1,3-dioxane-2,5-diyl, or pyrimidine-2,5-diyl; J is 1,4-cyclohexylene, 1,4-phenylene, pyrimidine-2,5-diyl or 1,4-phenylne in which at least one hydrogen is replaced by fluorine; $Z^6$ is —(CH$_2$)$_2$—, —COO—, —CF$_2$O—, OCF$_2$— or a single bond; $L^3$, $L^4$ and $L^5$ each independently is hydrogen or fluorine; and b, c and d each independently is 0 or 1.

33. A liquid crystal composition which contains at least one of the compounds described in claim 1 and at least one compound selected from the group consisting of compounds represented by Formula (8), Formula (9), Formula (10), Formula (11) and Formula (12) respectively, and may contain at least one optically active compound:

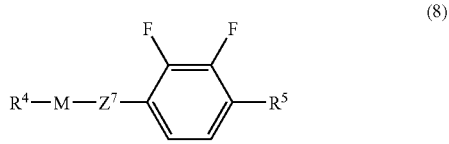

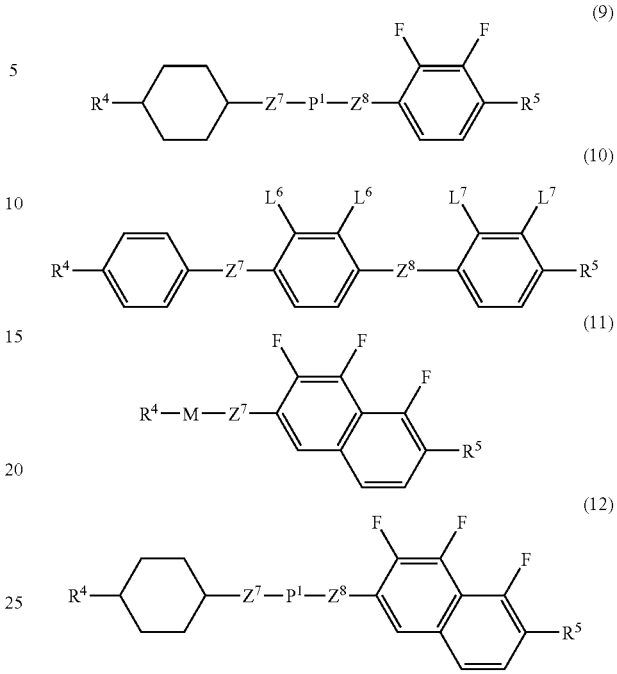

in which $R^4$ is alkyl of 1 to 10 carbon atoms and $R^5$ is fluorine or alkyl of 1 to 10 carbon atoms;
in the alkyls, arbitrary —CH$_2$— may be replaced by —O, arbitrary —(CH$_2$)$_2$— may be replaced by —CH=CH— and arbitrary hydrogen may be replaced by fluorine; M and $P^1$ each independently is 1,4-cyclohexylene, 1,4-phenylene, or decahydro-2,6-naphthylene; $Z^7$ and $Z^8$ each independently is —(CH$_2$)$_2$—, —COO—, or a single bond; $L^6$ and $L^7$ each independently is hydrogen or fluorine; and at least one of $L^6$ and $L^7$ is fluorine.

34. A liquid crystal composition which contains at least one of the compounds described in claim 1 and at least one compound selected from the group consisting of compounds represented by Formula (13), Formula (14) and Formula (15) respectively, and may contain at least one optically active compound:

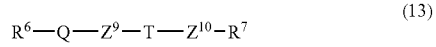
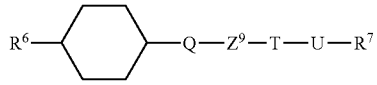

in which $R^6$ and $R^7$ each independently is alkyl of 1 to 10 carbon atoms; in the alkyl, arbitrary —CH$_2$— may be replaced by —O—, arbitrary —(CH$_2$)$_2$— may be replaced by —CH=CH—, and arbitrary hydrogen may be replaced by fluorine; Q, T and U each independently is 1,4-cyclohexylene, 1,4-phenylene, pyrimidine-2,5-diyl, or 1,4-phenylene in which at least one hydrogen is replaced by fluorine; and $Z^9$ and $Z^{10}$ each independently is —C≡C—, —COO—, —(CH$_2$)$_2$—, —CH=CH—, —CH$_2$O—, or a single bond.

35. The liquid crystal composition according to claim 31, which further contains at least one compound selected from the group consisting of compounds represented by Formula (6-1), Formula (6-2) and Formula (7), respectively:

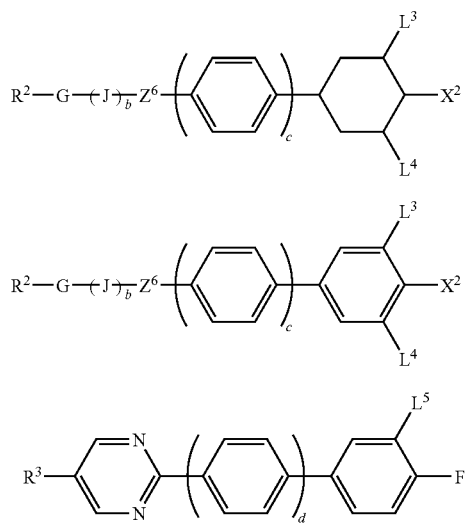

(6-1)

(6-2)

(7)

in which $R^2$ and $R^3$ each independently is alkyl of 1 to 10 carbon atoms; in the alkyl, arbitrary —$CH_2$— may be replaced by —O—, arbitrary —$(CH_2)_2$— may be replaced by —CH=CH—, and arbitrary hydrogen may be replaced by fluorine; $X^2$ is —CN or —C≡C—CN; G is 1,4-cyclohexylene, 1,4-phenylene, 1,3-dioxane-2,5-diyl, or pyrimidine-2,5-diyl; J is 1,4-cyclohexylene, 1,4-phenylene, pyrimidine-2,5-diyl, or 1,4-phenylene in which at least one hydrogen is replaced by fluorine; $Z^6$ is —$(CH_2)_2$—, —COO—, —$CF_2O$—, —$OCF_2$— or a single bond; $L^3$, $L^4$ and $L^5$ each independently is hydrogen or fluorine; and b, c, and d each independently is 0 or 1.

36. The liquid crystal composition according to claim 31, which further contains at least one compound selected from the group consisting of compounds represented by Formula (13), Formula (14) and Formula (15), respectively:

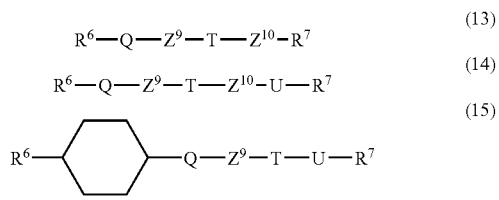

in which $R^6$ and $R^7$ each independently is alkyl of 1 to 10 carbon atoms; in the alkyl, arbitrary —$CH_2$—may be replaced by —O—, arbitrary —$(CH_2)_2$— may be replaced by —CH=CH—, and arbitrary hydrogen may be replaced by fluorine; Q, T and U each independently is 1,4-cyclohexylene, 1,4-phenylene, pyrimidine-2,5-diyl, or 1,4-phenylene in which at least one hydrogen is replaced by fluorine; and $Z^9$ and $Z^{10}$ each independently is —C≡C—, —COO—, —$(CH_2)_2$—, —CH=CH—, —$CH_2O$—, or a single bond.

37. The liquid crystal composition according to claim 32, which further contains at least one compound selected from the group consisting of compounds represented by Formula (13), Formula (14) and Formula (15), respectively:

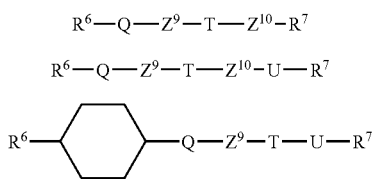

in which $R^6$ and $R^7$ each independently is alkyl of 1 to 10 carbon atoms; in the alkyl, arbitrary —$CH_2$— may be replaced by —O—, arbitrary —$(CH_2)_2$—may be replaced by —CH=CH—, and arbitrary hydrogen may be replaced by fluorine; Q, T and U each independently is 1,4-cyclohexylene, 1,4-phenylene, pyrimidine-2,5-diyl, or 1,4-phenylene in which at least one hydrogen is replaced by fluorine; and $Z^9$ and $Z^{10}$ each independently is —C≡C—, —COO—, —$(CH_2)_2$—, —CH=CH—, —$CH_2O$—, or a single bond.

38. The liquid crystal composition according to claim 33, which further contains at least one compound selected from the group consisting of compounds represented by Formula (13), Formula (14) and Formula (15), respectively:

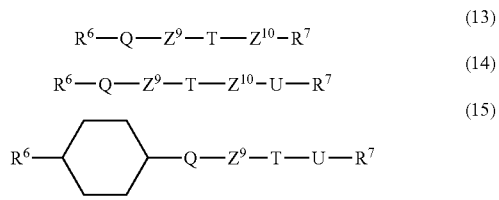

in which $R^6$ and $R^7$ each independently is alkyl of 1 to 10 carbon atoms; in the alkyl, arbitrary —$CH_2$—may be replaced by —O—, arbitrary —$(CH_2)_2$—may be replaced by —CH=CH—, and arbitrary hydrogen may be replaced by fluorine; Q, T and U each independently is 1,4-cyclohexylene, 1,4-phenylene, pyrimidine-2,5-diyl, or 1,4-phenylene in which at least one hydrogen is replaced by fluorine; and $Z^9$ and $Z^{10}$ each independently is —C≡C—, —COO—, —$(CH_2)_2$—, —CH=CH—, —$CH_2O$—, or a single bond.

39. A liquid crystal display device containing the liquid crystal composition described in claim 30.

* * * * *